(12) United States Patent
Voelker et al.

(10) Patent No.: US 7,405,344 B2
(45) Date of Patent: Jul. 29, 2008

(54) **ELEVATION OF OIL LEVELS IN *BRASSICA* PLANTS**

(75) Inventors: Toni A. Voelker, Davis, CA (US); Dale L. Val, Woodland, CA (US); Thomas J. Savage, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 168 days.

(21) Appl. No.: 10/742,350

(22) Filed: Dec. 19, 2003

(65) Prior Publication Data

US 2004/0172681 A1 Sep. 2, 2004

Related U.S. Application Data

(60) Provisional application No. 60/435,197, filed on Dec. 19, 2002.

(51) Int. Cl.
*C12N 5/04* (2006.01)
*C12N 15/82* (2006.01)

(52) U.S. Cl. .................. 800/281; 435/419; 435/468; 536/23.2

(58) Field of Classification Search .................. None
See application file for complete search history.

(56) References Cited

U.S. PATENT DOCUMENTS

| 5,510,255 | A | 4/1996 | Knauf et al. ............. 435/172.3 |
| 5,925,805 | A | 7/1999 | Ohlrogge et al. | |
| 6,268,550 | B1 | 7/2001 | Gengenbach et al. | |

OTHER PUBLICATIONS

Sweetlove et al. 1996, Biochem. J. 320:493-498.*
Kawaguchi et al., "Fatty Acid Synthase from *Brevibacterium ammoniagenes*", Methods in Enzymology, 71:120-127 (1981).
Lambalot et al., "A New Enzyme Superfamily—the Phosphopantetheinyl Transferases", Chem. Biol., 3:923-936 (1996).
Mootz et al., "4'-Phosphopantetheine Transfer in Primary and Secondary Metabolism of *Bacillus subtilis*", J. Biol.Chem., 276:37289:37298 (2001).
Sanchez et al., "Cloning and Characterization of a Phosphopantetheinyl Transferase from *Streptomyces verticillus* ATCC15003, the Producer of the Hybrid Peptide—Polyketide Antitumor Drug Bleomycin", Chem. Biol., 8:725-728 (2001).
Stuible et al., "Identification, Isolation and Biochemical Characterization of a Phosphopantetheine:Protein Transferase that Activates the Two Type-I Fatty Acid Synthases of *Brevibacterium ammoniagenes*", Eur. J. Biochem., 248:481-487 (1997).
Stuible et al., "Identification and Functional Differentiation of Two Type I Fatty Acid Synthases in *Brevibacterium ammoniagenes*", J. Bacteriol. 178:4787-4793 (1996).
Borchert et al., NCBI General Identifier No. 474184, Accession No. X76434 (Apr. 1994).
Cole et al., NCBI General Identifier No. 3261686, Accession No. CAB06201 (Jun. 2004).
Eiglmeier et al., NCBI General Identifier No. 4539127, Accession No. CAB39571 (Aug. 1999).
Fernandes et al., NCBI General Identifier No. 1036834, Accession No. U36763 (Aug. 2001).
Fraser et al., NCBI General Identifier No. 17507093, Accession No. NP_492417 (Nov. 2003).
Miller et al., NCBI General Identifier No. 929999, Accession No. U32586 (Oct. 1996).
Nakano et al., NCBI General Identifier No. 40138, Accession No. X63158 (Apr. 1992).
Oshima et al., NCBI General Identifier No. 1651238, Accession No. D90700 (Dec. 2002).
Saitoh et al., NCBI General Identifier No. 1199959, Accession No. D83412 (Feb. 1999).
Sanchez et al., NCBI General Identifier No. 12003273, Accession No. AF210311 (Nov. 2002).
Schweizer et al., NCBI General Identifier No. 56132, Accession No. X13415 (Sep. 1993).
Sofia et al., NCBI General Identifier No. 466582, Accession No. U00039 (Nov. 1996).
Southard et al., NCBI General Identifier No. 456442, Accession No. L29063 (Feb. 1994).
Urrestarazu et al., NCBI General Identifier No. 1370478, Accession No. CAA97948 (Aug. 1997).
Wiemann et al., NCBI General Identifier No. 486321, Accession No. CAA82025 (Aug. 1997).
Yuan et al., NCBI General Identifier No. 211766, Accession No. J03860 (Apr. 1993).
Zhao et al., NCBI General Identifier No. 402177, Accession No. CAA52907 (Dec. 1994).

* cited by examiner

*Primary Examiner*—Ashwin Mehta
*Assistant Examiner*—Li Zheng
(74) *Attorney, Agent, or Firm*—Sonnenschein Nath & Rosenthal LLP

(57) ABSTRACT

This present invention provides a method for increasing oil levels in the tissues of *Brassica* sp. plants by expression of a heterologous multifunctional fatty acid synthase (mfFAS) within the plant. In one embodiment, the present invention provides isolated nucleic acid molecules encoding mfFAS enzymes from various sources for this purpose, and vectors and plants containing same.

6 Claims, 19 Drawing Sheets

```
FASA pMON70058.SEQ  A T G T C G T T G A C C C C C T T G C A T A C C T T G T C T A A T G A C A G C A   40
X87822 orf.SEQ      A T G T C G T T G A C C C C C T T G C A T A C C T T G T C T A A T G A C A G C A   40

FASA pMON70058.SEQ  C T G C T C C C G C G G T G C T G T T T G C G G G T C A G G G T T C T G C A T G   80
X87822 orf.SEQ      C T G C T C C C G C G G T G C T G T T T G C G G G T C A G G G T T C T G C A T G   80

FASA pMON70058.SEQ  G C A A A A G G C C A T C G C T G A T G C C G C A G C C A G C C C T C A C C A G   120
X87822 orf.SEQ      G C A A A A G G C C A T C G C T G A T G C C G C A G C C A G C C C T C A C C A G   120

FASA pMON70058.SEQ  G G C G C A C A A T T G C G C G A C A T C C T A A A A G A A G T T C G C A C G A   160
X87822 orf.SEQ      G G C G C A C A A T T G C G C G A C A T C C T A A A A G A A G T T C G C A C G A   160

FASA pMON70058.SEQ  C C A C C G G C C C A G T A G C A C G C A T C A T T G C G T C G T C G T G C C C   200
X87822 orf.SEQ      C C A C C G G C C C A G T A G C A C G C A T C A T T G C G T C G T C G T G C C C   200

FASA pMON70058.SEQ  T G G C G T T T A T G A A C G C T T G G A A G A A C T T G C T C A G A C C C C C   240
X87822 orf.SEQ      T G G C G T T T A T G A A C G C T T G G A A G A A C T T G C T C A G A C C C C C   240

FASA pMON70058.SEQ  G C T G A C C A A G C A C C G G T G G C C A A G G A A T A T G A C G C G T A C C   280
X87822 orf.SEQ      G C T G A C C A A G C A C C G G T G G C C A A G G A A T A T G A C G C G T A C C   280

FASA pMON70058.SEQ  C G G C T T A C T C C A T C C C C G G C A T C G T C C T G G G A C A A A T T G G   320
X87822 orf.SEQ      C G G C T T A C T C C A T C C C C G G C A T C G T C C T G G G A C A A A T T G G   320

FASA pMON70058.SEQ  T G C C A T T G A G C A C C T G C G C G A G C T G G G C A T C G A T G T C G A T   360
X87822 orf.SEQ      T G C C A T T G A G C A C C T C G C G C A G C T G G G C A T C G A T G T C G A T   360

FASA pMON70058.SEQ  T C C G C G C A G T T A G C A G G C C A C T C C C A G G G T T C A T T A G G T G   400
X87822 orf.SEQ      T C C G C G C A G T T A G C A G G C C A C T C C C A G G G T T C A T T A G G T G   400

FASA pMON70058.SEQ  T T G C A G C C G T T A A G G A T G C A C G C C A G G C C C T G G C T A T T G C   440
X87822 orf.SEQ      T T G C A G C C G T T A A G G A T G C A C G C C A G G C C C T G G C T A T T G C   440

FASA pMON70058.SEQ  T G T T T T G A T G G G T A C T G C A G C A G C G G T G A C C C A G G G C G C G   480
X87822 orf.SEQ      T G T T T T G A T G G G T A C T G C A G C A G C G G T G A C C C A G G G C G C G   480

FASA pMON70058.SEQ  A A T G A T T C C C G C T C C C A C A T G C T G T C C G T G C G T G G C G T A C   520
X87822 orf.SEQ      A A T G A T T C C C G C A C C C A C A T G C T G T C C G T G C G T G G C G T A C   520

FASA pMON70058.SEQ  C A C G T G A G A T G G T C G A A G A A T A C C T C G C T G G T G A C G C T G C   560
X87822 orf.SEQ      C A C G T G A G A T G G T C G A A G A A T A C C T C G C T G G T G A C G C T G C   560

FASA pMON70058.SEQ  G A T T G C C G T G G T C A A C G G C C G C G T G C A C T T T G C A C T G T C G   600
X87822 orf.SEQ      G A T T G C C G T G G T C A A C G G C C G C G T G C A C T T T G C A C T G T C G   600

FASA pMON70058.SEQ  G G T A C C C C A G A G G A T C T G G C T A A G A C C G A G T C C A A C C T C A   640
X87822 orf.SEQ      G G T A C C C C A G A G G A T C T G G C T A A G A C C G A G T C C A A C C T C A   640

FASA pMON70058.SEQ  C C C A G G C T G C C G A G T C C T A C A A C G A C G C G C T G G A A G A A C G   680
X87822 orf.SEQ      C C C A G G C T G C C G A G T C C T A C A A C G A C G C G C T G G A A G A A C G   680

FASA pMON70058.SEQ  C C G C A T C G G C G G C T C C G A A A T T A A C C C A G T C T T C G A C G T A   720
X87822 orf.SEQ      C C G C A T C G G C G G C T C C G A A A T T A A C C C A G T C T T C G A C G T A   720

FASA pMON70058.SEQ  T T G G C C G T G G C A C T T C C T T T C C A C C A C G C A T C A C T G C A G G   760
X87822 orf.SEQ      T T G G C C G T G G C A C T T C C T T T C C A C C A C G C A T C A C T G C A G G   760

FASA pMON70058.SEQ  A T G C A G C G G A T C T G A C C G T G G A C T A C G C C A C C C A G T G T G G   800
X87822 orf.SEQ      A T G C A G C G G A T C T G A C C G T G G A C T A C G C C A C C C A G T G T G G   800

FASA pMON70058.SEQ  C C T G G A C G C T G A G C T T G C A C G C G A G C T G G C A G A T T C C A T C   840
X87822 orf.SEQ      C C T G G A C G C T G A G C T T G C A C G C G A G C T G G C A G A T T C C A T C   840

FASA pMON70058.SEQ  C T G G T T C A G C C A C A T A G C T G G G T T G A G A C C G T G G C C G G T C   880
X87822 orf.SEQ      C T G G T T C A G C C A C A T A G C T G G G T T G A G A C C G T G G C C G G T C   880

FASA pMON70058.SEQ  T C A A C T C C A C C T A C C T G C T C T C C T T A G A C C G T G G T C T G T C   920
X87822 orf.SEQ      T C A A C T C C A C C T A C C T G C T C T C C T T A G A C C G T G G T C T G T C   920

FASA pMON70058.SEQ  T T C G T T G A C T A C A C C T T T G A                                         940
X87822 orf.SEQ      T T C G T T G A C T A C A C C T T T G A                                         940
```

Boxed Residues Differ from pMON70058

Figure 2 (page 1 of 10)

| | | |
|---|---|---|
| FASA pMON70058.SEQ | T T G C C G G C A C C G G C A A G G T T G T G G T T C C A G C T G C T A C G C C | 980 |
| X87822 orf.SEQ | T T G C C G G C A C C G G C A A G G T T G T G G T T C C A G C T G C T A C G C C | 980 |
| FASA pMON70058.SEQ | A G C G G A G C G C G A T A A C C T G G C T A C C C C A G G C A C T G A G C T G | 1020 |
| X87822 orf.SEQ | A G C G G A G C G C G A T A A C C T G G C T A C C C C A G G C A C T G A G C T G | 1020 |
| FASA pMON70058.SEQ | C C T A C C G C G G T G A A C T A C G A G A A G T T C T C A C C A A A G C T C A | 1060 |
| X87822 orf.SEQ | C C T A C C G C G G T G A A C T A C G A G A A G T T C T C A C C A A A G C T C A | 1060 |
| FASA pMON70058.SEQ | T C T C C T T G C C C A A C G G C A A G T C C T A C A C T C A G A C T C G T T T | 1100 |
| X87822 orf.SEQ | T C T C C T T G C C C A A C G G C A A G T C C T A C A C T C A G A C T C G T T T | 1100 |
| FASA pMON70058.SEQ | C T C C G A G T G G A C C G G C A T G T C C C C C A T C A T T T T G G G C G G C | 1140 |
| X87822 orf.SEQ | C T C C G A G T G G A C C G G C A T G T C C C C C A T C A T T T T G G G C G G C | 1140 |
| FASA pMON70058.SEQ | A T G A C G C C G A C C A C G A T G G A T C C G G G C A T C G T T G C C G C A G | 1180 |
| X87822 orf.SEQ | A T G A C G C C G A C C A C G A T G G A T C C G G G C A T C G T T G C C G C A G | 1180 |
| FASA pMON70058.SEQ | C G G C C A A C G G T G G C T A C T G G T C A G A G A T G G C C G G T G G C G G | 1220 |
| X87822 orf.SEQ | C G G C C A A C G G T G G C T A C T G G T C A G A G A T G G C C G G T G G C G G | 1220 |
| FASA pMON70058.SEQ | T C A G T A C T C C G A T G A A G C T T T T A C C A T C A A C A A A G A C G G C | 1260 |
| X87822 orf.SEQ | T C A G T A C T C C G A T G A A G C T T T T A C C A T C A A C A A A G A C G G C | 1260 |
| FASA pMON70058.SEQ | A T G A T G G A G C T G C T G G A G C C A G G T C G C A C C G C A G C A T T T A | 1300 |
| X87822 orf.SEQ | A T G A T G G A G C T G C T G G A G C C A G G T C G C A C C G C A G C A T T T A | 1300 |
| FASA pMON70058.SEQ | A C A C C A T G T T C T T T G A C C G C T A C C T G T G G A A C C T A C A G T T | 1340 |
| X87822 orf.SEQ | A C A C C A T G T T C T T T G A C C G C T A C C T G T G G A A C C T A C A G T T | 1340 |
| FASA pMON70058.SEQ | C G G T G T C A C C C G C A T T G T T C C C A A G G C A C G C G C T A A T G G T | 1380 |
| X87822 orf.SEQ | C G G T G T C A C C C G C A T T [T G] T [T] C C A A G G C A C G C G C T A A T G G T | 1380 |
| FASA pMON70058.SEQ | G C T G C G T T T A C C G G C G T G A C C A T C T C C G C T G G T A T C C C A G | 1420 |
| X87822 orf.SEQ | G C T G C G T T T A C C G G C G T G A C C A T C T [G] C G C T G G T A T C C C A G | 1420 |
| FASA pMON70058.SEQ | A G C T G G A T G A A G C C A A G G A A T T G C T G G A C C A G C T C A C C T C | 1460 |
| X87822 orf.SEQ | A G C T G G A T G A A G C C A A G G A A T T G C T G G A C C A G C T C A C C T C | 1460 |
| FASA pMON70058.SEQ | C G A T G G C T T C C C A T A C A T C T C T T T C A A G C C G G G C A C C A C C | 1500 |
| X87822 orf.SEQ | C G A T G G C T T [T] C C A T A C A T C T C T T T C A A G C C G G G C A C C A C C | 1500 |
| FASA pMON70058.SEQ | A A G C A G A T T C A A G A C T G C A T C G C T A T C G C A G C G G A T A A C C | 1540 |
| X87822 orf.SEQ | A A G C A G A T T C A A G A C T G C [G] T C G C T A T C G C A G C G G A T A A C C | 1540 |
| FASA pMON70058.SEQ | C C A C C C A C C G C G T C A T C A T C C A A A T T G A A G A C G G C C A C G C | 1580 |
| X87822 orf.SEQ | C C A C C C A C C G C G T C A T C A T C C A A A T T G A A G A C G [C] C C A C G C | 1580 |
| FASA pMON70058.SEQ | T G G T G G C C A C C A C T C C T G G G T G G A T C T G G A T G A A A T G C T G | 1620 |
| X87822 orf.SEQ | T G G T G G C C A C C A C T C C T G G G T G G A T C T G G A T G A A A T G C T G | 1620 |
| FASA pMON70058.SEQ | C T G G C T A C C T A C G C A T C T G C C C G T G A G C A C G A C A A C C T G G | 1660 |
| X87822 orf.SEQ | C T G G C T A C C T A C G C A T [G] T G C C C G T G A G C A C G A C A A C C T G G | 1660 |
| FASA pMON70058.SEQ | C C A T C A C T G T T G G T G G C G G C A T C C A C T C C C C A G A C C G C G C | 1700 |
| X87822 orf.SEQ | C C A T C A C T G T T G G T G G C G G C A T C C A C T C C C C A G A C C G C G C | 1700 |
| FASA pMON70058.SEQ | A T C G G A A T A C C T G A C C G G T A C C T G G T C C A C C A A G T A C G G T | 1740 |
| X87822 orf.SEQ | A T C G G A A T A C C T G A C C G G T A C C T G G T C C A C C A A G T A C G G T | 1740 |
| FASA pMON70058.SEQ | T T G C C C A T C A T G C C G G T T G A T G G T G T C T T C T T G G G C A C C G | 1780 |
| X87822 orf.SEQ | T T G C C C A T C A T G C C G G T T G A T G G T G T C T T C T T G G G C A C C G | 1780 |
| FASA pMON70058.SEQ | T A G C C A T G G C G A C C A A G G A A G C A A C G G C T A A T G A T G A C G T | 1820 |
| X87822 orf.SEQ | T A G C C A T G G C G A C C A A G G A A G C A A C G G C T A A T G A T G A C G T | 1820 |
| FASA pMON70058.SEQ | T A A G C A G T T G C T A G T T G A T A C C C C A G G T A T T T C C C C A G A G | 1860 |
| X87822 orf.SEQ | T A A G C A G T T G C T A G T T G A T A C C C C A G G T A T T T C C C C A G A G | 1860 |
| FASA pMON70058.SEQ | A C C A A T G G C G G T T G G G T A G G C C G A C T A G A T G C C G A C G G C G | 1900 |
| X87822 orf.SEQ | A C C A A T G G C G G T T G G G T A G G C C G A C T A G A T G C C G A C G G C G | 1900 |

Boxed Residues Differ from pMON70058

Figure 2 (page 2 of 10)

| | | |
|---|---|---|
| FASA pMON70058.SEQ | G C G T C T C C T C C T C C C A G T C C C A C C T G T T G G C T G A C T T G C A | 1940 |
| X87822 orf.SEQ | G C G T [G] T C C T C C T C C C A G T C C C A C C T G T T G G C T G A C T T G C A | 1940 |
| FASA pMON70058.SEQ | C G A G A T T G A T A A C T C G T T T G C C A A G G C C T C G C G C A T G A T C | 1980 |
| X87822 orf.SEQ | C G A G A T T G A T A A C T C G T T T G C C A A G G C C T C G C G C A T G A T C | 1980 |
| FASA pMON70058.SEQ | A C C T C G A T C C C G A T C G A G G A G T A T G A C G A G C G T C G C G A C G | 2020 |
| X87822 orf.SEQ | A C C T C G A T C C C G A T C G A G G A G T A T G A C G A G C G T C G C G A C G | 2020 |
| FASA pMON70058.SEQ | A G A T C A T T G C T G C T C T G G A C A A G A C C T C C A A G C C A T A C T T | 2060 |
| X87822 orf.SEQ | A G A T C A T T G C T G C T C T G G A C A A G A C C T C C A A G C C A T A C T T | 2060 |
| FASA pMON70058.SEQ | C G G T G A C C T G T C G G A G A T G A C C T A C G A G G A T T G G G T C G C T | 2100 |
| X87822 orf.SEQ | C G G T G A C C T G T C G G A G A T G A C C T A C G A G G A T T G G G T C G C T | 2100 |
| FASA pMON70058.SEQ | C G T T T C G C A G A G C G C G C C T A C C C T T G G G T G G A T C C A A C C T | 2140 |
| X87822 orf.SEQ | C G T T T C G C A G A G C G C G C C T A C C C T T G G G T G G A T C C A A C C T | 2140 |
| FASA pMON70058.SEQ | G G C A C G A T C G T T T C C A C G A T C T G C T C C A G C G C G T A G A A G C | 2180 |
| X87822 orf.SEQ | G G C A C G A T C G T T T C C A C G A T C T G C T C C A G C G C G T A G A A G C | 2180 |
| FASA pMON70058.SEQ | G C G T C T C A A T G A C G C T G A C C A C G G C G A C A T C G A G A C C C T A | 2220 |
| X87822 orf.SEQ | G C G T C T C A A T G A C G C T G A C C A C G G C G A C A T C G A G A C C C T A | 2220 |
| FASA pMON70058.SEQ | T T C C C C A C A C T C G A C G A C T C C G A G A A C G C A C C A G A G G C A G | 2260 |
| X87822 orf.SEQ | T T C C C C A C A C T C G A C G A C T C C G A G A A C G C A C C A G A G G C A G | 2260 |
| FASA pMON70058.SEQ | T A G C C A A G C T G C T G G C T G C C T A C C C G A A T G C A A A G A C C A C | 2300 |
| X87822 orf.SEQ | T A G C C A A G C T G C T G G C T G C C T A C C C G A A T G C A A A G A C C A C | 2300 |
| FASA pMON70058.SEQ | C A A G G T C A A C A C C C G C G A T G A G G C A T G G T T C C C T A C C C T T | 2340 |
| X87822 orf.SEQ | C A A G G T C A A C A C C C G C G A T G A G G C A T G G T T C C C T A C C C T T | 2340 |
| FASA pMON70058.SEQ | A T C C G C A A G C A C G T C A A G C C A A T G C C G T G G A C C A C C G C T A | 2380 |
| X87822 orf.SEQ | A T C C G C A A G C A C G T C A A G C C A A T . G C C G T G G A C C A C C G C T A | 2380 |
| FASA pMON70058.SEQ | T T G A C G G T G A C C T G A A G G A A T G G T T T G C C A A G G A C A C C C T | 2420 |
| X87822 orf.SEQ | T T G A C G G T G A C C T G A A G G A A T G G T T T G C C A A G G A C A C C C T | 2420 |
| FASA pMON70058.SEQ | G T G G C A G G C C C A G G A C C C A C G C T A C G A C G C A G A C G G C G T A | 2460 |
| X87822 orf.SEQ | G T G G C A G G C C C A G G A C C C A C G C T A C G A C G C A G A C G G C G T A | 2460 |
| FASA pMON70058.SEQ | C G C A T C A T T C C A G G A C C G G T T T C G G T T G C T G G T A T C A C C A | 2500 |
| X87822 orf.SEQ | C G C A T C A T T C C A G G A C C G G T T T C G G T T G C T G G T A T C A C C A | 2500 |
| FASA pMON70058.SEQ | A G A A G A A T G A G C C C G T C G C A A A C C T G C T C G G T C G C T T C G A | 2540 |
| X87822 orf.SEQ | A G A A G A A T G A G C C C G T C G C A A A C C T G C T C G G T C G C T T C G A | 2540 |
| FASA pMON70058.SEQ | A G A C G C C A C C A C C G C A G C G C T T A A C G A T G C C G G C G T G G C A | 2580 |
| X87822 orf.SEQ | A G A C G C C A C C A C C G C A G C G C T T A A C G A T G C C G G C G T G G C A | 2580 |
| FASA pMON70058.SEQ | C C A G T T G A G C T C T A C T C C C G C T T G G C T T C T G C C A A G A A T G | 2620 |
| X87822 orf.SEQ | C C A G T T G A G C T C T A C T C C C G C T T G G C T T C T G C C A A G A A T G | 2620 |
| FASA pMON70058.SEQ | C A G A A G A G T T C C T G C G C A A T G C A C C A A C C A T C A T G T G G C A | 2660 |
| X87822 orf.SEQ | C A G A A G A G T T C C T G C G C A A T G C A C C A A C C A T C A T G T G G C A | 2660 |
| FASA pMON70058.SEQ | C G G T C A C C T C A T T G C C A A C C C G G C G T A T G A G C T G C C A G A A | 2700 |
| X87822 orf.SEQ | C G G T C A C C T C A T T G C C A A C C C G G C G T A T G A G C T G C C A G A A | 2700 |
| FASA pMON70058.SEQ | G A A G C T T T T G A C A T C G T C G A T G A C G G C G A A G G C T T T G C T A | 2740 |
| X87822 orf.SEQ | G A A G C T T T T G A C A T C G T C G A T G A C G G C G A A G G C T T T G C T A | 2740 |
| FASA pMON70058.SEQ | T T C G C A T C A A C T C T G A C T C C T A C T G G G A T A A C C T C C C A G A | 2780 |
| X87822 orf.SEQ | T T C G C A T C A A C T C T G A C T C C T A C [A] G G G A T A A C C T C C C A G A | 2780 |
| FASA pMON70058.SEQ | A G A G C A G C G T C C G T T C T A C G T C A A G C A C G T T G A T A T C C C C | 2820 |
| X87822 orf.SEQ | A G A G C A G C G T C C G T T C T A C G T C A A G C A C G T T G A T A T C C C C | 2820 |
| FASA pMON70058.SEQ | G T T G C G C T G T C G G A A G C C G T A G C A A C C G G T G C C T C C C C T G | 2860 |
| X87822 orf.SEQ | G T T G C G C T G T C G G A A G C C G T A G C A A C C G G T G C C T C C C C T G | 2860 |

Boxed Residues Differ from pMON70058

Figure 2 (page 3 of 10)

| | | |
|---|---|---|
| FASA pMON70058.SEQ | T T G T T G A T G A C G C G C G T T T G C C A A A G G C A G T C T T C G A C C T | 2900 |
| X87822 orf.SEQ | T T G T T G A T G A C G C G C G T T T G C C A A A G G C A G T C T T C G A C C T | 2900 |
| FASA pMON70058.SEQ | G C T C G C A G G C G T T G C T G G T G T C G G G T C T A T C T C T G A G A C C | 2940 |
| X87822 orf.SEQ | G C T C G C A G G C G T T G C T G G T G T C G G G T C T A T C T C T G A G A C C | 2940 |
| FASA pMON70058.SEQ | G G C G A T A A G A T C A C C G A A C T G C C G A A G G T C A T C G A A G G C T | 2980 |
| X87822 orf.SEQ | G G C G A T A A G A T C A C C G A A C T G C C G A A G G T C A T C G A A G G C T | 2980 |
| FASA pMON70058.SEQ | C T G T C T C C G A A G A A A A C C C T T A C G G C C T G G T G G A A T A C T C | 3020 |
| X87822 orf.SEQ | C T G T C T C C G A A G A A A A C C C T T A C G G C C T G G T G G A A T A C T C | 3020 |
| FASA pMON70058.SEQ | C T T T A C C T T G C C T T C T A C C C T G C T G A C C G C A C A C A C C G C G | 3060 |
| X87822 orf.SEQ | C T T T A C C T T G C C T T C T A C C C T G C T G A C C G C A C A C A C C G C G | 3060 |
| FASA pMON70058.SEQ | G T A A C C G G C G C T G C C T T G G G C A C C G C C A A C G C A G G C A C C C | 3100 |
| X87822 orf.SEQ | G T A A C C G G C G C T G C C T T G G G C A C C G C C A A C G C A G G C A C C C | 3100 |
| FASA pMON70058.SEQ | C A G A T G C G C T G G T T G G C C C C T G C T G G C C A G C A A T T T A C A C | 3140 |
| X87822 orf.SEQ | C A G A T G C G C T G G T T G G C C C C T G C T G G C C A G C A A T T T A C A C | 3140 |
| FASA pMON70058.SEQ | C G C G C T G G G C A C C G G T C G A T T G A C C G A A G A A C A C G G T G A G | 3180 |
| X87822 orf.SEQ | C G C G C T G G G C A C C G G T C G A T T G A C C G A A G A A C A C G G T G A G | 3180 |
| FASA pMON70058.SEQ | C C A G C C G G C A C C G A C T T C C C G G T C A T T G A A G G C C T G C T C A | 3220 |
| X87822 orf.SEQ | C C A G C C G G C A C C G A C T T C C C G G T C A T T G A A G G C C T G C T C A | 3220 |
| FASA pMON70058.SEQ | A C G C A G T C C A C C T C G A C C A C G T C G T C G A T G T G C G T G T T C C | 3260 |
| X87822 orf.SEQ | A C G C A G T C C A C C T C G A C C A C G T C G T C G A T G T G C G T G T T C C | 3260 |
| FASA pMON70058.SEQ | T C T T C A C G A A C T C G C A A A G G G T G A A A A G G G C G A A G G C C G T | 3300 |
| X87822 orf.SEQ | T C T T C A C G A A C T C G C A A A G G G T G A A A A G G G C G A A G G C [G] G T | 3300 |
| FASA pMON70058.SEQ | C G C A T T G A C G T C A C C T C C C G C T G T G C A T C C A T C G C G G A A T | 3340 |
| X87822 orf.SEQ | C G C A T T G A C G T C A C C T C C C G C T G T G C A T C C A T C G C G G A A T | 3340 |
| FASA pMON70058.SEQ | C C A A C T C C G G T C G C A T T G T C A C C G T G G A A C T T G A G T T G T G | 3380 |
| X87822 orf.SEQ | C C A A C T C C G G T C G C A T T G T C A C C G T G G A A C T T G A G T T G T G | 3380 |
| FASA pMON70058.SEQ | G G A T G C C G C A A C T C A A G A A G T T G T G G C G A C G C A G A T G C A G | 3420 |
| X87822 orf.SEQ | G G A T G C C G C A A C T C A A G A A G T T G T G G C G A C G C A G A T G C A G | 3420 |
| FASA pMON70058.SEQ | C G C T T T G C C A T C C G T G G C C G C G C T A C C G G C A C C T C C G T T C | 3460 |
| X87822 orf.SEQ | C G C T T T G C C A T C C G T G G C C G C G C T A C C G G C A C C T C C G T T C | 3460 |
| FASA pMON70058.SEQ | C G G T T T C T G C A C C A T C C T G G G G C G G C G G C A A G T C T C A G G A | 3500 |
| X87822 orf.SEQ | C G G T T T C T G C A C C A T C C T G G G G C G G C G G C A A G T C T C A G G A | 3500 |
| FASA pMON70058.SEQ | C A A G A T T G A G A C C A C C C C A C G T T C C T T C G T G G A T C G C G C C | 3540 |
| X87822 orf.SEQ | C A A G A T T G A G A C C A C C C C A C G T T C C T T C G T G G A T C G C G C C | 3540 |
| FASA pMON70058.SEQ | A T T G T C A C C G C G C C A T C G G A T A T G A C C C C A T T C G C G C T G G | 3580 |
| X87822 orf.SEQ | A T T G T C A C C G C G C C A T C G G A T A T G A C C C C A T T C G C G C T G G | 3580 |
| FASA pMON70058.SEQ | T C T C C G G T G A C T A C A A C C C A A T T C A C A C C T C C A C C A A C G C | 3620 |
| X87822 orf.SEQ | T C T C C G G T G A C T A C A A C C C A A T T C A C A C C T C C A C C A A C G C | 3620 |
| FASA pMON70058.SEQ | C G C G C G C T T G G T C A A C C T C G A C G C C C C A C T G G T G C A C G G C | 3660 |
| X87822 orf.SEQ | C G C G C G C T T G G T C A A C C T C G A C G C C C C A C T G G T G C A C G G C | 3660 |
| FASA pMON70058.SEQ | A T G T G G C T A T C T G C C A C C G C G C A G C A C C T A G C T G G C A A C C | 3700 |
| X87822 orf.SEQ | A T G T G G C T A T C T G C C A C C G C G C A G C A C C T A G C T G G C A A C C | 3700 |
| FASA pMON70058.SEQ | A C G G C A C C G T G G T G G G T T G G A C C T A T T C C A T G T A C G G C A T | 3740 |
| X87822 orf.SEQ | A C G G C A C C G T G G T G G G T T G G A C C T A T T C C A T G T A C G G C A T | 3740 |
| FASA pMON70058.SEQ | G G T C C A G C T C A A C G A T G A A G T A G A A A T C A C C G T C G A A C G C | 3780 |
| X87822 orf.SEQ | G G T C C A G C T C A A C G A T G A A G T A G A A A T C A C C G T C G A A C G C | 3780 |
| FASA pMON70058.SEQ | G T A G G C C G C A A G G G C A T T C A C G C A G C A T T C G A G G T C A C C T | 3820 |
| X87822 orf.SEQ | G T A G G C C G C A A G G G C A T T C A C G C A G C A T T C G A G G T C A C C T | 3820 |

Boxed Residues Differ from pMON70058

Figure 2 (page 4 of 10)

```
FASA pMON70058.SEQ  G C C G C A T C G A C G G C G A A G T A G T C T C C C G C G G C C A G G C G C T  3860
X87822 orf.SEQ      G C C G C A T C G A C G G C G A A G T A G T C T C C C G C G G C C A G G C G C T  3860

FASA pMON70058.SEQ  C A T G G C A C A G C C A C G C A C C G C T T A T G T C T A C C C A G G C C A G  3900
X87822 orf.SEQ      C A T G G C A C A G C C A C G C A C C G C T T A T G T C T A C C C A G G C C A G  3900

FASA pMON70058.SEQ  G G C A T C C A G G C C G A G G G C A T G G G C C G T G G T G A C C G C G A T G  3940
X87822 orf.SEQ      G G C A T C C A G G C C G A G G G C A T G G G C C G T G G T G A C C G C G A T G  3940

FASA pMON70058.SEQ  C T T C G G C A G C A G C G C G T G A G G T A T G G C G T C G T G C A G A C C G  3980
X87822 orf.SEQ      C T T C G G C A G C A G C G C G T G A G G T A T G G C G T C G T G C A G A C C G  3980

FASA pMON70058.SEQ  C C A C A C C C G C A C C G C A A T G G G C T T T T C T A T T C G C C A G A T C  4020
X87822 orf.SEQ      C C A C A C C C G C A C C G C A[C]T G G G C T T T T C T A T T C G C C A G A T C  4020

FASA pMON70058.SEQ  A T C G A T G A C A A C C C C A C C G A G C T C G T C G T T C G C G G C A C C A  4060
X87822 orf.SEQ      A T C G A T G A C A A C C C C A C C G A G C T C G T C G T T C G C G G C A C C A  4060

FASA pMON70058.SEQ  A G T T C G T C C A C C C C A A T G G C G T G C T G C A C T T A A C G C A G T T  4100
X87822 orf.SEQ      A G T T C G T C C A C C C C A A T G G C G T G C T G C A C T T A A C G C A G T T  4100

FASA pMON70058.SEQ  C A C T C A G G T T G C C C T C G C A G T C G T T G C T T A T G C A C A A A C C  4140
X87822 orf.SEQ      C A C T C A G G T T G C C C T C G C A G T C G T T G C T T A T G, C A C A A A C C  4140

FASA pMON70058.SEQ  G A G C G C C T G C G C G A A G C A G A T G C T C T G G G C A C C A A C T C C A  4180
X87822 orf.SEQ      G A G C G C C T G C G C G A A G C A G A T G C T C T G G G C A C C A A C T C C A  4180

FASA pMON70058.SEQ  T G T A C G C C G G T C A C T C A C T G G G T G A G T A C A C C G C G C T G G C  4220
X87822 orf.SEQ      T G T A C G C C G G T C A C T C A C T G G G T G A G T A C A C C G C G C T G G C  4220

FASA pMON70058.SEQ  A T C G T T G G C G A A T A T C T T T G A C C T C G A A G C G G T T A T C G A C  4260
X87822 orf.SEQ      A T C G T T G G C G A A T A T C T T T G A C C T C G A A G C G G T T A T C G A C  4260

FASA pMON70058.SEQ  A T C G T C T A C T C C C G T G G C T C T G C C A T G G G C A C C T T G G T C G  4300
X87822 orf.SEQ      A T C G T C T A C T C C C G T G G C T C T G C C A T G G G C A C C T T G G T C G  4300

FASA pMON70058.SEQ  A A C G T G A T G A A A A C G G T A A C T C C A A C T A C G G C A T G G G C G C  4340
X87822 orf.SEQ      A A C G T G A T G A A A A C G G T A A C T C C A A C T A C G G C A T G G G C G C  4340

FASA pMON70058.SEQ  G C T G C G T C C A A A C A T G A T T G G T G T T C C C G C A G A C C A G G T T  4380
X87822 orf.SEQ      G C T G C G T C C A A A C A T G A T T G G T G T T C C C G C A G A C C A G G T T  4380

FASA pMON70058.SEQ  G A G G C C T A C A T C G C G C A G A C C G C G G A A G A A A C T G G C G A A T  4420
X87822 orf.SEQ      G A G G C C T A C A T C G C G C A G A C C G C G G A A G A A A C T G G C G A A T  4420

FASA pMON70058.SEQ  T C C T C G A A A T C G T C A A C T A C A A C A T C G C T G G T C A G C A G T A  4460
X87822 orf.SEQ      T C C T C G A A A T C G T C A A C T A C A A C A T C G C T G G T C A G C A G T A  4460

FASA pMON70058.SEQ  C T C C A T C G C G G G T A C C A A G G C T G G T T T G G C C G C C C T G A A G  4500
X87822 orf.SEQ      C T C C A T C G C G G G T A C C A A G G C T G G T T T G G C C G C C C T G A A G  4500

FASA pMON70058.SEQ  A A A A A G G C C A A C T C C G T C A A G G A C C G T G C T T A T G T C A C G G  4540
X87822 orf.SEQ      A A A A A G G C C A A C T C C G T C A A G G A C C G T G C T T A T G T C A C G G  4540

FASA pMON70058.SEQ  T T C C A G G C A T C G A T G T A C C T T T C C A C T C C C A G G T A C T G C G  4580
X87822 orf.SEQ      T T C C A G G C A T C G A T G T A C C T T T C C A C T C C C A G G T A C T G C G  4580

FASA pMON70058.SEQ  C G A C G G C G T T C C T G C T T T C G C A G A A A A G C T C G A T G A A C T G  4620
X87822 orf.SEQ      C G A C G G C G T T C C T G C T T T C G C A G A A A A G C T C G A T G A A C T G  4620

FASA pMON70058.SEQ  T T G C C A G A A A C C T T G G A C C T G G A C G C C C T G G T C G G C C G C T  4660
X87822 orf.SEQ      T T G C C A G A A A C C T T G G A C C T G G A C G C C C T G G T C G G C C G C T  4660

FASA pMON70058.SEQ  A C G T G C C G A A C C T G G T G G C G C T G C C A T T C G A G C T G A C C C A  4700
X87822 orf.SEQ      A C G T G C C G A A C C T G G T G G C G C T G C C A T T C G A G C T G A C C C A  4700

FASA pMON70058.SEQ  G G A A T T T G T C G A T A A G G T C A A G C C T T T G G C T C C T T C C G G C  4740
X87822 orf.SEQ      G G A A T T T G T C G A T A A G G T C A A G C C T T T G G C T C C T T C C G G C  4740

FASA pMON70058.SEQ  A A G C T G G A T A A C C T C A A G G T C G A A G A C A C C G A T G A G C A A G  4780
X87822 orf.SEQ      A A G C T G G A T A A C C T C A A G G T C G A A G A C A C C G A T G A G C A A G  4780
```

Boxed Residues Differ from pMON70058

Figure 2  (page 5 of 10)

```
FASA pMON70058.SEQ  C C C T T G C T C G C C T G C T C A T G A T T G A G C T A T T G T C C T G G C A  4820
X87822 orf.SEQ      C C C C T C T C G C C T G C T C A T G A T T G A G C T A T T G T C C T G G C A  4820

FASA pMON70058.SEQ  G T T C G C A T C A C C T G T G C G C T G G A T T G A A A C C C A G C A G C T G  4860
X87822 orf.SEQ      G T T C G C A T C A C C T G T G C G C T G G A T T G A A A C C C A G C A G C T G  4860

FASA pMON70058.SEQ  C T C T T T G A A G A A G T A G A C C A G A T C A T C G A A G T C G G T C T C G  4900
X87822 orf.SEQ      C T C T T T G A A G A A G T A G A C C A G A T C A T C G A A G T C G G T C T C G  4900

FASA pMON70058.SEQ  C G G C A T C C C C A A C G C T G A C C A A C T T G G C C A A G C G C T C C A T  4940
X87822 orf.SEQ      C T T C A T C C C C A A C G C T G A C C A A C T T G G C C A A G C G C T C C A T  4940

FASA pMON70058.SEQ  G G A T A T C G C C G G C G T G G A C C T C C C G G T C T T C A A C G T C G A A  4980
X87822 orf.SEQ      G G A T A T C G C C G G C G T G G A C C T C C C G G T C T T C A A C G T C G A A  4980

FASA pMON70058.SEQ  C G C G A C C A A G A C C A G G T C A T G C T C C A A G A C G T T C A G G A A G  5020
X87822 orf.SEQ      C G C G A C C A A G A C C A G G T C A T G C T C C A A G A C G T T C A G G A A G  5020

FASA pMON70058.SEQ  C A C C A G C T G C C T C C T T C G A C G T C G A G G A A G G A G A G G C C A C  5060
X87822 orf.SEQ      C A C C A G C T G C C T C C T T C G A C G T C G A G G A A G G A G A G G C C A C  5060

FASA pMON70058.SEQ  C T C T T C G A C C G C A G C G T C T G A A A C C C C A G G T G A A T C C G C T  5100
X87822 orf.SEQ      C T C T T C G A C C G C A G C G T C T G A A A C C C C A G G T G A A T C C G C T  5100

FASA pMON70058.SEQ  G C G G C G G C C T C G G A T A A T A C C C A G G C C A T C C C A T C G G C T G  5140
X87822 orf.SEQ      G C G G C G G C C T C G G A T A A T A C C C A G G C C A T C C C A T C G G C T G  5140

FASA pMON70058.SEQ  A G C C A C A A A C G G T G G C A G A G G C A C C A G C A C C A T C C G C C G C  5180
X87822 orf.SEQ      A G C C A C A A A C G G T G G C A G A G G C A C C A G C A C C A T C C G C C G C  5180

FASA pMON70058.SEQ  A C C A G C T G G C G G C A C C G C T G C C G C A G A T G C T C C T G A C C T G  5220
X87822 orf.SEQ      A C C A G C T G G C G G C A C C C G T G C C G C A G A T G C T C C T G A C C T G  5220

FASA pMON70058.SEQ  C C A T T T A C C G C A G C A G A A G C C A T C A T G G T T C T G T T C G C T T  5260
X87822 orf.SEQ      C C A T T T A C C G C A G C A G A A G C C A T C A T G G T T C T G T T C G C T T  5260

FASA pMON70058.SEQ  T C C A G A A C A A G A T C C G C C A G G A C C A G A T C A A T G A C T C G G A  5300
X87822 orf.SEQ      T C C A G A A C A A G A T C C G C C A G G A C C A G A T C A A T G A C T C G G A  5300

FASA pMON70058.SEQ  T A C G G T C G A A G A G C T C A C C A A C G G T G T C T C C T C C C G C C G T  5340
X87822 orf.SEQ      T A C G G T C G A A G A G C T C A C C A A C G G T G T C T C C T C C C G C C G T  5340

FASA pMON70058.SEQ  A A C C A A C T G T T G A T G G A T A T G T C C G C A G A A A T C G G C G T G C  5380
X87822 orf.SEQ      A A C C A A C T G T T G A T G G A T A T G T C C G C A G A A A A T C G C G T G C  5380

FASA pMON70058.SEQ  C C G C C A T T G A C G G T G C A G C C G A T G C T G A C G T G G C A A C C T T  5420
X87822 orf.SEQ      C C G C C A T T G A C G G T G C A G C C G A T G C T G A C G T G G C A A C C T T  5420

FASA pMON70058.SEQ  G C G T G A G C G C G T C A A G A C T G C C G C T C C G G G C T A C T C G C C A  5460
X87822 orf.SEQ      G C G T G A G C G C G T C A A G A C T G C C G C T C C G G G C T A C T C G C C A  5460

FASA pMON70058.SEQ  T T C G G C A C C G T C T T G T C T G A G G C T A T T A C C G C T C G T C T G C  5500
X87822 orf.SEQ      T T C G G C A C C G T C T T G T C T G A G G C T A T T A C C G C T C G T C T G C  5500

FASA pMON70058.SEQ  G C C A G C T C A C T G G T G C A G C A G G C G T C A A G C C G G C C T A C A T  5540
X87822 orf.SEQ      G C C A G C T C A C T G G T G C A G C A G G C G T C A A G C C G G C C T A C A T  5540

FASA pMON70058.SEQ  T T C A G A G C G C G T G A C C G G A A C T T G G G G C T T G C C T A T G T C C  5580
X87822 orf.SEQ      T T C A G A G C G C G T G A C C G G A A C T T G G G G G C T G C C T A T G T C C  5580

FASA pMON70058.SEQ  T G G G C A G C C C A C G T T G A G G C T G A A A T C T T G C T C G G C T C C C  5620
X87822 orf.SEQ      T G G G C A G C C C A C G T T G A G G C T G A A A T C T T G C T C G G C T C C C  5620

FASA pMON70058.SEQ  G T G A A G A A G A C T C C G T G C G C G G T G G C T C C T T G T C C A C C G T  5660
X87822 orf.SEQ      G T G A A G A A G A C T C A G T G C G C G G T G G C T C C T T G T C C A C C G T  5660

FASA pMON70058.SEQ  T C C T T C C G C G G C G T C G T C G A A G G C C G A T G T C G A T G C G C T T  5700
X87822 orf.SEQ      T C C T T C C G C G G C G T C G T C G A A G G C C G A T G T C G A T G C G C T T  5700

FASA pMON70058.SEQ  G T C G A T G C C G C G G T C C A G G C C G T A G C C G C A G C A C A C G G C A  5740
X87822 orf.SEQ      G T C G A T G C C G C G G T C C A G G C C G T A G C C G C A G C A C A C G G C A  5740
```

Boxed Residues Differ from pMON70058

Figure 2 (page 6 of 10)

```
FASA pMON70058.SEQ  C C T C G G T A T C C A T G G G T G C T G C G A G T G G C G C C G G C G G C C G G  5780
X87822 orf.SEQ       C C T C G G T A T C C[C A T]G G T G C T G C G A G T G G C G C C G G C G G C G G  5780

FASA pMON70058.SEQ  T G G A G T C G T C G A C T C C G C A G C C T T G G A T G C T T A C G C A G A T  5820
X87822 orf.SEQ       T G G A G T C G T C G A C T C C G C A G C C T T G G A T G C T T A C G C A G A T  5820

FASA pMON70058.SEQ  A T C G T C A C C G G T G A A A A C G G T G T C C T C G C T A C T G C T G C T C  5860
X87822 orf.SEQ       A T C G T C A C C G G T G A A A A C G G T G T C C T C G C T A C T G C T G C T C  5860

FASA pMON70058.SEQ  G C C A G G T T C T G G C T C A G C T G G G C T T G G T C G A G G A A G C C C C  5900
X87822 orf.SEQ       G C C A G G T T C T G G C T C A G C T G G G C T T G G T C G A G G A A G C C C C  5900

FASA pMON70058.SEQ  T G A G A C C C C T G A G A C C G A T A A C A C C T T G T T C G A G A C C G T C  5940
X87822 orf.SEQ       T G A G A C C C C T G A G A C C G A T A A C A C C T T G T T C G[C]G A C C G T C  5940

FASA pMON70058.SEQ  G A G G C C G A G C T G G G T T C C G G T T G G G A A A A G A C C G T T A C C C  5980
X87822 orf.SEQ       G A G G C C G A G C T G G G T T C C G G T T G G G A A A A G A C C G T T A C C C  5980

FASA pMON70058.SEQ  C A T C C T T T G A C G C C A A G C G C G C A G T G C T T T T C G A T G A C C G  6020
X87822 orf.SEQ       C A T C C T T T G A C G C C A A G C G C G C A G T G C T T T T C G A T G A C C G  6020

FASA pMON70058.SEQ  C T G G G C G T C T G C T C G C G A A G A T C T C G C C C G C G T G G C A C T C  6060
X87822 orf.SEQ       C T G G G C G T C T G C T C G C G A A G A T C T C G C C C G C G T G G C A C T C  6060

FASA pMON70058.SEQ  G G C G A G A T C G A C T T G C C A G T C A A G C G T T T C C A G G G A A C C G  6100
X87822 orf.SEQ       G G C G A G A T C G A C T T G C C A G T C A A G C G T T T C C A G G G A A C C G  6100

FASA pMON70058.SEQ  G A G A G A C C A T C G C C A A G C A A G C G G A A T G G T G G G C G G A G A A  6140
X87822 orf.SEQ       G A G A G A C C A T C G C C A A G C A A G C G G A A T G G T G G G C G G A G A A  6140

FASA pMON70058.SEQ  C A C C G C T G C T T C C A C T G G T G C G C A C G C G A A G G C A A C C T C T  6180
X87822 orf.SEQ       C A C C G C T G C T T C C A C T G G T G C G C A C G C G A A G G C A A C C[G]C T  6180

FASA pMON70058.SEQ  G C C G A G A C C C T G C A T G C T A T T G C T G C C G C A G C G C G C G A A G  6220
X87822 orf.SEQ       G C C G A G A C C C T G C A T G C T A T T G C T G C C G C A G C G C G C G A A G  6220

FASA pMON70058.SEQ  A A C T C G A C G G C G A A T T C G C T G G C G A T G T C G C G T T G G T C A C  6260
X87822 orf.SEQ       A A C T C G A C G G C G A A T T C G C T G G C G A T G T C G C G T T G G T C A C  6260

FASA pMON70058.SEQ  C G G T G C A G C C C C A G G C T C C A T T G C T A C C G C T C T C G T A G A A  6300
X87822 orf.SEQ       C G G T G C A G C C C C A G G C T C C A T T G C T A C C G C T C T C G T A G A A  6300

FASA pMON70058.SEQ  C G C C T G C T G G A A G G C G G C G C G A C C G T C A T C A T G A C T G C G T  6340
X87822 orf.SEQ       C G C C T G C T G G A A G G C G G C G C G A C C G T C A T C A T G A C T G C G T  6340

FASA pMON70058.SEQ  C A C G T G T C A G C C A G T C C C G T A A G G A A T T T G C A C G C A A G C T  6380
X87822 orf.SEQ       C A C G T G T C A G C C A G T C C C G T A A G G A A T T T G C A C G C A A G C T  6380

FASA pMON70058.SEQ  C T A C G C T G C A C A C G C G A T T C C T G G C G C T G C C C T G T G G G T T  6420
X87822 orf.SEQ       C T A C G C T G C A C A C G C G A T T C C T G G C G C T G C C C T G T G G G T T  6420

FASA pMON70058.SEQ  G T T C C T G C G A A C T T G A G C T C C T A C C G C G A T G T T G A T G C T C  6460
X87822 orf.SEQ       G T T C C T G C G A A C T T G[C]G C T C C T A C C G C G A T G T T G A T G C T C  6460

FASA pMON70058.SEQ  T C A T T G A C T G G A T T G G T A A T G A G C A G C G T G A A T C T G T C G G  6500
X87822 orf.SEQ       T C A T T G A C T G G A T T G G T A A T G A G C A G C G T G[C C]T C T G T C G G  6500

FASA pMON70058.SEQ  C A A C G A A G T C A A G A T C A C C A A G C C A G C G T T G A C C C C A A C C  6540
X87822 orf.SEQ       C A A C G A A G T C A A G A T C A C C A A G C C A G C G T T G A C C C C A A C C  6540

FASA pMON70058.SEQ  T T G G C C T T T C C C A T T C G C G G C A C C T T C C G T G T C C G G T T C T G  6580
X87822 orf.SEQ       T T G G C C T T T C C C A T T C G C G G C A C C T T C C G T G T C C G G T T C T G  6580

FASA pMON70058.SEQ  T G G C C G A T G C C G G C C C A C A G G C T G A A A A C C A G A C T C G C C T  6620
X87822 orf.SEQ       T G G C C G A T G C C G G C C C A C A G G C T G A A A A C C A G A C T C G C C T  6620

FASA pMON70058.SEQ  G C T G C T G T G G T C T G T T G A G C G C A C C A T C G C T G G T C T G T C C  6660
X87822 orf.SEQ       G C T G C T G T G G T C T G T T G A G C G C A C C A T C G C T G G T C T G T C C  6660

FASA pMON70058.SEQ  A A C C T G G C G C A G C A A G G C G T G G A T A C C C G C T G C C A C A T T G  6700
X87822 orf.SEQ       A A C C T G G C G C A G C A A G G C G T G G A T A C C C G C T G C C A C A T T G  6700
```

Boxed Residues Differ from pMON70058

Figure 2 (page 7 of 10)

```
FASA pMON70058.SEQ  T G C T G C C T G G T T C T C C G A A C C G C G G C A T G T T C G G T G G C G A   6740
X87822 orf.SEQ      T G C T G C C T G G T T C T C C G A A C C G C G G C A T G T T C G G T G G C G A   6740

FASA pMON70058.SEQ  C G G C G C T T A C G G C G A A G T C A A G G C A G C C T T G G A C G C T A T T   6780
X87822 orf.SEQ      C G G C G C T T A C G G C G A A G T C A A G G C A G C C T T G G A C G C T A T T   6780

FASA pMON70058.SEQ  T T G G C C A A G T G G T C T G C A G A A G C A G G C T G G C C A G A A G G T G   6820
X87822 orf.SEQ      T T G G C C A A G T G G T C T G C A G A A G C A G G C T G G C C A G A A G G T G   6820

FASA pMON70058.SEQ  T T A C C T T G G C A C A A G C C A A G A T T G G C T G G G T C T C T G G T A C   6860
X87822 orf.SEQ      T T A C C T T G G C A C A A G C C A A G A T T G G C T G G G T C T C T G G T A C   6860

FASA pMON70058.SEQ  C T C C C T G A T G G G C G G C A A C G A C G T T C T G A T T C C G G C A G C G   6900
X87822 orf.SEQ      C T C C C T G A T G G G C G G C A A C G A C G T T C T G A T T C C G G C A G C G   6900

FASA pMON70058.SEQ  G A A G C C G C T G G C A T C C A C G T G T G G G A C C C A G A A G A G A T T T   6940
X87822 orf.SEQ      G A A G C C G C T G G C A T C C A C G T G T G G G A C C C A G A A G A G A T T T   6940

FASA pMON70058.SEQ  C T T C C C A G C T C A T C T C C C T A G C T T C C G A A G A A T C C C G C G C   6980
X87822 orf.SEQ      C T T C C C A G C T C A T C T C C C T A G C T T C C G A A G A A T C C C G C G C   6980

FASA pMON70058.SEQ  G A A G G C A G C C G A G G C T C C A C T A G A G C T G G A T C T G A C C G G T   7020
X87822 orf.SEQ      G A A G G C A G C C G A G G C T C C A C T A G A G C T G G A T C T G A C C G G T   7020

FASA pMON70058.SEQ  G G T C T G G G C T C G T C C A A G A T C T C C A T C T C C G A G C T G G C T G   7060
X87822 orf.SEQ      G G T C T G G G C T C G T C C A A [C] A T C T C C A T C T C C G A G C T G G C T G   7060

FASA pMON70058.SEQ  C C C A G G C C C G C G A G G A C G C C G A G G C A C A A G C T G C T T C C G G   7100
X87822 orf.SEQ      C C C A G G C C C G C G A G G A C G C C G A G G C A C A A G C T G C T T C C G G   7100

FASA pMON70058.SEQ  T G A T A A T G C A G A C G C A G C T G C G G A A G C T C C T G C A G C C A C G   7140
X87822 orf.SEQ      T G A T A A T G C A G A C G C A G C T G C G G A A G C T C C T G C A G C C A C G   7140

FASA pMON70058.SEQ  A T T C C A G C A C T G C C T A A T A C C C G T T C A G T A G A G C T G C C T G   7180
X87822 orf.SEQ      A T T C C A G C A C T G C C T A A T A C C C G T T C A G T A G A G C T G C C T G   7180

FASA pMON70058.SEQ  C A G C G C T A C C G G A A G G T G A A G T G G G C G A C G T A A C C A C G G A   7220
X87822 orf.SEQ      C A G C G C T A C C G G A A G G T G A A G T G G G C G A C G T A A C C A C G G A   7220

FASA pMON70058.SEQ  T C T G G A T G A C A T G G T C G T C A T C G C A G G T G T C G G C G A A G T C   7260
X87822 orf.SEQ      T C T G G A T G A C A T G G T C G T C A T C G C A G G T G T C G G C G A A G T C   7260

FASA pMON70058.SEQ  T C C T C G T G G G G T T C G G G C C G T A C C C G C T T T G A G G C A G A A T   7300
X87822 orf.SEQ      T C C T C G T G G G G T T C G G G C C G T A C C C G C T T T G A G G C A G A A T   7300

FASA pMON70058.SEQ  A T G G C T T G C A G C G C G A T G G C G C T G T G G A C C T G A C C G C C G C   7340
X87822 orf.SEQ      A T G G C T T G C A G C G C G A T G G C G C T G T G G A C C T G A C C G C C G C   7340

FASA pMON70058.SEQ  T G G T G T C T T G G A A T T G G C A T G G A T G A C C G G A C T G A T T T C C   7380
X87822 orf.SEQ      T G G T G T C T T G G A A T T G G C A T G G A T G A C C G G A C T G A T T T C C   7380

FASA pMON70058.SEQ  T G G T C C A A T G A C C C A C G T C C A G C C T G G T A C G A C G A A G A G G   7420
X87822 orf.SEQ      T G G T C C A A T G A C C C A C G T C C A G C C T G G T A C G A C G A A G A G G   7420

FASA pMON70058.SEQ  G C A C C G A A G T C G A T G A A G C A G A T A T C T A C G C T C G C T T C C G   7460
X87822 orf.SEQ      G C A C C G A A G T C G A T G A A G C A G A T A T C T A C G C T C G C T T C C G   7460

FASA pMON70058.SEQ  C G A C G A G G T T G T A G C T C G C T C C G G T A T C C G T A C C T T G A C C   7500
X87822 orf.SEQ      C G A C G A G G T T G T A G C T C G C T C C G G T A T C C G T A C C T T G A C C   7500

FASA pMON70058.SEQ  G A T A A G T A C A A C A T G G T T G A C C A G G G C T C C A T T G A C C T G A   7540
X87822 orf.SEQ      G A T A A G T A C A A C A T G G T T G A C C A G G G C T C C A T T G A C C T G A   7540

FASA pMON70058.SEQ  C T T C T G T G T T C T T G G A C C G C G A T A T C G T C T T C A C C G T T C C   7580
X87822 orf.SEQ      C T T C T G T G T T C T T G G A C C G C G A T A T C G T C T T C A C C G T T C C   7580

FASA pMON70058.SEQ  T A C C G A A C A A G A A G C A C T C G A T A T T G A A G A A G C C G A C C C A   7620
X87822 orf.SEQ      T A C C G A A C A A G A A G C A C T C G A T A T T G A A G A A G C C G A C C C A   7620

FASA pMON70058.SEQ  T C G T T T A C C A A G C T G C G C G A A G T C G A C G G C G A G T G G G A A G   7660
X87822 orf.SEQ      T C G T T T A C C A A G C T G C G C G A A G T C G A C G G C G A G T G G G A A G   7660
```

Boxed Residues Differ from pMON70058

Figure 2 (page 8 of 10)

| | | |
|---|---|---|
| FASA pMON70058.SEQ | T C A C C C G T T T G A A G G G T G C C A C C G C C C G C G T G C C A C G C A A | 7700 |
| X87822 orf.SEQ | T C A C C C G T T T G A A G G G T G C C A C C G C C C G C G T G C C A C G C A A | 7700 |
| FASA pMON70058.SEQ | G G C A A C G T T G A C T C G T A C C G T T G C T G G T C A A A T G C C G G A T | 7740 |
| X87822 orf.SEQ | G G C A A C G T T G A C T C G T A C C G T T G C T G G T C A A A T G C C G G A T | 7740 |
| FASA pMON70058.SEQ | C A C T T C G A T G C T G C C A A G T G G G G C A T T C C A G A C C A C A T G C | 7780 |
| X87822 orf.SEQ | C A C T T C G A T G C T G C C A A G T G G G G C A T T C C A G A C C A C A T G C | 7780 |
| FASA pMON70058.SEQ | T G G A T G C A C T C G A C C G C A T G G C C G T G T G G A A C C T G G T G A C | 7820 |
| X87822 orf.SEQ | T G G A T G C A C T C G A C C G C A T G G C C G T G T G G A A C C T G G T G A C | 7820 |
| FASA pMON70058.SEQ | C G C A G T C G A T G C C T T T A C C C A G G C G G G C T T T A G C C C G G C T | 7860 |
| X87822 orf.SEQ | C G C A G T C G A T G C C T T T A C C C A G G C G G G C T T T A G C C C G G C T | 7860 |
| FASA pMON70058.SEQ | G A G T T G C T G C A G G T T A T T C A C C C A G C G C A G G T T G C T A C C A | 7900 |
| X87822 orf.SEQ | G A G T T G C T G C A G G T T A T T C A C C C A G C G C A G G T T G C T A C C A | 7900 |
| FASA pMON70058.SEQ | C C C A G G G C A C C G G T A T C G G C G G C A T G G A A T C C C T G C A C A A | 7940 |
| X87822 orf.SEQ | C C C A G G G C A C C G G T A T C G G C G G C A T G G A A T C C C T G C A C A A | 7940 |
| FASA pMON70058.SEQ | G G T C T T C G T G A C C C G T C T G C T C G G T G A A G A C C G T C C T T C C | 7980 |
| X87822 orf.SEQ | G G T C T T C G T G A C C C G T C T G C T C G G T G A A G A C C G T C C T T C C | 7980 |
| FASA pMON70058.SEQ | G A C A T C C T G C A G G A A G C A C T G C C T A A C G T T A T T G C A G C G C | 8020 |
| X87822 orf.SEQ | G A C A T C C T G C A G G A A G C A C T G C C T A A C G T T A T T G C A G C G C | 8020 |
| FASA pMON70058.SEQ | A C A C C A T G C A G T C T T T G G T G G G C G G C T A C G G T T C G A T G A T | 8060 |
| X87822 orf.SEQ | A C A C C A T G C A G T C T T T G G T G G G C G G C T A C G G T T C G A T G A T | 8060 |
| FASA pMON70058.SEQ | T C A C C C T A T C G G T G C T T G T G C C A C C G C T G C G G T G T C C A T C | 8100 |
| X87822 orf.SEQ | T C A C C C T A T C G G T G C T T G T G C C A C C G C T G C G G T G T C C A T C | 8100 |
| FASA pMON70058.SEQ | G A A G A A G G C G T G G A C A A G A T T G C C C T G G G C A A G G C C G A C C | 8140 |
| X87822 orf.SEQ | G A A G A A G G C G T G G A C A A G A T T G C C C T G G G C A A G G C C G A C C | 8140 |
| FASA pMON70058.SEQ | T G G T C G T T G C C G G T G G T A T C G A T G A C G T C C A A G T T G A G T C | 8180 |
| X87822 orf.SEQ | T G G T C G T T G C C G G T G G T A T C G A T G A C G T C C A A G T T G A G T C | 8180 |
| FASA pMON70058.SEQ | T T T G A C C G G C T T C G G C G A C A T G A A C G C C A C C G C T G A G A C C | 8220 |
| X87822 orf.SEQ | T T T G A C C G G C T T C G G C G A C A T G A A C G C C A C C G C T G A G A C C | 8220 |
| FASA pMON70058.SEQ | A A G A A G A T G A C C G A T C A G G G C A T T G A T G A C C G C T T C A T C T | 8260 |
| X87822 orf.SEQ | A A G A A G A T G A C C G A T C A G G G C A T T G A T G A C C G C T T C A T C T | 8260 |
| FASA pMON70058.SEQ | C C C G T G C G A A T G A C C G C C G T C G T G G C G G C T T C C T C G A G G C | 8300 |
| X87822 orf.SEQ | C C C G T G C G A A T G A C C G C C G T C G T G G C G G C T T C C T C G A G G C | 8300 |
| FASA pMON70058.SEQ | A G A A G G C G G C G G T A C C G T G C T T C T G G T T C G C G G T T C C C T G | 8340 |
| X87822 orf.SEQ | A G A A G G C G G C G G T A C C G T G C T T C T G G T T C G C G G T T C C C T G | 8340 |
| FASA pMON70058.SEQ | G C T C G T G A G A T G G G T C T G C C G G T C T A C G C G G T C G T T G C G C | 8380 |
| X87822 orf.SEQ | G C T C G T G A G A T G G G T C T G C C G G T C T A C G C G G T C G T T G C G C | 8380 |
| FASA pMON70058.SEQ | A C G C G G C G T C C T A C G G C G A C G G T G C C C A C A C C T C C A T T C C | 8420 |
| X87822 orf.SEQ | A C G [A] G G C G T C C T A C G G [- - - - -] T G C C C A C A C C T C C A T T C C | 8420 |
| FASA pMON70058.SEQ | T G C T C C A G G T T T G G G T G C T T T G G G C G C T G G C C G T G G C C G G | 8460 |
| X87822 orf.SEQ | T G C T C C A G G T T T G G G T G C T T T G G G C G C T G G C C G T G G C C G G | 8460 |
| FASA pMON70058.SEQ | A A G A A C T C C C G C C T G G C C A A G G G C T T G G C T G G T T T G G G T C | 8500 |
| X87822 orf.SEQ | A A G A A C T C C C G C C T G G C C A A G G G C T T G G C T G G T T T G G G T C | 8500 |
| FASA pMON70058.SEQ | T G A C T C C A A A T G A C G T C T C G G T A C T G T C C A A G C A C G A C A C | 8540 |
| X87822 orf.SEQ | T G A C T C C A A A T G A C G T C T C G G T A C T G T C C A A G C A C G A C A C | 8540 |
| FASA pMON70058.SEQ | C T C G A C C A A C G C C A A T G A C C C G A A T G A G T C G G A A C T G C A C | 8580 |
| X87822 orf.SEQ | C T C G A C C A A C G C C A A T G A C C C G A A T G A G T C G G A A C T G C A C | 8580 |
| FASA pMON70058.SEQ | T C C A T C T T G T G G C C T G C T A T T G G C C G C G A T G T G G A C C A G C | 8620 |
| X87822 orf.SEQ | T C C A T C T T G T G G C C T G C T A T T G G C C G C G A T G T G G A C C A G C | 8614 |

Boxed Residues Differ from pMON70058

Figure 2 (page 9 of 10)

```
FASA pMON70058.SEQ   C A C T G T T T G T G A T T T C G C A G A A G T C A C T G A C T G G T C A C T C   8660
X87822 orf.SEQ       C A C T G T T T G T G A T T T C G C A G A A G T C A C T G A C T G G T C A C T C   8654

FASA pMON70058.SEQ   C A A G G C T G G T G C C G C G C T G T T C C A G A C C G G C G G T T T G A T T   8700
X87822 orf.SEQ       C A A G G C T G G T G C C G C G C T G T T C C A G A C C G G C G G T T T G A T T   8694

FASA pMON70058.SEQ   G A C G T C T T C C G C A C G G G A C G C A T T C C A G C T A A C C T G T C G C   8740
X87822 orf.SEQ       G A C G T C T T C C G C A C G G G A C G C A T T C C A G C T A A C C T G T C G C   8734

FASA pMON70058.SEQ   T G G A T T G T G T G G A T C C A T T G A T T G A G C C A A A G G C C A C G A A   8780
X87822 orf.SEQ       T G G A T T G T G T G G A T C C A T T G A T T G A G C C A A A G G C C A C G A A   8774

FASA pMON70058.SEQ   C T T G G T C T G G C T A C G C T C C C C A C T A G A T G T G G A A G C A G C C   8820
X87822 orf.SEQ       C T T G G T C T G G C T A C G C T C C C C A C T A G A T G T G G A A G C A G C C   8814

FASA pMON70058.SEQ   A A C C G C C C G G T C A A G G C C G C G G C G C T C A C C T C G C T C G G C T   8860
X87822 orf.SEQ       A A C C G C C C G G T C A A G G C C G C G G C G C T C A C C T C G C T C G G C T   8854

FASA pMON70058.SEQ   T C G G T C A C G T C G G T G C A T T G A T T G T C T A C G C G C A C C C A G G   8900
X87822 orf.SEQ       T C G G T C A C G T C G G T G C A T T G A T T G T C T A C G C G C A C C C A G G   8894

FASA pMON70058.SEQ   T G T C T T C G A G G C T G C C G T T G C C C A G C A G G T T T C G G C C G A G   8940
X87822 orf.SEQ       T G T C T T C G A G G C T G C C G T T G C C C A G C A G G T T T C G G C C G A G   8934

FASA pMON70058.SEQ   G C T G C T G C C G A A T G G C G C G A G A A G G C A A A T G C C C G C C T C G   8980
X87822 orf.SEQ       G C T G C T G C C G A A T G G C G C G A G A A G G C A A A T G C C C G C C T C G   8974

FASA pMON70058.SEQ   C C G C C G G T G C A G C A C G C T T C G A A G C C G G C A T G A T T G G C A A   9020
X87822 orf.SEQ       C C G C C G G T G C A G C A C G C T T C G A A G C C G G C A T G A T T G G C A A   9014

FASA pMON70058.SEQ   G G A A A C C T T G T T C G A G G T C A T C G A C G G C C G C C G C C T G C C T   9060
X87822 orf.SEQ       G G A A A C C T T G T T C G A G G T C A T C G A C G G C C G C C G C C T G C C T   9054

FASA pMON70058.SEQ   G A C G C A G C G G G C A C C G T T G A G A T T G A G A A C T A C G G C C C A G   9100
X87822 orf.SEQ       G A C G C A G C G G G C A C C G T T G A G A T T G A G A A C T A C G G C C C A G̈   9094

FASA pMON70058.SEQ   T C G C C G C C G A C A A G G C C G C A G A A A T T G C G C T C T T G C T T G A   9140
X87822 orf.SEQ       T C G C C G C C G A C A A G G C C G C A G A A [-] T T G C G C T C T T G C T T G A   9133

FASA pMON70058.SEQ   C G A C G A C A T C C G T C T T A C C G C C G A A G G C A C T T T C C C T C C G   9180
X87822 orf.SEQ       C G A C G A C A T C C G T C T T A C C G C C G A A G G C A C T T T C C C T C C G   9173

FASA pMON70058.SEQ   G C G A A G T A G                                                                 9189
X87822 orf.SEQ       G C G A A G T A G G A C A A A G T A G                                             9192
```

Boxed Residues Differ from pMON70058

Figure 2 (page 10 of 10)

| | | |
|---|---|---|
| FASA pmon70058.PRO | M S L T P L H T L S N D S T A P A V L F A G Q G S A W Q K A I A D A A A S P H Q | 40 |
| FASA X87822.PRO    | M S L T P L H T L S N D S T A P A V L F A G Q G S A W Q K A I A D A A A S P H Q | 40 |
| FASA pmon70058.PRO | G A Q L R D I L K E V R T T T G P V A R I I A S S C P G V Y E R L E E L A Q T P | 80 |
| FASA X87822.PRO    | G A Q L R D I L K E V R T T T G P V A R I I A S S C P G V Y E R L E E L A Q T P | 80 |
| FASA pmon70058.PRO | A D Q A P V A K E Y D A Y P A Y S I P G I V L G Q I G A I E H L R E L G I D V D | 120 |
| FASA X87822.PRO    | A D Q A P V A K E Y D A Y P A Y S I P G I V L G Q I G A I E H L [A Q] L G I D V D | 120 |
| FASA pmon70058.PRO | S A Q L A G H S Q G S L G V A A V K D A R Q A L A I A V L M G T A A A V T Q G A | 160 |
| FASA X87822.PRO    | S A Q L A G H S Q G S L G V A A V K D A R Q A L A I A V L M G T A A A V T Q G A | 160 |
| FASA pmon70058.PRO | N D S R S H M L S V R G V P R E M V E E Y L A G D A A I A V V N G R V H F A L S | 200 |
| FASA X87822.PRO    | N D S R [T] H M L S V R G V P R E M V E E Y L A G D A A I A V V N G R V H F A L S | 200 |
| FASA pmon70058.PRO | G T P E D L A K T E S N L T Q A A E S Y N D A L E E R R I G G S E I N P V F D V | 240 |
| FASA X87822.PRO    | G T P E D L A K T E S N L T Q A A E S Y N D A L E E R R I G G S E I N P V F D V | 240 |
| FASA pmon70058.PRO | L A V A L P F H H A S L Q D A A D L T V D Y A T Q C G L D A E L A R E L A D S I | 280 |
| FASA X87822.PRO    | L A V A L P F H H A S L Q D A A D L T V D Y A T Q C G L D A E L A R E L A D S I | 280 |
| FASA pmon70058.PRO | L V Q P H S W V E T V A G L N S T Y L L S L D R G L S S L T T P L I A G T G K V | 320 |
| FASA X87822.PRO    | L V Q P H S W V E T V A G L N S T Y L L S L D R G L S S L T T P L I A G T G K V | 320 |
| FASA pmon70058.PRO | V V P A A T P A E R D N L A T P G T E L P T A V N Y E K F S P K L I S L P N G K | 360 |
| FASA X87822.PRO    | V V P A A T P A E R D N L A T P G T E L P T A V N Y E K F S P K L I S L P N G K | 360 |
| FASA pmon70058.PRO | S Y T Q T R F S E W T G M S P I I L G G M T P T T M D P G I V A A A A N G G Y W | 400 |
| FASA X87822.PRO    | S Y T Q T R F S E W T G M S P I I L G G M T P T T M D P G I V A A A A N G G Y W | 400 |
| FASA pmon70058.PRO | S E M A G G G Q Y S D E A F T I N K D G M M E L L E P G R T A A F N T M F F D R | 440 |
| FASA X87822.PRO    | S E M A G G G Q Y S D E A F T I N K D G M M E L L E P G R T A A F N T M F F D R | 440 |
| FASA pmon70058.PRO | Y L W N L Q F G V T R I V P K A R A N G A A F T G V T I S A G I P E L D E A K E | 480 |
| FASA X87822.PRO    | Y L W N L Q F G V T R I [C S] K A R A N G A A F T G V T I [C] A G I P E L D E A K E | 480 |
| FASA pmon70058.PRO | L L D Q L T S D G F P Y I S F K P G T T K Q I Q D C I A I A A D N P T H R V I I | 520 |
| FASA X87822.PRO    | L L D Q L T S D G F P Y I S F K P G T T K Q I Q D C [V] A I A A D N P T H R V I I | 520 |
| FASA pmon70058.PRO | Q I E D G H A G G H H S W V D L D E M L L A T Y A S A R E H D N L A I T V G G G | 560 |
| FASA X87822.PRO    | Q I E D [A] H A G G H H S W V D L D E M L L A T Y A [C] A R E H D N L A I T V G G G | 560 |
| FASA pmon70058.PRO | I H S P D R A S E Y L T G T W S T K Y G L P I M P V D G V F L G T V A M A T K E | 600 |
| FASA X87822.PRO    | I H S P D R A S E Y L T G T W S T K Y G L P I M P V D G V F L G T V A M A T K E | 600 |
| FASA pmon70058.PRO | A T A N D D V K Q L L V D T P G I S P E T N G G W V G R L D A D G G V S S S Q S | 640 |
| FASA X87822.PRO    | A T A N D D V K Q L L V D T P G I S P E T N G G W V G R L D A D G G V S S S Q S | 640 |
| FASA pmon70058.PRO | H L L A D L H E I D N S F A K A S R M I T S I P I E E Y D E R R D E I I A A L D | 680 |
| FASA X87822.PRO    | H L L A D L H E I D N S F A K A S R M I T S I P I E E Y D E R R D E I I A A L D | 680 |
| FASA pmon70058.PRO | K T S K P Y F G D L S E M T Y E D W V A R F A E R A Y P W V D P T W H D R F H D | 720 |
| FASA X87822.PRO    | K T S K P Y F G D L S E M T Y E D W V A R F A E R A Y P W V D P T W H D R F H D | 720 |
| FASA pmon70058.PRO | L L Q R V E A R L N D A D H G D I E T L F P T L D D S E N A P E A V A K L L A A | 760 |
| FASA X87822.PRO    | L L Q R V E A R L N D A D H G D I E T L F P T L D D S E N A P E A V A K L L A A | 760 |
| FASA pmon70058.PRO | Y P N A K T T K V N T R D E A W F P T L I R K H V K P M P W T T A I D G D L K E | 800 |
| FASA X87822.PRO    | Y P N A K T T K V N T R D E A W F P T L I R K H V K P M P W T T A I D G D L K E | 800 |
| FASA pmon70058.PRO | W F A K D T L W Q A Q D P R Y D A D G V R I I P G P V S V A G I T K K N E P V A | 840 |
| FASA X87822.PRO    | W F A K D T L W Q A Q D P R Y D A D G V R I I P G P V S V A G I T K K N E P V A | 840 |
| FASA pmon70058.PRO | N L L G R F E D A T T A A L N D A G V A P V E L Y S R L A S A K N A E E F L R N | 880 |
| FASA X87822.PRO    | N L L G R F E D A T T A A L N D A G V A P V E L Y S R L A S A K N A E E F L R N | 880 |
| FASA pmon70058.PRO | A P T I M W H G H L I A N P A Y E L P E E A F D I V D D G E G F A I R I N S D S | 920 |
| FASA X87822.PRO    | A P T I M W H G H L I A N P A Y E L P E E A F D I V D D G E G F A I R I N S D S | 920 |
| FASA pmon70058.PRO | Y W D N L P E E Q R P F Y V K H V D I P V A L S E A V A T G A S P V V D D A R L | 960 |
| FASA X87822.PRO    | Y [R] D N L P E E Q R P F Y V K H V D I P V A L S E A V A T G A S P V V D D A R L | 960 |

Boxed Residues Differ from pMON70058

Figure 3 (page 1 of 4)

```
FASA pmon70058.PRO    P K A V F D L L A G V A G V G S I S E T G D K I T E L P K V I E G S V S E E N P    1000
FASA X87822.PRO       P K A V F D L L A G V A G V G S I S E T G D K I T E L P K V I E G S V S E E N P    1000

FASA pmon70058.PRO    Y G L V E Y S F T L P S T L L T A H T A V T G A A L G T A N A G T P D A L V G P    1040
FASA X87822.PRO       Y G L V E Y S F T L P S T L L T A H T A V T G A A L G T A N A G T P D A L V G P    1040

FASA pmon70058.PRO    C W P A I Y T A L G T G R L T E E H G E P A G T D F P V I E G L L N A V H L D H    1080
FASA X87822.PRO       C W P A I Y T A L G T G R L T E E H G E P A G T D F P V I E G L L N A V H L D H    1080

FASA pmon70058.PRO    V V D V R V P L H E L A K G E K G E G R R I D V T S R C A S I A E S N S G R I V    1120
FASA X87822.PRO       V V D V R V P L H E L A K G E K G E G [G] R I D V T S R C A S I A E S N S G R I V    1120

FASA pmon70058.PRO    T V E L E L W D A A T Q E V V A T Q M Q R F A I R G R A T G T S V P V S A P S W    1160
FASA X87822.PRO       T V E L E L W D A A T Q E V V A T Q M Q R F A I R G R A T G T S V P V S A P S W    1160

FASA pmon70058.PRO    G G G K S Q D K I E T T P R S F V D R A I V T A P S D M T P F A L V S G D Y N P    1200
FASA X87822.PRO       G G G K S Q D K I E T T P R S F V D R A I V T A P S D M T P F A L V S G D Y N P    1200

FASA pmon70058.PRO    I H T S T N A A R L V N L D A P L V H G M W L S A T A Q H L A G N H G T V V G W    1240
FASA X87822.PRO       I H T S T N A A R L V N L D A P L V H G M W L S A T A Q H L A G N H G T V V G W    1240

FASA pmon70058.PRO    T Y S M Y G M V Q L N D E V E I T V E R V G R K G I H A A F E V T C R I D G E V    1280
FASA X87822.PRO       T Y S M Y G M V Q L N D E V E I T V E R V G R K G I H A A F E V T C R I D G E V    1280

FASA pmon70058.PRO    V S R G Q A L M A Q P R T A Y V Y P G Q G I Q A E G M G R G D R D A S A A A R E    1320
FASA X87822.PRO       V S R G Q A L M A Q P R T A Y V Y P G Q G I Q A E G M G R G D R D A S A A A R E    1320

FASA pmon70058.PRO    V W R R A D R H T R T A M G F S I R Q I I D D N P T E L V V R G T K F V H P N G    1360
FASA X87822.PRO       V W R R A D R H T R T A [L] G F S I R Q I I D D N P T E L V V R G T K F V H P N G    1360

FASA pmon70058.PRO    V L H L T Q F T Q V A L A V V A Y A Q T E R L R E A D A L G T N S M Y A G H S L    1400
FASA X87822.PRO       V L H L T Q F T Q V A L A V V A Y A Q T E R L R E A D A L G T N S M Y A G H S L    1400

FASA pmon70058.PRO    G E Y T A L A S L A N I F D L E A V I D I V Y S R G S A M G T L V E R D E N G N    1440
FASA X87822.PRO       G E Y T A L A S L A N I F D L E A V I D I V Y S R G S A M G T L V E R D E N G N    1440

FASA pmon70058.PRO    S N Y G M G A L R P N M I G V P A D Q V E A Y I A Q T A E E T G E F L E I V N Y    1480
FASA X87822.PRO       S N Y G M G A L R P N M I G V P A D Q V E A Y I A Q T A E E T G E F L E I V N Y    1480

FASA pmon70058.PRO    N I A G Q Q Y S I A G T K A G L A A L K K K A N S V K D R A Y V T V P G I D V P    1520
FASA X87822.PRO       N I A G Q Q Y S I A G T K A G L A A L K K K A N S V K D R A Y V T V P G I D V P    1520

FASA pmon70058.PRO    F H S Q V L R D G V P A F A E K L D E L L P E T L D L D A L V G R Y V P N L V A    1560
FASA X87822.PRO       F H S Q V L R D G V P A F A E K L D E L L P E T L D L D A L V G R Y V P N L V A    1560

FASA pmon70058.PRO    L P F E L T Q E F V D K V K P L A P S G K L D N L K V E D T D E Q A L A R L L M    1600
FASA X87822.PRO       L P F E L T Q E F V D K V K P L A P S G K L D N L K V E D T D E Q A [P S] R L L M    1600

FASA pmon70058.PRO    I E L L S W Q F A S P V R W I E T Q Q L L F E E V D Q I I E V G L A A S P T L T    1640
FASA X87822.PRO       I E L L S W Q F A S P V R W I E T Q Q L L F E E V D Q I I E V G L A [S] S P T L T    1640

FASA pmon70058.PRO    N L A K R S M D I A G V D L P V F N V E R D Q D Q V M L Q D V Q E A P A A S F D    1680
FASA X87822.PRO       N L A K R S M D I A G V D L P V F N V E R D Q D Q V M L Q D V Q E A P A A S F D    1680

FASA pmon70058.PRO    V E E G E A T S S T A A S E T P G E S A A A A S D N T Q A I P S A E P Q T V A E    1720
FASA X87822.PRO       V E E G E A T S S T A A S E T P G E S A A A A S D N T Q A I P S A E P Q T V A E    1720

FASA pmon70058.PRO    A P A P S A A P A G G T A A A D A P D L P F T A A E A I M V L F A F Q N K I R Q    1760
FASA X87822.PRO       A P A P S A A P A G G T [R] A A D A P D L P F T A A E A I M V L F A F Q N K I R Q    1760

FASA pmon70058.PRO    D Q I N D S D T V E E L T N G V S S R R N Q L L M D M S A E I G V P A I D G A A    1800
FASA X87822.PRO       D Q I N D S D T V E E L T N G V S S R R N Q L L M D M S A E [N R] V P A I D G A A    1800

FASA pmon70058.PRO    D A D V A T L R E R V K T A A P G Y S P F G T V L S E A I T A R L R Q L T G A A    1840
FASA X87822.PRO       D A D V A T L R E R V K T A A P G Y S P F G T V L S E A I T A R L R Q L T G A A    1840

FASA pmon70058.PRO    G V K P A Y I S E R V T G T W G L P M S W A A H V E A E I L L G S R E E D S V R    1880
FASA X87822.PRO       G V K P A Y I S E R V T G T W G L P M S W A A H V E A E I L L G S R E E D S V R    1880

FASA pmon70058.PRO    G G S L S T V P S A A S S K A D V D A L V D A A V Q A V A A A H G T S V S M G A    1920
FASA X87822.PRO       G G S L S T V P S A A S S K A D V D A L V D A A V Q A V A A A H G T S V S [H] G A    1920
```

Boxed Residues Differ from pMON70058

Figure 3 (page 2 of 4)

```
FASA pmon70058.PRO   A S G A G G G G V V D S A A L D A Y A D I V T G E N G V L A T A A R Q V L A Q L   1960
FASA X87822.PRO      A S G A G G G G V V D S A A L D A Y A D I V T G E N G V L A T A A R Q V L A Q L   1960

FASA pmon70058.PRO   G L V E E A P E T P E T D N T L F E T V E A E L G S W E K T V T P S F D A K R   2000
FASA X87822.PRO      G L V E E A P E T P E T D N T L F[A]T V E A E L G S W E K T V T P S F D A K R   2000

FASA pmon70058.PRO   A V L F D D R W A S A R E D L A R V A L G E I D L P V K R F Q G T G E T I A K Q   2040
FASA X87822.PRO      A V L F D D R W A S A R E D L A R V A L G E I D L P V K R F Q G T G E T I A K Q   2040

FASA pmon70058.PRO   A E W W A E N T A A S T G A H A K A T S A E T L H A I A A A A R E E L D G E F A   2080
FASA X87822.PRO      A E W W A E N T A A S T G A H A K A T[A]A E T L H A I A A A A R E E L D G E F A   2080

FASA pmon70058.PRO   G D V A L V T G A A P G S I A T A L V E R L L E G G A T V I M T A S R V S Q S R   2120
FASA X87822.PRO      G D V A L V T G A A P G S I A T A L V E R L L E G G A T V I M T A S R V S Q S R   2120

FASA pmon70058.PRO   K E F A R K L Y A A H A I P G A A L W V V P A N L S S Y R D V D A L I D W I G N   2160
FASA X87822.PRO      K E F A R K L Y A A H A I P G A A L W V V P A N L[R]S Y R D V D A L I D W I G N   2160

FASA pmon70058.PRO   E Q R E S V G N E V K I T K P A L T P T L A F P F A A P S V S G S V A D A G P Q   2200
FASA X87822.PRO      E Q R[A]S V G N E V K I T K P A L T P T L A F P F A A P S V S G S V A D A G P Q   2200

FASA pmon70058.PRO   A E N Q T R L L L W S V E R T I A G L S N L A Q Q G V D T R C H I V L P G S P N   2240
FASA X87822.PRO      A E N Q T R L L L W S V E R T I A G L S N L A Q Q G V D T R C H I V L P G S P N   2240

FASA pmon70058.PRO   R G M F G G D G A Y G E V K A A L D A I L A K W S A E A G W P E G V T L A Q A K   2280
FASA X87822.PRO      R G M F G G D G A Y G E V K A A L D A I L A K W S A E A G W P E G V T L A Q A K   2280

FASA pmon70058.PRO   I G W V S G T S L M G G N D V L I P A A E A A G I H V W D P E E I S S Q L I S L   2320
FASA X87822.PRO      I G W V S G T S L M G G N D V L I P A A E A A G I H V W D P E E I S S Q L I S L   2320

FASA pmon70058.PRO   A S E E S R A K A A E A P L E L D L T G G L G S S K I S I S E L A A Q A R E D A   2360
FASA X87822.PRO      A S E E S R A K A A E A P L E L D L T G G L G S S[N]I S I S E L A A Q A R E D A   2360

FASA pmon70058.PRO   E A Q A A S G D N A D A A A E A P A A T I P A L P N T R S V E L P A A L P E G E   2400
FASA X87822.PRO      E A Q A A S G D N A D A A A E A P A A T I P A L P N T R S V E L P A A L P E G E   2400

FASA pmon70058.PRO   V G D V T T D L D D M V V I A G V G E V S S W G S G R T R F E A E Y G L Q R D G   2440
FASA X87822.PRO      V G D V T T D L D D M V V I A G V G E V S S W G S G R T R F E A E Y G L Q R D G   2440

FASA pmon70058.PRO   A V D L T A A G V L E L A W M T G L I S W S N D P R P A W Y D E E G T E V D E A   2480
FASA X87822.PRO      A V D L T A A G V L E L A W M T G L I S W S N D P R P A W Y D E E G T E V D E A   248

FASA pmon70058.PRO   D I Y A R F R D E V V A R S G I R T L T D K Y N M V D Q G S I D L T S V F L D R   2520
FASA X87822.PRO      D I Y A R F R D E V V A R S G I R T L T D K Y N M V D Q G S I D L T S V F L D R   2520

FASA pmon70058.PRO   D I V F T V P T E Q E A L D I E E A D P S F T K L R E V D G E W E V T R L K G A   2560
FASA X87822.PRO      D I V F T V P T E Q E A L D I E E A D P S F T K L R E V D G E W E V T R L K G A   2560

FASA pmon70058.PRO   T A R V P R K A T L T R T V A G Q M P D H F D A A K W G I P D H M L D A L D R M   2600
FASA X87822.PRO      T A R V P R K A T L T R T V A G Q M P D H F D A A K W G I P D H M L D A L D R M   2600

FASA pmon70058.PRO   A V W N L V T A V D A F T Q A G F S P A E L L Q V I H P A Q V A T T Q G T G I G   2640
FASA X87822.PRO      A V W N L V T A V D A F T Q A G F S P A E L L Q V I H P A Q V A T T Q G T G I G   2640

FASA pmon70058.PRO   G M E S L H K V F V T R L L G E D R P S D I L Q E A L P N V I A A H T M Q S L V   2680
FASA X87822.PRO      G M E S L H K V F V T R L L G E D R P S D I L Q E A L P N V I A A H T M Q S L V   2680

FASA pmon70058.PRO   G G Y G S M I H P I G A C A T A A V S I E E G V D K I A L G K A D L V V A G G I   2720
FASA X87822.PRO      G G Y G S M I H P I G A C A T A A V S I E E G V D K I A L G K A D L V V A G G I   2720

FASA pmon70058.PRO   D D V Q V E S L T G F G D M N A T A E T K K M T D Q G I D D R F I S R A N D R R   2760
FASA X87822.PRO      D D V Q V E S L T G F G D M N A T A E T K K M T D Q G I D D R F I S R A N D R R   2760

FASA pmon70058.PRO   R G G F L E A E G G G T V L L V R G S L A R E M G L P V Y A V V A H A A S Y G D   2800
FASA X87822.PRO      R G G F L E A E G G G T V L L V R G S L A R E M G L P V Y A V V A H[E]A S Y G[-]  2799

FASA pmon70058.PRO   G A H T S I P A P G L G A L G A G R G R K N S R L A K G L A G L G L T P N D V S   2840
FASA X87822.PRO     [-]A H T S I P A P G L G A L G A G R G R K N S R L A K G L A G L G L T P N D V S   2838

FASA pmon70058.PRO   V L S K H D T S T N A N D P N E S E L H S I L W P A I G R D V D Q P L F V I S Q   2880
FASA X87822.PRO      V L S K H D T S T N A N D P N E S E L H S I L W P A I G R D V D Q P L F V I S Q   2878
```

Boxed Residues Differ from pMON70058

Figure 3 (page 3 of 4)

```
FASA pmon70058.PRO   K S L T G H S K A G A A L F Q T G G L I D V F R T G R I P A N L S L D C V D P L   2920
FASA X87822.PRO      K S L T G H S K A G A A L F Q T G G L I D V F R T G R I P A N L S L D C V D P L   2918

FASA pmon70058.PRO   I E P K A T N L V W L R S P L D V E A A N R P V K A A A L T S L G F G H V G A L   2960
FASA X87822.PRO      I E P K A T N L V W L R S P L D V E A A N R P V K A A A L T S L G F G H V G A L   2958

FASA pmon70058.PRO   I V Y A H P G V F E A A V A Q Q V S A E A A A E W R E K A N A R L A A G A A R F   3000
FASA X87822.PRO      I V Y A H P G V F E A A V A Q Q V S A E A A A E W R E K A N A R L A A G A A R F   2998

FASA pmon70058.PRO   E A G M I G K E T L F E V I D G R R L P D A A G T V E I E N Y G P V A A D K A A   3040
FASA X87822.PRO      E A G M I G K E T L F E V I D G R R L P D A A G T V E I E N Y G P V A A D K A A   3038

FASA pmon70058.PRO   E I A L L L D D D I R L T A E G T F P P A K .                                     3063
FASA X87822.PRO      E [L R S C] L [T T T S V] L [P P K A L S L R R S R] T K .                       3064
```

Boxed Residues Differ from pMON70058

Figure 3 (page 4 of 4)

| Pedigree | Relative Expression measured by Taqman mfFAS probe* Expt A | Relative Expression measured by Taqman mfFAS probe* Expt B | Relative Expression measured by Taqman PPT probe* Expt A | Relative Expression measured by Taqman PPT probe* Expt B | Western | Oil Increase observed at R2 |
|---|---|---|---|---|---|---|
| BN_G1198[a,b] | 1 | 1.34 | 36.76 | 61.82 | + | |
| BN_G1299 | 1.21 | 1 | 32.45 | 89.88 | w | |
| BN_G1220[a,b] | 1.64 | 1.59 | 36.25 | 34.06 | + | |
| BN_G1217[a] | 2.6 | 1.97 | 48.5 | 26 | + | |
| BN_G1135 | 2.93 | 1.83 | 22.16 | 30.06 | w | |
| BN_G1185 | 3.23 | 1.20 | 30.27 | 43.11 | w | |
| BN_G1182 | 3.32 | 2.25 | 58.49 | 34.54 | w | |
| BN_G1180 | 3.43 | 1.95 | 50.21 | 32.45 | w | |
| BN_G1091 | 3.71 | 4.11 | 50.91 | 81.57 | w | |
| BN_G1216 | 3.94 | 1.99 | 1 | 1 | + | + |
| BN_G1195 | 7.46 | 7.67 | 64.89 | 85.04 | w | |
| BN_G1193[a,b] | 9.25 | 6.77 | 65.34 | 57.28 | w | |
| BN_G1184 | 10.56 | 17.15 | 104.69 | 364.56 | w | |
| BN_G1183 | 11.08 | 19.3 | 227.54 | 352.14 | w | |
| BN_G1214[a,b] | 12.47 | 5.24 | 90.51 | 77.17 | + | |
| BN_G1239 | 12.82 | 3.97 | 124.5 | 67.18 | + | |
| BN_G1194 | 14.22 | 6.06 | 28.44 | 16.8 | w | |
| BN_G1218 | 17.88 | 6.73 | 254.23 | 213.78 | w | |
| BN_G1179 | 21.56 | 15.89 | 35.75 | 60.97 | w | |
| BN_G1139 | 32.22 | 7.06 | 121.10 | 105.42 | w | |
| BN_G1196 | 32.45 | 21.11 | 53.45 | 60.55 | w | |
| BN_G1225 | 53.45 | 11.47 | 19.16 | 24.25 | + | |
| BN_G1223 | 67.65 | 7.52 | 97.68 | 54.19 | + | |

Data is normalized to 18S RNA and then relative expression is obtained by comparing the value for each event to an event chosen as the lowest expressor for that experiment.

(a) R1 transplant grown in Brawley, CA.

(b) R1 seed planted in Thief River Falls, MN.

The letter w denotes a weak signal and therefore not conclusively positive or negative.

Figure 6

Oneway Analysis of %Oil By mFAS

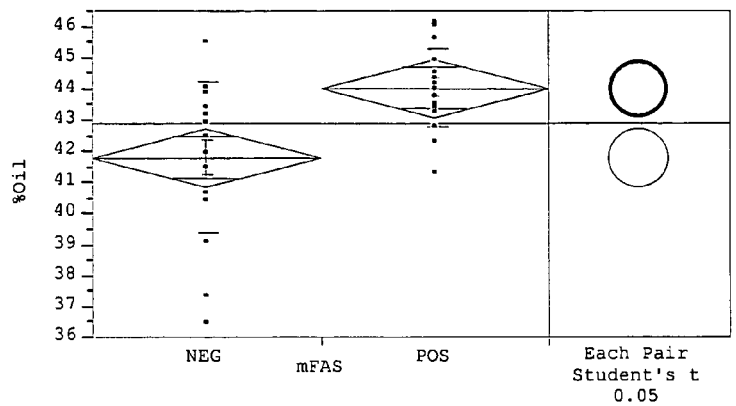

Oneway Anova
Summary of Fit

| | |
|---|---|
| Rsquare | 0.263684 |
| Adj Rsquare | 0.240674 |
| Root Mean Square Error | 1.916516 |
| Mean of Response | 42.92029 |
| Observations (or Sum Wgts) | 34 | t-Test

| | Difference | t-Test | DF | Prob>|t| |
|---|---|---|---|---|
| Estimate | -2.2253 | -3.385 | 32 | 0.0019 |
| Std Error | 0.6574 | | | |
| Lower 95% | -3.5643 | | | |
| Upper 95% | -0.8863 | | | |

Assuming equal variances

Analysis of Variance

| Source | DF | Sum of Squares | Mean Square | F Ratio | Prob > F |
|---|---|---|---|---|---|
| mFAS | 1 | 42.09144 | 42.0914 | 11.4596 | 0.0019 |
| Error | 32 | 117.53706 | 3.6730 | | |
| C. Total | 33 | 159.62850 | | | |

Means for Oneway Anova

| Level | Number | Mean | Std Error | Lower 95% | Upper 95% |
|---|---|---|---|---|---|
| NEG | 17 | 41.8076 | 0.46482 | 40.861 | 42.754 |
| POS | 17 | 44.0329 | 0.46482 | 43.086 | 44.980 |

Std Error uses a pooled estimate of error variance

Means and Std Deviations

| Level | Number | Mean | Std Dev | Std Err Mean | Lower 95% | Upper 95% |
|---|---|---|---|---|---|---|
| NEG | 17 | 41.8076 | 2.38814 | 0.57921 | 40.580 | 43.036 |
| POS | 17 | 44.0329 | 1.28174 | 0.31087 | 43.374 | 44.692 |

Means Comparisons

| Dif=Mean[i]-Mean[j] | POS | NEG |
|---|---|---|
| POS | 0.0000 | 2.2253 |
| NEG | -2.2253 | 0.0000 |

Alpha=
0.05

Comparisons for each pair using Student's t t
2.03693

| Abs(Dif)-LSD | POS | NEG |
|---|---|---|
| POS | -1.3390 | 0.8863 |

Figure 7

ELEVATION OF OIL LEVELS IN *BRASSICA* PLANTS

This patent application claims the benefit of U.S. Provisional Patent Application No. 60/435,197, filed Dec. 19, 2002, incorporated herein by reference.

The present invention relates to the fields of nucleic acid chemistry and agricultural biotechnology. In particular, the present invention is directed at the identification of nucleic acids that encode proteins useful for increasing oil levels in *Brassica* plants and creating *Brassica* plants that include such nucleic acids.

*Brassica* plants are a source of polyunsaturated oils. While tissues of most *Brassica* plant species contain little oil, the cultivation of certain plant types, over many acres, permit large quantities of *Brassica* plant oils to be produced. If the oil content of these *Brassica* plants could be increased, then *Brassica* plant oils could be produced more efficiently.

Higher plants such as *Brassica* synthesize fatty acids via a common metabolic pathway involving the co-factor ACP and the fatty acid synthase (FAS) enzyme complex. The FAS complex consists of about 8 separate enzymes that catalyze 30 or more individual reaction steps, all of which, in plants, are located in the plastids. In developing seeds, for example, where fatty acids are stored, the fatty acid synthase (FAS) enzyme complex is located in the plastids, synthesizes the fatty acids therein, and then the fatty acids are transported to the cytosol in accordance with energy needs there.

Certain workers have attempted to increase or modulate the oil content of plants. For example, U.S. Pat. No. 6,268,550 to Gengenbach et al., provides maize acetyl CoA carboxylase nucleic acids for altering the oil content of plants. Additionally, U.S. Pat. No. 5,925,805 to Ohlrogge et al., provides an *Arabidopsis* acetyl CoA carboxylase gene that can be used to increase the oil content of plants.

SUMMARY OF THE INVENTION

A need exists for a method to increase the oil content of *Brassica* plants and seeds. Moreover, it would be more energy efficient to provide the plant with a capability to synthesize fatty acids in the cytosol directly. This present invention provides a *Brassica* sp. plant comprising a heterologous nucleic acid encoding a multifunctional fatty acid synthase. In one embodiment, the plant further comprises a second nucleic acid encoding a phosphopantetheine:protein transferase. In one preferred embodiment the *Brassica* plant produces increased oil levels in the seed tissue as a result of the multifunctional fatty acid synthase. In another preferred embodiment the multifunctional fatty acid synthase is substantially located in the cytosol of the plant cell.

This present invention further provides a method for increasing oil levels in the tissues of a *Brassica* sp. plant by expressing a gene encoding a multifunctional fatty acid synthase on either a single or multiple polypeptide chains. In one preferred embodiment of this present invention, the gene encodes a cytosol-targeted mfFAS. Preferably, the source of the mfFAS is selected from the group consisting of bacteria, fungae, planta, mycoplasma, and the like; more preferably, the source of the mfFAS is bacteria or fungae; most preferably, the source of the mfFAS is bacteria. In another embodiment of this present invention, the expression of the mfFAS gene is in the seed tissue of the *Brassica* plant, preferably resulting in the accumulation of oil in the seed.

In another embodiment the present invention provides plant transformation vectors for *Brassica* containing a mfFAS gene, as well as transformed *Brassica* plants and seeds are also provided.

In another embodiment, the present invention provides a method of producing a *Brassica* oil, comprising the steps of: a) growing an oilseed *Brassica* plant, the genome of which contains a nucleic acid molecule encoding a multifunctional fatty acid synthase, to produce oil-containing seeds; and b) extracting oil from the seeds. In another embodiment, the present invention provides a method of producing a *Brassica* oil, comprising the steps of: a) growing an oilseed *Brassica* plant, the genome of which contains a nucleic acid molecule encoding a phosphopantetheine:protein transferase, to produce oil-containing seeds; and b) extracting oil from the seeds.

DESCRIPTION OF THE FIGURES

FIG. 2 provides an alignment of the fasA *Brevibacterium ammoniagenes* nucleic acid sequence [SEQ ID NO: 1] provided herein with a published fasA *Brevibacterium ammoniagenes* nucleic acid sequence (Stuible et al., *J. Bacteriol.*, 178:4787, 1996). A number of differences at the DNA level were observed.

FIG. 3 provides an alignment of the fasA *Brevibacterium ammoniagenes* amino acid sequence [SEQ ID NO: 2] provided herein with a published fasA *Brevibacterium ammoniagenes* amino acid sequence (Stuible et al., *J. Bacteriol.*, 178:4787, 1996). A number of differences at the protein level were observed.

FIG. 6 shows the results of the analyses of R2 seed from events generated from the transformation of canola explants with the vector pMON75201.

FIG. 7 shows the statistical analysis of the oil results from positive and negative isolines of event BN_G1216.

BRIEF DESCRIPTION OF THE SEQUENCES

Figure 1:
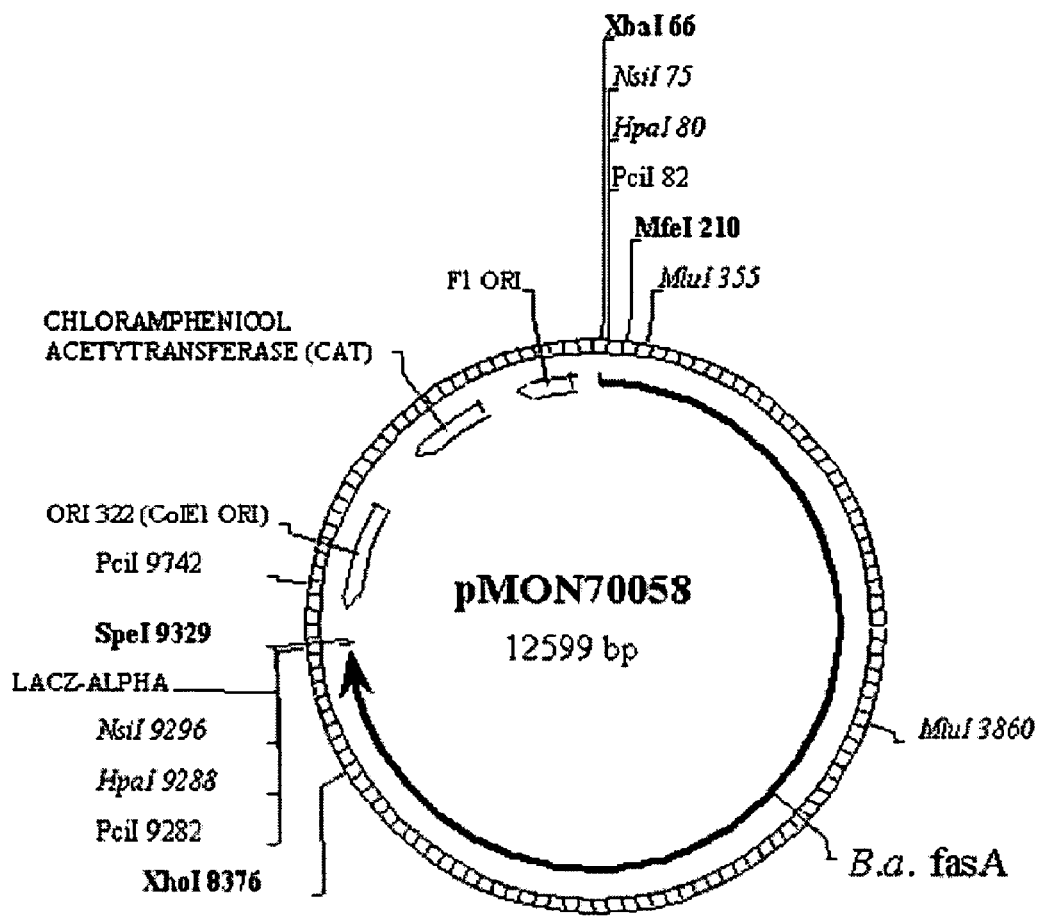
FIG. 1 provides a map of the plasmid pMON70058 that contains the 8 KB fasA gene from *Brevibacterium ammoniagenes*.

SEQ ID NO: 1 is a DNA encoding FasA from *Brevibacterium ammoniagenes*.

SEQ ID NO: 2 is a protein known as FasA from *Brevibacterium ammoniagenes*.

SEQ ID NO: 3 is a DNA encoding a phosphopantetheine:protein transferase (PPT1) enzyme from *B. ammoniagenes*.

SEQ ID NO: 4 is a protein known as phosphopantetheine:protein transferase (PPT1) enzyme from *B. ammoniagenes*.

SEQ ID NO: 5 is a nucleic acid used as a PCR primer.
SEQ ID NO: 6 is a nucleic acid used as a PCR primer.
SEQ ID NO: 7 is a nucleic acid used as a PCR primer.
SEQ ID NO: 8 is a nucleic acid used as a PCR primer.
SEQ ID NO: 9 is a nucleic acid used as a PCR primer.
SEQ ID NO: 10 is a nucleic acid used as a PCR primer.

SEQ ID NO: 11 is a nucleic acid used as a PCR primer.

SEQ ID NO: 12 is a nucleic acid used as a PCR primer.

SEQ ID NO: 13 is a nucleic acid used as a PCR primer.

SEQ ID NO: 14 is a nucleic acid used as a PCR primer.

SEQ ID NO: 15 is a protein known as fatty acid synthase 1 of *Schizosaccharomyces pombe*; NCBI Accession No. CAB54157.

SEQ ID NO: 16 is a DNA encoding fatty acid synthase subunit beta of *Schizosaccharomyces pombe*.

SEQ ID NO: 17 is a protein known as fatty acid synthase subunit alpha of *Schizosaccharomyces pombe*; NCBI Accession No. D83412.

SEQ ID NO: 18 is a protein known as fatty acid synthase subunit beta of *Saccharomyces cerevisiae*; NCBI Accession No. CAA82025.

SEQ ID NO: 19 is a protein known as fatty acid synthase subunit alpha of *Saccharomyces cerevisiae*; NCBI Accession No. CAA97948.

SEQ ID NO: 20 is a protein known as fatty acid synthase subunit beta of *Candida albicans*; NCBI Accession No. CAA52907.

SEQ ID NO: 21 is a DNA encoding fatty acid synthase subunit alpha of *Candida albicans*; NCBI Accession No. L29063.

SEQ ID NO: 22 is a protein known as fatty acid synthase subunit alpha of *Candida albicans*; NCBI Accession No. L29063.

SEQ ID NO: 23 is a protein known as fatty acid synthase of *Mycobacterium tuberculosis* H37Rv; NCBI Accession No. CAB06201.

SEQ ID NO: 24 is a protein known as fatty acid synthase of *Mycobacterium leprae*; NCBI Accession No. CAB39571.

SEQ ID NO: 25 is a protein known as fatty acid synthase of *Caenorhabditis elegans*; NCBI Accession No. NP492417.

SEQ ID NO: 26 is a DNA encoding fatty acid synthase (FAS) of *Rattus norvegicus*; NCBI Accession No. X13415.

SEQ ID NO: 27 is a protein known as fatty acid synthase (FAS) of *Rattus norvegicus*; NCBI Accession No. X13415.

SEQ ID NO: 28 is a DNA encoding fatty acid synthase (FAS) of chicken (*Gallus gallus*); NCBI Accession No. J03860 M22987.

SEQ ID NO: 29 is a protein known as fatty acid synthase (FAS) of chicken (*Gallus gallus*); NCBI Accession No. J03860 M22987.

SEQ ID NO: 30 is a DNA encoding fatty acid synthase (FAS) of *Mycobacterium bovis*; NCBI Accession No. U36763.

SEQ ID NO: 31 is a protein known as fatty acid synthase (FAS) of *Mycobacterium bovis*; NCBI Accession No. U36763.

SEQ ID NO: 32 is a DNA encoding a phosphopantetheine: protein transferase (sfp gene product) enzyme from *Bacillus subtilis*; NCBI Accession No. X63158.

SEQ ID NO: 33 is a protein known as phosphopantetheine: protein transferase (sfp gene product) enzyme from *Bacillus subtilis*; NCBI Accession No. X63158.

SEQ ID NO: 34 is a DNA encoding a phosphopantetheine: protein transferase (gsp gene product) enzyme from *Brevibacillus brevis* (ATCC 9999); NCBI Accession No. X76434.

SEQ ID NO: 35 is a protein known as phosphopantetheine: protein transferase (gsp gene product) enzyme from *Brevibacillus brevis* (ATCC 9999); NCBI Accession No. X76434.

SEQ ID NO: 36 is a DNA encoding a phosphopantetheine: protein transferase (entD gene product) enzyme from *Escherichia coli*; NCBI Accession No. D90700.

SEQ ID NO: 37 is a protein known as phosphopantetheine: protein transferase (entD gene product) enzyme from *Escherichia coli*; NCBI Accession No. D90700.

SEQ ID NO: 38 is a DNA encoding a phosphopantetheine: protein transferase (pptA gene product) enzyme from *Streptomyces verticillus*; NCBI Accession No. AF210311.

SEQ ID NO: 39 is a protein known as phosphopantetheine: protein transferase (pptA gene product) enzyme from *Streptomyces verticillus*; NCBI Accession No. AF210311.

SEQ ID NO: 40 is a DNA encoding an α-aminoadipate reductase small subunit (lys5 gene product) enzyme from *Saccharomyces cerevisiae*; NCBI Accession No. U32586.

SEQ ID NO: 41 is a protein known as the small subunit (lys5 gene product) of an α-aminoadipate reductase from *Saccharomyces cerevisiae*; NCBI Accession No. U32586.

SEQ ID NO: 42 is a DNA encoding an open reading frame o195 from *Escherichia coli*; NCBI Accession No. U00039.

SEQ ID NO: 43 is a protein encoded by open reading frame o195 from *Escherichia coli*; NCBI Accession No. U00039.

Definitions

The following definitions are provided as an aid to understanding the detailed description of the present invention.

The phrases "coding sequence," "coding region," "structural sequence," and "structural nucleic acid sequence" refer to a physical structure comprising an orderly arrangement of nucleotides. The nucleotides are arranged in a series of triplets that each form a codon. Each codon encodes a specific amino acid. Thus, the coding sequence, coding region, structural sequence, and structural nucleic acid sequence encode a series of amino acids forming a protein, polypeptide, or peptide sequence. The coding sequence, coding region, structural sequence, and structural nucleic acid sequence may be contained within a larger nucleic acid molecule, vector, or the like. In addition, the orderly arrangement of nucleotides in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The phrase "expression of antisense RNA" refers to the transcription of a DNA to produce a first RNA molecule capable of hybridizing to a second RNA molecule, which second RNA molecule encodes a gene product that is desirably down-regulated.

The term "homology" refers to the level of similarity between 2 or more nucleic acid or amino acid sequences in terms of percent of positional identity (i.e., sequence similarity or identity). Homology also refers to the concept of similar functional properties among different nucleic acids or proteins.

The term "heterologous" refers to the relationship between 2 or more nucleic acid or protein sequences that are derived from different sources. For example, a promoter is heterologous with respect to a coding sequence if such a combination is not normally found in nature. In addition, a particular nucleic acid molecule may be "heterologous" with respect to a cell or organism into which it is inserted (i.e., does not naturally occur in that particular cell or organism).

The term "hybridization" refers to the ability of a first strand of nucleic acid to join with a second strand via hydrogen bond base pairing when the 2 nucleic acid strands have sufficient sequence complementarity. Hybridization occurs when the 2 nucleic acid molecules anneal to one another under appropriate conditions.

The phrase "operably linked" refers to the functional spatial arrangement of 2 or more nucleic acid regions or nucleic acid sequences. For example, a promoter region may be positioned relative to a nucleic acid sequence such that transcription of the nucleic acid sequence is directed by the promoter region. Thus, a promoter region is operably linked to the nucleic acid sequence.

In the context of the present invention, the terms "plant" or "plants" refer to plants of the species Brassica.

The terms "promoter" or "promoter region" refers to a nucleic acid sequence, usually found upstream (5') to a coding sequence, that is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The term "5'-UTR" refers to the untranslated region of DNA upstream, or 5', of the coding region of a gene.

The term "3'-UTR" refers to the untranslated region of DNA downstream, or 3', of the coding region of a gene.

The phrase "recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

The phrase "regulatory sequence" refers to a nucleotide sequence located upstream (5'), within, or downstream (3') with respect to a coding sequence. Transcription and expression of the coding sequence is typically impacted by the presence or absence of the regulatory sequence.

The phrase "substantially homologous" refers to 2 sequences that are at least about 90% identical in sequence, as measured by the CLUSTAL W method in the Omiga program, using default parameters (Version 2.0; Accelrys, San Diego, Calif.).

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, the phrase "transgenic Brassica plant" refers to a Brassica plant having an introduced nucleic acid stably introduced into a genome of that plant, for example, the nuclear or plastid genomes.

As used herein, the phrase "substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state.

DETAILED DESCRIPTION OF THE INVENTION

The present invention provides a multifunctional fatty acid synthase ("mfFAS") that encodes the enzymatic functions required to synthesize palmitoyl (16:0) CoA, stearoyl (18:0) CoA, and oleoyl (18:1) CoA, the fatty acids used as precursors for other long chain saturated and unsaturated fatty acids. Obtaining nucleic acid sequences capable of producing increased oil content in Brassica plants is problematic because many non-associated, monofunctional enzymes are used to make fatty acids in Brassica plants. Accordingly, cloning and genetic manipulation of plant fatty acid synthases ("FASs") would require isolation and coordinated expression of at least 8 separate genes. In particular, plant fatty acid synthesis depends on availability of the following plastid-localized FAS enzymes: Malonyl-CoA:ACP transacylase, β-ketoacyl-ACP synthase III, β-ketoacyl-ACP synthase I, β-ketoacyl-ACP synthase II, β-ketoacyl-ACP reductase, β-hydroxyacyl-ACP dehydratase, enoyl-ACP reductase, and stearoyl-ACP desaturase. For movement of the end-product, acyl-ACP, from the plastid to the cytosol of the cell, two more enzymatic activities are required: acyl-ACP thioesterase and acyl-CoA synthase.

However, the present invention solves this problem by providing a multifunctional fatty acid synthase that encodes all of the FAS enzymatic functions in a single, long polypeptide chain or in two chains that combine together, which may be employed in the cytosol or plastid, preferably in both, more preferably in the cytosol. Such a multifunctional fatty acid synthase is surprisingly effective in Brassica plants even though its structure is so dissimilar from plant endogenous fatty acid synthases. Most preferably, the mfFAS of the present invention is employed in the cytosol of a Brassica plant, and in this way the need for an acyl carrier protein ("ACP") in fatty acid synthesis and the enzymes acyl-ACP thioesterase and acyl-CoA synthase is removed. Accordingly, not only does the present invention remove the need to clone at least 8 different genes to accomplish altered fatty acid synthesis in a Brassica plant, but when the mfFAS is employed in the cytosol, it replaces the function of 11 different plant gene products.

Fatty Acid Synthases: Fatty acid synthases are among the functionally most complex multienzyme systems known, which can be formed from a single polypeptide or multiple polypeptides. For mfFASs formed of a single polypeptide, there are multiple regions included thereon that perform the various enzymatic activities; such regions are referred to as "domains." Multifunctional fatty acid synthases formed of multiple polypeptides include various FAS domains as well, which require the interaction of the constituent polypeptides to function. Such polypeptides, whether a multi-domain or single-domain polypeptide, can be isolated from an organism, or can be generated by combining domains or parts of domains together at the nucleic acid level using conventional recombinant technology. Accordingly, recombinant chimeric nucleic acids that combine some mfFAS domains from one source with the remainder of the mfFAS domains from one or more second sources are preferred embodiments of the present invention. In the same fashion, the nucleic acid sequences in a mfFAS gene that encodes a particular domain can be replaced with a homologous nucleic acid sequence from a second source that encodes the same domain.

Fatty acid synthases usually comprise a set of 8 different functional domains and catalyze more than about 30 individual reaction steps. Two structurally distinct classes of fatty acid synthases exist. Type I fatty acid synthases are multifunctional synthases, commonly found in non-plant eukaryotes and in a few bacterial species. Type II fatty acid synthases constitute a set of separate, monofunctional polypeptides that are found in most bacteria and in the plastids of higher plants. These polypeptides must properly assemble into a multimeric complex before the synthase becomes active. The fatty acid synthase from some bacteria, such as *Brevibacterium ammoniagenes*, is unlike plant and animal synthases in that it has a ninth catalytic activity (Seyama and Kawaguchi (1987), in Dolthin et al., (eds.), Pyridine Nucleotide Coenzymes: Chemical, Biochemical and Medical Aspects, vol. 2B, Wiley, N.Y., pp. 381-431), the 3-hydroxydecanoyl β,γ-dehydratase, which enables synthesis of both saturated and unsaturated fatty acids.

For transgenic purposes, type I multifunctional fatty acid synthases may have certain advantages over the type II "monofunctional" fatty acid synthases. For example, the type I multifunctional fatty acid synthases may have greater stability and/or better-coordinated expression. Addition of a single polypeptide specific for one of the enzymatic fatty acid synthase activities to a plant by transgenic means may not provide overproduction of the entire fatty acid synthase complex because there may not be sufficient endogenous amounts of the other non-transgenic FAS polypeptides to substantially increase levels of the functional complex. In contrast, nucleic acids encoding a type I multifunctional fatty acid synthase can reliably be used to overproduce all of the enzymatic functions of fatty acid synthase.

According to the present invention, nucleic acids encoding one or more of the separate domains from a type II monofunctional fatty acid synthase can be fused or linked to provide a synthetic multifunctional fatty acid synthase that can generate high oil levels when expressed within a host, such as, for example, a *Brassica* plant cell, plant tissue, or seed. Such a fused, synthetic multifunctional fatty acid synthase can be made by fusing or linking the separate enzymatic functions associated with the various polypeptides of type II fatty acid synthases by chemically linking the nucleic acids that encode the various polypeptides. The overall sequence of such a synthetic gene generally aligns with that of a type I multifunctional fatty acid synthase. Using such sequence alignments, the spacing and orientation of polypeptides that contain the various fatty acid synthase activities can be adjusted or modified by altering the lengths of linking DNA between coding regions to generate a synthetic multifunctional fatty acid synthase DNA construct that optimally aligns with a natural type I multifunctional fatty acid synthase gene.

The fatty acid synthase polypeptides of the present invention can therefore encode more than one of the enzymes associated with fatty acid synthase, such as, for example, 2 through and including 9, thereby enabling up to the same 9 catalytic activities as are found in the mfFAS of *Brevibacterium ammoniagenes*. Any of the enzymes involved in the various steps of fatty acid synthesis can be joined. The first step in initiation stage of fatty acid synthesis is the carboxylation of the 2-carbon acetyl-CoA to form the 3-carbon β-ketoacid malonyl-CoA by acetyl-CoA carboxylase (ACCase). The ACCase step is irreversible, so once this step is accomplished, the resultant carbon compound is committed to fatty acid synthesis. All subsequent steps are catalyzed by the FAS.

Malonyl-ACP is synthesized from malonyl-CoA and ACP by the enzyme malonyl-CoA:ACP transacylase. An acetyl moiety from acetyl-CoA is joined to a malonyl-ACP in a condensation reaction catalyzed by β-ketoacyl-ACP synthase III. Elongation of acetyl-ACP to 16- and 18-carbon fatty acids involves the cyclical action of the following sequence of reactions. After acetyl-CoA is condensed with malonyl-ACP using β-ketoacyl-ACP synthase, a β-ketoacyl-ACP is formed. The keto group on the β-ketoacyl-ACP is then reduced to an alcohol by β-ketoacyl-ACP reductase. The alcohol is removed in a dehydration reaction to form an enoyl-ACP by β-hydroxyacyl-ACP dehydratase. Finally, the enoyl-ACP is reduced to form the elongated saturated acyl-ACP by enoyl-ACP reductase.

The enzyme β-ketoacyl-ACP synthase I catalyzes elongation up to palmitoyl-ACP (C16:0), which is generally the end product from which other types of fatty acids are made. The enzyme β-ketoacyl-ACP synthase II catalyzes the final elongation of palmitoyl-ACP to stearoyl-ACP (C18:0).

Common plant unsaturated fatty acids, such as oleic, linoleic, and α-linolenic acids, originate from the desaturation of stearoyl-ACP to form oleoyl-ACP (C18:1) in a reaction catalyzed by a soluble plastid enzyme, Δ-9 desaturase (also often referred to as "stearoyl-ACP desaturase"). Molecular oxygen is required for desaturation and reduced ferredoxin serves as an electron co-donor.

Hence, the present invention contemplates polypeptides encoding several functions, for example, those relating to acyl carrier protein, malonyl CoA-ACP acyltransferase, β-ketoayl-ACP synthase III, β-ketoayl-ACP reductase, β-hydroxyacyl-ACP dehydratase, enoyl-ACP reductase, β-ketoacyl-ACP synthase I, β-ketoacyl-ACP synthase II, and Δ-9 desaturase.

In one embodiment, the present invention provides an isolated mfFAS polypeptide from a species of the group consisting of *Brevibacterium ammoniagenes, Schizosaccharomyces pombe, Saccharomyces cerevesiae, Candida albicans, Mycobacterium tuberculosis, Caenorhabditis elegans, Rattus norvegicus, Gallus gallus, Lipomyces starkeyi, Rhodosporidium toruloides*, and *Mycobacterium bovis*. Preferably, the mfFAS polypeptide is isolated from *Brevibacterium ammoniagenes, Schizosaccharomyces pombe, Saccharomyces cerevesiae, Candida albicans*; more preferably, the mfFAS polypeptides is isolated from *Brevibacterium ammoniagenes*. Such mfFAS polypeptides include one selected from the group consisting of SEQ ID NOs: 2, 15, 17, 18, 19, 20, 22, 23, 24, 25, 27, 29, and 31. Preferably, the mfFAS polypeptide used in the context of the present invention is one selected from the group consisting of SEQ ID NOs: 2, 15, 17, 18, 19, 20, and 22; more preferably, the mfFAS is SEQ ID NO: 2. Any of the aforementioned mfFAS polypeptides functions to increase the oil content of *Brassica* plant tissues.

mfFAS Nucleic Acids: The present invention uses nucleic acids that encode multifunctional fatty acid synthases, which are used in the context of the present invention for increasing the oil content of *Brassica* plant tissues. Such nucleic acids can encode a type I multifunctional fatty acid synthase that has been isolated from an organism. Preferred organisms from which nucleic acids encoding mfFAS can be isolated include, without limitation: bacteria, preferably *Brevibacteria* and *Bacilli*; fungae, preferably *Saccharomycetes, Schizosaccharomycetes, Lipomyces starkeyi, Rhodosporidium toruloides*, or *Candidae*; mycobacteria; nematodes, preferably *Caenorhabdites*; and mammals, preferably rat or chicken. Alternatively, the nucleic acids can encode a multifunctional fatty acid synthase that has been recombinantly generated to contain a fusion of 2 or more regions that encode monofunctional enzymatic domains that facilitate 2 or more of the steps required to make a fatty acid.

In one embodiment, the present invention uses an isolated nucleic acid that encodes a protein having mfFAS activity, which nucleic acid is selected from the group consisting of SEQ ID NOs: 1, 16, 21, 26, 28, and 30, and complements thereof, and nucleic acids having at least about 70% sequence identity thereof. Preferred nucleic acid is SEQ ID NO: 1, 16, 21, 26, 28, or 30; more preferred is SEQ ID NO: 1. The percent sequence identity of included nucleic acids in the group is preferably at least about 75%, more preferably at least about 80%, yet more preferably at least about 85%, and yet more preferably at least about 90%; even more preferably at least about 95%; and most preferably at least about 98%. The nucleic acids of the present invention can be isolated from any species that has a multifunctional fatty acid synthase, including without limitation *Brevibacterium ammoniagenes* (source of SEQ ID NO: 1), *Schizosaccharomyces pombe* (source of SEQ ID NO: 16), *Saccharomyces cerevesiae, Candida albicans* (source of SEQ ID NO: 21), *Mycobacterium tuberculosis, Mycobacterium leprae, Mycobacterium bovis* (source of SEQ ID NO: 30), *Caenorhabditis elegans*, rat (source of SEQ ID NO: 26), and chicken (source of SEQ ID NO: 28). In a preferred embodiment, the present invention provides a nucleic acid that encodes mfFAS from *Brevibacterium ammoniagenes, Schizosaccharomyces pombe, Saccharomyces cerevesiae,* or *Candida albicans*; more preferably, the mfFAS polypeptides are isolated from *Brevibacterium ammoniagenes*.

In yet another embodiment, the present invention uses a nucleic acid that encodes a multifunctional fatty acid synthase having an amino acid sequence comprising a protein selected from the group consisting of SEQ ID NOs: 2, 15, 17, 18, 19, 20, 22, 23, 24, 25, 27, 29, and 31. Preferably, the protein is SEQ ID NO: 2. The present invention also uses the set of nucleic acids that includes those nucleic acids that are at least about 80% identical to those that encode SEQ ID NO: 2, 15, 17, 18, 19, 20, 22, 23, 24, 25, 27, 29, or 31; more preferably, the set of nucleic acids are at least about 85% identical to one or more of the nucleic acids that encode one or more of the identified SEQ ID NOs; yet more preferably, at least about 90% identical; even more preferably, at least about 95% identical; and most preferably, at least about 98% identical.

The present invention also uses vectors containing such multifunctional fatty acid synthase nucleic acids. As set forth in further detail hereinbelow, preferred nucleic acids include appropriate regulatory elements operably linked thereto that facilitate efficient expression of the inventive nucleic acids in a host, including without limitation, *Brassica* plant hosts. Vectors useful in the context of the present invention can include such regulatory elements.

In a preferred embodiment of the present invention, the nucleic acid molecules of the present invention encode enzymes that are allelic to those defined. As used herein, a mutant enzyme is any enzyme that contains an amino acid that is different from the amino acid in the same position of an enzyme of the same type.

The nucleic acids and vectors described herein need not have the exact nucleic acid sequences described herein. Instead, the sequences of these nucleic acids and vectors can vary, so long as the nucleic acid either performs the function for which it is intended or has some other utility, for example, as a nucleic acid probe for complementary nucleic acids. For example, some sequence variability in any part of a multifunctional fatty acid synthase nucleic acid is permitted so long as the mutant or variant polypeptide or polypeptides retains at least about 10% of the fatty acid synthase (FasA) activity observed under similar conditions for an analogous wild type fatty acid synthase enzyme, more preferably, the polypeptide(s) retain at least about 25% of the FasA activity; more preferably at least about 50% of the FasA activity; even more preferably, at least about 75% of the FasA activity; and yet more preferably, at least about 90% of the FasA activity. Most preferably, the aforementioned sequence variability results in increased FasA activity. In a preferred embodiment, the comparison of enzymatic activity is with the wild type *Brevibacterium ammoniagenes* fatty acid synthase [SEQ ID NO: 2].

Fragment and variant nucleic acids, for example, of SEQ ID NO: 1, are also encompassed by the present invention. Nucleic acid "fragments" encompassed by the present invention are of 3 general types. First, fragment nucleic acids that are not full length but do perform their intended function (fatty acid synthesis) are encompassed within the present invention. Second, fragments of nucleic acids identified herein that are useful as hybridization probes, but generally are not functional for fatty acid synthesis, are also included in the present invention. And, third, fragments of nucleic acids identified herein can be used in suppression technologies known in the art, such as, for example, anti-sense technology or RNA inhibition (RNAi), which provides for reducing carbon flow in a plant into oil, making more carbon available for protein or starch accumulation, for example. Thus, fragments of a nucleotide sequence, such as SEQ ID NO: 1, 16, 21, 26, 28, or 30, without limitation, may range from at least about 15 nucleotides, at least about 17 nucleotides, at least about 18 nucleotides, at least about 20 nucleotides, at least about 50 nucleotides, at least about 100 nucleotides, or more. In general, a fragment nucleic acid of the present invention can have any upper size limit so long as it is related in sequence to the nucleic acids of the present invention but does not include the full length.

In another embodiment, the present invention provides DNA molecules comprising a sequence encoding a consensus amino acid sequence, and complements thereof. In another aspect, the present invention provides DNA molecules comprising a sequence encoding a polypeptide comprising a conserved fragment of an amino acid consensus sequence. The present invention includes the use of consensus sequence and fragments thereof in transgenic *Brassica* plants, other organisms, and for other uses including those described below.

As used herein, "variants" have substantially similar or substantially homologous sequences when compared to reference or wild type sequence. For nucleotide sequences that encode proteins, variants also include those sequences that, because of the degeneracy of the genetic code, encode the identical amino acid sequence of the reference protein. Variant nucleic acids also include those that encode polypeptides that do not have amino acid sequences identical to that of the proteins identified herein, but which encode an active protein with conservative changes in the amino acid sequence.

As is known by one of skill in the art, the genetic code is "degenerate," meaning that several trinucleotide codons can encode the same amino acid. This degeneracy is apparent from Table 1.

TABLE 1

| 1st Position | 2nd Position | | | | 3rd Position |
|---|---|---|---|---|---|
| | T | C | A | G | |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid. Therefore, a particular nucleic acid of the present invention also encompasses variants with degenerate codon substitutions, and complementary sequences thereof, as well as the sequence explicitly specified by a SEQ ID NO as set forth herein. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., *Nucleic Acid Res.*, 19:5081 (1991) and/or Ohtsuka et al., *J. Biol. Chem.*, 260:2605 (1985); Rossolini et al., *Mol. Cell. Probes*, 8:91 (1994).

A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any disclosed nucleic acid or amino acid sequence may be modified to reflect the preferred codon usage of a host cell or organism in which they are contained. Modification of a structural nucleic acid sequence for optimal codon usage in plants is described in U.S. Pat. No. 5,689,052, which is incorporated herein by reference. In a preferred embodiment, the present invention includes nucleic acids that encode mfFAS and that are codon-optimized in a *Brassica* plant. In a preferred embodiment the plants are of the *Brassica* species, and most preferably *Brassica napus* (canola).

However, the present invention is not limited to silent changes in the present nucleotide sequences but also includes variant nucleic acid sequences that conservatively alter the amino acid sequence of a polypeptide of the present invention. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode the peptides, without appreciable loss of their biological utility or activity. According to the present invention, then, variant and reference nucleic acids of the present invention may differ in the encoded amino acid sequence by one or more substitutions, additions, insertions, deletions, fusions, and truncations, which may be present in any combination, so long as an active mfFAS protein is encoded by the variant nucleic acid. Such variant nucleic acids will not encode exactly the same amino acid sequence as the reference nucleic acid, but have conservative sequence changes. It is known that codons capable of coding for such conservative amino acid substitutions are known in the art.

Another approach to identifying conservative amino acid substitutions require analysis of the hydropathic index of amino acids may be considered. The importance of the hydropathic amino acid index in conferring interactive biological function on a protein is generally understood in the art (Kyte and Doolittle, *J. Mol. Biol.*, 157:105-132, 1982). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.*, 157:105-132, 1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), glutamine (+0.3), asparagine (+0.2), glutamine (+0.2), glycine (0), threonine (−0.4), proline (+0.2), alninea (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

Variant nucleic acids with silent and conservative changes can be defined and characterized by the degree of homology to the reference nucleic acid. Preferred variant nucleic acids are "substantially homologous" to the reference nucleic acids of the present invention. As recognized by one of skill in the art, such substantially similar nucleic acids can hybridize under stringent conditions with the reference nucleic acids identified by SEQ ID NO herein. These types of substantially homologous nucleic acids are encompassed by this present invention.

Generally, nucleic acid derivatives and variants of the present invention will have at least about 90%, at least about 91%, at least about 92%, at least about 93%, or at least about 94% sequence identity to the reference nucleotide sequence defined herein. Preferably, nucleic acids of the present invention will have at least about 95%, at least about 96%, at least about 97%, or at least about 98% sequence identity to the reference nucleotide sequence defined herein.

Variant nucleic acids can be detected and isolated by standard hybridization procedures. Hybridization to detect or isolate such sequences is generally carried out under "moderately stringent" and preferably under "stringent" conditions. Moderately stringent hybridization conditions and associated moderately stringent and stringent hybridization wash conditions used in the context of nucleic acid hybridization experiments, such as Southern and Northern hybridization, are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular Biology-Hybridization with Nucleic Acid Probes, page 1, Chapter 2, *Overview of principles of hybridization and the strategy of nucleic acid probe assays*, Elsevier, N.Y. (1993). See also, J. Sambrook et al., Molecular Cloning: A Laboratory Manual, Cold Spring Harbor Press, NY, pp. 9.31-9.58 (1989); J. Sambrook et al., Molecular Cloning: A Laboratory Manual, Cold Spring Harbor Press, NY (3rd ed. 2001).

The present invention also provides methods for detection and isolation of derivative or variant nucleic acids encoding the proteins provided herein. The methods involve hybridizing at least a portion of a nucleic acid comprising any part of SEQ ID NO: 1, 16, 21, 26, 28, or 30, with respect to FAS-related sequences; and any part of SEQ ID NO: 3, 32, 34, 36, 38, 40, or 42, with respect to phosphopantetheine:protein transferase to a sample nucleic acid, thereby forming a hybridization complex; and detecting the hybridization complex. The presence of the complex correlates with the presence of a derivative or variant nucleic acid that can be further characterized by nucleic acid sequencing, expression of RNA and/or protein and testing to determine whether the derivative or variant retains activity. In general, the portion of a nucleic acid comprising any part of the aforementioned DNAs identified by SEQ ID NO used for hybridization is preferably at least about 15 nucleotides, and hybridization is under hybridization conditions that are sufficiently stringent to permit detection and isolation of substantially homologous nucleic acids; preferably, the hybridization conditions are "moderately stringent"; more preferably the hybridization conditions are "stringent", as defined herein and in the context of conventional molecular biological techniques well known in the art.

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or the washing conditions, nucleic acids having 100% complementary can be identified and isolated.

Alternatively, stringency conditions can be adjusted to allow some mismatching in sequences so that lower degrees of similarity are detected (heterologous probing) using, for example, moderately stringent conditions. Appropriate stringency conditions that promote DNA hybridization under moderately stringent conditions are, for example, about 2× sodium chloride/sodium citrate (SSC) at about 65° C., followed by a wash of 2×SSC at 20-25° C., are known to those skilled in the art and can be found in *Current Protocols in Molecular Biology*, John Wiley & Sons, NY, 6.3.1-6.3.6 (1989). Both temperature and salt may be varied, or either the temperature or the salt concentration may be held constant while the other variable is changed.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide, in which case hybridization temperatures can be decreased. Dextran sulfate and/or Denhardt's solution (50× Denhardt's is 5% Ficoll, 5% polyvinylpyrrolidone, 5% BSA) can also be included in the hybridization reactions.

Exemplary low stringency conditions include hybridization with a buffer solution of 30 to 50% formamide, 5×SSC (20×SSC is 3M NaCl, 0.3 M trisodium citrate), 50 mM sodium phosphate, pH7, 5 mM EDTA, 0.1% SDS (sodium dodecyl sulfate), 5× Denhardt's with 100 μg/ml denatured salmon sperm DNA at 37° C., and a wash in 1× to 5×SSC (20×SSC=3.0 M NaCl and 0.3 M trisodium citrate), 0.1% SDS at 37° C. Exemplary moderate stringency conditions include hybridization in 40 to 50% formamide, 5×SSC 50 mM sodium phosphate, pH 7, 5 mM EDTA, 0.1% SDS, 5× Denhardt's with 100 μg/ml denatured salmon sperm DNA at 42° C., and a wash in 0.1× to 2×SSC, 0.1% SDS at 42 to 55° C. Exemplary high stringency conditions include hybridization in 50% formamide, 5×SSC, 50 mM sodium phosphate, pH 7.0, 5 mM EDTA, 0.1% SDS, 5× Denhardt's with 100 μg/ml denatured salmon sperm DNA at 42° C., and a wash in 0.1×SSC, 0.1% SDS at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl, *Anal. Biochem.*, 138:267-284 (1984);

$$T_m=81.5° C.+16.6(\log M)+0.41 (\% GC)-0.61(\% \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Very stringent conditions are selected for hybridization to derivative and variant nucleic acids having a $T_m$ equal to the exact complement of a particular probe, less stringent conditions are selected for hybridization to derivative and variant nucleic acids having a $T_m$ less than the exact complement of the probe.

In general, $T_m$ is reduced by about 1° C. for each 1% of mismatching. Thus, $T_m$, hybridization, and/or wash conditions can be adjusted to hybridize to sequences of the desired sequence identity. For example, if sequences with greater than about 90% identity are sought, the $T_m$ can be decreased by about 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at about 1, about 2, about 3, or about 4° C. lower than the thermal melting point ($T_m$); moderately stringent conditions can utilize a hybridization and/or wash at about 6, about 7, about 8, about 9, or about 10° C. lower than the thermal melting point ($T_m$); low stringency conditions can utilize a hybridization and/or wash at about 11, about 12, about 13, about 14, about 15, or about 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2, Elsevier, N.Y.; Ausubel et al., eds. (1995) Current Protocols in Molecular Biology, Chapter 2, Greene Publishing and Wiley—Interscience, N.Y. See Sambrook et al., (1989) Molecular Cloning: A Laboratory Manual, 2d ed., Cold Spring Harbor Laboratory Press, Plainview, N.Y. Using these references and the teachings herein on the relationship between $T_m$, mismatch, and hybridization and wash conditions, those of ordinary skill can generate variants of the present nucleic acids.

In another preferred embodiment of the present invention, the inventive nucleic acids are defined by the percent identity relationship between particular nucleic acids and other members of the class using analytic protocols well known in the art. Such analytic protocols include, but are not limited to: CLUSTAL in the PC/Gene program (available from Intelligenetics, Mountain View, Calif., or in the Omiga program version 2.0 Accelrys Inc., San Diego, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis.). Alignments using these programs can be performed using the default parameters. The CLUSTAL program is well described by Higgins et al., Gene, 73:237-244 (1988); Higgins et al., *CABIOS*, 5:151-153 (1989); Corpet et al., *Nucleic Acids Res.*, 16:10881-90 (1988); Huang et al., *CABIOS*, 8:155-65 (1992); and Pearson et al., *Meth. Mol. Biol.*, 24:307-331 (1994). The ALIGN program is based on the algorithm of Meyers and Miller, *Computer Applic. Biol. Sci.*, 4:11-17 (1988). The BLAST programs of Altschul et al., *J. Mol. Biol.*, 215:403 (1990), are based on the algorithm of Karlin and Altschul *Proc. Natl. Acad. Sci.* (U.S.A.), 87:2264-2268 (1990). To obtain gapped alignments for comparison purposes, Gapped BLAST (in BLAST 2.0) can be utilized as described in Altschul et al., *Nucleic Acids Res.*, 25:3389 (1997). Alternatively, PSI-BLAST (in BLAST 2.0) can be used to perform an iterated search that detects distant relationships between molecules. See, Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see, Henikoff & Henikoff, *Proc. Natl. Acad. Sci.* (U.S.A.), 89:10915, 1989). Alignment may also be performed manually by inspection.

For purposes of the present invention, comparison of nucleotide sequences for determination of percent sequence identity to the nucleic acid sequences disclosed herein is preferably made using the BLASTN program (version 1.4.7 or later) with its default parameters or any equivalent program. By "equivalent program" is intended any sequence comparison program that, for any 2 sequences in question, generates an alignment having identical nucleotide or amino acid residue matches and an identical percent sequence identity when compared to the corresponding alignment generated by the preferred program.

Isolation of Nucleic Acids Encoding Multifunctional Fatty Acid Synthases: Nucleic acids encoding a multifunctional fatty acid synthase can be identified and isolated by standard methods, as described by Sambrook et al., *Molecular Cloning: A Laboratory Manual*, Cold Spring Harbor, N.Y. (1989). For example, a DNA sequence encoding a type I multifunctional fatty acid synthase can be identified by screening of a DNA or cDNA library generated from nucleic acid derived from a particular cell type, cell line, primary cells, or tissue. Examples of libraries useful for identifying and isolating a multifunctional fatty acid synthase include libraries made from the genomic DNA or cDNA of any organism encoding a type I fatty acid synthase, preferably a bacteria or non-plant eukaryote.

Screening for DNA fragments that encode a multifunctional fatty acid synthase can be accomplished by screening colonies or plaques from a genomic or cDNA library for hybridization to a probe of an available multifunctional fatty acid synthase from other organisms or by screening colonies or plaques from a cDNA expression library for binding to antibodies that specifically recognize a multifunctional fatty acid synthase. DNA fragments that hybridize to multifunctional fatty acid synthase probes from other organisms and/or colonies or plaques carrying DNA fragments that are immunoreactive with antibodies to multifunctional fatty acid synthase can be subcloned into a vector and sequenced and/or used as probes to identify other cDNA or genomic sequences encoding all or a portion of the desired multifunctional fatty acid synthase gene. Probes for isolation of multifunctional fatty acid synthase genes can also include DNA fragments of type II fatty acid synthase genes or antibodies to the type II proteins, as noted herein above.

A cDNA library can be prepared, for example, by random oligo priming or oligo dT priming. Plaques containing DNA fragments can be screened with probes or antibodies specific for multifunctional fatty acid synthase. DNA fragments encoding a portion of a multifunctional fatty acid synthase gene can be subcloned and sequenced and used as probes to identify a genomic multifunctional fatty acid synthase gene. DNA fragments encoding a portion of a multifunctional fatty acid synthase can be verified by determining sequence homology with other known multifunctional fatty acid synthase genes or by hybridization to multifunctional fatty acid synthase-specific messenger RNA. Once cDNA fragments encoding portions of the 5', middle and 3' ends of a multifunctional fatty acid synthase are obtained, they can be used as probes to identify and clone a complete genomic copy of the multifunctional fatty acid synthase gene from a genomic library.

Portions of the genomic copy or copies of an multifunctional fatty acid synthase gene can be sequenced and the 5' end of the gene identified by standard methods, including either DNA sequence homology to other multifunctional fatty acid synthase genes or by RNAase protection analysis, as described by Sambrook et al., *Molecular Cloning: A Laboratory Manual*, Cold Spring Harbor Press, Cold Spring Harbor, N.Y. (1989). The 3' and 5' ends of the target gene can also be located by computer searches of genomic sequence databases using known fatty acid synthase coding regions. Once portions of the 5' end of the gene are identified, complete copies of the multifunctional fatty acid synthase gene can be obtained by standard methods, including cloning or polymerase chain reaction (PCR) synthesis using oligonucleotide primers complementary to the DNA sequence at the 5' end of the gene. The presence of an isolated full-length copy of the multifunctional fatty acid synthase gene can be verified by hybridization, partial sequence analysis, or by expression of the multifunctional fatty acid synthase enzyme.

Phosphopantetheine:Protein Transferases: During the process of fatty acid synthesis, the growing acyl chain is preferably covalently linked by a thioester bond to the cysteamine thiol of a phosphopantetheinyl (P-Pan) moiety, which is preferably attached at the other end to a specific serine residue of acyl carrier protein (ACP), in the case of type II FAS systems, or the ACP-domain of a type I FAS. This P-Pan moiety acts as a "swinging arm," carrying the growing acyl chain between the active sites of the different enzymes or domains of the FAS complex. Accordingly, the transgenic mfFAS used in the context of the present invention is preferably phosphopantetheinylated, which phosphopantetheinylation is accomplished by a co-transformed gene that encodes a suitable PPTase or by a host PPTase that has sufficient substrate range of activity for the purpose of modifying the transgenic mfFAS.

The enzymatic post-translational attachment of the P-Pan group to an ACP protein or domain is carried out by a phosphopantetheinyl transferase (PPTase). Any suitable PPTase can be used in the context of the present invention, the suitability of which is determined by the ability of the PPTase to phosphopantetheinylate a mfFAS used herein. For example, the *Brevibacterium ammoniagenes* FasA protein [SEQ ID NO: 2] can be suitably combined with the PPTase from the same species, which is identified herein as SEQ ID NO: 4. In another embodiment of the present invention, the gene encoding the mfFAS includes its own PPTase activity, such as the mfFAS derived from yeast (e.g., SEQ ID NOs: 15-19), and thus the transgenic mfFAS is suitably modified to be active upon expression in the host. Particularly preferred PPTases have broad specificity, such as, for example, those referred to as being of the sfp-type, as further discussed hereinbelow. More preferred, the mfFAS employed in the context of the present invention is pantethenylated by an enzyme having PPTase activity that is native to the host *Brassica* plant into which the mfFAS transgene has been inserted.

A PPTase from *Bacillus subtillis*, the sfp gene product, has a remarkably broad range of substrate specificity, being able to phosphopantetheinylate non-native substrates both in vitro (Lambalot et al., *Chem. Biol.*, 3:923-936, 1996) and in vivo (Mootz et al., *J. Biol. Chem.*, 276:37389-37298, 2001); see FIG. 23 for recital of the sequences of the sfp gene and its product. Mootz and co-workers have shown that the sfp gene product not only complements heterologous PPTases, such as *E. coli* ACPS, but it in vivo phosphopantetheinylates all the different acceptor domains in natural host cells (e.g., *Bacillus subtillis*) that include ACP and PCP (petide carrier protein) of type I polyketide synthases (PKS) and non-ribosomal peptide synthetases (NRPS) involved in secondary metabolism as well as the type II ACP protein required for fatty acid synthesis (primary metabolism). Indeed, this broad range of specificity appears to be a general feature of many sfp-type PPTases. *Streptomyces verticullus svp* PPTase (see FIG. 26), another sfp-type enzyme, was also found to be able to phosphopantetheinylate a broad range of substrates, including type I and II ACP and PCP domains from various *Streptomyces* species (Sáanchez et al., *Chem. Biol.*, 8:725-728, 2001). Other useful sfp-type PPTases include those found in *Brevibacillus brevis* (SEQ ID NO: 35), and *Escherichia coli* (SEQ ID NO: 36), which are listed here without any intention to limit the sfp-type PPTases that are usefully employed in the context of the present invention. Preferably, the *Bacillus subtilis* PPTase, that is the gene that encodes it, is used.

In the case of the multifunctional FasA and FasB proteins from *Brevibacterium ammoniagenes*, Stuible and co-workers found that the *E. coli* ACPS was unable to phosphopantetheinylate these type I FAS proteins either in vivo when the genes were introduced into *E. coli* or in vitro when mixed with the proteins. The *B. ammoniagenes* PPT1 protein was required to phosphopantetheinylate both of these type I FAS proteins (Stuible et al., *Eur. J. Biochem.*, 248:481-487, 1997).

A preferred embodiment of the present invention relates to the use of an mfFAS that can be phosphopantetheinylated by a PPTase that is innate to a *Brassica* plant. An alternative preferred embodiment relates to the use of a PPTase specific for the introduced multifunctional FAS that is inserted in a *Brassica* plant, such as ppt1 in the case of the *B. ammoniagenes* fasA and fasB genes, which specific PPTase could be co-expressed in order to engineer functional multifunctional FAS expression in *Brassica* plants. As a further embodiment of the present invention, a PPTase of broad specificity, such as a sfp-type PPTase, may be co-expressed with a type II FAS gene in order to engineer functional multifunctional FAS expression in *Brassica* plants.

Expression Vectors and Cassettes: The expression vectors and cassettes of the present invention include nucleic acids encoding multifunctional fatty acid synthases. When inclusion of a heterologous phosphopantetheine protein transferase enzyme (PPTase) is desired, such expression vectors and cassettes can also include a nucleic acid encoding a PPTase that can post-translationally activate the multifunctional fatty acid synthase polypeptide. Alternatively, a separate expression vector or cassette can encode a phosphopantetheine protein transferase enzyme. One such PPTase is encoded by the *B. ammoniagenes* ppt1 gene. Other sources of PPTase having broad spectrum activity include: *Bacillus sub-*

*tilis, Brevibacillus brevis, Escherichia coli, Streptomyces verticullus,* and *Saccharomyces cerevisiae.*

A transgene comprising a multifunctional fatty acid synthase can be subcloned into an expression vector or cassette, and fatty acid synthase expression can be detected and/or quantified. This method of screening is useful to identify transgenes providing for an expression of a multifunctional fatty acid synthase, and expression of a multifunctional fatty acid synthase in a transformed *Brassica* plant cell.

Plasmid vectors that provide for easy selection, amplification, and transformation of the transgene in prokaryotic and eukaryotic cells include, for example, pUC-derived vectors, pSK-derived vectors, pGEM-derived vectors, pSP-derived vectors, pBS-derived vectors, pFastBac (Invitrogen) for baculovirus expression and pYES2 (Invitrogen) for yeast expression. Additional elements may be present in such vectors, including origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells. One vector that is useful for expression in both plant and prokaryotic cells is the binary Ti plasmid (as disclosed in Schilperoot et al., U.S. Pat. No. 4,940,838), as exemplified by vector pGA582. This binary Ti plasmid vector has been previously characterized by An, *Methods in Enzymology,* 153:292 (1987). This binary Ti vector can be replicated in prokaryotic bacteria, such as *E. coli* and *Agrobacterium.* The *Agrobacterium* plasmid vectors can also be used to transfer the transgene to *Brassica* plant cells. The binary Ti vectors preferably include the nopaline T DNA right and left borders to provide for efficient *Brassica* plant cell transformation, a selectable marker gene, unique multiple cloning sites in the T border regions, the colE1 replication of origin and a wide host range replicon. The binary Ti vectors carrying a transgene of the present invention can be used to transform both prokaryotic and eukaryotic cells, but is preferably used to transform plant cells. See, for example, Glassman et al., U.S. Pat. No. 5,258,300.

In general, the expression vectors and cassettes of the present invention contain at least a promoter capable of expressing RNA in a *Brassica* plant cell and a terminator, in addition to a nucleic acid encoding a multifunctional fatty acid synthase. Other elements may also be present in the expression cassettes of the present invention. For example, expression cassettes can also contain enhancers, introns, untranslated leader sequences, cloning sites, matrix attachment regions for silencing the effects of chromosomal control elements, and other elements known to one of skill in the art.

Nucleic acids encoding fatty acid synthases are operably linked to regulatory elements, such as a promoter, termination signals, and the like. Operably linking a nucleic acid under the regulatory control of a promoter or a regulatory element means positioning the nucleic acid such that the expression of the nucleic acid is controlled by these sequences. In general, promoters are found positioned 5' (upstream) to the nucleic acid that they control. Thus, in the construction of heterologous promoter/nucleic acid combinations, the promoter is preferably positioned upstream to the nucleic acid and at a distance from the transcription start site of the nucleic acid that the distance between the promoter and the transcription start site approximates the distance observed in the natural setting. As is known in the art, some variation in this distance can be tolerated without loss of promoter function. Similarly, the preferred positioning of a regulatory element with respect to a heterologous nucleic acid placed under its control is the natural position of the regulatory element relative to the structural gene it naturally regulates. Again, as is known in the art, some variation in this distance can be accommodated.

Expression cassettes have promoters that can regulate gene expression. Promoter regions are typically found in the flanking DNA sequence upstream from coding regions in both prokaryotic and eukaryotic cells. A promoter sequence provides for regulation of transcription of the downstream gene sequence and typically includes from about 50 to about 2,000 nucleotide base pairs. Promoter sequences also contain regulatory sequences, such as enhancer sequences that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired. Transcription initiation regions that are preferentially expressed in seed tissue, and that are undetectable in other *Brassica* plant parts, are considered desirable for seed oil modifications in order to minimize any disruptive or adverse effects of the gene product.

Promoters of the present invention will generally include, but are not limited to, promoters that function in bacteria, bacteriophage, plastids, or plant cells. Useful promoters include the globulin promoter (see, for example, Belanger and Kriz, *Genet.,* 129:863-872, 1991), gamma zein Z27 promoter (see, for example, U.S. Ser. No. 08/763,705; also Lopes et al., *Mol Gen Genet.,* 247:603-613, 1995), L3 oleosin promoter (U.S. Pat. No. 6,433,252), USP promoter and 7Sα promoter (U.S. Ser. No. 10/235,618), 7Sα' promoter (see, for example, Beachy et al., *EMBO J.,* 4:3047, 1985; Schuler et al., *Nucleic Acid Res.,* 10(24):8225-8244, 1982), CaMV 35S promoter (Odell et al., *Nature,* 313:810, 1985), the CaMV 19S (Lawton et al., *Plant Mol. Biol.,* 9:31F, 1987), nos (Ebert et al., *Proc. Natl. Acad. Sci. (U.S.A.),* 84:5745, 1987), Adh (Walker et al., *Proc. Natl. Acad. Sci. (U.S.A.),* 84:6624, 1987), sucrose synthase (Yang et al., *Proc. Natl. Acad. Sci. (U.S.A.),* 87:4144, 1990), tubulin, actin (Wang et al., *Mol. Cell. Biol.,* 12:3399, 1992), cab (Sullivan et al., *Mol. Gen. Genet.,* 215: 431, 1989), PEPCase promoter (Hudspeth et al., *Plant Mol. Biol.,* 12:579, 1989), or those associated with the R gene complex (Chandler et al., *The Plant Cell,* 1:1175, 1989). Other useful promoters include the Figwort Mosaic Virus (FMV) promoter (Richins et al., *Nucleic Acids Res.,* 20:8451, 1987), arcelin, tomato E8, patatin, ubiquitin, mannopine synthase (mas), soybean seed protein glycinin (Gly), soybean vegetative storage protein (vsp), bacteriophage SP6, T3, and T7 promoters.

Indeed, in a preferred embodiment, the promoter used is a seed-specific promoter. Examples of seed regulated genes and transcriptional regions are disclosed in U.S. Pat. Nos. 5,420,034; 5,608,152; and 5,530,194. Examples of such promoters include the 5' regulatory regions from such genes as napin (Kridl et al., *Seed Sci. Res.,* 1:209-219, 1991), phaseolin (Bustos et al., *Plant Cell,* 1(9):839-853, 1989), soybean trypsin inhibitor (Riggs et al., *Plant Cell,* 1(6):609-621, 1989), ACP (Baerson et al., *Plant Mol. Biol.,* 22(2):255-267, 1993), stearoyl-ACP desaturase (Slocombe et al., *Plant Physiol.,* 104(4):167-176, 1994), soybean a' subunit of β-conglycinin (Chen et al., *Proc. Natl. Acad. Sci.,* 83:8560-8564, 1986), *Lesquerella* hydroxylase promoter (described in Broun et al., *Plant Journal,* 12(2):201-210, 1998; U.S. Pat. No. 5,965,793), delta 12 desaturase and oleosin (Hong et al., *Plant Mol. Biol.,* 34(3):549-555, 1997). Further examples include the promoter for β-conglycinin (Chen et al., *Dev. Genet.,* 10:112-122, 1989), the GL2 promoter (Szymanski et al., *Development,* 125:1161-1171, 1998), the tt2 promoter (Nesi et al., *The Plant Cell,* 13:2099-114, 2001), the LDOX promoter (Pelletier et al., *Plant Physiology,* 113:1437-1445, 1997), the CPC promoter (Wada et al., *Science,* 277:1113-1116, 1997).

Plastid promoters can also be used. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al., *EMBO J.,* 16:4041-4048 (1997), which is hereby in its entirety incorporated by reference.

Examples of plastid promoters that can be used include the *Zea mays* plastid RRN (ZMRRN) promoter. The ZMRRN promoter can drive expression of a gene when the *Arabidopsis thaliana* plastid RNA polymerase is present. Similar promoters that can be used in the present invention are the Glycine max plastid RRN(SOYRRN) and the *Nicotiana tabacum* plastid RRN (NTRRN) promoters. All three promoters can be recognized by the *Arabidopsis* plastid RNA polymerase. The general features of RRN promoters are described by Hajdukiewicz et al., supra, and U.S. Pat. No. 6,218,145.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, *Nucl. Acid Res.,* 15:6643, 1987). The choice of such sequences is at the discretion of those of skill in the art. Sequences that are derived from genes that are highly expressed in *Brassica* in particular are contemplated.

An inducible promoter can be turned on or off by an exogenously added agent so that expression of an operably linked nucleic acid is also turned on or off. For example, a bacterial promoter, such as the $P_{tac}$ promoter can be induced to varying levels of gene expression depending on the level of isothiopropylgalactoside added to the transformed bacterial cells. It may also be preferable to combine the nucleic acid encoding the polypeptide of interest with a promoter that provides tissue specific expression or developmentally regulated gene expression in plants.

Expression cassettes of the present invention will also include a sequence near the 3' end of the cassette that acts as a signal to terminate transcription from a heterologous nucleic acid and that directs polyadenylation of the resultant mRNA. Some 3' elements that can act as termination signals include those from the nopaline synthase gene of *Agrobacterium tumefaciens* (Bevan et al., *Nucl. Acid Res.,* 11:369, 1983), a napin 3' untranslated region (Kridl et al., *Seed Sci Res.,* 1:209-219, 1991), a globulin 3' untranslated region (Belanger and Kriz, *Genetics,* 129:863-872, 1991), or one from a zein gene, such as Z27 (Lopes et al., *Mol Gen Genet.,* 247: 603-613, 1995). Other 3' elements known by one of skill in the art also can be used in the vectors of the present invention.

Regulatory elements, such as Adh intron 1 (Callis et al., *Genes Develop.,* 1:1183, 1987), a rice actin intron (McElroy et al., *Mol. Gen. Genet.,* 231(1):150-160, 1991), sucrose synthase intron (Vasil et al., *Plant Physiol.,* 91:5175, 1989), the maize HSP70 intron (Rochester et al., *EMBO J.,* 5:451-458, 1986), or TMV omega element (Gallie et al., *The Plant Cell,* 1:301, 1989) may further be included where desired. These 3' nontranslated regulatory sequences can be obtained as described in An, *Methods in Enzymology,* 153:292 (1987) or are already present in plasmids available from commercial sources, such as Clontech, Palo Alto, Calif. The 3' nontranslated regulatory sequences can be operably linked to the 3' terminus of any heterologous nucleic acid to be expressed by the expression cassettes contained within the present vectors. Other such regulatory elements useful in the practice of the present invention are known by one of skill in the art and can also be placed in the vectors of the present invention.

The vectors of the present invention, as well as the coding regions claimed herein, can be optimized for expression in *Brassica* plants by having one or more codons replaced by other codons encoding the same amino acids so that the polypeptide is optimally translated by the translation machinery of the *Brassica* plant species in which the vector is used.

Selectable Markers: Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can 'select' for by chemical means, i.e., through the use of a selective agent (e.g., a herbicide, antibiotic, or the like). Reporter genes or screenable genes, confer a trait that one can identify through observation or testing, i.e., by 'screening' (e.g., the R-locus trait). Of course, many examples of suitable marker genes are known to the art and can be employed in the practice of the present invention.

Possible selectable markers for use in connection with the present invention include, but are not limited to, a neo gene (Potrykus et al., *Mol. Gen. Genet.,* 199:183, 1985) which codes for kanamycin resistance and can be selected for by applying kanamycin, a kanamycin analog such as geneticin (Sigma Chemical Company, St. Louis, Mo.), and the like; a bar gene that codes for bialaphos resistance; a gene that encodes an altered EPSP synthase protein (Hinchee et al., *Biotech.,* 6:915, 1988) thus conferring glyphosate resistance; a nitrilase gene, such as bxn from *Klebsiella ozaenae,* which confers resistance to bromoxynil (Stalker et al., *Science,* 242: 419, 1988); a mutant acetolactate synthase gene (ALS) that confers resistance to imidazolinone, sulfonylurea, or other ALS-inhibiting chemicals (EP 154 204A1, 1985); a methotrexate-resistant DHFR gene (Thillet et al., *J. Biol. Chem.,* 263:12500, 1988); a dalapon dehalogenase gene that confers resistance to the herbicide dalapon. Where a mutant EPSP synthase gene is employed, additional benefit may be realized through the incorporation of a suitable plastid transit peptide (CTP).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin that inhibits glutamine synthetase, (Murakami et al., *Mol. Gen. Genet.*, 205:42, 1986; Twell et al., *Plant Physiol.*, 91:1270, 1989) causing rapid accumulation of ammonia and cell death.

Screenable markers that may be employed include, but are not limited to, a β-glucuronidase or uidA gene (GUS), which encodes an enzyme for which various chromogenic substrates are known; an R-locus gene, which encodes a product that regulates the production of anthocyanin pigments (red color) in plant tissues (Dellaporta et al., *Chromosome Structure and Function*, 263-282, 1988); a β-lactamase gene (Sutcliffe, *Proc. Natl. Acad. Sci. (U.S.A.)*, 75:3737, 1978), which encodes an enzyme for which various chromogenic substrates are known (e.g., PADAC, a chromogenic cephalosporin); a xylE gene (Zukowsky et al., *Proc. Natl. Acad. Sci. (U.S.A.)*, 80:1101, 1983) that encodes a catechol dioxygenase that can convert chromogenic catechols; an α-amylase gene (Ikuta et al., *Biotech.*, 8:241, 1990); a tyrosinase gene (Katz et al., *J. Gen. Microbiol.*, 129:2703, 1983) that encodes an enzyme capable of oxidizing tyrosine to DOPA and dopaquinone, which in turn condenses to form the easily detectable compound melanin; a β-galactosidase gene, which encodes an enzyme for which there are chromogenic substrates; a luciferase (lux) gene (Ow et al., *Science*, 234:856, 1986), which allows for bioluminescence detection; or an aequorin gene (Prasher et al., *Biochem. Biophys. Res. Comm.*, 126:1259, 1985), which may be employed in calcium-sensitive bioluminescence detection, or a green fluorescent protein gene (Niedz et al., *Plant Cell Reports*, 14:403, 1995). The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for populational screening for bioluminescence, such as on tissue culture plates, or even for whole plant screening.

Transit Peptides: Additionally, transgenes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit or signal peptide will transport the protein to a particular intracellular, or extracellular destination, respectively, and may then be post-translationally removed. Transit or signal peptides act by facilitating the transport of proteins through intracellular membranes, e.g., vacuole, vesicle, plastid, and mitochondrial membranes, whereas signal peptides direct proteins through the extracellular membrane. By facilitating transport of the protein into compartments inside or outside the cell, these sequences may increase the accumulation of gene product.

An example of such a use concerns the direction of a fatty acid synthase to a particular organelle, such as to a plastid rather than to the cytoplasm. This is exemplified by the use of the *Arabidopsis* SSU1A transit peptide that confers plastid-specific targeting of proteins. Alternatively, the transgene can comprise a plastid transit peptide-encoding DNA sequence or a DNA sequence encoding the rbcS (RuBISCO) transit peptide operably linked between a promoter and the DNA sequence encoding a fatty acid synthase (for a review of plastid targeting peptides, see Heijne et al., *Eur. J. Biochem.*, 180:535, 1989; Keegstra et al., *Ann. Rev. Plant Physiol. Plant Mol. Biol.*, 40:471, 1989). If the transgene is to be introduced into a plant cell, the transgene can also contain plant transcriptional termination and polyadenylation signals and translational signals linked to the 3' terminus of a plant fatty acid synthase gene.

A heterologous plastid transit peptide can be linked to a multifunctional fatty acid synthase gene. A plastid transit peptide is typically 40 to 70 amino acids in length and functions post-translationally to direct a protein to the plastid. The transit peptide is cleaved either during or just after import into the plastid to yield the mature protein.

Heterologous plastid transit peptide encoding sequences can be obtained from a variety of plant nuclear genes, so long as the products of the genes are expressed as preproteins comprising an amino terminal transit peptide and transported into plastid. Examples of plant gene products known to include such transit peptide sequences include, but are not limited to, the small subunit of ribulose biphosphate carboxylase, chlorophyll a/b binding protein, plastid ribosomal proteins encoded by nuclear genes, certain heat shock proteins, amino acid biosynthetic enzymes, such as acetolactate acid synthase, 3-enolpyruvylphosphoshikimate synthase, dihydrodipicolinate synthase, fatty acid synthase, and the like. In some instances, a plastid transport protein already may be encoded in the fatty acid synthase gene of interest, in which case there may be no need to add such plastid transit sequences. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon, for example, an ATG codon, and be expressed as an amino acid sequence that is recognized by and will function properly in plastids of the host plant. Attention should also be given to the amino acid sequence at the junction between the transit peptide and the fatty acid synthase enzyme, where it is cleaved to yield the mature enzyme. Certain conserved amino acid sequences have been identified and may serve as a guideline. Precise fusion of the transit peptide coding sequence with the fatty acid synthase coding sequence may require manipulation of one or both DNA sequences to introduce, for example, a convenient restriction site. This may be accomplished by methods including site-directed mutagenesis, insertion of chemically synthesized oligonucleotide linkers, and the like.

Precise fusion of the nucleic acids encoding the plastid transport protein may not be necessary so long as the coding sequence of the plastid transport protein is in-frame with that of the fatty acid synthase. For example, additional peptidyl or amino acids can often be included without adversely affecting the expression or localization of the protein of interest.

Once obtained, and when desired, the plastid transit peptide sequence can be appropriately linked to the promoter and a fatty acid synthase coding region in a transgene using standard methods. A plasmid containing a promoter functional in plant cells and having multiple cloning sites downstream can be constructed or obtained from commercial sources. The plastid transit peptide sequence can be inserted downstream from the promoter using restriction enzymes. A fatty acid synthase coding region can then be translationally fused or inserted immediately downstream from and in frame with the 3' terminus of the plastid transit peptide sequence. Hence, the plastid transit peptide is preferably linked to the amino terminus of the fatty acid synthase. Once formed, the transgene can be subcloned into other plasmids or vectors.

In addition to nuclear plant transformation, the present invention also extends to direct transformation of the plastid genome of *Brassica* plants. Hence, targeting of the gene product to an intracellular compartment within plant cells may also be achieved by direct delivery of a gene to the intracellular compartment. In some embodiments, direct transformation of plastid genome may provide additional benefits over nuclear transformation. For example, direct plastid transformation of fatty acid synthase eliminates the requirement for a plastid targeting peptide and post-translational transport and processing of the pre-protein derived from the corresponding nuclear transformants. Plastid transformation of plants has been described by Maliga, *Current Opinion in Plant Biology*, 5:164-172 (2002); Heifetz, *Biochimie*, 82:655-666 (2000); Bock, *J. Mol. Biol.*, 312:425-438 (2001); and Daniell et al., *Trends in Plant Science*, 7:84-91 (2002), and references cited therein.

After constructing a transgene containing a multifunctional fatty acid synthase, the expression vector or cassette can then be introduced into a *Brassica* plant cell. Depending on the type of plant cell, the level of gene expression, and the activity of the enzyme encoded by the gene, introduction of DNA encoding a multifunctional fatty acid synthase into the plant cell can lead to increased oil content in *Brassica* plant tissues.

Plant Transformation: There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules, such as, for example, by PEG-mediated transformation, by electroporation or by acceleration of DNA coated particles, and the like. (Potrykus, *Ann. Rev. Plant Physiol. Plant Mol. Biol.*, 42:205-225, 1991; Vasil, *Plant Mol. Biol.*, 25:925-937, 1994). For example, electroporation has been used to transform maize protoplasts (Fromm et al., *Nature*, 312:791-793, 1986).

Other vector systems suitable for introducing transforming DNA into a host plant cell include but are not limited to binary artificial chromosome (BIBAC) vectors (Hamilton et al., *Gene*, 200:107-116, 1997); and transfection with RNA viral vectors (Della-Cioppa et al., *Ann. N.Y. Acad. Sci.*, (1996), 792 (Engineering Plants for Commercial Products and Applications, 57-61)). Additional vector systems also include plant selectable YAC vectors, such as those described in Mullen et al., *Molecular Breeding*, 4:449-457 (1988).

Technology for introduction of DNA into cells is well known by one of skill in the art. Four general methods for delivering a gene into cells have been described: (1) chemical methods (Graham and van der Eb, *Virology*, 54:536-539, 1973); (2) physical methods, such as microinjection (Capecchi, *Cell*, 22:479-488, 1980), electroporation (Wong and Neumann, Biochem. Biophys. Res. Commun., 107:584-587, 1982; Fromm et al., *Proc. Natl. Acad. Sci. (U.S.A.)*, 82:5824-5828, 1985; U.S. Pat. No. 5,384,253); the gene gun (Johnston and Tang, *Methods Cell Biol.*, 43:353-365, 1994); and vacuum infiltration (Bechtold et al., *C.R. Acad. Sci. Paris, Life Sci.*, 316:1194-1199, 1993); (3) viral vectors (Clapp, *Clin. Perinatol.*, 20:155-168, 1993; Lu et al., *J. Exp. Med.*, 178:2089-2096, 1993; Eglitis and Anderson, *Biotechniques*, 6:608-614, 1988); and (4) receptor-mediated mechanisms (Curiel et al., *Hum. Gen. Ther.*, 3:147-154, 1992; Wagner et al., *Proc. Natl. Acad. Sci. (U.S.A.)*, 89:6099-6103, 1992).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994). Non-biological particles (microprojectiles) may be coated with nucleic acids and delivered into cells by a propelling force. Exemplary particles include those comprised of tungsten, gold, platinum, and the like.

A particular advantage of microprojectile bombardment, in addition to it being an effective means of reproducibly transforming monocots, is that neither the isolation of protoplasts (Cristou et al., *Plant Physiol.*, 87:671-674, 1988) nor the susceptibility to *Agrobacterium* infection is required. An illustrative embodiment of a method for delivering DNA into maize cells by acceleration is a biolistics $\alpha$-particle delivery system, which can be used to propel particles coated with DNA through a screen, such as a stainless steel or Nytex screen, onto a filter surface covered with maize cells cultured in suspension. Gordon-Kamm et al., describes the basic procedure for coating tungsten particles with DNA (Gordon-Kamm et al., *Plant Cell*, 2:603-618, 1990). The screen disperses the tungsten nucleic acid particles so that they are not delivered to the recipient cells in large aggregates. A particle delivery system suitable for use with the present invention is the helium acceleration PDS-1000/He gun, which is available from Bio-Rad Laboratories (Bio-Rad, Hercules, Calif.) (also, see, Sanford et al., *Technique*, 3:3-16, 1991).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from 1 to 10, and average 1 to 3.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of the microprojectiles. Biological factors include all steps involved in manipulation of cells before and immediately after bombardment, the osmotic adjustment of target cells to help alleviate the trauma associated with bombardment and, also, the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)*, 87:8526-8530, 1990; Svab and Maliga, *Proc. Natl. Acad. Sci. (U.S.A.)*, 90:913-917, 1993; Staub and Maliga, *EMBO J.*, 12:601-606, 1993; U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and which may therefore influence transformation and integration efficiencies. For example, the osmotic state, tissue hydration, and the subculture stage or cell cycle of the recipient cells may be adjusted for optimum transformation. The execution of other routine adjustments will be known by one of skill in the art in light of the present invention.

*Agrobacterium*—mediated transfer is a widely applicable system for introducing genes into plant cells because the DNA can be introduced into whole plant tissues, thereby bypassing the need for regeneration of an intact plant from a protoplast. The use of *Agrobacterium*—mediated plant integrating vectors to introduce DNA into plant cells is well known in the art. See, for example the methods described by Fraley et al., *BioTechnology*, 3:629-635 (1985) and Rogers et al., *Methods Enzymol.*, 153:253-277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.*, 205:34, 1986).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, NY, pp. 179-203, 1985). Moreover, technological advances in vectors for *Agrobacterium*—mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.*, 153:253-277, 1987). In addition, *Agrobacterium* containing both armed and disarmed Ti genes can be used for the transformations. In those plant strains where *Agrobacterium*—mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains 2 added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation, and combinations of these treatments (see, for example, Potrykus et al., *Mol. Gen. Genet.*, 205:193-200, 1986; Lorz et al., *Mol. Gen. Genet.*, 199:178, 1985; Fromm et al., *Nature*, 319:791, 1986; Uchimiya et al., *Mol. Gen. Genet.*, 204:204, 1986; Marcotte et al., *Nature*, 335:454-457, 1988).

Application of these systems to different plant strains depends upon the ability to regenerate that particular plant strain from protoplasts. Illustrative methods for the regeneration of cereals from protoplasts are described (Fujimura et al., *Plant Tissue Culture Letters*, 2:74, 1985; Toriyama et al., *Theor. Appl. Genet.*, 205:34, 1986; Yamada et al., *Plant Cell Rep.*, 4:85, 1986; Abdullah et al., *Biotechnology*, 4:1087, 1986).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology*, 6:397, 1988). In addition, "particle gun" or high-velocity microprojectile technology can be utilized (Vasil et al., *Bio/Technology*, 10:667, 1992).

Using the latter technology, DNA is carried through the cell wall and into the cytoplasm on the surface of small metal particles as described (Klein et al., *Nature*, 328:70, 1987; Klein et al., *Proc. Natl. Acad. Sci. (U.S.A.)*, 85:8502-8505, 1988; McCabe et al., *Bio/Technology*, 6:923, 1988). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.*, 107:367, 1987; Luo et al., *Plant Mol. Biol. Reporter*, 6:165, 1988), by direct injection of DNA into reproductive organs of a plant (Pena et al., *Nature*, 325:274, 1987), or by direct injection of DNA into the cells of immature embryos followed by the rehydration of desiccated embryos (Neuhaus et al., *Theor. Appl. Genet.*, 75:30, 1987).

The regeneration, development, and cultivation of plants from single plant protoplast transformants or from various transformed explants is well known in the art (Weissbach and Weissbach, In: *Methods for Plant Molecular Biology*, Academic Press, San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 6,384,301; 5,569,834; and 5,416,011; McCabe et al., *Biotechnology*, 6:923, 1988; Christou et al., *Plant Physiol.*, 87:671-674, 1988); *Brassica* (U.S. Pat. No. 5,463,174); peanut (Cheng et al., *Plant Cell Rep.*, 15:653-657, 1996; McKently et al., *Plant Cell Rep.*, 14:699-703, 1995); papaya; pea (Grant et al., *Plant Cell Rep.*, 15:254-258, 1995); and *Arabidopsis thaliana* (Bechtold et al., *C.R. Acad. Sci. Paris, Life Sci.*, 316:1194-1199, 1993). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci. (U.S.A.)*, 84:5354, 1987); barley (Wan and Lemaux, *Plant Physiol.*, 104:37, 1994); maize (Rhodes et al., *Science*, 240: 204, 1988; Gordon-Kamm et al., *Plant Cell*, 2:603-618, 1990; Fromm et al., *Bio/Technology*, 8:833, 1990; Koziel et al., *Bio/Technology*, 11:194, 1993; Armstrong et al., *Crop Science*, 35:550-557, 1995); oat (Somers et al., *Bio/Technology*, 10:1589, 1992); orchard grass (Horn et al., *Plant Cell Rep.*, 7:469, 1988); rice (Toriyama et al., *Theor Appl. Genet.*, 205: 34, 1986; Part et al., *Plant Mol. Biol.*, 32:1135-1148, 1996; Abedinia et al., *Aust. J. Plant Physiol.*, 24:133-141, 1997; Zhang and Wu, *Theor. Appl. Genet.*, 76:835, 1988; Zhang et al., *Plant Cell Rep.*, 7:379, 1988; Battraw and Hall, *Plant Sci.*, 86:191-202, 1992; Christou et al., *Bio/Technology*, 9:957, 1991); rye (DelaPena et al., *Nature*, 325:274, 1987); sugarcane (Bower and Birch, *Plant J.*, 2:409, 1992); tall fescue (Wang et al., *Bio/Technology*, 10:691, 1992); and wheat (Vasil et al., *Bio/Technology*, 10:667, 1992; U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature*, 335:454-457, 1988; Marcotte et al., *Plant Cell*, 1:523-532, 1989; McCarty et al., *Cell*, 66:895-905, 1991; Hattori et al., *Genes Dev.*, 6:609-618, 1992; Goff et al., *EMBO J.*, 9:2517-2522, 1990). Transient expression systems may be used to functionally dissect gene constructs (see generally, Maliga et al., *Methods in Plant Molecular Biology*, Cold Spring Harbor Press, 1995).

Any of the nucleic acid molecules of the present invention may be introduced into a plant cell in a permanent or transient manner in combination with other genetic elements such as vectors, promoters, enhancers, etc. Further, any of the nucleic acid molecules of the present invention may be introduced into a plant cell in a manner that allows for expression or overexpression of the protein or fragment thereof encoded by the nucleic acid molecule.

It is also to be understood that 2 different transgenic *Brassica* plants can also be mated to produce offspring that contain 2 independently segregating added, exogenous genes. Selfing of appropriate progeny can produce plants that are homozygous for both added, exogenous genes that encode a polypeptide of interest. Backcrossing to a parental plant and outcrossing with a non-transgenic plant are also contemplated, as is vegetative propagation.

Transgenic *Brassica* plants may find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic *Brassica* plants may also be used in commercial breeding programs, or may be crossed or bred to plants of related crop species. Improvements encoded by the recombinant DNA may be transferred, e.g., from cells of one species to cells of other species, e.g., by protoplast fusion.

The present invention also provides for a method of stably expressing a fatty acid synthase of interest in a *Brassica* plant, which includes, contacting the plant cell with a vector of the present invention that has a selectable marker gene and a nucleic acid encoding the fatty acid synthase of interest, under conditions effective to transform the plant cell. A promoter within the expression cassette can be any of the promoters provided herein, for example, a constitutive promoter, an inducible promoter, a tissue-specific promoter or a seed specific promoter. Such promoters can provide expression of an encoded fatty acid synthase at a desired time, or at a desired developmental stage, or in a desired tissue.

The present invention also provides for a method of stably expressing a fatty acid synthase of interest in a plant, which includes, contacting the plant cell with a vector of the present invention that has a nucleic acid encoding the fatty acid synthase of interest, under conditions effective to transfer and integrate the vector into the nuclear genome of the cell. The vector can also include a selectable marker gene. When using the vector with *Agrobacterium tumefaciens*, the vector can have an *Agrobacterium tumefaciens* origin of replication.

In another embodiment, the present invention provides a method of producing a *Brassica* oil, comprising the steps of: a) growing an oilseed *Brassica* plant, the genome of which contains a nucleic acid molecule encoding a multifunctional fatty acid synthase, to produce oil-containing seeds; and b) extracting oil from the seeds. In another embodiment, the present invention provides a method of producing a *Brassica* oil, comprising the steps of: a) growing an oilseed *Brassica* plant, the genome of which contains a nucleic acid molecule encoding a phosphopantetheine:protein transferase, to produce oil-containing seeds; and b) extracting oil from the seeds.

Plants: Plants for use with the vectors of the present invention include *Brassica* sp., particularly those *Brassica* species useful as sources of seed oil (e.g., *B. napus*, *B. rapa*, *B. juncea*).

The following examples are provided to illustrate the present invention and are not intended to limit the present invention in any way.

EXAMPLE 1

This example describes the isolation of the fasA and ppt1 genes from *Brevibacterium ammoniagenes*.

Genomic DNA was isolated from *B. ammoniagenes* (ATCC 6871) using standard methodologies. A genomic library was prepared by partially digesting *B. ammoniagenes* genomic DNA with the restriction enzyme Sau3A, isolating DNA fragments ranging from 30-42 kb in size and generating the library using the SuperCos 1 Cosmid Vector kit from Stratagene, Inc. (La Jolla, Calif.). The genomic library was screened by hybridization and washing under stringent conditions with a 32P-labelled 1.1 kb fasA PCR fragment generated from isolated genomic DNA using the following PCR primers:

```
14713 (forward):
5'-CCAGCTCAACGATGAAGTAG-3'        [SEQ ID NO: 5]

and 14714 (reverse):
5'-TCGATGATCTGGTCTACTTC-3'        [SEQ ID NO: 6]
```

Rehybridization was in a solution of 40% formamide, 5×SSC, 50 mM sodium phosphate, pH 7.0, 5×Denhardt's, 0.1% SDS, 5 mM EDTA, 0.1 µg/ml salmon sperm DNA, and 5% Dextran sulfate for 2 hrs at 42° C. The filters were rinsed briefly in 0.1×SSC, 0.1% SDS at RT and then washed 2 times for 20 mm each in 0.1×SSC, 0.1% SDS at 50° C. FasA-containing clones were identified by autoradiography and restriction mapping. Selected cosmid clones were analyzed in more detail and one clone was confirmed to have the full-length fasA gene by restriction mapping and comparison with the restriction sites in the published sequence (Stuible et al., *J Bacteriol.*, 178:4787-4793, 1996).

The full-length fasA gene was assembled so as to introduce convenient flanking restriction sites for sub-cloning by using the following basic steps: a) PCR amplification of the 5' and 3' ends; b) assembling the 5' and 3' ends of the gene together by an overlapping PCR strategy resulting in deletion of the fasA sequence between the internal MfeI and XhoI sites; c) cloning the "5'-3' fused" PCR fragment; d) insertion of the 8166 bp fasA MfeI/XhoI fragment between the MfeI and XhoI sites in the "5'-3' fused" PCR fragment so as to re-generate the full-length fasA gene with convenient flanking cloning sites. The details for each of these steps are outlined below.

A 5' 280 bp fasA PCR fragment was generated using the following primers:

16393 (forward)

The forward primer, 16393, introduced XbaI, NsiI, HpaI, and PciI flanking restriction sites.

A 3' 946 bp fasA PCR fragment was generated using the following primers:

16385 (forward)

The reverse primer, 16394, introduced 3' flanking NsiI, HpaI, and PciI restriction sites. The forward primer, 16385, contained 20 bp of sequence matching the 3'-end of the 5' 280 bp restriction fragment described above to allow the 2 fragments to anneal together. The 5' 280 bp fasA PCR fragment and the 3' 946 bp fasA PCR fragment were fused together by annealing the 2 fragments and PCR amplifying the full length (1206 bp) overlapped fragment using the external primers 16393 (forward) and 16394 (reverse). The 1206 bp 5'-3'-fused PCR fragment was cloned into pCR-Blunt II-TOPO (Invitrogen Corporation, Carlsbad, Calif.) and the correct DNA sequence was confirmed by sequencing. The 1206 bp 5'-3'-fused PCR fragment was then sub-cloned as an SpeI/XbaI fragment into a Bluescript pBC KS+ (Stratagene Inc., La Jolla, Calif.) vector which contained a modified multiple cloning sequence (pCGN3686). The full-length fasA gene was then obtained by ligation of the 3505 bp MluI/MluI and 4516 bp MluI/XhoI internal fasA fragments isolated from the full-length cosmid clone between the MluI and XhoI sites in the 5'-3' fused PCR fragment to make pMON70058 (FIG. 1).

The complete double-stranded sequence of the full-length fasA gene open reading frame in pMON70058 was determined using a Perkin Elmer ABI 377 DNA sequencer (SEQ ID NO: 1). The corresponding protein sequence (SEQ ID NO: 2) was predicted based on standard genetic code using the program Omiga (Accelrys, Inc., Cambridge, UK) and compared with the published fasA sequence (FIG. 2). Alignment of both the nucleic acid and predicted amino acid sequences to the published sequences (Stuible et al., *J. Bacteriol.*, 178: 4787, 1996) revealed a number of differences both at the DNA and protein levels (FIGS. 2 and 3).

The *B. ammoniagenes* ppt1 gene was PCR amplified from isolated genomic DNA using the following primers:

```
5'- TCTAGATGCATAGTTAACATGTCGTTGACCCCCTTGC -3'     [SEQ ID NO: 9]

and 14873 (reverse)
5'-GGTACGCGTCATATTCCTTG -3'                      [SEQ ID NO: 10]
```

```
5'-CAAGGAATATGACGCGTACCCTCGAGGCAGAAGGCGGCGG- 3'  [SEQ ID NO: 11]

and 16394 (reverse)
5'-ATGCATGTTAACATGTCTACTTTGTCCTACTTCGCCG-3'      [SEQ ID NO: 12]
```

16117 (forward):
5'-GTCGACATGCTCGACAACCGTGAAGCG-3'   [SEQ ID NO: 7]

and 16118 (reverse):
5'-AGATCTTCACTGGTGGCTTGCCGTAGATCG   [SEQ ID NO: 8]
C-3'

The PCR-amplified fragment was then cloned into the commercially available cloning vector pCR-Blunt II TOPO (Invitrogen Corporation, Carlsbad, Calif.). The complete double stranded sequence of the full-length ppt1 gene (SEQ ID NO: 3) was determined using a Perkin Elmer ABI 377 DNA sequencer. The corresponding protein sequence (SEQ ID NO: 4) was predicted based on standard genetic code using the program Omiga and compared with the published ppt1 sequence. Alignment of both the nucleic acid and predicted amino acid sequences to the published sequences (Stuible et al., *J. Bacteriol.*, 178:4787, 1996) revealed that the cloned ppt1 gene was identical to the published sequence.

EXAMPLE 2

This example describes the transformation of *E. coli* with fasA gene constructs for functional testing.

The full-length, sequence-confirmed *B. ammoniagenes* ppt1 gene in the pCR-Blunt II TOPO vector described in Example 1 was cut out of the pCR-Blunt II TOPO backbone as a Sal I/Bgl II fragment, and ligated into the SalI/BamHI sites, respectively, of pSU19 (Bartolome et al., *Gene*, 102(1): 75-78, 1991). The SalI sites of both the ppt1 and the pSU19 fragments were blunt-ended with the Klenow fragment of DNA polymerase I prior to ligation to enable inframe insertion of the ppt1 coding sequence into the lacZ coding sequence of pSU19. The PPT1 protein was thus expressed in *E. coli* as a lacZ fusion protein upon induction of the lacZ promoter in pSU19 by the use of isopropyl-1-thio-β-D-galactopyranoside (IPTG). This ppt1-containing vector was then transformed into *E. coli* strain VCS257 from Stratagene (cat#200256-51), along with the mfFAS cosmid clone, described in Example 1, for functional testing.

Because the plasmid pSU19 has a pACYC184 origin of replication and conveys chloramphenicol resistance, the ppt1 expressing plasmid could be stably maintained along with the cosmid (ampicillin resistance) expressing the fasA gene.

Based on the published report of Stuible et al., *Eur. J. Biochem.*, 248:481-487 (1997), the endogenous fasA promoter was used to express the mfFAS polypeptide encoded by fasA in *E. coli*. As a result, *E. coli* transformants containing the fasA cosmid alone, the pSU19/ppt1 construct alone, and both the fasA cosmid and the pSU19/ppt1 construct were made for functional testing. The full-length fasA gene was also subcloned as a PciI fragment from pMON70058 into the *E. coli* expression vector pQE60 (QIAGEN, Inc., Valencia, Calif.) to enable inducible expression from an *E. coli* promoter (pMON70081).

EXAMPLE 3

This example sets forth the functional testing of transgene activity in *E. coli* using enzymatic assays.

In order to assay the *E. coli* strains containing the fasA cosmid and ppt1 gene construct the fasA gene product was partially purified essentially as outlined in Kawaguchi et al., *Methods in Enzymology*, 71:120-127 (1981). Frozen cells from the strain containing either the fasA cosmid alone, the pSU19/ppt1 construct alone, both the fasA cosmid and the pSU19/ppt1 construct, or the untransformed cell line alone were thawed in 0.1M potassium phosphate buffer (~1 ml/1 gm) and cells lysed by high speed mixing with glass beads. The supernatant was centrifuged at 105,000×g for 60 minutes and removed. Ammonium sulphate was slowly added to the supernatant to give a final concentration of 30% w/v followed by 30 minutes of stirring. A second centrifugation step (25,000×g) was performed and the precipitate was re-suspended in 0.5M potassium phosphate buffer before passing through a Sephadex G-25 column.

Figure 4:
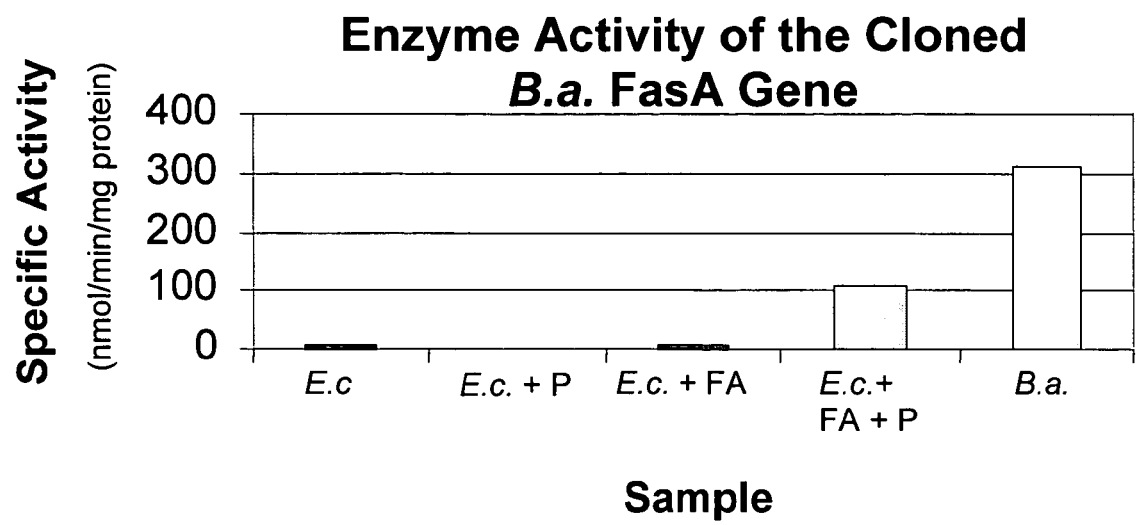
FIG. 4 illustrates FasA enzyme activity of the cloned fasA gene from *B. ammoniagenes*. The FasA enzyme activity was determined as outlined in Kawaguchi et al., *Methods in Enzymology*, 71:120-127 (1981) for partially purified enzyme preparations from *B. ammoniagenes* (B.a.), for an untransformed *E. coli* strain VCS257 (E.c.), and for the same strain transformed with the ppt1 expressing plasmid (E.c.+P), the fasA cosmid (E.c.+FA), or the ppt1 expressing plasmid and the fasA cosmid (E.c.+P+FA).

The fasA activity in each of the extracts was determined by a radiochemical assay at 37° C. for 15 minutes using the conditions outlined in Kawaguchi et al., (1981). The results of these assays (shown in FIG. 4) demonstrated that only when the fasA cosmid (FA) and the pSU19/ppt1 (P) construct were both present was there any measurable fasA activity. Furthermore, they demonstrated that the fasA gene that was cloned and used for preparation of *Brassica* transformation constructs did encode a functional fasA enzyme.

EXAMPLE 4

This example describes the construction of a plant binary vector for seed-specific expression of the fasA gene in canola plants. The construction is shown graphically in FIGS. 5 and 6. The vector pMON75201 was designed to produce seed-specific expression of the *B. ammoniagenes* fasA and ppt1 genes in canola.

Figure 5:
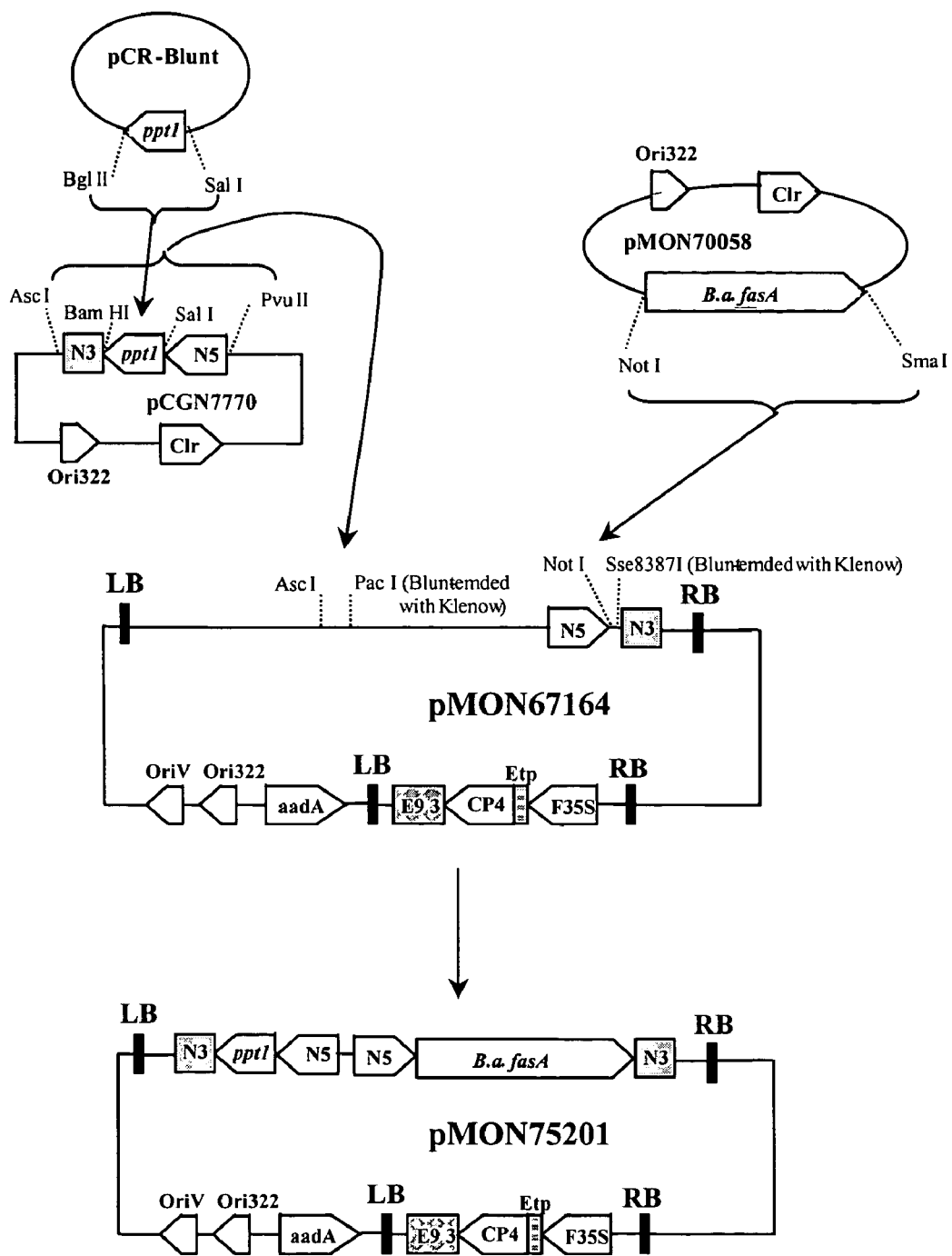
FIG. 5 provides a schematic representation of the preparation of pMON75201 as well as a map of pMON75201.

The full-length, sequence-confirmed *B. ammoniagenes* ppt1 gene in the pCR-Blunt II TOPO vector described in Example 1 was cut out of the pCR-Blunt II TOPO backbone using the Sal I and Bgl II sites engineered into the PCR primers 16117 and 16118 (SEQ ID NOs: 7 and 8, respectively) used in the cloning and ligated to the Sal I and BamHI sites between the napin promoter (base pairs 407-2151 of the *Brassica campestris* napin gene, N5, GenBank Accession Number M64632) and the napin 3' untranslated region (UTR), N3, (base pairs 2728-3982 of the *Brassica campestris* napin gene, GenBank Accession Number M64632) found in the plant/*E. coli* binary vector pCGN7770 (FIG. 5). The napin promoter/*B. ammoniagenes* ppt1/napin 3' UTR cassette was combined with the *B. ammoniagenes* fasA gene for simultaneous expression in *Brassica* plants as described below.

The full-length, sequence-confirmed *B. ammoniagenes* fasA gene was removed from pMON70058 (described in Example 1 and FIG. 1) using the restriction enzymes NotI and SmaI and was ligated into the NotI and blunted Sse8387II restriction sites between a napin promoter and napin 3' UTR (as described above) contained in a two T-DNA binary vector pMON67164. The Sse8387II site was blunt-ended by the action of Klenow fragment of DNA polymerase I. The resultant vector, containing the pMON67164 backbone and the *B. ammoniagenes* fasA gene flanked by the napin expression sequences, was digested with PacI, blunt-ended by the action of Klenow fragment of DNA polymerase I, and then digested with AscI. The AscI/PvuII fragment containing the napin promoter/*B. ammoniagenes* ppt1 gene/napin 3' UTR cassette in pCGN7770 (described above) was then inserted into the PacI blunt/AscI sites to form pMON75201. pMON75201 is a two T-DNA vector containing both the *B. ammoniagenes* fasA gene and the *B. ammoniagenes* ppt1 gene each under the control of seed-specific napin expression sequences (napin promoter and 3' UTR) and located within one set of T-DNA left and right borders. A selectable marker for plant transformation, containing the FMV 35S promoter, (F35S, base pairs 6927-6474 of the FMV promoter which is the promoter for ORF VII, GenBank Accession Number X06166) driving a CP4 selectable marker gene (a chloroplast targeting sequence from the Arabidopsis EPSP gene linked to a synthetic EPSP synthase coding region as described in U.S. Pat. No. 5,633, 435) and a E93' UTR (Coruzzi et al., *EMBO J.*, 3(8):1671-1679, 1984) is located within a second set of T-DNA left and right borders.

EXAMPLE 5

This example describes the transformation of canola plants with fasA and ppt1 genes.

Canola plants (*Brassica napus*) are transformed using a modification of the protocol described by Radke et al., *Plant Cell Reports*, 11:499-505 (1992). Briefly canola seed of the cultivar 'Ebony' (Monsanto Canada, Inc., Winnipeg, Canada) are disinfected and germinated in vitro as described in Radke et al., 1992. Precocultivation with tobacco feeder plates, explant preparation and inoculation of explants with *Agrobacterium tumefaciens* strain ABI (Koncz and Schell, *Mol Gen Genet.*, 204:383-396, 1986) containing the vector pMON75201 are as described with the *Agrobacterium* being maintained in LB media (solid or liquid) containing 75 mg/l spectinomycin, 25 mg/l chloramphenicol, and 50 mg/l kanamycin. For plant transformation including callus induction, shoot regeneration, maturation and rooting, glyphosate selection is used rather than the kanamycin selection as described in Radke et al., 1992. Specifically, the B5-1 callus induction medium is supplemented with 500 mg/l carbenicillin and 50 mg/l Timentin (Duchefa Biochemie BV) to inhibit the *Agrobacterium* growth and kanamycin is omitted from the media. B5BZ shoot regeneration medium contains 500 mg/l carbenicillin, 50 mg/l Timentin, and 45 mg/l glyphosate with explants being transferred to fresh medium every 2 weeks. Glyphosate selected shoots are transferred to hormone-free B5-0 shoot maturation medium containing 300 mg/l carbenicillin and 45 mg/l glyphosate for 2 weeks and finally shoots are transferred to B5 root induction medium containing 45 mg/l glyphosate. Rooted green plantlets are transplanted to potting soil and acclimated to green house conditions. Plants are maintained in a greenhouse under standard conditions.

Developing seed is harvested at various stages after pollination and stored at −70° C. Mature seed is collected and stored under controlled conditions consisting of about 17° C. and 30% humidity.

EXAMPLE 6

This example describes the evaluation and selection of R2 seed from canola plants transformed with the fasA and ppt1 genes as described above in Example 5.

From the transformation of canola ex-plants with pMON75201, as described above, 110 events were generated. These events were analyzed for the presence of the gene of interest (GOI) by PCR, for transcription expression of the GOI by TaqMan methodology, and for the presence of the FasA protein by western blot analysis. The events testing positive for the GOI by PCR were considered for selection to advance in the development of high oil varieties.

The western blot analysis for the presence of the FasA protein was done using methods well known in the art. Briefly, antibodies were generated by a contract laboratory (Zymed Laboratories Inc., South San Francisco, Calif.) to 4 synthetic peptides located in different regions of the fasA gene; fasA$_{2843-2858}$=(C)SKHDTSTNANDPNESE (SEQ ID NO: 44),fasA$_{1755-1768}$=(C)QNKIRQDQINDSDT (SEQ ID NO: 45), fasA$_{915-930}$=(C)RINSDSYWDNLPEEQR (SEQ ID NO: 46), and fasA$_{1431-1444}$=(C)TLVERDENGNSNYG (SEQ ID NO: 47). A protein extract from each of the events was separated using SDS-PAGE according to Laemmli, *Nature*, 227: 680 (1970), and transferred to a polyvinylidene difluoride (PVDF) membrane in Tris buffered saline (TBS; 25 mM Tris, 150 mM NaCl) (BioRad, Bulletin #9016). The membrane was blocked with TBST (TBS with 0.05% Tween 20) containing 1% bovine serum albumin (BSA) for 10 minutes then incubated overnight at room temperature with a combined solution of primary antibodies from fasA$_{2843-2858}$, faSA$_{1755-1768}$, and fasA$_{1431-1444}$, at a 1:2000 dilution of each antibody in TBST with 1% BSA. The membrane was washed 3×15 minutes with TBST then exposed to a reporting, secondary antibody (Anti-rabbit-AP conjugate, Promega S3731, Madison, Wis., 1:5000 in TBST) for one hour. The membrane was washed 3×15 minutes with TBST followed by 2 minutes with TBS to remove residual Tween 20. Western Blue Stabilized Substrate for Alkaline Phosphatase (Promega S3841, Madison, Wis.) was added to visualize protein. Development was stopped by rinsing the membrane with purified water. Of the events tested, 23 were determined to be potentially western positive by exhibiting at least a weak response, and 8 of those confirmed to be positive by exhibiting a strong response. The results are shown in FIG. 7.

Mature R1 seed from all 23 events were planted and a selection test was performed to identify gene positive and gene negative lines for each event. For the event selection test, plants from each event were analyzed for the presence of the gene of interest (GOI) by PCR using primers from the GOI and promoter region. DNA for the PCR was isolated from leaf tissue using DNeasy 96 Plant Kit from Qiagen (Cat. No. 69181). The forward primer, located in the promoter region, was primer # 6456 (5'-TTCATAAGATGTCACGCCAGG-3') (SEQ ID NO: 48), and the reverse primer, located in the GOI, was primer # 14873 (5'-GGTACGCGTCATATTCCTTG-3') (SEQ ID NO: 49). PCR protocol was set at 97° C. for 1 minute, 40 cycles of [94° C. 15 seconds, 60° C. 30 seconds, 72° C. 30 second], and 72° C. for 5 minutes. Fourteen events (indicated by $^a$ in FIG. 7) were advanced to the R2 seed stage by growing R1 plants to maturity in the greenhouse under standard conditions. Ten of these events were identified as single locus (indicated by $^b$ in FIG. 7) and were also planted in field trials (Brawley, Calif.) as R1 transplants. The R2 seed from gene positive and null segregants from 4 events (BN_G1193, BN_G1198, BN_G1214, and BN_G1220) as well as commercial control lines, were planted in a randomized complete bloc experiment in field trials (Thief River Falls, Minn.).

In addition to the PCR gene confirmation and the western blot analysis, developing R1 seed (approximately 20/event) of the 23 events were analyzed for transcript expression of the genes of interest, fasA and ppt1, by TaqMan. TaqMan analysis was performed using the TaqMan One-Step RT-PCR Master Mix Reagents Kit and Protocol (#4310299 rev. C, Applied Biosystems, Foster City, Calif.). Low, medium, and high GOI-expressing lines are carried forward. Two separate experiments were performed on the same, pooled sample from each event. The results of both experiments are shown in tabular form in FIG. 7.

On the occasion when multiple gene copies of the GOI or marker are present, additional work is required to generate a null segregant from which phenotypic comparisons can be made. In addition to the original 14 events that were advanced, two GOI multicopy events (BN_G1223 and BN_G1239) were identified that exhibited a strong response in the western blot analysis. These events were crossed to the variety Ebony in order to produce gene positive as well as null segregants from an F1 population. Event BN_G1216 contained multiple copies of the marker gene, therefore it was out-crossed to Ebony as well. F1 transplants were generated for these events and were planted in the field and greenhouse. These 3 events are identified by $^c$ in FIG. 7. A comparison of the gene positive and null segregant selections is made in the F2 seed generation.

Oil and protein content of the F1 and R2 seed were established by near-infrared reflectance (NIR) spectroscopy (Williams and Norris, eds., *Near-infrared Technology in the Agricultural and Food Industries*, American Association of Cereal Chemists, Inc., St. Paul, Minn. (1987)), using a standard curve generated from analysis of canola seed with varying oil and protein levels. Briefly, mature canola seeds previously dried to less than 10% moisture were equilibrated to ambient humidity in paper envelopes at room temperature. Single replicate sub-samples (2-3 g) were placed in NIR ring cups (aluminum/quartz; 2 inch diameter by 0.5 inch thick, Foss North America Inc., Silver Springs, Md.) and sealed with a paperboard disk. The loaded ring cups were placed in an autoloader and scanned sequentially on a Foss Analytical model 6500 Spectrometer, (Foss North America Inc., Silver Springs, Md.). Each sample was scanned 25 times from 400 to 2500 nm (resolution 2 nm) and the average spectrum was compiled. The averaged spectrum was reduced to second derivative spectra, smoothed, and transformed to a series of principal component scores. The total oil and protein levels were predicted based on a previously prepared calibration models. Commercially available software (WinISI ver 1.00, Infrasoft International LLC, State College, Pa.) was used for calibration development and instrument operation.

One-way analysis of variance and the Student's T-test (JMP software, version 4.04, SAS Institute Inc., Cary, N.C.) was performed to identify significant differences between transgenic and non-transgenic seed pools as determined by transgene-specific PCR. As a result of the statistical analysis of the oil results, R2 seed from event BN_G1216 was determined to have a statistically significant increase in oil content as compared to a negative isoline control. The mean oil content determined by a one-way analysis of variance (ANOVA) for the positive isoline was 44.0%, as compared to 41.8% for the negative isoline control. The results are shown in FIG. 8.

EXAMPLE 7

This example describes the generation and evaluation of R3 seed and F2 seed from canola plants transformed with the fasA and ppt1 genes as described above in Example 5.

The event that showed a significant increase in oil in the greenhouse (BN_G1216) is included in a randomized complete bloc field test. This event did not show a positive phenotype as an R1 transplant in a first field trial (described above in Example 6). However, because field conditions are variable and have been shown to affect phenotype, and because of the positive phenotype in the greenhouse trial, this second field trial is determined to be warranted. In this second field trial, the gene positive line is compared to its null segregant to determine phenotype. Ebony is included in this experiment as a varietal control. The resulting seed is analyzed for oil and protein and the data is analyzed for statistical differences as described above in Example 6. The results of the R3 seed corroborate the results from the greenhouse grown R2 seed, described above in Example 6.

Three additional events, BN_G1223, BN_G1216, and BN_G1239, that were Western positive but contained multiple gene copies, are crossed to the variety Ebony in order to produce null segregants from an F1 population of seed that contained gene positive as well as the null segregants. The 3 out-crossed events, BN_G1233xEbony, BN_G1239xEbony, and BN_G1216xEbony, are grown in the field and greenhouse as F1 single plants. They are randomized as positive and negative selections and are grown with Ebony control lines. These events are individually isolated to produce selfed seed. The resulting F2 seed is harvested and analyzed for oil and protein, and the data is analyzed for statistical differences, as described above. The results of the F2 seed corroborate the results from the greenhouse grown R2 seed, described above in Example 6.

The present invention is not limited to the precise details shown and set forth hereinabove, for it should be understood that many variations and modifications may be made while still remaining within the spirit and scope of the present invention defined by the claims.

---

What is claimed:

1. A *Brassica* sp. plant comprising a heterologous nucleic acid molecule encoding multifunctional fatty acid synthase of SEQ ID NO: 2 and further comprising a second heterologous nucleic acid molecule encoding a phosphopantetheine:protein transferase enzyme of SEQ ID NO: 4.

2. The plant of claim 1, wherein the multifunctional fatty acid synthase increases oil levels in a seed of said plant that has been transformed with said nucleic acid encoding multifunctional fatty acid synthase.

3. The plant of claim 1, that further comprises a promoter that is operably linked to the nucleic acid encoding a multifunctional fatty acid synthase or the second nucleic acid encoding a phosphopantetheine:protein transferase enzyme, wherein the promoter is functional in a plant cell.

4. The plant of claim 3, wherein the promoter provides expression within plant seeds of the multifunctional fatty acid synthase or the phosphopantetheine:protein transferase enzyme.

5. The plant of claim 1, wherein the multifunctional fatty acid synthase is located in the cytosol of a plant cell.

6. A method of producing a *Brassica* oil, comprising the steps of:
 a) obtaining the *Brassica* plant of claim 1; and
 b) extracting oil from the seeds of said plant.

* * * * *

SEQUENCE LISTING

<160> NUMBER OF SEQ ID NOS: 49

<210> SEQ ID NO 1
<211> LENGTH: 9122
<212> TYPE: DNA
<213> ORGANISM: Brevibacterium ammoniagenes

<400> SEQUENCE: 1

```
atgtcgttga cccccttgca taccttgtct aatgacagca ctgctcccgc ggtgctgttt        60
gcgggtcagg gttctgcatg gcaaaaggcc atcgctgatg ccgcagccag ccctcaccag      120
ggcgcacatt gcgcgacatc ctaaaagaag ttcgcacgac caccggccca gtagcacgca      180
tcattgcgtc gtcgtgccct ggcgtttatg aacgcttgga agaacttgct cagaccccg       240
```

-continued

```
ctgaccaagc accgtggcca aggaatatga cgcgtacccg gcttactcca tccccggcat    300
cgtcctggga caaattggtg ccattgagca cctcgcgcag ctgggcatcg atgtcgattc    360
cgcgcagtta gcaggccact ccagggttca ttaggtgttg cagccgttaa ggatgcacgc    420
caggccctgg ctattgctgt tttgatgggt actgcagcag cggtgaccca gggcgcgaat    480
gattcccgca cccacatgct gtccgtgctg gcgtaccacg tgagatggtc gaagaatacc    540
tcgctggtga cgctgcgatt gccgtggtca acggccgcgt gcactttgca ctgtcgggta    600
cccccagagga tctggctaag accgagtcca acctccccag gctgccgagt cctacaacga    660
cgcgctggaa gaacgccgca tcggcggctc cgaaattaac ccagtcttcg acgtattggc    720
cgtggcactt cctttccacc acgcatcact gcaggatgca gcgatctgac cgtggactac    780
gccacccagt gtggcctgga cgctgagctt gcacgcgagc tggcagattc catcctggtt    840
cagccacata gctgggttga ccgtggccc ggtctcaact ccacctaccg ctctccttag    900
accgtggtct gtcttcgttg actacacctt tgattgccgg caccggcaag gttgtggttc    960
cagctgctac gccagcggag cgcgataacc tggctacccc aggcactgag ctgcctccgc   1020
ggtgaactac gagaagttct caccaaagct catctccttg cccaacggca gtcctacac   1080
tcagactcgt ttctccgagt ggaccggcat gtccccatc attttgggcg gcatgacgcc   1140
gacacgatgg atccgggcat cgttgccgca gcggccaacg tggctactg gtcagagatg   1200
gccggtggcg tcagtactc cgatgaagct tttaccatca caaagacgg catgatggag   1260
ctgctggagc aggtcgcacc gcagcattta acaccatgtt ctttgaccgc tacctgtgga   1320
acctacagtt cggtgtcacc cgcatttgtt ccaaggcacg cgctaatggt gctgcgttta   1380
ccggcgtgac catctgcctg gtatcccaga gctggatgaa gccaaggaat tgctggacca   1440
gctcacctcc gatggctttc catacatctc tttcaagccg gcaccacca agcagattca   1500
agactgcgtc gctatcgcag cggaaacccc acccaccgcg tcatcatcca aattgaagac   1560
gcccacgctg gtggccacca ctcctgggtg gatctggatg aaatgctgct ggctacctac   1620
gcatgtgccc gtgagcacga caacctggcc acactgttgg tggcggcatc cactccccag   1680
accgcgcatc ggaatacctg accggtacct ggtccaccaa gtacggtttg cccatcatgc   1740
cggttgatgg tgtcttcttg ggcaccgtag ccatggcgcc aaggaagcaa cggctaatga   1800
tgacgttaag cagttgctag ttgatacccc aggtatttcc ccagagacca atggcggttg   1860
ggtaggccga ctagatgccg acggcggcgt gtcctcctcc cagtccacct gttggctgac   1920
ttgcacgaga ttgataactc gtttgccaag gcctcgcgca tgatcacctc gatcccgatc   1980
gaggagtatg acgagcgtcg cgacgagatc attgctgctc tggacaagac ctcaagccat   2040
acttcggtga cctgtcggag atgacctacg aggattgggt cgctcgtttc gcagagcgcg   2100
cctacccttg ggtggatcca acctggcacg atcgtttcca cgatctgctc cagcgcgtaa   2160
agcgcgtctc aatgacgctg accacggcga catcgagacc ctattcccca cactcgacga   2220
ctccgagaac gcaccagagg cagtagccaa gctgctggct gcctacccga atgcaaagac   2280
caccaagtca acaccgcga tgaggcatgg ttccctaccc ttatccgcaa gcacgtcaag   2340
ccaatgccgt ggaccaccgc tattgacggt gacctgaagg aatggtttgc caaggacacc   2400
ctgtggcagg cccggaccca cgctacgacg cagacggcgt acgcatcatt ccaggaccgg   2460
tttcggttgc tggtatcacc aagaagaatg agcccgtcgc aaacctgctc ggtcgcttcg   2520
aagacgccac caccgcagcg ttaacgatgc cggcgtggca ccagttgagc tctactcccg   2580
```

```
cttggcttct gccaagaatg cagaagagtt cctgcgcaat gcaccaacca tcatgtggca    2640
cggtcacctc attgccaacc cggcgtatga gctgccagaa gaagcttttg acatcgtcga    2700
tgacggcgaa ggcttttgcta ttcgcatcaa ctcgactcct acagggataa cctcccagaa    2760
gagcagcgtc cgttctacgt caagcacgtt gatatccccg ttgcgctgtc ggaagccgta    2820
gcaaccggtg cctcccctgt tgttgatgac gcgcgtttgc aaaggcagtc ttcgacctgc    2880
tcgcaggcgt tgctggtgtc gggtctatct ctgagaccgg cgataagatc accgaactgc    2940
cgaaggtcat cgaaggctct gtctccgaag aaaaccctta cggcctgtgg aatactcctt    3000
taccttgcct tctaccctgc tgaccgcaca caccgcggta accggcgctg ccttgggcac    3060
cgccaacgca ggcacccccag atgcgctggt tggcccctgc tggccagcaa tttaaccgcg    3120
ctgggcaccg gtcgattgac cgaagaacac ggtgagccag ccggcaccga cttcccggtc    3180
attgaaggcc tgctcaacgc agtccacctc gaccacgtcg tcgatgtgcg tgttcctctt    3240
ccgaactcgc aaagggtgaa aagggcgaag gcggtcgcat tgacgtcacc tcccgctgtg    3300
catccatcgc ggaatccaac tccggtcgca ttgtcaccgt ggaacttgag ttgtgggatg    3360
ccgcaactaa gaagttgtgg cgacgcagat gcagcgcttt gccatccgtg gccgcgctac    3420
cggcacctcc gttccggttt ctgcaccatc ctggggcggc ggcaagtctc aggacaagat    3480
tgagaccacc ccacgtcctt cgtggatcgc gccattgtca ccgcgccatc ggatatgacc    3540
ccattcgcgc tggtctccgg tgactacaac ccaattcaca cctccaccaa cgccgcgcgc    3600
ttggtcaacc tcgacgcccc acggtgcacg gcatgtggct atctgccacc gcgcagcacc    3660
tagctggcaa ccacggcacc gtggtgggtt ggacctattc catgtacggc atggtccagc    3720
tcaacgatga agtagaaatc accgtcgaag cgtaggccgc aagggcattc acgcagcatt    3780
cgaggtcacc tgccgcatcg acggcgaagt agtctcccgc ggccaggcgc tcatggcaca    3840
gccacgcacc gcttatgtct acccaggcca gggcatcagg ccgagggcat gggccgtggt    3900
gaccgcgatg cttcggcagc agcgcgtgag gtatggcgtc gtgcagaccg ccacacccgc    3960
accgcactgg gcttttctat tcgccagatc atcgatgaca cccaccgag ctcgtcgttc    4020 gcggcaccaa gttcgtccac cccaatggcg tgctgcactt aacgcagttc actcaggttg    4080
ccctcgcagt cgttgcttat gcacaaaccg agcgcctgcg cgaagcagat ctctgggcac    4140
caactccatg tacgccggtc actcactggg tgagtacacc gcgctggcat cgttggcgaa    4200
tatctttgac ctcgaagcgg ttatcgacat cgtctactcc cgtggctctg ccatgggacc    4260
ttggtcgaac gtgatgaaaa cggtaactcc aactacggca tgggcgcgct gcgtccaaac    4320
atgattggtg ttcccgcaga ccaggttgag gcctacatcg cgcagaccgc ggaagaaact    4380
ggcgattcct cgaaatcgtc aactacaaca tcgctggtca gcagtactcc atcgcgggta    4440
ccaaggctgg tttggccgcc ctgaagaaaa aggccaactc cgtcaaggac cgtgcttatg    4500
tcacggttcc agcatcgatg tacctttcca ctcccaggta ctgcgcgacg cgttcctgc     4560 tttcgcagaa aagctcgatg aactgttgcc agaaaccttg gacctggacg ccctggtcgg    4620
ccgctacgtg ccgaacctgt ggcgctgcca ttcgagctga cccaggaatt tgtcgataag    4680
gtcaagcctt tggctccttc cggcaagctg gataacctca aggtcgaaga caccgatgag    4740 caagccccttt ctcgcctgct catgatgagc tattgtcctg gcagttcgca tcacctgtgc    4800
gctggattga aacccagcag ctgctctttg aagaagtaga ccagatcatc gaagtcggtc    4860
tcgcttcatc cccaacgctg accaacttgg ccagcgctcc atggatatcg ccggcgtgga    4920
cctcccggtc ttcaacgtcg aacgcgacca agaccaggtc atgctccaag acgttcagga    4980
```

-continued

```
agcaccagct gcctccttcg acgtcgagga aggagaggca cctcttcgac cgcagcgtct   5040 gaaacccag gtgaatccgc tgcggcggcc tcggataata cccaggccat cccatcggct     5100
gagccacaaa cggtggcaga ggcaccagca ccatccgccg caccagtggc ggcacccgtg    5160
ccgcagatgc tcctgacctg ccatttaccg cagcagaagc catcatggtt ctgttcgctt    5220
tccagaacaa gatccgccag gaccagatca atgactcgga tacggtcgaa gagtcaccaa    5280
cggtgtctcc tcccgccgta accaactgtt gatggatatg tccgcagaaa atcgcgtgcc    5340
cgccattgac ggtgcagccg atgctgacgt ggcaaccttg cgtgagcgcg tcaagactgc    5400
cgctccgggc tactcgccat tcggcaccgt cttgtctgag gctataccgc tcgtctgcgc    5460
cagctcactg gtgcagcagg cgtcaagccg gcctacattt cagagcgcgt gaccggaact    5520
tgggggctgc ctatgtcctg ggcagcccac gttgaggctg aaatcttgct cgctcccgtg    5580
aagaagactc agtgcgcggt ggctccttgt ccaccgttcc ttccgcggcg tcgtcgaagg    5640
ccgatgtcga tgcgcttgtc gatgccgcgg tccaggccgt agccgcagca cacggcaccc    5700
ggtatcccat ggtgctgcga gtggcgccgg cggcggtgga gtcgtcgact ccgcagcctt    5760
ggatgcttac gcagatatcg tcaccggtga aaacggtgtc ctcgctactg ctgctcgcca    5820
ggttctgctc agctgggctt ggtcgaggaa gcccctgaga cccctgagac cgataacacc    5880
ttgttcgcga ccgtcgaggc cgagctgggt tccggttggg aaaagaccgt tacccccatcc   5940 tttgacgcca gccgcagtg cttttcgatg accgctgggc gtctgctcgc gaagatctcg     6000
cccgcgtggc actcggcgag atcgacttgc cagtcaagcg tttccaggga accggagaga    6060
ccatcgccaa gcaagcggaa ggtgggcgga gaacaccgct gcttccactg gtgcgcacgc    6120
gaaggcaacc gctgccgaga ccctgcatgc tattgctgcc gcagcgcgcg aagaactcga    6180
cggcgaattc gctggcgatg tcgcgttgtc accggtgcag ccccaggctc cattgctacc    6240
gctctcgtag aacgcctgct ggaaggcggc gcgaccgtca tcatgactgc gtcacgtgtc    6300
agccagtccc gtaaggaatt tgcacgcaag ctctcgctgc acacgcgatt cctggcgctg    6360
ccctgtgggt tgttcctgcg aacttgcgct cctaccgcga tgttgatgct tcattgact    6420 ggattggtaa tgagcagcgt gcctctgtcg gcaacgaagt cagatcacca agccagcgtt    6480
gaccccaacc ttggccttcc cattcgcggc accttccgtg tccggttctg tggccgatgc    6540
cggcccacag gctgaaaacc agactcgcct gctgctgtgg tctgttgacg caccatcgct    6600
ggtctgtcca acctggcgca gcaaggcgtg ataccccgct gccacattgt gctgcctggt    6660
tctccgaacc gcggcatgtt cggtggcgac ggcgcttacg gcgaagtcaa ggcagcttgg    6720
acgctatttt ggccaagtgg tctgcagaag caggctggcc agaaggtgtt accttggcac    6780
aagccaagat tggctgggtc tctggtacct ccctgatggg cggcaacgac gttctgattc    6840
cgcagcggaa gccgctggca tccacgtgtg ggacccagaa gagatttctt cccagctcat    6900
ctccctagct tccgaagaat cccgcgcgaa ggcagccgag gctccactag agctggatct    6960
gaccggtggc tgggctcgtc caacatctcc atctccgagc tggctgccca ggcccgcgag    7020
gacgccgagg cacaagctgc ttccggtgat aatgcagacg cagctgcgga agctcctgca    7080
gccacgattc cagcacgcct aatacccgtt cagtagagct gcctgcagcg ctaccggaag    7140
gtgaagtggg cgacgtaacc acggatctgg atgacatggt cgtcatcgca ggtgtcggcg    7200
aagtctcctc gtggggttcg ggcgtacccg ctttgaggca gaatatggct tgcagcgcga    7260
tggcgctgtg gacctgaccg ccgctggtgt cttggaattg gcatggatga ccggactgat    7320
```

```
ttcctggtcc aatgacccac gtccagcctg tacgacgaag agggcaccga agtcgatgaa    7380
gcagatatct acgctcgctt ccgcgacgag gttgtagctc gctccggtat ccgtaccttg    7440
accgataagt acaacatggt tgaccagggc tccattgcct gacttctgtg ttcttggacc    7500
gcgatatcgt cttcaccgtt cctaccgaac aagaagcact cgatattgaa gaagccgacc    7560
catcgtttac caagctgcgc gaagtcgacg gcgagtggga agtccccgtt tgaagggtgc    7620
caccgcccgc gtgccacgca aggcaacgtt gactcgtacc gttgctggtc aaatgccgga    7680
tcacttcgat gctgccaagt ggggcattcc agaccacatg ctggatgcac tgaccgcatg    7740
gccgtgtgga acctggtgac cgcagtcgat gcctttaccc aggcgggctt tagcccggct    7800
gagttgctgc aggttattca cccagcgcag gttgctacca cccagggcac cggtatcgcg    7860
gcatggaatc cctgcacaag gtcttcgtga cccgtctgct cggtgaagac cgtccttccg    7920
acatcctgca ggaagcactg cctaacgtta ttgcagcgca caccatgcag tctttggtgg    7980
gcggcacggt tcgatgattc accctatcgg tgcttgtgcc accgctgcgg tgtccatcga    8040
agaaggcgtg gacaagattg ccctgggcaa ggccgacctg gtcgttgccg gtggtatcga    8100
tgacgtccaa gttgagtctt tgaccggctt cggcgacatg aacgccaccg ctgagaccaa    8160
aagatgaccg atcagggcat tgatgaccgc ttcatctccc gtgcgaatga ccgccgtcgt    8220
ggcggcttcc tcgaggcaga aggcggcggt accgtgcttc tggttcgcgg ttccctggct    8280
cgtgagaggg tctgccggtc tacgcggtcg ttgcgcacga ggcgtcctac ggtgcccaca    8340
cctccattcc tgctccaggt ttgggtgctt gggcgctgg ccgtggccgg aagaactccc    8400
gcctggccaa gggctggctg gtttgggtct gactccaaat gacgtctcgg tactgtccaa    8460
gcacgacacc tcgaccaacg ccaatgaccc gaatgagtcg gaactgcact ccatcttgtg    8520
gcctgctatt ggccgcgatg tgaccagcca ctgtttgtga tttcgcagaa gtcactgact    8580
ggtcactcca aggctggtgc cgcgctgttc cagaccggcg gtttgattga cgtcttccgc    8640
acgggacgca ttccagctaa cctgtcgcgg attgtgtgga tccattgatt gagccaaagg    8700
ccacgaactt ggtctggcta cgctccccac tagatgtgga agcagccaac cgcccggtca    8760
aggccgcggc gctcacctcg ctcggcttcg gtcactcggt gcattgattg tctacgcgca    8820
cccaggtgtc ttcgaggctg ccgttgccca gcaggtttcg gccgaggctg ctgccgaatg    8880
gcgcgagaag gcaaatgccc gcctcgccgc cggtgcagca cgttcgaagc cggcatgatt    8940
ggcaaggaaa ccttgttcga ggtcatcgac ggccgccgcc tgcctgacgc agcgggcacc    9000
gttgagattg agaactacgg cccagtcgcc gccgacaagg ccgcagaatg cgctcttgct    9060
tgacgacgac atccgtctta ccgccgaagg cactttccct ccggcgaagt aggacaaagt    9120
ag                                                                  9122
```

<210> SEQ ID NO 2
<211> LENGTH: 3040
<212> TYPE: PRT
<213> ORGANISM: Brevibacterium ammoniagenes

<400> SEQUENCE: 2

Met Ser Leu Thr Pro Leu His Thr Leu Ser Asn Asp Ser Thr Ala Pro
1               5                   10                  15

Ala Val Leu Phe Ala Gly Gln Gly Ser Ala Trp Gln Lys Ala Ile Ala
            20                  25                  30

Asp Ala Ala Ala Ser Pro His Gln Gly Ala Gln Leu Arg Asp Ile Leu
        35                  40                  45

-continued

```
Lys Glu Val Arg Thr Thr Gly Pro Val Ala Arg Ile Ile Ala Ser
 50                  55                  60

Ser Cys Pro Gly Val Tyr Glu Arg Leu Glu Glu Leu Ala Gln Thr Pro
 65                  70                  75                  80

Ala Asp Gln Ala Pro Val Ala Lys Glu Tyr Asp Ala Tyr Pro Ala Tyr
                 85                  90                  95

Ser Ile Pro Gly Ile Val Leu Gly Gln Ile Gly Ala Ile Glu His Leu
            100                 105                 110

Ala Gln Leu Gly Ile Asp Val Asp Ser Ala Gln Leu Ala Gly His Gln
        115                 120                 125

Gly Ser Leu Gly Val Ala Ala Val Lys Asp Ala Arg Gln Ala Leu Ala
    130                 135                 140

Ile Ala Val Leu Met Gly Thr Ala Ala Val Thr Gln Gly Ala Asn
145                 150                 155                 160

Asp Ser Arg Thr His Met Leu Ser Val Arg Gly Val Pro Arg Glu Met
                165                 170                 175

Val Glu Glu Tyr Leu Ala Gly Asp Ala Ala Ile Ala Val Val Asn Gly
            180                 185                 190

Arg Val His Phe Ala Leu Ser Gly Thr Pro Glu Asp Leu Ala Lys Thr
        195                 200                 205

Glu Ser Asn Leu Thr Gln Ala Ala Glu Ser Tyr Asn Asp Ala Leu Glu
    210                 215                 220

Glu Arg Arg Ile Gly Gly Ser Glu Ile Asn Pro Val Phe Asp Val Leu
225                 230                 235                 240

Ala Val Ala Leu Pro Phe His His Ala Ser Leu Gln Asp Ala Asp Leu
                245                 250                 255

Thr Val Asp Tyr Ala Thr Gln Cys Gly Leu Asp Ala Glu Leu Ala Arg
            260                 265                 270

Glu Leu Ala Asp Ser Ile Leu Val Gln Pro His Ser Trp Val Glu Thr
        275                 280                 285

Val Ala Gly Leu Asn Ser Thr Tyr Leu Leu Ser Leu Asp Arg Gly Leu
    290                 295                 300

Ser Ser Leu Thr Thr Pro Leu Ile Ala Gly Thr Gly Lys Val Val Val
305                 310                 315                 320

Pro Ala Ala Thr Pro Ala Glu Arg Asp Asn Leu Ala Thr Pro Gly Thr
                325                 330                 335

Glu Leu Pro Thr Ala Val Asn Tyr Glu Lys Phe Ser Pro Lys Leu Ile
            340                 345                 350

Ser Leu Pro Asn Gly Lys Ser Tyr Thr Gln Thr Arg Phe Ser Glu Trp
        355                 360                 365

Thr Gly Met Ser Pro Ile Ile Leu Gly Gly Met Thr Pro Thr Met Asp
    370                 375                 380

Pro Gly Ile Val Ala Ala Ala Asn Gly Gly Tyr Trp Ser Glu Met
385                 390                 395                 400

Ala Gly Gly Gly Gln Tyr Ser Asp Glu Ala Phe Thr Ile Asn Lys Asp
                405                 410                 415

Gly Met Met Glu Leu Leu Glu Pro Gly Arg Thr Ala Ala Phe Asn Thr
            420                 425                 430

Met Phe Phe Asp Arg Tyr Leu Trp Asn Leu Gln Phe Gly Val Thr Arg
        435                 440                 445

Ile Cys Ser Lys Ala Arg Ala Asn Gly Ala Ala Phe Thr Gly Val Thr
    450                 455                 460

Ile Cys Ala Gly Ile Pro Glu Leu Asp Glu Ala Lys Glu Leu Leu Asp
```

```
                   465                 470                 475                 480
Gln Leu Thr Ser Asp Gly Phe Pro Tyr Ile Ser Phe Lys Pro Gly Thr
                            485                 490                 495

Thr Lys Gln Ile Gln Asp Cys Val Ala Ile Ala Ala Asn Pro Thr His
            500                 505                 510

Arg Val Ile Ile Gln Ile Glu Asp Ala His Ala Gly Gly His His Ser
            515                 520                 525

Trp Val Asp Leu Asp Glu Met Leu Leu Ala Thr Tyr Ala Cys Ala Arg
            530                 535                 540

Glu His Asp Asn Leu Ala Ile Thr Val Gly Gly Ile His Ser Pro
545                 550                 555                 560

Asp Arg Ala Ser Glu Tyr Leu Thr Gly Thr Trp Ser Thr Lys Tyr Gly
                565                 570                 575

Leu Pro Ile Met Pro Val Asp Gly Val Phe Leu Gly Thr Val Ala Met
                580                 585                 590

Ala Thr Lys Glu Ala Thr Ala Asn Asp Asp Val Lys Gln Leu Leu Val
            595                 600                 605

Asp Thr Pro Gly Ile Ser Pro Glu Thr Asn Gly Gly Trp Val Gly Arg
            610                 615                 620

Leu Asp Ala Asp Gly Gly Val Ser Ser Gln His Leu Leu Ala Asp
625                 630                 635                 640

Leu His Glu Ile Asp Asn Ser Phe Ala Lys Ala Ser Arg Met Ile Thr
                645                 650                 655

Ser Ile Pro Ile Glu Glu Tyr Asp Glu Arg Arg Asp Glu Ile Ile Ala
            660                 665                 670

Ala Leu Asp Lys Thr Ser Lys Pro Tyr Phe Gly Asp Leu Ser Glu Met
            675                 680                 685

Thr Tyr Glu Asp Trp Val Ala Arg Phe Ala Glu Arg Ala Tyr Pro Trp
            690                 695                 700

Val Asp Pro Thr Trp His Asp Arg Phe His Asp Leu Leu Gln Arg Val
705                 710                 715                 720

Glu Ala Arg Leu Asn Asp Ala Asp His Gly Asp Ile Glu Thr Leu Phe
                725                 730                 735

Pro Thr Leu Asp Asp Ser Glu Asn Ala Pro Glu Ala Val Ala Lys Leu
            740                 745                 750

Leu Ala Ala Tyr Pro Asn Ala Lys Thr Thr Val Asn Thr Arg Asp Glu
            755                 760                 765

Ala Trp Phe Pro Thr Leu Ile Arg Lys His Val Lys Pro Met Pro Trp
            770                 775                 780

Thr Thr Ala Ile Asp Gly Asp Leu Lys Glu Trp Phe Ala Lys Asp Thr
785                 790                 795                 800

Leu Trp Gln Ala Gln Asp Pro Arg Tyr Asp Ala Asp Gly Val Arg Ile
                805                 810                 815

Ile Pro Gly Pro Val Ser Val Ala Gly Ile Thr Lys Lys Asn Glu Pro
            820                 825                 830

Val Ala Asn Leu Leu Gly Arg Phe Glu Asp Ala Thr Thr Ala Ala Leu
            835                 840                 845

Asn Asp Ala Gly Val Ala Pro Val Glu Leu Tyr Ser Arg Leu Ala Ser
850                 855                 860

Ala Lys Asn Ala Glu Glu Phe Leu Arg Asn Ala Pro Thr Ile Met Trp
865                 870                 875                 880

His Gly His Leu Ile Ala Asn Pro Ala Glu Leu Pro Glu Glu Ala Phe
                885                 890                 895
```

```
Asp Ile Val Asp Asp Gly Glu Gly Phe Ala Ile Arg Ile Asn Ser Asp
            900                 905                 910

Ser Tyr Arg Asp Asn Leu Pro Glu Glu Gln Arg Pro Phe Tyr Val Lys
        915                 920                 925

His Val Asp Ile Pro Val Ala Leu Ser Glu Ala Val Ala Thr Gly Ala
    930                 935                 940

Ser Pro Val Val Asp Asp Ala Arg Leu Pro Lys Ala Val Phe Asp Leu
945                 950                 955                 960

Leu Ala Gly Val Ala Gly Val Gly Ser Ile Ser Glu Thr Gly Asp Lys
                965                 970                 975

Ile Thr Glu Leu Pro Lys Val Ile Glu Gly Ser Val Ser Glu Glu Asn
            980                 985                 990

Pro Tyr Gly Leu Val Glu Tyr Ser Phe Thr Leu Pro Ser Thr Leu Leu
        995                 1000                1005

Thr Ala His Thr Ala Val Thr Gly Ala Leu Gly Thr Ala Asn Ala
    1010                1015                1020

Gly Thr Pro Asp Ala Leu Val Gly Pro Cys Trp Pro Ala Ile Tyr
    1025                1030                1035

Thr Ala Leu Gly Thr Gly Arg Leu Thr Glu Glu His Gly Glu Pro
    1040                1045                1050

Ala Gly Thr Asp Phe Pro Val Ile Glu Gly Leu Leu Asn Ala Val
    1055                1060                1065

His Leu Asp His Val Val Asp Val Arg Val Pro Leu His Glu Leu
    1070                1075                1080

Ala Lys Gly Glu Lys Gly Glu Gly Gly Arg Ile Asp Val Thr Ser
    1085                1090                1095

Arg Cys Ala Ser Ile Ala Glu Ser Asn Ser Gly Arg Ile Val Thr
    1100                1105                1110

Val Glu Leu Glu Leu Trp Asp Ala Ala Thr Gln Glu Val Val Ala
    1115                1120                1125

Thr Gln Met Gln Arg Phe Ala Ile Arg Gly Arg Ala Thr Gly Thr
    1130                1135                1140

Val Pro Val Ser Ala Pro Ser Trp Gly Gly Gly Lys Ser Gln Asp
    1145                1150                1155

Lys Ile Glu Thr Thr Pro Arg Ser Phe Val Asp Arg Ala Ile Val
    1160                1165                1170

Thr Ala Pro Ser Asp Met Thr Pro Phe Ala Leu Val Ser Gly Asp
    1175                1180                1185

Tyr Asn Pro Ile His Thr Ser Thr Asn Ala Ala Arg Leu Val Asn
    1190                1195                1200

Leu Asp Ala Pro Leu Val His Gly Met Trp Leu Ser Ala Thr Ala
    1205                1210                1215

Gln His Leu Ala Gly Asn His Gly Thr Val Val Gly Trp Thr Tyr
    1220                1225                1230

Ser Met Tyr Gly Met Val Gln Leu Asn Asp Glu Val Glu Ile Thr
    1235                1240                1245

Val Glu Arg Val Gly Arg Lys Gly Ile His Ala Ala Phe Glu Val
    1250                1255                1260

Thr Cys Arg Ile Asp Gly Glu Val Ser Arg Gly Gln Ala Leu Met
    1265                1270                1275

Ala Gln Pro Arg Thr Ala Tyr Val Tyr Pro Gly Gln Gly Ile Gln
    1280                1285                1290
```

-continued

```
Ala Glu Gly Met Gly Arg Gly Asp Arg Asp Ser Ala Ala Ala
    1295            1300            1305

Arg Glu Val Trp Arg Arg Ala Asp Arg His Thr Arg Thr Ala Leu
    1310            1315            1320

Gly Phe Ser Ile Arg Gln Ile Ile Asp Asp Asn Pro Thr Glu Leu
    1325            1330            1335

Val Val Arg Gly Thr Lys Phe Val His Pro Asn Gly Val Leu His
    1340            1345            1350

Leu Thr Gln Phe Thr Gln Val Ala Leu Ala Val Val Ala Tyr Ala
    1355            1360            1365

Gln Thr Glu Arg Leu Arg Glu Ala Asp Ala Leu Gly Thr Asn Ser
    1370            1375            1380

Met Tyr Ala Gly His Ser Leu Gly Glu Tyr Thr Ala Leu Ala Leu
    1385            1390            1395

Ala Asn Ile Phe Asp Leu Glu Ala Val Ile Asp Ile Val Tyr Ser
    1400            1405            1410

Arg Gly Ser Ala Met Gly Thr Leu Val Glu Arg Asp Glu Asn Gly
    1415            1420            1425

Asn Ser Asn Tyr Gly Met Gly Ala Leu Arg Pro Asn Met Ile Gly
    1430            1435            1440

Val Pro Ala Asp Gln Val Glu Ala Tyr Ile Ala Gln Thr Ala Glu
    1445            1450            1455

Glu Thr Gly Glu Phe Leu Glu Ile Val Asn Tyr Asn Ile Ala Gly
    1460            1465            1470

Gln Gln Tyr Ser Ile Ala Gly Thr Lys Ala Gly Leu Ala Ala Leu
    1475            1480            1485

Lys Lys Lys Ala Asn Ser Val Lys Asp Arg Ala Tyr Val Thr Val
    1490            1495            1500

Pro Gly Ile Asp Val Pro Phe His Ser Gln Val Leu Arg Asp Gly
    1505            1510            1515

Val Pro Ala Phe Ala Glu Leu Asp Glu Leu Leu Pro Glu Thr Leu
    1520            1525            1530

Asp Leu Asp Ala Leu Val Gly Arg Tyr Val Pro Asn Leu Val Ala
    1535            1540            1545

Leu Pro Phe Glu Leu Thr Gln Glu Phe Val Asp Lys Val Lys Pro
    1550            1555            1560

Leu Ala Pro Ser Gly Lys Leu Asp Asn Leu Lys Val Glu Asp Thr
    1565            1570            1575

Asp Glu Gln Ala Pro Ser Arg Leu Leu Met Ile Glu Leu Leu Ser
    1580            1585            1590

Trp Gln Phe Ala Ser Pro Val Arg Trp Ile Glu Thr Gln Gln Leu
    1595            1600            1605

Leu Phe Glu Glu Val Asp Gln Ile Ile Glu Val Gly Leu Ala Ser
    1610            1615            1620

Ser Pro Thr Leu Thr Asn Leu Ala Lys Arg Ser Met Asp Ile Ala
    1625            1630            1635

Gly Val Asp Leu Pro Val Phe Asn Val Glu Arg Asp Gln Gln Val
    1640            1645            1650

Met Leu Gln Asp Val Gln Glu Ala Pro Ala Ala Ser Phe Asp Val
    1655            1660            1665

Glu Glu Gly Glu Ala Thr Ser Ser Thr Ala Ala Ser Glu Thr Pro
    1670            1675            1680

Gly Glu Ser Ala Ala Ala Ala Ser Asp Asn Thr Gln Ala Ile Pro
```

```
                    1685                1690                1695

Ser Ala Glu Pro Gln Thr Val Ala Glu Pro Ala Pro Ser Ala
    1700                1705                1710

Ala Pro Ala Gly Gly Thr Arg Ala Ala Asp Ala Pro Asp Leu Pro
    1715                1720                1725

Phe Thr Ala Ala Glu Ala Ile Met Val Leu Phe Ala Phe Gln Asn
    1730                1735                1740

Lys Ile Arg Gln Asp Gln Ile Asn Asp Ser Asp Thr Val Glu Glu
    1745                1750                1755

Leu Thr Asn Gly Val Ser Ser Arg Arg Asn Gln Leu Leu Met Asp
    1760                1765                1770

Met Ser Ala Glu Asn Val Pro Ala Ile Asp Gly Ala Ala Asp Ala
    1775                1780                1785

Asp Val Ala Thr Leu Arg Glu Arg Val Lys Thr Ala Ala Pro Gly
    1790                1795                1800

Tyr Ser Pro Phe Gly Thr Val Leu Ser Glu Ala Ile Thr Ala Arg
    1805                1810                1815

Leu Arg Gln Leu Thr Gly Ala Ala Gly Val Lys Pro Ala Tyr Ile
    1820                1825                1830

Ser Glu Arg Val Thr Gly Thr Trp Gly Leu Pro Met Ser Trp Ala
    1835                1840                1845

Ala His Val Glu Ala Glu Ile Leu Leu Gly Ser Arg Glu Glu Asp
    1850                1855                1860

Ser Val Arg Gly Gly Ser Leu Ser Thr Val Pro Ser Ala Ala Ser
    1865                1870                1875

Ser Lys Ala Asp Val Asp Ala Leu Val Asp Ala Ala Val Gln Ala
    1880                1885                1890

Val Ala Ala His Gly Thr Ser Val Ser His Gly Ala Ser Gly
    1895                1900                1905

Ala Gly Gly Gly Gly Val Val Asp Ser Ala Ala Leu Asp Ala Tyr
    1910                1915                1920

Ala Asp Ile Val Thr Gly Glu Asn Gly Val Leu Ala Thr Ala Ala
    1925                1930                1935

Arg Gln Val Leu Ala Gln Leu Gly Leu Val Glu Glu Ala Pro Glu
    1940                1945                1950

Thr Pro Glu Thr Asp Asn Thr Leu Phe Ala Thr Val Glu Ala Glu
    1955                1960                1965

Leu Gly Ser Gly Trp Glu Lys Thr Val Thr Pro Ser Phe Asp Ala
    1970                1975                1980

Lys Arg Ala Val Leu Phe Asp Asp Arg Trp Ala Ser Ala Arg Glu
    1985                1990                1995

Asp Leu Ala Arg Val Ala Leu Gly Glu Ile Asp Leu Pro Val Lys
    2000                2005                2010

Arg Phe Gln Gly Thr Gly Glu Thr Ile Ala Lys Gln Ala Glu Trp
    2015                2020                2025

Trp Ala Glu Asn Ala Ala Ser Thr Gly Ala His Ala Lys Ala Thr
    2030                2035                2040

Ala Ala Glu Thr Leu His Ala Ile Ala Ala Ala Arg Glu Glu
    2045                2050                2055

Leu Asp Gly Glu Phe Ala Gly Asp Val Ala Leu Val Thr Gly Ala
    2060                2065                2070

Ala Pro Gly Ser Ile Ala Thr Ala Leu Val Glu Arg Leu Leu Glu
    2075                2080                2085
```

-continued

```
Gly Gly Ala Thr Val Ile Met Thr Ala Ser Arg Val Ser Gln Ser
2090                2095                2100

Arg Lys Glu Phe Ala Arg Lys Leu Tyr Ala Ala His Ala Ile Pro
2105                2110                2115

Gly Ala Ala Leu Trp Val Val Pro Ala Asn Leu Arg Ser Tyr Arg
2120                2125                2130

Asp Val Asp Ala Leu Ile Asp Trp Ile Gly Asn Glu Gln Arg Ala
2135                2140                2145

Ser Val Gly Asn Glu Val Lys Ile Thr Lys Pro Leu Thr Pro Thr
2150                2155                2160

Leu Ala Phe Pro Phe Ala Ala Pro Ser Val Ser Gly Ser Val Ala
2165                2170                2175

Asp Ala Gly Pro Gln Ala Glu Asn Gln Thr Arg Leu Leu Leu Trp
2180                2185                2190

Ser Val Glu Arg Thr Ile Ala Gly Leu Ser Asn Leu Ala Gln Gln
2195                2200                2205

Gly Val Asp Thr Arg Cys His Ile Val Leu Pro Gly Ser Pro Asn
2210                2215                2220

Arg Gly Met Phe Gly Gly Asp Gly Ala Tyr Gly Glu Val Lys Ala
2225                2230                2235

Ala Leu Asp Ala Ile Leu Ala Lys Trp Ser Ala Glu Ala Gly Trp
2240                2245                2250

Pro Glu Gly Val Thr Leu Ala Gln Ala Lys Ile Gly Trp Val Ser
2255                2260                2265

Gly Thr Ser Leu Met Gly Gly Asn Asp Val Leu Ile Pro Ala Ala
2270                2275                2280

Glu Ala Ala Ile His Val Trp Asp Pro Glu Glu Ile Ser Ser Gln
2285                2290                2295

Leu Ile Ser Leu Ala Ser Glu Glu Ser Arg Ala Lys Ala Ala Glu
2300                2305                2310

Ala Pro Leu Glu Leu Asp Leu Thr Gly Gly Leu Gly Ser Ser Asn
2315                2320                2325

Ile Ser Ile Ser Glu Leu Ala Ala Gln Ala Arg Glu Asp Ala Glu
2330                2335                2340

Ala Gln Ala Ala Ser Gly Asp Asn Ala Asp Ala Ala Glu Ala
2345                2350                2355

Pro Ala Ala Thr Ile Pro Ala Leu Pro Asn Thr Arg Ser Val Glu
2360                2365                2370

Leu Pro Ala Ala Leu Pro Glu Gly Glu Val Gly Asp Val Thr Thr
2375                2380                2385

Asp Leu Asp Asp Met Val Val Ile Ala Gly Val Gly Glu Val Ser
2390                2395                2400

Ser Trp Gly Ser Gly Arg Thr Arg Phe Glu Glu Tyr Gly Leu Gln
2405                2410                2415

Arg Asp Gly Ala Val Asp Leu Thr Ala Ala Gly Val Leu Glu Leu
2420                2425                2430

Ala Trp Met Thr Gly Leu Ile Ser Trp Ser Asn Asp Pro Arg Pro
2435                2440                2445

Ala Trp Tyr Asp Glu Glu Gly Thr Glu Val Asp Glu Ala Asp Ile
2450                2455                2460

Tyr Ala Arg Phe Arg Asp Glu Val Val Ala Arg Ser Gly Ile Arg
2465                2470                2475
```

```
Thr Leu Thr Asp Lys Tyr Asn Met Val Asp Gln Gly Ser Ile Asp
2480                2485                2490

Leu Thr Ser Val Phe Leu Asp Arg Asp Ile Val Phe Thr Val Pro
    2495                2500                2505

Thr Glu Gln Glu Ala Leu Asp Ile Glu Glu Ala Asp Pro Ser Phe
2510                2515                2520

Thr Lys Leu Arg Glu Val Asp Gly Glu Trp Glu Val Thr Arg Leu
2525                2530                2535

Lys Gly Thr Ala Arg Val Pro Arg Lys Ala Thr Leu Thr Arg Thr
2540                2545                2550

Val Ala Gly Gln Met Pro Asp His Phe Asp Ala Ala Lys Trp Gly
2555                2560                2565

Ile Pro Asp His Met Leu Asp Ala Leu Asp Arg Met Ala Val Trp
2570                2575                2580

Asn Leu Val Thr Ala Val Asp Ala Phe Thr Gln Ala Gly Phe Ser
2585                2590                2595

Pro Ala Glu Leu Leu Gln Val Ile His Pro Ala Gln Val Ala Thr
2600                2605                2610

Thr Gln Gly Thr Gly Ile Gly Gly Met Glu Ser Leu His Lys Val
2615                2620                2625

Phe Val Thr Arg Leu Leu Gly Glu Asp Arg Pro Ser Asp Ile Leu
2630                2635                2640

Gln Glu Ala Leu Pro Asn Val Ile Ala Ala His Thr Met Gln Ser
2645                2650                2655

Leu Val Gly Gly Tyr Gly Ser Met Ile Pro Ile Gly Ala Cys Ala
2660                2665                2670

Thr Ala Ala Val Ser Ile Glu Glu Gly Val Asp Lys Ile Ala Leu
2675                2680                2685

Gly Lys Ala Asp Leu Val Val Ala Gly Gly Ile Asp Asp Val Gln
2690                2695                2700

Val Glu Ser Leu Thr Gly Phe Gly Asp Met Asn Ala Thr Ala Glu
2705                2710                2715

Thr Lys Lys Met Thr Asp Gln Gly Ile Asp Asp Arg Phe Ile Ser
2720                2725                2730

Arg Ala Asn Asp Arg Arg Arg Gly Gly Phe Leu Glu Ala Glu Gly
2735                2740                2745

Gly Gly Thr Val Leu Leu Val Arg Gly Ser Leu Ala Arg Glu Met
2750                2755                2760

Gly Leu Pro Val Tyr Ala Val Val Ala His Glu Ala Ser Tyr Gly
2765                2770                2775

Ala His Thr Ser Ile Pro Ala Pro Gly Leu Gly Ala Leu Gly Ala
2780                2785                2790

Gly Arg Gly Arg Lys Asn Ser Arg Leu Ala Lys Gly Leu Ala Gly
2795                2800                2805

Leu Gly Leu Thr Pro Asn Asp Val Ser Val Leu Ser Lys His Asp
2810                2815                2820

Thr Ser Thr Asn Asn Asp Pro Asn Glu Ser Glu Leu His Ser Ile
2825                2830                2835

Leu Trp Pro Ala Ile Gly Arg Asp Val Asp Gln Pro Leu Phe Val
2840                2845                2850

Ile Ser Gln Lys Ser Leu Thr Gly His Ser Lys Ala Gly Ala Ala
2855                2860                2865

Leu Phe Gln Thr Gly Gly Leu Ile Asp Val Phe Arg Thr Gly Arg
```

```
            2870                2875                2880
Ile Pro Ala Asn Leu Ser  Leu Asp Cys Val Asp Pro  Leu Ile Glu
    2885                2890                2895

Pro Lys Ala Thr Asn Leu  Val Trp Leu Arg Ser Pro  Leu Asp Val
    2900                2905                2910

Glu Ala Ala Asn Arg Pro  Val Lys Ala Ala Ala Leu  Thr Ser Leu
    2915                2920                2925

Gly Phe Gly His Val Gly  Ala Leu Ile Val Tyr Ala  His Pro Gly
    2930                2935                2940

Val Phe Glu Ala Ala Val  Ala Gln Gln Val Ser Glu  Ala Ala Ala
    2945                2950                2955

Glu Trp Arg Glu Lys Ala  Asn Ala Arg Leu Ala Ala  Gly Ala Ala
    2960                2965                2970

Arg Phe Glu Ala Gly Met  Ile Gly Lys Glu Thr Leu  Phe Glu Val
    2975                2980                2985

Ile Asp Gly Arg Arg Leu  Pro Asp Ala Ala Gly Thr  Val Glu Ile
    2990                2995                3000

Glu Asn Tyr Gly Pro Val  Ala Ala Asp Lys Ala Ala  Glu Leu Arg
    3005                3010                3015

Ser Cys Leu Thr Thr Thr  Ser Val Leu Pro Pro Lys  Ala Leu Ser
    3020                3025                3030

Leu Arg Arg Ser Arg Thr  Lys
    3035                3040

<210> SEQ ID NO 3
<211> LENGTH: 459
<212> TYPE: DNA
<213> ORGANISM: Brevibacterium ammoniagenes

<400> SEQUENCE: 3
gtgctcgaca accgtgaagc gatgaccgtg ggtgtggact tggtccacat ccccggcttt      60
gccgagcaat tgtcgcgccc tggttcgact tttgagcaag tgttttcgcc gttggaacgt     120
cgtcatgtca aacgcgccgt gacgctgcag cggatgctac gaattcgagc cttgcgggtt     180
cacggactga gcacctggct gggcggtggg cggcaaaaga gcgttcatc aaggcgtggt      240 cgcaagcgat ctacgcaagc caccagtgat tgaaccagac tggtgaact tcgcagagat      300 cgaagtcttg cccgaccgct ggggcagggt agcgctgcag cttaaaggtg aagttgctgc     360
aaaacttcag gaatcaatag ggacgtggag ctggcgctga gcatcagcca tgatggcgat     420
tacgccaccg cgcagtgcct gctgcggtac cagcggtaa                           459

<210> SEQ ID NO 4
<211> LENGTH: 152
<212> TYPE: PRT
<213> ORGANISM: Brevibacterium ammoniagenes

<400> SEQUENCE: 4

Met Leu Asp Asn Arg Glu  Ala Met Thr Val Gly Val  Asp Leu Val His
1               5                   10                  15

Ile Pro Gly Phe Ala Glu  Gln Leu Ser Arg Pro Gly  Ser Thr Phe Glu
            20                  25                  30

Gln Val Phe Ser Pro Leu  Glu Arg Arg His Ala Gln  Thr Arg Arg Asp
        35                  40                  45

Ala Ala Ala Asp Ala Thr  Asn Ser Ser Leu Ala Gly  Ser Arg Thr Glu
    50                  55                  60
```

```
His Leu Ala Gly Arg Trp Ala Ala Lys Glu Ala Phe Ile Lys Ala Trp
 65                  70                  75                  80

Ser Gln Ala Ile Tyr Gly Lys Pro Pro Val Ile Glu Pro Asp Leu Val
                 85                  90                  95

Asn Phe Ala Glu Ile Glu Val Leu Pro Asp Arg Trp Gly Arg Val Ala
            100                 105                 110

Leu Gln Leu Lys Gly Glu Val Ala Ala Lys Leu Gln Glu Ser Ile Asp
        115                 120                 125

Val Glu Leu Ala Leu Ser Ile Ser His Asp Gly Asp Tyr Ala Thr Ala
    130                 135                 140

Gln Cys Leu Leu Arg Tyr Gln Arg
145                 150

<210> SEQ ID NO 5
<211> LENGTH: 20
<212> TYPE: DNA
<213> ORGANISM: Artificial
<220> FEATURE:
<223> OTHER INFORMATION: PCR primer sequence

<400> SEQUENCE: 5
ccagctcaac gatgaagtag                                               20

<210> SEQ ID NO 6
<211> LENGTH: 20
<212> TYPE: DNA
<213> ORGANISM: Artificial
<220> FEATURE:
<223> OTHER INFORMATION: PCR primer sequence

<400> SEQUENCE: 6
tcgatgatct ggtctacttc                                               20

<210> SEQ ID NO 7
<211> LENGTH: 27
<212> TYPE: DNA
<213> ORGANISM: Artificial
<220> FEATURE:
<223> OTHER INFORMATION: Primer Sequence

<400> SEQUENCE: 7
gtcgacatgc tcgacaaccg tgaagcg                                       27

<210> SEQ ID NO 8
<211> LENGTH: 31
<212> TYPE: DNA
<213> ORGANISM: Artificial
<220> FEATURE:
<223> OTHER INFORMATION: Primer Sequence

<400> SEQUENCE: 8
agatcttcac tggtggcttg ccgtagatcg c                                  31

<210> SEQ ID NO 9
<211> LENGTH: 37
<212> TYPE: DNA
<213> ORGANISM: Artificial
<220> FEATURE:
<223> OTHER INFORMATION: Primer Sequence

<400> SEQUENCE: 9
tctagatgca tagttaacat gtcgttgacc cccttgc                            37
```

```
<210> SEQ ID NO 10
<211> LENGTH: 20
<212> TYPE: DNA
<213> ORGANISM: Artificial
<220> FEATURE:
<223> OTHER INFORMATION: Primer Sequence

<400> SEQUENCE: 10
ggtacgcgtc atattccttg                                               20

<210> SEQ ID NO 11
<211> LENGTH: 40
<212> TYPE: DNA
<213> ORGANISM: Artificial
<220> FEATURE:
<223> OTHER INFORMATION: Primer Sequence

<400> SEQUENCE: 11
caaggaatat gacgcgtacc ctcgaggcag aaggcggcgg                         40

<210> SEQ ID NO 12
<211> LENGTH: 37
<212> TYPE: DNA
<213> ORGANISM: Artificial
<220> FEATURE:
<223> OTHER INFORMATION: Primer Sequence

<400> SEQUENCE: 12
atgcatgtta acatgtctac tttgtcctac ttcgccg                            37

<210> SEQ ID NO 13
<211> LENGTH: 33
<212> TYPE: DNA
<213> ORGANISM: Artificial
<220> FEATURE:
<223> OTHER INFORMATION: Primer Sequence

<400> SEQUENCE: 13
gtcgacatgc atatgctcga caaccgtgaa gcg                                33

<210> SEQ ID NO 14
<211> LENGTH: 30
<212> TYPE: DNA
<213> ORGANISM: Artificial
<220> FEATURE:
<223> OTHER INFORMATION: Primer Sequence

<400> SEQUENCE: 14
agatctatgc attaccgctg gtaccgcagc                                    30

<210> SEQ ID NO 15
<211> LENGTH: 2073
<212> TYPE: PRT
<213> ORGANISM: Schizosaccharomyces pombe

<400> SEQUENCE: 15
```

| Met | Val | Glu | Ala | Glu | Gln | Val | His | Gln | Ser | Leu | Arg | Ser | Leu | Val | Leu |
|---|---|---|---|---|---|---|---|---|---|---|---|---|---|---|---|
| 1 |  |  |  | 5 |  |  |  |  | 10 |  |  |  |  | 15 |  |

| Ser | Tyr | Ala | His | Phe | Ser | Pro | Ser | Ile | Leu | Ile | Pro | Ala | Ser | Gln | Tyr |
|---|---|---|---|---|---|---|---|---|---|---|---|---|---|---|---|
|  |  |  | 20 |  |  |  |  | 25 |  |  |  |  | 30 |  |  |

| Leu | Leu | Ala | Ala | Gln | Leu | Arg | Asp | Glu | Phe | Leu | Ser | Leu | His | Pro | Ala |
|---|---|---|---|---|---|---|---|---|---|---|---|---|---|---|---|
|  |  |  | 35 |  |  |  |  | 40 |  |  |  |  | 45 |  |  |

| Pro | Ser | Ala | Glu | Ser | Val | Glu | Lys | Glu | Gly | Ala | Glu | Leu | Glu | Phe | Glu |
|---|---|---|---|---|---|---|---|---|---|---|---|---|---|---|---|
|  | 50 |  |  |  |  | 55 |  |  |  |  | 60 |  |  |  |  |

-continued

```
His Glu Leu His Leu Leu Ala Gly Phe Leu Gly Leu Ile Ala Ala Lys
 65                  70                  75                  80

Glu Glu Glu Thr Pro Gly Gln Tyr Thr Gln Leu Leu Arg Ile Ile Thr
                 85                  90                  95

Leu Glu Phe Glu Arg Thr Phe Leu Ala Gly Asn Glu Val His Ala Val
            100                 105                 110

Val His Ser Leu Gly Leu Asn Ile Pro Ala Gln Lys Asp Val Val Arg
        115                 120                 125

Phe Tyr Tyr His Ser Cys Ala Leu Ile Gly Gln Thr Thr Lys Phe His
    130                 135                 140

Gly Ser Ala Leu Leu Asp Glu Ser Ser Val Lys Leu Ala Ala Ile Phe
145                 150                 155                 160

Gly Gly Gln Gly Tyr Glu Asp Tyr Phe Asp Glu Leu Ile Glu Leu Tyr
                165                 170                 175

Glu Val Tyr Ala Pro Phe Ala Ala Glu Leu Ile Gln Val Leu Ser Lys
            180                 185                 190

His Leu Phe Thr Leu Ser Gln Asn Glu Gln Ala Ser Lys Val Tyr Ser
        195                 200                 205

Lys Gly Leu Asn Val Leu Asp Trp Leu Ala Gly Glu Arg Pro Glu Arg
    210                 215                 220

Asp Tyr Leu Val Ser Ala Pro Val Ser Leu Pro Leu Val Gly Leu Thr
225                 230                 235                 240

Gln Leu Val His Phe Ser Val Thr Ala Gln Ile Leu Gly Leu Asn Pro
                245                 250                 255

Gly Glu Leu Ala Ser Arg Phe Ser Ala Ala Ser Gly His Ser Gln Gly
            260                 265                 270

Ile Val Val Ala Ala Val Ser Ala Ser Thr Asp Ser Ala Ser Phe
        275                 280                 285

Met Glu Asn Ala Lys Val Ala Leu Thr Thr Leu Phe Trp Ile Gly Val
    290                 295                 300

Arg Ser Gln Gln Thr Phe Pro Thr Thr Thr Leu Pro Pro Ser Val Val
305                 310                 315                 320

Ala Asp Ser Leu Ala Ser Ser Glu Gly Asn Pro Thr Pro Met Leu Ala
                325                 330                 335

Val Arg Asp Leu Pro Ile Glu Thr Leu Asn Lys His Ile Glu Thr Thr
            340                 345                 350

Asn Thr His Leu Pro Glu Asp Arg Lys Val Ser Leu Ser Leu Val Asn
        355                 360                 365

Gly Pro Arg Ser Phe Val Val Ser Gly Pro Ala Arg Ser Leu Tyr Gly
    370                 375                 380

Leu Asn Leu Ser Leu Arg Lys Glu Lys Ala Asp Gly Gln Asn Gln Ser
385                 390                 395                 400

Arg Ile Pro His Ser Lys Arg Lys Leu Arg Phe Ile Asn Arg Phe Leu
                405                 410                 415

Ser Ile Ser Val Pro Phe His Ser Pro Tyr Leu Ala Pro Val Arg Ser
            420                 425                 430

Leu Leu Glu Lys Asp Leu Gln Gly Leu Gln Phe Ser Ala Leu Lys Val
        435                 440                 445

Pro Val Tyr Ser Thr Asp Asp Ala Gly Asp Leu Arg Phe Glu Gln Pro
    450                 455                 460

Ser Lys Leu Leu Leu Ala Leu Ala Val Met Ile Thr Glu Lys Val Val
465                 470                 475                 480

His Trp Glu Glu Ala Cys Gly Phe Pro Asp Val Thr His Ile Ile Asp
```

-continued

```
                485                 490                 495
Phe Gly Pro Gly Gly Ile Ser Gly Val Gly Ser Leu Thr Arg Ala Asn
            500                 505                 510
Lys Asp Gly Gln Gly Val Arg Val Ile Val Ala Asp Ser Phe Glu Ser
            515                 520                 525
Leu Asp Met Gly Ala Lys Phe Glu Ile Phe Asp Arg Asp Ala Lys Ser
            530                 535                 540
Ile Glu Phe Ala Pro Asn Trp Val Lys Leu Tyr Ser Pro Lys Leu Val
545                 550                 555                 560
Lys Asn Lys Leu Gly Arg Val Tyr Val Asp Thr Arg Leu Ser Arg Met
                565                 570                 575
Leu Gly Leu Pro Pro Leu Trp Val Ala Gly Met Thr Pro Thr Ser Val
            580                 585                 590
Pro Trp Gln Phe Cys Ser Ala Ile Ala Lys Ala Gly Phe Thr Tyr Glu
            595                 600                 605
Leu Ala Gly Gly Gly Tyr Phe Asp Pro Lys Met Met Arg Glu Ala Ile
            610                 615                 620
His Lys Leu Ser Leu Asn Ile Pro Pro Gly Ala Gly Ile Cys Val Asn
625                 630                 635                 640
Val Ile Tyr Ile Asn Pro Arg Thr Tyr Ala Trp Gln Ile Pro Leu Ile
                645                 650                 655
Arg Asp Met Val Ala Glu Gly Tyr Pro Ile Arg Gly Val Thr Ile Ala
            660                 665                 670
Ala Gly Ile Pro Ser Leu Glu Val Ala Asn Glu Leu Ile Ser Thr Leu
            675                 680                 685
Gly Val Gln Tyr Leu Cys Leu Lys Pro Gly Ser Val Glu Ala Val Asn
            690                 695                 700
Ala Val Ile Ser Ile Ala Lys Ala Asn Pro Thr Phe Pro Ile Val Leu
705                 710                 715                 720
Gln Trp Thr Gly Gly Arg Ala Gly Gly His His Ser Phe Glu Asp Phe
                725                 730                 735
His Ser Pro Ile Leu Leu Thr Tyr Ser Ala Ile Arg Arg Cys Asp Asn
            740                 745                 750
Ile Val Leu Ile Ala Gly Ser Gly Phe Gly Gly Ala Asp Asp Thr Glu
            755                 760                 765
Pro Tyr Leu Thr Gly Glu Trp Ser Ala Ala Phe Lys Leu Pro Pro Met
            770                 775                 780
Pro Phe Asp Gly Ile Leu Phe Gly Ser Arg Leu Met Val Ala Lys Glu
785                 790                 795                 800
Ala His Thr Ser Leu Ala Ala Lys Glu Ala Ile Val Ala Ala Lys Gly
                805                 810                 815
Val Asp Asp Ser Glu Trp Glu Lys Thr Tyr Asp Gly Pro Thr Gly Gly
            820                 825                 830
Ile Val Thr Val Leu Ser Glu Leu Gly Glu Pro Ile His Lys Leu Ala
            835                 840                 845
Thr Arg Gly Ile Met Phe Trp Lys Glu Leu Asp Asp Thr Ile Phe Ser
            850                 855                 860
Leu Pro Arg Pro Lys Arg Leu Pro Ala Leu Ala Lys Lys Gln Tyr
865                 870                 875                 880
Ile Ile Lys Arg Leu Asn Asp Asp Phe Gln Lys Val Tyr Phe Pro Ala
                885                 890                 895
His Ile Val Glu Gln Val Ser Pro Glu Lys Phe Lys Phe Glu Ala Val
            900                 905                 910
```

```
Asp Ser Val Glu Asp Met Thr Tyr Ala Glu Leu Leu Tyr Arg Ala Ile
        915                 920                 925

Asp Leu Met Tyr Val Thr Lys Glu Lys Arg Trp Ile Asp Val Thr Leu
    930                 935                 940

Arg Thr Phe Thr Gly Lys Leu Met Arg Arg Ile Glu Glu Arg Phe Thr
945                 950                 955                 960

Gln Asp Val Gly Lys Thr Thr Leu Ile Glu Asn Phe Gly Asp Leu Asn
            965                 970                 975

Asp Pro Tyr Pro Val Ala Ala Arg Phe Leu Asp Ala Tyr Pro Glu Ala
                980                 985                 990

Ser Thr Gln Asp Leu Asn Thr Gln Asp Ala Gln Phe Phe Tyr Ser Leu
        995                 1000                1005

Cys Ser Asn Pro Phe Gln Lys Pro Val Pro Phe Ile Pro Ala Ile
    1010                1015                1020

Asp Asp Thr Phe Glu Phe Tyr Phe Lys Lys Asp Ser Leu Trp Gln
    1025                1030                1035

Ser Glu Asp Leu Ala Ala Val Val Gly Glu Asp Val Gly Arg Val
    1040                1045                1050

Ala Ile Leu Gln Gly Pro Met Ala Ala Lys His Ser Thr Lys Val
    1055                1060                1065

Asn Glu Pro Ala Lys Glu Leu Leu Asp Gly Ile Asn Glu Thr His
    1070                1075                1080

Ile Gln His Phe Ile Lys Lys Phe Tyr Ala Gly Asp Glu Lys Lys
    1085                1090                1095

Ile Pro Ile Val Glu Tyr Phe Gly Gly Val Pro Pro Val Asn Val
    1100                1105                1110

Ser His Lys Ser Leu Glu Ser Val Ser Val Thr Glu Glu Ala Gly
    1115                1120                1125

Ser Lys Val Tyr Lys Leu Pro Glu Ile Gly Ser Asn Ser Ala Leu
    1130                1135                1140

Pro Ser Lys Lys Leu Trp Phe Glu Leu Leu Ala Gly Pro Glu Tyr
    1145                1150                1155

Thr Trp Phe Arg Ala Ile Phe Thr Thr Gln Arg Val Ala Lys Gly
    1160                1165                1170

Trp Lys Leu Glu His Asn Pro Val Arg Arg Ile Phe Ala Pro Arg
    1175                1180                1185

Tyr Gly Gln Arg Ala Val Val Lys Gly Lys Asp Asn Asp Thr Val
    1190                1195                1200

Val Glu Leu Tyr Glu Thr Gln Ser Gly Asn Tyr Val Leu Ala Ala
    1205                1210                1215

Arg Leu Ser Tyr Asp Gly Glu Thr Ile Val Val Ser Met Phe Glu
    1220                1225                1230

Asn Arg Asn Ala Leu Lys Lys Glu Val His Leu Asp Phe Leu Phe
    1235                1240                1245

Lys Tyr Glu Pro Ser Ala Gly Tyr Ser Pro Val Ser Glu Ile Leu
    1250                1255                1260

Asp Gly Arg Asn Asp Arg Ile Lys His Phe Tyr Trp Ala Leu Trp
    1265                1270                1275

Phe Gly Glu Glu Pro Tyr Pro Gly Asn Ala Ser Ile Thr Asp Thr
    1280                1285                1290

Phe Thr Gly Pro Glu Val Thr Val Thr Gly Asn Met Ile Glu Asp
    1295                1300                1305
```

-continued

```
Phe Cys Arg Thr Val Gly Asn His Asn Glu Ala Tyr Thr Lys Arg
1310                1315                1320

Ala Ile Arg Lys Arg Met Ala Pro Met Asp Phe Ala Ile Val Val
1325                1330                1335

Gly Trp Gln Ala Ile Thr Lys Ala Ile Phe Pro Lys Ala Ile Asp
1340                1345                1350

Gly Asp Leu Leu Arg Leu Val His Leu Ser Asn Ser Phe Arg Met
1355                1360                1365

Val Gly Ser His Ser Leu Met Glu Gly Asp Lys Val Thr Thr Ser
1370                1375                1380

Ala Ser Ile Ile Ala Ile Leu Asn Asn Asp Ser Gly Lys Thr Val
1385                1390                1395

Thr Val Lys Gly Thr Val Tyr Arg Asp Gly Lys Glu Val Ile Glu
1400                1405                1410

Val Ile Ser Arg Phe Leu Tyr Arg Gly Thr Phe Thr Asp Phe Glu
1415                1420                1425

Asn Thr Phe Glu His Thr Gln Glu Thr Pro Met Gln Leu Thr Leu
1430                1435                1440

Ala Thr Pro Lys Asp Val Ala Val Leu Gln Ser Lys Ser Trp Phe
1445                1450                1455

Gln Leu Leu Asp Pro Ser Gln Asp Leu Ser Gly Ser Ile Leu Thr
1460                1465                1470

Phe Arg Leu Asn Ser Tyr Val Arg Phe Lys Asp Gln Lys Val Lys
1475                1480                1485

Ser Ser Val Glu Thr Lys Gly Ile Val Leu Ser Glu Leu Pro Ser
1490                1495                1500

Lys Ala Ile Ile Gln Val Ala Ser Val Asp Phe Gln Ser Val Asp
1505                1510                1515

Cys His Gly Asn Pro Val Ile Glu Phe Leu Lys Arg Asn Gly Lys
1520                1525                1530

Pro Ile Glu Gln Pro Val Glu Phe Glu Asn Gly Gly Tyr Ser Val
1535                1540                1545

Ile Gln Val Met Asp Glu Gly Tyr Ser Pro Val Phe Val Thr Pro
1550                1555                1560

Pro Thr Asn Ser Pro Tyr Ala Glu Val Ser Gly Asp Tyr Asn Pro
1565                1570                1575

Ile His Val Ser Pro Thr Phe Ala Ala Phe Val Glu Leu Pro Gly
1580                1585                1590

Thr His Gly Ile Thr His Gly Met Tyr Thr Ser Ala Ala Ala Arg
1595                1600                1605

Arg Phe Val Glu Thr Tyr Ala Ala Gln Asn Val Pro Glu Arg Val
1610                1615                1620

Lys His Tyr Glu Val Thr Phe Val Asn Met Val Leu Pro Asn Thr
1625                1630                1635

Glu Leu Ile Thr Lys Leu Ser His Thr Gly Met Ile Asn Gly Arg
1640                1645                1650

Lys Ile Ile Lys Val Glu Val Leu Asn Gln Glu Thr Ser Glu Pro
1655                1660                1665

Val Leu Val Gly Thr Ala Glu Val Glu Gln Pro Val Ser Ala Tyr
1670                1675                1680

Val Phe Thr Gly Gln Gly Ser Gln Glu Gln Gly Met Gly Met Asp
1685                1690                1695

Leu Tyr Ala Ser Ser Pro Val Ala Arg Lys Ile Trp Asp Ser Ala
```

```
                1700                1705                1710

Asp Lys His Phe Leu Thr Asn Tyr Gly Phe Ser Ile Ile Asp Ile
1715                1720                1725

Val Lys His Asn Pro His Ser Ile Thr Ile His Phe Gly Gly Ser
1730                1735                1740

Lys Gly Lys Lys Ile Arg Asp Asn Tyr Met Ala Met Ala Tyr Glu
1745                1750                1755

Lys Leu Met Glu Asp Gly Thr Ser Lys Val Val Pro Val Phe Glu
1760                1765                1770

Thr Ile Thr Lys Asp Ser Thr Ser Phe Ser Phe Thr His Pro Ser
1775                1780                1785

Gly Leu Leu Ser Ala Thr Gln Phe Thr Gln Pro Ala Leu Thr Leu
1790                1795                1800

Met Glu Lys Ser Ala Phe Glu Asp Met Arg Ser Lys Gly Leu Val
1805                1810                1815

Gln Asn Asp Cys Ala Phe Ala Gly His Ser Leu Gly Glu Tyr Ser
1820                1825                1830

Ala Leu Ser Ala Met Gly Asp Val Leu Ser Ile Glu Ala Leu Val
1835                1840                1845

Asp Leu Val Phe Leu Arg Gly Leu Thr Met Gln Asn Ala Val His
1850                1855                1860

Arg Asp Glu Leu Gly Arg Ser Asp Tyr Gly Met Val Ala Ala Asn
1865                1870                1875

Pro Ser Arg Val Ser Ala Ser Phe Thr Asp Ala Ala Leu Arg Phe
1880                1885                1890

Ile Val Asp His Ile Gly Gln Gln Thr Asn Leu Leu Glu Ile
1895                1900                1905

Val Asn Tyr Asn Val Glu Asn Gln Gln Tyr Val Val Ser Gly Asn
1910                1915                1920

Leu Leu Ser Leu Ser Thr Leu Gly His Val Leu Asn Phe Leu Lys
1925                1930                1935

Val Gln Lys Ile Asp Phe Glu Lys Leu Lys Glu Thr Leu Thr Ile
1940                1945                1950

Glu Gln Leu Lys Glu Gln Leu Thr Asp Ile Val Glu Ala Cys His
1955                1960                1965

Ala Lys Thr Leu Glu Gln Gln Lys Lys Thr Gly Arg Ile Glu Leu
1970                1975                1980

Glu Arg Gly Tyr Ala Thr Ile Pro Leu Lys Ile Asp Val Pro Phe
1985                1990                1995

His Ser Ser Phe Leu Arg Gly Gly Val Arg Met Phe Arg Glu Tyr
2000                2005                2010

Leu Val Lys Lys Ile Phe Pro His Gln Ile Asn Val Ala Lys Leu
2015                2020                2025

Arg Gly Lys Tyr Ile Pro Asn Leu Thr Ala Lys Pro Phe Glu Ile
2030                2035                2040

Ser Lys Glu Tyr Phe Gln Asn Val Tyr Asp Leu Thr Gly Ser Gln
2045                2050                2055

Arg Ile Lys Lys Ile Leu Gln Asn Trp Asp Glu Tyr Glu Ser Ser
2060                2065                2070

<210> SEQ ID NO 16
<211> LENGTH: 6232
<212> TYPE: DNA
<213> ORGANISM: Schizosaccharomyces pombe
```

<400> SEQUENCE: 16

```
aagcttacta tactgtgtag tagagagtga taaaatgtta attatgccac aagcagttgc      60
taattcgcta tatttgataa cgatgcgtta aatattcgtt acatgcttca aagctgatag     120
gtttaacctg agtgttccca cgcgatagta aaggatcaag ttaactagaa ccaacaacta     180
aagcaggtgt tggagttttg ttaaaccatt tgaataatga gaccagaagt tgagcaggag     240
cttgctcata ctttattatt ggagttgctt gcataccagt ttgcatctcc tgtccgttgg     300
attgagacgc aagatgtaat tctttctcct ccagtatcgg ctgaacgtat cgtcgaaatt     360
ggacctagtc ctaccttagc tggtatggct aagcgtacct tgaaattgaa atatgagaac     420
atggatgccg ctttaagtat taatcgtgaa gttctttgct actctaaaga tgctcgtgaa     480
atctattaca actttgagga cgaggttgct gatgaacctg ccgaagcccc agcttcaacc     540
agctccactc caaaggttga aactgctgct gctgccgctc ccgctgccac gccagcccct     600
gccccagcac aaacatcagc cccagctgct gctttacctg acgagcctcc caaagctctt     660
gaggtacttc atactcttgt tgcccaaaag ttgaagaaaa gcatcgagga agtctcccct     720
caaaaatcta tcaaagattt ggttggcggt aagtccactt tgcaaaacga aattcttggt     780
gatttacaga aggagttcgg tgccactccc gagaagccag aggaggttcc attggatgag     840
cttggagcta tcatgcagtc aagctttaac ggatctcttg gtaaacaatc gtcttctctt     900
atctcacgaa tgatttcctc aaaaatgcct ggtggtttca ataattctgc tgttcgtggt     960
tatttaggaa accgttatgg tttgggtcct ggtcgtttgg agtctgtgct tttgttagcg    1020
cttaccatgg aacctgcatc acgtttgggc tcggaagctg atgctaaagc ttggcttgat    1080
agtgtagctc aaaaatatgc tgctcgtaat ggtgttacat tatcttctcc tactgctgaa    1140
ggcggttctt cgtccggttc tgcagctgtt atcgatgaag aaacctttaa gaaactcacc    1200
aagaataata ccatgcttgt tactcagcaa ttagaactat ttgctcgata cctcaataaa    1260
gaccttcgtg ctggccaaaa ggctcaagtt gctgaaaagg ttatttccga taccttacgc    1320
gctcaattag atttatggaa cgaagaacat ggtgaatttt atgcatcagg aattgctcct    1380
atttttcgc ctttaaaagc tcgcgtttac gactccgact ggaattgggc tcgtcaagat    1440
gctcttaaga tgttttttga cattatcttt ggtcgtctta ggcatgttga tactgaaata    1500
gtcgctcgtt gtatttctgt tatgaataga tccaacccta ctttacttga atttatgcaa    1560
tatcatattg atcattgtcc cgccgaaaag ggtgaaacat atcaacttgc taaaaccttg    1620
ggccaacagc taattgataa ttgcaaatcc gtgatagatg ctcctccagt tttcaaaaat    1680
gtgaatcatc caactgctcc ttctacgacg attgacgaac gtggtaattt gaattatgaa    1740
gaaatcccta gaccaggtgt tcgcaaatta actcattacg ttactgagat ggccaaaggt    1800
ggtaaattac caacggagtc caaaaacaaa gctaaggtac aaaacgattt ggctcgaatt    1860
tatcgcatta ttaagtctca aaacaaaatg tctcgttcgt ctaagttgca gattaaacag    1920
ttgtacggtc aggttttaca tgcccttttcc cttccattgc cttcttccaa cgatgaacaa    1980
acgcctgtta aagaaaccat tcctttcctt catattagga agaagtccgt tgatggtaat    2040
tgggaattca acaagtcatt gactggcact tatttgagatg ttttagaatc gggtgctaag    2100
aatggtataa cataccaaga caaatatgct ctagtgactg gtgcaggtgc aggctccatt    2160
ggtgctcaga ttgttgaagg tctccttgct ggtggtgcta agttgtagt tactacatcc    2220
cggttttcgc gcaaggttac tgaattttat caatcccttg acacccgcca tggaagccgt    2280
```

```
ggttcatgtc tgatcgtggt tccatttaac caaggatcta agacagacgt agaagctctt    2340
attgattata tttatgacga aaagaagggt cttggatgga acttggacta cattgttcct    2400
ttcgctgcca ttccagaaaa tggtcgtgaa attgatggca ttgattctcg ttccgagttt    2460
gctcaccgta ttatgttgac aaacattttg agactgcttg gcgccgtcaa aagtcaaaag    2520
gcctctcgtg gtatggatac ccgacccgct caagttattt tgcctctttc tcccaatcac    2580
ggtacctttg gaaacgatgg tttatactcg gaatctaagt taggtttaga aactttgttt    2640
aaccgttggt actccgagtc atgggctaat tacctaacca tttgtggggc tgtcattggt    2700
tggactcgtg gtacaggctt aatggcacct aataatattg tttctcaggg aatcgaaaaa    2760
tatggtgttc gtactttttc gcagagtgag atggctttta acattttggg tttgatgtcc    2820
cagaaagtcg tcgacttgtg tcaatctgaa ccaatttatg ccaaccttaa cggtggtctt    2880
gagcttttac ctgatctcaa ggacctttcc actcgtttgc gtaccgaatt gttagaaact    2940
gccgaaatcc gccgcgctgt tgccgcagag actgcctttg atcatagcat taccaacgga    3000
cctgactctg aagcagtttt ccagaaaact gccattcagc ctagggccaa tcttaaattt    3060
aatttccccca aattgaaacc ttatgaagcc ctttctcatt tatctgatct tcgtggaatg    3120
gttgatttag aaaaagttcc tgttgttact ggttttttccg aagtaggtcc atggggtaac    3180
tctcgtacta gatgggatat ggagtgttat ggtgagtttt cactagaagg atgtgtcgaa    3240
attgcttgga ttatgggatt aattaaaaac ttcaatggca agggcaaaga cggcaagccc    3300
tattcaggtt gggttgatac aaagaccggt gaacctgtgg acgacaaaga cgttaaagct    3360
aagtatgaga agtatatact ggagcattgc ggtatccgta ttattgaagc tgaactcttc    3420
catggatata atcctgaaaa gaaagagctt ttgcaagaag ttgttattga tcatgactta    3480
gagccttttg aagcatccaa agaggctgct catgagttca agcttcgtca tggtgatcaa    3540
gttgaaattt ttgaaattcc tgattctacc gaatggtccg tacgcttcaa gcgcggtaca    3600
agtatgctaa ttcctaaggc tttgcgcttt gatcgatttg ttgctggcca gattccactt    3660
ggttgggatc ccaaacgtta tggcattcct gacgatatta tttctcaagt tgaccctaca    3720
actttgtacg ttttagtgtc tactgtagaa gctctggttg catcaggtat tacagatcct    3780
tatgaatgct ataagtatat tcacgtatct gaacttggta atacagttgg ttctggtatt    3840
ggtggtatgt ctgctcttcg tggaatgtac aaggaccgct ggactgataa acctgttcaa    3900
aaagatattt tacaagaatc attcattaac actgccaatg cttggattaa catgcttttg    3960
ctctctgcct ctggtcctat taagactcct gttggtgctt gcgctaccgc tgtcgaatct    4020
gttgatgcag ctgtcgactt gatcacttct ggtaaggcca ggatatgtat tagcggtggt    4080
tatgacgact tttcagaaga aggttcatac gagtttgcga acatgggtgc tacatcaaat    4140
gctgctaagg aaacagaaag gggacgtact cctcaagaaa tgtctcgtcc tgctacttct    4200
actcgtgatg gatttatgga gtctcaaggt gctggtgtac agattatcat gcaagcaaag    4260
cttgctattg agatgggtgt ccctatacat ggtattgttg ttatgtttc cacagctatg    4320
gataaacaag tcgttcggt tcctgcccct gggcaaggta ttttgactgg tgctcgtgaa    4380
atcgcgacta agacacccct tcccatagtt gaccttaaat tccgttctcg tcaactccaa    4440
cgccgccgtt ctcaaattgg tgaatgggcc gaacgcgagt atctttattt agaagaagaa    4500
cttgatgcga tgaaggttca aaatcctgac ttggatttag aggcttaccg tatagagcgt    4560
atcaacgtta ttaaggagga ggttgttcga caagaaaagg aggcgctcaa tacttttgga    4620
aatgaatttt ggaaacgtga tcctactatt gctcctatcc gtggtgcatt agctgttttgg    4680
```

-continued

```
ggtcttacta ttgacgattt gggcgttgca tcattccatg gtacctctac caaagccaat    4740
gagaagaatg aatgcgatgt cattgacagt cagttaacac atctcggacg ctctaagggt    4800
aacgctgtgt acggtgtttt ccagaaatat ctcactggac atagcaaggg tggtgctgga    4860
gcttggatgc tcaacggagc tctccaaatt cttcgctctg gtttgttcc gggtaatcgt     4920 aacgccgata acattgatga gtatctagca cgattcgacc gggttatgtt ccctagtgaa    4980
ggtatacaaa ctgatggcat aaaggcagca tctgttactg catttggttt tggacaagtt    5040
ggtggacaag ttatagttat ccatcctgat tacatttacg gtgtgattga tgaggctact    5100
tataatgctt acaaagctaa aactgctgct cgttataagg catcttatcg ttacacccac    5160
gatgcgctgg tttacaacaa tttggtccgc gccaaggatt ctcctcctta caccaaagaa    5220
caagagaaag ccgtttatct caatcctttg gcacgcgctt cgaagagcaa agctggcact    5280
tggactttcc ctgccacact gcctgctgaa tccgacattt ctaaaaccaa cgaaactaca    5340
cgtactctac aaagcctaac aacctcattg accaactcca atgaaaatgt tggcgtggat    5400
gttgaacttg tatcagcgat tagcattgat aatgagacct ttatagaaag gaattttact    5460
gataccgagc gaaagtactg ttttgcagct cctaatcccc aagctagctt tgccggacgt    5520
tggtcagcca agaggctgt ctttaagtct ttgggtattt ccggtaaagg cgctgcagct    5580
ccattgaagg atatcgaaat tatttcttca gagtctggtg ctcctgaagt agttttgcac    5640
ggagaggctg cgaaggctgc aacgaccgcc ggtgtgaaga gtgtttccgt cagtatttcc    5700
cacgatgata atcaaagtgt cagtgttgct ttggctcaca gtaatttac gttatattgt     5760 ctttcaacat tggtatgcgg attttcgcat tcccttcaat cgtttgattt aatacactat    5820
ctttaatctt tttgtttacc tcaaatgctt tgaaatggtt atcgattttt gtagtcgtta    5880
tatacgcagt tagaaataaa ttactttttaa ccttataaat tattatgctc taaaaaaatg    5940
cagtatcatt aaatttaaac gaatgtcctt acacgtatga gtatttaaac tgatattgag    6000
ttatcttcat aaatttctga agccaggcag cggttgttgt tcatcgaaa gaaatggggt      6060 tcatatatgc tgttgaagtg ttttgctcga acaaaatttc agttagatgc ttaatcactg    6120
tccaaccgta agcattcgga aaccgcctac gacaatcatg gtattgtgtg catcaccatc    6180
gagtctaaca gcaaccttc tccacgcaag cctatgccag ttttggcaa tg              6232
```

<210> SEQ ID NO 17
<211> LENGTH: 1842
<212> TYPE: PRT
<213> ORGANISM: Schizosaccharomyces pombe

<400> SEQUENCE: 17

```
Met Arg Pro Glu Val Glu Gln Glu Leu Ala His Thr Leu Leu Leu Glu
1               5                   10                  15

Leu Leu Ala Tyr Gln Phe Ala Ser Pro Val Arg Trp Ile Glu Thr Gln
            20                  25                  30

Asp Val Ile Leu Ser Pro Pro Val Ser Ala Glu Arg Ile Val Glu Ile
        35                  40                  45

Gly Pro Ser Pro Thr Leu Ala Gly Met Ala Lys Arg Thr Leu Lys Leu
    50                  55                  60

Lys Tyr Glu Asn Met Asp Ala Ala Leu Ser Ile Asn Arg Glu Val Leu
65                  70                  75                  80

Cys Tyr Ser Lys Asp Ala Arg Glu Ile Tyr Tyr Asn Phe Glu Asp Glu
                85                  90                  95
```

-continued

```
Val Ala Asp Glu Pro Ala Glu Ala Pro Ala Ser Thr Ser Ser Thr Pro
            100                 105                 110

Lys Val Glu Thr Ala Ala Ala Ala Pro Ala Ala Thr Pro Ala Pro
            115                 120                 125

Ala Pro Ala Gln Thr Ser Ala Pro Ala Ala Leu Pro Asp Glu Pro
            130                 135                 140

Pro Lys Ala Leu Glu Val Leu His Thr Leu Val Ala Gln Lys Leu Lys
145                 150                 155                 160

Lys Ser Ile Glu Glu Val Ser Pro Gln Lys Ser Ile Lys Asp Leu Val
                165                 170                 175

Gly Gly Lys Ser Thr Leu Gln Asn Glu Ile Leu Gly Asp Leu Gln Lys
            180                 185                 190

Glu Phe Gly Ala Thr Pro Glu Lys Pro Glu Glu Val Pro Leu Asp Glu
            195                 200                 205

Leu Gly Ala Ile Met Gln Ser Ser Phe Asn Gly Ser Leu Gly Lys Gln
            210                 215                 220

Ser Ser Ser Leu Ile Ser Arg Met Ile Ser Ser Lys Met Pro Gly Gly
225                 230                 235                 240

Phe Asn Asn Ser Ala Val Arg Gly Tyr Leu Gly Asn Arg Tyr Gly Leu
                245                 250                 255

Gly Pro Gly Arg Leu Glu Ser Val Leu Leu Leu Ala Leu Thr Met Glu
            260                 265                 270

Pro Ala Ser Arg Leu Gly Ser Glu Ala Asp Ala Lys Ala Trp Leu Asp
            275                 280                 285

Ser Val Ala Gln Lys Tyr Ala Ala Arg Asn Gly Val Thr Leu Ser Ser
            290                 295                 300

Pro Thr Ala Glu Gly Gly Ser Ser Gly Ser Ala Ala Val Ile Asp
305                 310                 315                 320

Glu Glu Thr Phe Lys Lys Leu Thr Lys Asn Asn Thr Met Leu Val Thr
                325                 330                 335

Gln Gln Leu Glu Leu Phe Ala Arg Tyr Leu Asn Lys Asp Leu Arg Ala
            340                 345                 350

Gly Gln Lys Ala Gln Val Ala Glu Lys Val Ile Ser Asp Thr Leu Arg
            355                 360                 365

Ala Gln Leu Asp Leu Trp Asn Glu Glu His Gly Glu Phe Tyr Ala Ser
            370                 375                 380

Gly Ile Ala Pro Ile Phe Ser Pro Leu Lys Ala Arg Val Tyr Asp Ser
385                 390                 395                 400

Asp Trp Asn Trp Ala Arg Gln Asp Ala Leu Lys Met Phe Phe Asp Ile
                405                 410                 415

Ile Phe Gly Arg Leu Arg His Val Asp Thr Glu Ile Val Ala Arg Cys
            420                 425                 430

Ile Ser Val Met Asn Arg Ser Asn Pro Thr Leu Leu Glu Phe Met Gln
            435                 440                 445

Tyr His Ile Asp His Cys Pro Ala Glu Lys Gly Glu Thr Tyr Gln Leu
            450                 455                 460

Ala Lys Thr Leu Gly Gln Gln Leu Ile Asp Asn Cys Lys Ser Val Ile
465                 470                 475                 480

Asp Ala Pro Pro Val Phe Lys Asn Val Asn His Pro Thr Ala Pro Ser
                485                 490                 495

Thr Thr Ile Asp Glu Arg Gly Asn Leu Asn Tyr Glu Glu Ile Pro Arg
            500                 505                 510

Pro Gly Val Arg Lys Leu Thr His Tyr Val Thr Glu Met Ala Lys Gly
```

-continued

```
            515                 520                 525
Gly Lys Leu Pro Thr Glu Ser Lys Asn Lys Ala Lys Val Gln Asn Asp
        530                 535                 540

Leu Ala Arg Ile Tyr Arg Ile Ile Lys Ser Gln Asn Lys Met Ser Arg
545                 550                 555                 560

Ser Ser Lys Leu Gln Ile Lys Gln Leu Tyr Gly Gln Val Leu His Ala
                565                 570                 575

Leu Ser Leu Pro Leu Pro Ser Ser Asn Asp Glu Gln Thr Pro Val Lys
                580                 585                 590

Glu Thr Ile Pro Phe Leu His Ile Arg Lys Lys Ser Val Asp Gly Asn
            595                 600                 605

Trp Glu Phe Asn Lys Ser Leu Thr Gly Thr Tyr Leu Asp Val Leu Glu
        610                 615                 620

Ser Gly Ala Lys Asn Gly Ile Thr Tyr Gln Asp Lys Tyr Ala Leu Val
625                 630                 635                 640

Thr Gly Ala Gly Ala Gly Ser Ile Gly Ala Gln Ile Val Glu Gly Leu
                645                 650                 655

Leu Ala Gly Gly Ala Lys Val Val Val Thr Thr Ser Arg Phe Ser Arg
            660                 665                 670

Lys Val Thr Glu Phe Tyr Gln Ser Leu Tyr Thr Arg His Gly Ser Arg
        675                 680                 685

Gly Ser Cys Leu Ile Val Val Pro Phe Asn Gln Gly Ser Lys Thr Asp
        690                 695                 700

Val Glu Ala Leu Ile Asp Tyr Ile Tyr Asp Glu Lys Lys Gly Leu Gly
705                 710                 715                 720

Trp Asn Leu Asp Tyr Ile Val Pro Phe Ala Ala Ile Pro Glu Asn Gly
                725                 730                 735

Arg Glu Ile Asp Gly Ile Asp Ser Arg Ser Glu Phe Ala His Arg Ile
            740                 745                 750

Met Leu Thr Asn Ile Leu Arg Leu Leu Gly Ala Val Lys Ser Gln Lys
        755                 760                 765

Ala Ser Arg Gly Met Asp Thr Arg Pro Ala Gln Val Ile Leu Pro Leu
        770                 775                 780

Ser Pro Asn His Gly Thr Phe Gly Asn Asp Gly Leu Tyr Ser Glu Ser
785                 790                 795                 800

Lys Leu Gly Leu Glu Thr Leu Phe Asn Arg Trp Tyr Ser Glu Ser Trp
                805                 810                 815

Ala Asn Tyr Leu Thr Ile Cys Gly Ala Val Ile Gly Trp Thr Arg Gly
            820                 825                 830

Thr Gly Leu Met Ala Pro Asn Asn Ile Val Ser Gln Gly Ile Glu Lys
        835                 840                 845

Tyr Gly Val Arg Thr Phe Ser Gln Ser Glu Met Ala Phe Asn Ile Leu
        850                 855                 860

Gly Leu Met Ser Gln Lys Val Val Asp Leu Cys Gln Ser Glu Pro Ile
865                 870                 875                 880

Tyr Ala Asn Leu Asn Gly Gly Leu Glu Leu Leu Pro Asp Leu Lys Asp
                885                 890                 895

Leu Ser Thr Arg Leu Arg Thr Glu Leu Leu Glu Thr Ala Glu Ile Arg
            900                 905                 910

Arg Ala Val Ala Ala Glu Thr Ala Phe Asp His Ser Ile Thr Asn Gly
        915                 920                 925

Pro Asp Ser Glu Ala Val Phe Gln Lys Thr Ala Ile Gln Pro Arg Ala
        930                 935                 940
```

```
Asn Leu Lys Phe Asn Phe Pro Lys Leu Lys Pro Tyr Glu Ala Leu Ser
945                 950                 955                 960

His Leu Ser Asp Leu Arg Gly Met Val Asp Leu Glu Lys Val Pro Val
            965                 970                 975

Val Thr Gly Phe Ser Glu Val Gly Pro Trp Gly Asn Ser Arg Thr Arg
        980                 985                 990

Trp Asp Met Glu Cys Tyr Gly Glu Phe Ser Leu Glu Gly Cys Val Glu
        995                 1000                1005

Ile Ala Trp Ile Met Gly Leu Ile Lys Asn Phe Asn Gly Lys Gly
    1010                1015                1020

Lys Asp Gly Lys Pro Tyr Ser Gly Trp Val Asp Thr Lys Thr Gly
    1025                1030                1035

Glu Pro Val Asp Asp Lys Asp Val Lys Ala Lys Tyr Glu Lys Tyr
    1040                1045                1050

Ile Leu Glu His Cys Gly Ile Arg Ile Ile Glu Ala Glu Leu Phe
    1055                1060                1065

His Gly Tyr Asn Pro Glu Lys Lys Glu Leu Leu Gln Glu Val Val
    1070                1075                1080

Ile Asp His Asp Leu Glu Pro Phe Glu Ala Ser Lys Glu Ala Ala
    1085                1090                1095

His Glu Phe Lys Leu Arg His Gly Asp Gln Val Glu Ile Phe Glu
    1100                1105                1110

Ile Pro Asp Ser Thr Glu Trp Ser Val Arg Phe Lys Arg Gly Thr
    1115                1120                1125

Ser Met Leu Ile Pro Lys Ala Leu Arg Phe Asp Arg Phe Val Ala
    1130                1135                1140

Gly Gln Ile Pro Leu Gly Trp Asp Pro Lys Arg Tyr Gly Ile Pro
    1145                1150                1155

Asp Asp Ile Ile Ser Gln Val Asp Pro Thr Thr Leu Tyr Val Leu
    1160                1165                1170

Val Ser Thr Val Glu Ala Leu Val Ala Ser Gly Ile Thr Asp Pro
    1175                1180                1185

Tyr Glu Cys Tyr Lys Tyr Ile His Val Ser Glu Leu Gly Asn Thr
    1190                1195                1200

Val Gly Ser Gly Ile Gly Gly Met Ser Ala Leu Arg Gly Met Tyr
    1205                1210                1215

Lys Asp Arg Trp Thr Asp Lys Pro Val Gln Lys Asp Ile Leu Gln
    1220                1225                1230

Glu Ser Phe Ile Asn Thr Ala Asn Ala Trp Ile Asn Met Leu Leu
    1235                1240                1245

Leu Ser Ala Ser Gly Pro Ile Lys Thr Pro Val Gly Ala Cys Ala
    1250                1255                1260

Thr Ala Val Glu Ser Val Asp Ala Ala Val Asp Leu Ile Thr Ser
    1265                1270                1275

Gly Lys Ala Arg Ile Cys Ile Ser Gly Gly Tyr Asp Asp Phe Ser
    1280                1285                1290

Glu Glu Gly Ser Tyr Glu Phe Ala Asn Met Gly Ala Thr Ser Asn
    1295                1300                1305

Ala Ala Lys Glu Thr Glu Arg Gly Arg Thr Pro Gln Glu Met Ser
    1310                1315                1320

Arg Pro Ala Thr Ser Thr Arg Asp Gly Phe Met Glu Ser Gln Gly
    1325                1330                1335
```

```
Ala Gly Val Gln Ile Ile Met Gln Ala Lys Leu Ala Ile Glu Met
    1340                1345                1350

Gly Val Pro Ile His Gly Ile Val Gly Tyr Val Ser Thr Ala Met
    1355                1360                1365

Asp Lys Gln Gly Arg Ser Val Pro Ala Pro Gly Gln Gly Ile Leu
    1370                1375                1380

Thr Gly Ala Arg Glu Ile Ala Thr Lys Thr Pro Leu Pro Ile Val
    1385                1390                1395

Asp Leu Lys Phe Arg Ser Arg Gln Leu Gln Arg Arg Arg Ser Gln
    1400                1405                1410

Ile Gly Glu Trp Ala Glu Arg Glu Tyr Leu Tyr Leu Glu Glu Glu
    1415                1420                1425

Leu Asp Ala Met Lys Val Gln Asn Pro Asp Leu Asp Leu Glu Ala
    1430                1435                1440

Tyr Arg Ile Glu Arg Ile Asn Val Ile Lys Glu Val Val Arg
    1445                1450                1455

Gln Glu Lys Glu Ala Leu Asn Thr Phe Gly Asn Glu Phe Trp Lys
    1460                1465                1470

Arg Asp Pro Thr Ile Ala Pro Ile Arg Gly Ala Leu Ala Val Trp
    1475                1480                1485

Gly Leu Thr Ile Asp Asp Leu Gly Val Ala Ser Phe His Gly Thr
    1490                1495                1500

Ser Thr Lys Ala Asn Glu Lys Asn Glu Cys Asp Val Ile Asp Ser
    1505                1510                1515

Gln Leu Thr His Leu Gly Arg Ser Lys Gly Asn Ala Val Tyr Gly
    1520                1525                1530

Val Phe Gln Lys Tyr Leu Thr Gly His Ser Lys Gly Gly Ala Gly
    1535                1540                1545

Ala Trp Met Leu Asn Gly Ala Leu Gln Ile Leu Arg Ser Gly Phe
    1550                1555                1560

Val Pro Gly Asn Arg Asn Ala Asp Asn Ile Asp Glu Tyr Leu Ala
    1565                1570                1575

Arg Phe Asp Arg Val Met Phe Pro Ser Glu Gly Ile Gln Thr Asp
    1580                1585                1590

Gly Ile Lys Ala Ala Ser Val Thr Ala Phe Gly Phe Gly Gln Val
    1595                1600                1605

Gly Gly Gln Val Ile Val Ile His Pro Asp Tyr Ile Tyr Gly Val
    1610                1615                1620

Ile Asp Glu Ala Thr Tyr Asn Ala Tyr Lys Ala Lys Thr Ala Ala
    1625                1630                1635

Arg Tyr Lys Ala Ser Tyr Arg Tyr Thr His Asp Ala Leu Val Tyr
    1640                1645                1650

Asn Asn Leu Val Arg Ala Lys Asp Ser Pro Pro Tyr Thr Lys Glu
    1655                1660                1665

Gln Glu Lys Ala Val Tyr Leu Asn Pro Leu Ala Arg Ala Ser Lys
    1670                1675                1680

Ser Lys Ala Gly Thr Trp Thr Phe Pro Ala Thr Leu Pro Ala Glu
    1685                1690                1695

Ser Asp Ile Ser Lys Thr Asn Glu Thr Thr Arg Thr Leu Gln Ser
    1700                1705                1710

Leu Thr Thr Ser Leu Thr Asn Ser Asn Glu Asn Val Gly Val Asp
    1715                1720                1725

Val Glu Leu Val Ser Ala Ile Ser Ile Asp Asn Glu Thr Phe Ile
```

```
        1730                1735                1740

Glu Arg Asn Phe Thr Asp Thr Glu Arg Lys Tyr Cys Phe Ala Ala
    1745                1750                1755

Pro Asn Pro Gln Ala Ser Phe Ala Gly Arg Trp Ser Ala Lys Glu
    1760                1765                1770

Ala Val Phe Lys Ser Leu Gly Ile Ser Gly Lys Gly Ala Ala Ala
    1775                1780                1785

Pro Leu Lys Asp Ile Glu Ile Ile Ser Ser Glu Ser Gly Ala Pro
    1790                1795                1800

Glu Val Val Leu His Gly Glu Ala Ala Lys Ala Ala Thr Thr Ala
    1805                1810                1815

Gly Val Lys Ser Val Ser Val Ser Ile Ser His Asp Asp Asn Gln
    1820                1825                1830

Ser Val Ser Val Ala Leu Ala His Lys
    1835                1840

<210> SEQ ID NO 18
<211> LENGTH: 2051
<212> TYPE: PRT
<213> ORGANISM: Saccharomyces cerevisiae

<400> SEQUENCE: 18

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
                100                 105                 110

Asp Thr Thr Leu Val Lys Thr Lys Glu Leu Ile Lys Asn Tyr Ile Thr
            115                 120                 125

Ala Arg Ile Met Ala Lys Arg Pro Phe Asp Lys Lys Ser Asn Ser Ala
        130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
    210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255
```

-continued

```
Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Val Ser Val Arg Lys Ala Ile Thr Val Leu Phe
    290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Gly Val Pro Ser
            325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
        355                 360                 365

Ser Leu Val Asn Gly Ala Lys Asn Leu Val Val Ser Gly Pro Pro Gln
    370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
            405                 410                 415

Ser Asn Arg Phe Leu Pro Val Ala Ser Pro Phe His Ser His Leu Leu
            420                 425                 430

Val Pro Ala Ser Asp Leu Ile Asn Lys Asp Leu Val Lys Asn Asn Val
        435                 440                 445

Ser Phe Asn Ala Lys Asp Ile Gln Ile Pro Val Tyr Asp Thr Phe Asp
    450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
            485                 490                 495

Lys Ala Thr His Ile Leu Asp Phe Gly Pro Gly Gly Ala Ser Gly Leu
            500                 505                 510

Gly Val Leu Thr His Arg Asn Lys Asp Gly Thr Gly Val Arg Val Ile
        515                 520                 525

Val Ala Gly Thr Leu Asp Ile Asn Pro Asp Asp Tyr Gly Phe Lys
    530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
            565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
        595                 600                 605

Ala Thr Thr Asn Ala Gly Tyr Thr Ile Glu Leu Ala Gly Gly Gly Tyr
    610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
            645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
```

-continued

```
            675                 680                 685
Glu Val Ala Ser Glu Tyr Ile Glu Thr Leu Gly Leu Lys Tyr Leu Gly
690                 695                 700
Leu Lys Pro Gly Ser Ile Asp Ala Ile Ser Gln Val Ile Asn Ile Ala
705                 710                 715                 720
Lys Ala His Pro Asn Phe Pro Ile Ala Leu Gln Trp Thr Gly Gly Arg
                    725                 730                 735
Gly Gly Gly His His Ser Phe Glu Asp Ala His Thr Pro Met Leu Gln
                740                 745                 750
Met Tyr Ser Lys Ile Arg Arg His Pro Asn Ile Met Leu Ile Phe Gly
            755                 760                 765
Ser Gly Phe Gly Ser Ala Asp Asp Thr Tyr Pro Tyr Leu Thr Gly Glu
        770                 775                 780
Trp Ser Thr Lys Phe Asp Tyr Pro Pro Met Pro Phe Asp Gly Phe Leu
785                 790                 795                 800
Phe Gly Ser Arg Val Met Ile Ala Lys Glu Val Lys Thr Ser Pro Asp
                    805                 810                 815
Ala Lys Lys Cys Ile Ala Ala Cys Thr Gly Val Pro Asp Asp Lys Trp
                820                 825                 830
Glu Gln Thr Tyr Lys Lys Pro Thr Gly Gly Ile Val Thr Val Arg Ser
            835                 840                 845
Glu Met Gly Glu Pro Ile His Lys Ile Ala Thr Arg Gly Val Met Leu
        850                 855                 860
Trp Lys Glu Phe Asp Glu Thr Ile Phe Asn Leu Pro Lys Asn Lys Leu
865                 870                 875                 880
Val Pro Thr Leu Glu Ala Lys Arg Asp Tyr Ile Ile Ser Arg Leu Asn
                    885                 890                 895
Ala Asp Phe Gln Lys Pro Trp Phe Ala Thr Val Asn Gly Gln Ala Arg
                900                 905                 910
Asp Leu Ala Thr Met Thr Tyr Glu Glu Val Ala Lys Arg Leu Val Glu
            915                 920                 925
Leu Met Phe Ile Arg Ser Thr Asn Ser Trp Phe Asp Val Thr Trp Arg
        930                 935                 940
Thr Phe Thr Gly Asp Phe Leu Arg Arg Val Glu Glu Arg Phe Thr Lys
945                 950                 955                 960
Ser Lys Thr Leu Ser Leu Ile Gln Ser Tyr Ser Leu Leu Asp Lys Pro
                    965                 970                 975
Asp Glu Ala Ile Glu Lys Val Phe Asn Ala Tyr Pro Ala Ala Arg Glu
                980                 985                 990
Gln Phe Leu Asn Ala Gln Asp Ile Asp His Phe Leu Ser Met Cys Gln
            995                 1000                1005
Asn Pro Met Gln Lys Pro Val Pro Phe Val Pro Val Leu Asp Arg
        1010                1015                1020
Arg Phe Glu Ile Phe Phe Lys Lys Asp Ser Leu Trp Gln Ser Glu
        1025                1030                1035
His Leu Glu Ala Val Val Asp Gln Asp Val Gln Arg Thr Cys Ile
        1040                1045                1050
Leu His Gly Pro Val Ala Ala Gln Phe Thr Lys Val Ile Asp Glu
        1055                1060                1065
Pro Ile Lys Ser Ile Met Asp Gly Ile His Asp Gly His Ile Lys
        1070                1075                1080
Lys Leu Leu His Gln Tyr Tyr Gly Asp Asp Glu Ser Lys Ile Pro
        1085                1090                1095
```

-continued

```
Ala Val Glu Tyr Phe Gly Gly Glu Ser Pro Val Asp Val Gln Ser
    1100                1105                1110
Gln Val Asp Ser Ser Val Ser Glu Asp Ser Ala Val Phe Lys
    1115            1120                1125
Ala Thr Ser Ser Thr Asp Glu Glu Ser Trp Phe Lys Ala Leu Ala
    1130                1135                1140
Gly Ser Glu Ile Asn Trp Arg His Ala Ser Phe Leu Cys Ser Phe
    1145                1150                1155
Ile Thr Gln Asp Lys Met Phe Val Ser Asn Pro Ile Arg Lys Val
    1160                1165                1170
Phe Lys Pro Ser Gln Gly Met Val Val Glu Ile Ser Asn Gly Asn
    1175                1180                1185
Thr Ser Ser Lys Thr Val Val Thr Leu Ser Glu Pro Val Gln Gly
    1190                1195                1200
Glu Leu Lys Pro Thr Val Ile Leu Lys Leu Leu Lys Glu Asn Ile
    1205                1210                1215
Ile Gln Met Glu Met Ile Glu Asn Arg Thr Met Asp Gly Lys Pro
    1220                1225                1230
Val Ser Leu Pro Leu Leu Tyr Asn Phe Asn Pro Asp Asn Gly Phe
    1235                1240                1245
Ala Pro Ile Ser Glu Val Met Glu Asp Arg Asn Gln Arg Ile Lys
    1250                1255                1260
Glu Met Tyr Trp Lys Leu Trp Ile Asp Glu Pro Phe Asn Leu Asp
    1265                1270                1275
Phe Asp Pro Arg Asp Val Ile Lys Gly Lys Asp Phe Glu Ile Thr
    1280                1285                1290
Ala Lys Glu Val Tyr Asp Phe Thr His Ala Val Gly Asn Asn Cys
    1295                1300                1305
Glu Asp Phe Val Ser Arg Pro Asp Arg Thr Met Leu Ala Pro Met
    1310                1315                1320
Asp Phe Ala Ile Val Val Gly Trp Arg Ala Ile Ile Lys Ala Ile
    1325                1330                1335
Phe Pro Asn Thr Val Asp Gly Asp Leu Leu Lys Leu Val His Leu
    1340                1345                1350
Ser Asn Gly Tyr Lys Met Ile Pro Gly Ala Lys Pro Leu Gln Val
    1355                1360                1365
Gly Asp Val Val Ser Thr Thr Ala Val Ile Glu Ser Val Val Asn
    1370                1375                1380
Gln Pro Thr Gly Lys Ile Val Asp Val Val Gly Thr Leu Ser Arg
    1385                1390                1395
Asn Gly Lys Pro Val Met Glu Val Thr Ser Ser Phe Phe Tyr Arg
    1400                1405                1410
Gly Asn Tyr Thr Asp Phe Glu Asn Thr Phe Gln Lys Thr Val Glu
    1415                1420                1425
Pro Val Tyr Gln Met His Ile Lys Thr Ser Lys Asp Ile Ala Val
    1430                1435                1440
Leu Arg Ser Lys Glu Trp Phe Gln Leu Asp Asp Glu Asp Phe Asp
    1445                1450                1455
Leu Leu Asn Lys Thr Leu Thr Phe Glu Thr Glu Thr Glu Val Thr
    1460                1465                1470
Phe Lys Asn Ala Asn Ile Phe Ser Ser Val Lys Cys Phe Gly Pro
    1475                1480                1485
```

```
Ile Lys Val Glu Leu Pro Thr Lys Glu Thr Val Glu Ile Gly Ile
1490                1495                1500

Val Asp Tyr Glu Ala Gly Ala Ser His Gly Asn Pro Val Val Asp
1505                1510                1515

Phe Leu Lys Arg Asn Gly Ser Thr Leu Glu Gln Lys Val Asn Leu
1520                1525                1530

Glu Asn Pro Ile Pro Ile Ala Val Leu Asp Ser Tyr Thr Pro Ser
1535                1540                1545

Thr Asn Glu Pro Tyr Ala Arg Val Ser Gly Asp Leu Asn Pro Ile
1550                1555                1560

His Val Ser Arg His Phe Ala Ser Tyr Ala Asn Leu Pro Gly Thr
1565                1570                1575

Ile Thr His Gly Met Phe Ser Ser Ala Ser Val Arg Ala Leu Ile
1580                1585                1590

Glu Asn Trp Ala Ala Asp Ser Val Ser Ser Arg Val Arg Gly Tyr
1595                1600                1605

Thr Cys Gln Phe Val Asp Met Val Leu Pro Asn Thr Ala Leu Lys
1610                1615                1620

Thr Ser Ile Gln His Val Gly Met Ile Asn Gly Arg Lys Leu Ile
1625                1630                1635

Lys Phe Glu Thr Arg Asn Glu Asp Asp Val Val Val Leu Thr Gly
1640                1645                1650

Glu Ala Glu Ile Glu Gln Pro Val Thr Thr Phe Val Phe Thr Gly
1655                1660                1665

Gln Gly Ser Gln Glu Gln Gly Met Gly Met Asp Leu Tyr Lys Thr
1670                1675                1680

Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
1700                1705                1710

Pro Val Asn Leu Thr Ile His Phe Gly Gly Glu Lys Gly Lys Arg
1715                1720                1725

Ile Arg Glu Asn Tyr Ser Ala Met Ile Phe Glu Thr Ile Val Asp
1730                1735                1740

Gly Lys Leu Lys Thr Glu Lys Ile Phe Lys Glu Ile Asn Glu His
1745                1750                1755

Ser Thr Ser Tyr Thr Phe Arg Ser Glu Lys Gly Leu Leu Ser Ala
1760                1765                1770

Thr Gln Phe Thr Gln Pro Ala Leu Thr Leu Met Glu Lys Ala Ala
1775                1780                1785

Phe Glu Asp Leu Lys Ser Lys Gly Leu Ile Pro Ala Asp Ala Thr
1790                1795                1800

Phe Ala Gly His Ser Leu Gly Glu Tyr Ala Ala Leu Ala Ser Leu
1805                1810                1815

Ala Asp Val Met Ser Ile Glu Ser Leu Val Glu Val Val Phe Tyr
1820                1825                1830

Arg Gly Met Thr Met Gln Val Ala Val Pro Arg Asp Glu Leu Gly
1835                1840                1845

Arg Ser Asn Tyr Gly Met Ile Ala Ile Asn Pro Gly Arg Val Ala
1850                1855                1860

Ala Ser Phe Ser Gln Glu Ala Leu Gln Tyr Val Val Glu Arg Val
1865                1870                1875

Gly Lys Arg Thr Gly Trp Leu Val Glu Ile Val Asn Tyr Asn Val
```

```
               1880                1885                1890
Glu Asn Gln Gln Tyr Val Ala Ala Gly Asp Leu Arg Ala Leu Asp
        1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Glu Val Glu Gly
    1925                1930                1935

His Leu Phe Glu Ile Ile Asp Glu Ala Ser Lys Lys Ser Ala Val
    1940                1945                1950

Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050

<210> SEQ ID NO 19
<211> LENGTH: 1887
<212> TYPE: PRT
<213> ORGANISM: Saccharomyces cerevisiae

<400> SEQUENCE: 19

Met Lys Pro Glu Val Glu Gln Glu Leu Ala His Ile Leu Leu Thr Glu
1               5                   10                  15

Leu Leu Ala Tyr Gln Phe Ala Ser Pro Val Arg Trp Ile Glu Thr Gln
                20                  25                  30

Asp Val Phe Leu Lys Asp Phe Asn Thr Glu Arg Val Val Glu Ile Gly
            35                  40                  45

Pro Ser Pro Thr Leu Ala Gly Met Ala Gln Arg Thr Leu Lys Asn Lys
        50                  55                  60

Tyr Glu Ser Tyr Asp Ala Ala Leu Ser Leu His Arg Glu Ile Leu Cys
65                  70                  75                  80

Tyr Ser Lys Asp Ala Lys Glu Ile Tyr Tyr Thr Pro Asp Pro Ser Glu
                85                  90                  95

Leu Ala Ala Lys Glu Glu Pro Ala Lys Glu Ala Pro Ala Pro Thr
            100                 105                 110

Pro Ala Ala Ser Ala Pro Ala Pro Ala Ala Ala Pro Ala Pro Val
        115                 120                 125

Ala Ala Ala Ala Pro Ala Ala Ala Ala Glu Ile Ala Asp Glu Pro
    130                 135                 140

Val Lys Ala Ser Leu Leu Leu His Val Leu Val Ala His Lys Leu Lys
145                 150                 155                 160

Lys Ser Leu Asp Ser Ile Pro Met Ser Lys Thr Ile Lys Asp Leu Val
                165                 170                 175

Gly Gly Lys Ser Thr Val Gln Asn Glu Ile Leu Gly Asp Leu Gly Lys
            180                 185                 190
```

-continued

```
Glu Phe Gly Thr Thr Pro Glu Lys Pro Glu Glu Thr Pro Leu Glu Glu
        195                 200                 205

Leu Ala Glu Thr Phe Gln Asp Thr Phe Ser Gly Ala Leu Gly Lys Gln
        210                 215                 220

Ser Ser Ser Leu Leu Ser Arg Leu Ile Ser Ser Lys Met Pro Gly Gly
225                 230                 235                 240

Phe Thr Ile Thr Val Ala Arg Lys Tyr Leu Gln Thr Arg Trp Gly Leu
                245                 250                 255

Pro Ser Gly Arg Gln Asp Gly Val Leu Leu Val Ala Leu Ser Asn Glu
            260                 265                 270

Pro Ala Ala Arg Leu Gly Ser Glu Ala Asp Ala Lys Ala Phe Leu Asp
            275                 280                 285

Ser Met Ala Gln Lys Tyr Ala Ser Ile Val Gly Val Asp Leu Ser Ser
        290                 295                 300

Ala Ala Ser Ala Ser Gly Ala Ala Gly Ala Gly Ala Ala Ala Gly Ala
305                 310                 315                 320

Ala Met Ile Asp Ala Gly Ala Leu Glu Glu Ile Thr Lys Asp His Lys
                325                 330                 335

Val Leu Ala Arg Gln Gln Leu Gln Val Leu Ala Arg Tyr Leu Lys Met
            340                 345                 350

Asp Leu Asp Asn Gly Glu Arg Lys Phe Leu Lys Glu Lys Asp Thr Val
            355                 360                 365

Ala Glu Leu Gln Ala Gln Leu Asp Tyr Leu Asn Ala Glu Leu Gly Glu
        370                 375                 380

Phe Phe Val Asn Gly Val Ala Thr Ser Phe Ser Arg Lys Lys Ala Arg
385                 390                 395                 400

Thr Phe Asp Ser Ser Trp Asn Trp Ala Lys Gln Ser Leu Leu Ser Leu
                405                 410                 415

Tyr Phe Glu Ile Ile His Gly Val Leu Lys Asn Val Asp Arg Glu Val
            420                 425                 430

Val Ser Glu Ala Ile Asn Ile Met Asn Arg Ser Asn Asp Ala Leu Ile
            435                 440                 445

Lys Phe Met Glu Tyr His Ile Ser Asn Thr Asp Glu Thr Lys Gly Glu
        450                 455                 460

Asn Tyr Gln Leu Val Lys Thr Leu Gly Glu Gln Leu Ile Glu Asn Cys
465                 470                 475                 480

Lys Gln Val Leu Asp Val Asp Pro Val Tyr Lys Asp Val Ala Lys Pro
                485                 490                 495

Thr Gly Pro Lys Thr Ala Ile Asp Lys Asn Gly Asn Ile Thr Tyr Ser
            500                 505                 510

Glu Glu Pro Arg Glu Lys Val Arg Lys Leu Ser Gln Tyr Val Gln Glu
        515                 520                 525

Met Ala Leu Gly Gly Pro Ile Thr Lys Glu Ser Gln Pro Thr Ile Glu
        530                 535                 540

Glu Asp Leu Thr Arg Val Tyr Lys Ala Ile Ser Ala Gln Ala Asp Lys
545                 550                 555                 560

Gln Asp Ile Ser Ser Ser Thr Arg Val Glu Phe Glu Lys Leu Tyr Ser
                565                 570                 575

Asp Leu Met Lys Phe Leu Glu Ser Ser Lys Glu Ile Asp Pro Ser Gln
            580                 585                 590

Thr Thr Gln Leu Ala Gly Met Asp Val Glu Asp Ala Leu Asp Lys Asp
        595                 600                 605

Ser Thr Lys Glu Val Ala Ser Leu Pro Asn Lys Ser Thr Ile Ser Lys
```

-continued

```
            610                 615                 620
Thr Val Ser Ser Thr Ile Pro Arg Glu Thr Ile Pro Phe Leu His Leu
625                 630                                 640

Arg Lys Lys Thr Pro Ala Gly Asp Trp Lys Tyr Asp Arg Gln Leu Ser
                    645                 650                 655

Ser Leu Phe Leu Asp Gly Leu Glu Lys Ala Ala Phe Asn Gly Val Thr
                660                 665                 670

Phe Lys Asp Lys Tyr Val Leu Ile Thr Gly Ala Gly Lys Gly Ser Ile
            675                 680                 685

Gly Ala Glu Val Leu Gln Gly Leu Leu Gln Gly Ala Lys Val Val
690                 695                 700

Val Thr Thr Ser Arg Phe Ser Lys Gln Val Thr Asp Tyr Tyr Gln Ser
705                 710                 715                 720

Ile Tyr Ala Lys Tyr Gly Ala Lys Gly Ser Thr Leu Ile Val Val Pro
                    725                 730                 735

Phe Asn Gln Gly Ser Lys Gln Asp Val Glu Ala Leu Ile Glu Phe Ile
                740                 745                 750

Tyr Asp Thr Glu Lys Asn Gly Gly Leu Gly Trp Asp Leu Asp Ala Ile
            755                 760                 765

Ile Pro Phe Ala Ala Ile Pro Glu Gln Gly Ile Glu Leu Glu His Ile
770                 775                 780

Asp Ser Lys Ser Glu Phe Ala His Arg Ile Met Leu Thr Asn Ile Leu
785                 790                 795                 800

Arg Met Met Gly Cys Val Lys Lys Gln Lys Ser Ala Arg Gly Ile Glu
                    805                 810                 815

Thr Arg Pro Ala Gln Val Ile Leu Pro Met Ser Pro Asn His Gly Thr
                820                 825                 830

Phe Gly Gly Asp Gly Met Tyr Ser Glu Ser Lys Leu Ser Leu Glu Thr
            835                 840                 845

Leu Phe Asn Arg Trp His Ser Glu Ser Trp Ala Asn Gln Leu Thr Val
            850                 855                 860

Cys Gly Ala Ile Ile Gly Trp Thr Arg Gly Thr Gly Leu Met Ser Ala
865                 870                 875                 880

Asn Asn Ile Ile Ala Glu Gly Ile Glu Lys Met Gly Val Arg Thr Phe
                    885                 890                 895

Ser Gln Lys Glu Met Ala Phe Asn Leu Leu Gly Leu Leu Thr Pro Glu
                900                 905                 910

Val Val Glu Leu Cys Gln Lys Ser Pro Val Met Ala Asp Leu Asn Gly
            915                 920                 925

Gly Leu Gln Phe Val Pro Glu Leu Lys Glu Phe Thr Ala Lys Leu Arg
930                 935                 940

Lys Glu Leu Val Glu Thr Ser Glu Val Arg Lys Ala Val Ser Ile Glu
945                 950                 955                 960

Thr Ala Leu Glu His Lys Val Val Asn Gly Asn Ser Ala Asp Ala Ala
                    965                 970                 975

Tyr Ala Gln Val Glu Ile Gln Pro Arg Ala Asn Ile Gln Leu Asp Phe
                980                 985                 990

Pro Glu Leu Lys Pro Tyr Lys Gln Val Lys Gln Ile Ala Pro Ala Glu
            995                 1000                1005

Leu Glu Gly Leu Leu Asp Leu Glu Arg Val Ile Val Val Thr Gly
            1010                1015                1020

Phe Ala Glu Val Gly Pro Trp Gly Ser Ala Arg Thr Arg Trp Glu
            1025                1030                1035
```

-continued

```
Met Glu Ala Phe Gly Glu Phe Ser Leu Glu Gly Cys Val Glu Met
    1040                1045                1050
Ala Trp Ile Met Gly Phe Ile Ser Tyr His Asn Gly Asn Leu Lys
    1055                1060                1065
Gly Arg Pro Tyr Thr Gly Trp Val Asp Ser Lys Thr Lys Glu Pro
    1070                1075                1080
Val Asp Asp Lys Asp Val Lys Ala Lys Tyr Glu Thr Ser Ile Leu
    1085                1090                1095
Glu His Ser Gly Ile Arg Leu Ile Glu Pro Glu Leu Phe Asn Gly
    1100                1105                1110
Tyr Asn Pro Glu Lys Lys Glu Met Ile Gln Glu Val Ile Val Glu
    1115                1120                1125
Glu Asp Leu Glu Pro Phe Glu Ala Ser Lys Glu Thr Ala Glu Gln
    1130                1135                1140
Phe Lys His Gln His Gly Asp Lys Val Asp Ile Phe Glu Ile Pro
    1145                1150                1155
Glu Thr Gly Glu Tyr Ser Val Lys Leu Leu Lys Gly Ala Thr Leu
    1160                1165                1170
Tyr Ile Pro Lys Ala Leu Arg Phe Asp Arg Leu Val Ala Gly Gln
    1175                1180                1185
Ile Pro Thr Gly Trp Asn Ala Lys Thr Tyr Gly Ile Ser Asp Asp
    1190                1195                1200
Ile Ile Ser Gln Val Asp Pro Ile Thr Leu Phe Val Leu Val Ser
    1205                1210                1215
Val Val Glu Ala Phe Ile Ala Ser Gly Ile Thr Asp Pro Tyr Glu
    1220                1225                1230
Met Tyr Lys Tyr Val His Val Ser Glu Val Gly Asn Cys Ser Gly
    1235                1240                1245
Ser Gly Met Gly Gly Val Ser Ala Leu Arg Gly Met Phe Lys Asp
    1250                1255                1260
Arg Phe Lys Asp Glu Pro Val Gln Asn Asp Ile Leu Gln Glu Ser
    1265                1270                1275
Phe Ile Asn Thr Met Ser Ala Trp Val Asn Met Leu Leu Ile Ser
    1280                1285                1290
Ser Ser Gly Pro Ile Lys Thr Pro Val Gly Ala Cys Ala Thr Ser
    1295                1300                1305
Val Glu Ser Val Asp Ile Gly Val Glu Thr Ile Leu Ser Gly Lys
    1310                1315                1320
Ala Arg Ile Cys Ile Val Gly Gly Tyr Asp Asp Phe Gln Glu Glu
    1325                1330                1335
Gly Ser Phe Glu Phe Gly Asn Met Lys Ala Thr Ser Asn Thr Leu
    1340                1345                1350
Glu Glu Phe Glu His Gly Arg Thr Pro Ala Glu Met Ser Arg Pro
    1355                1360                1365
Ala Thr Thr Thr Arg Asn Gly Phe Met Glu Ala Gln Gly Ala Gly
    1370                1375                1380
Ile Gln Ile Ile Met Gln Ala Asp Leu Ala Leu Lys Met Gly Val
    1385                1390                1395
Pro Ile Tyr Gly Ile Val Ala Met Ala Ala Thr Ala Thr Asp Lys
    1400                1405                1410
Ile Gly Arg Ser Val Pro Ala Pro Gly Lys Gly Ile Leu Thr Thr
    1415                1420                1425
```

-continued

```
Ala Arg Glu His His Ser Ser Val Lys Tyr Ala Ser Pro Asn Leu
1430                    1435                1440

Asn Met Lys Tyr Arg Lys Arg Gln Leu Val Thr Arg Glu Ala Gln
1445                    1450                1455

Ile Lys Asp Trp Val Glu Asn Glu Leu Glu Ala Leu Lys Leu Glu
1460                    1465                1470

Ala Glu Glu Ile Pro Ser Glu Asp Gln Asn Glu Phe Leu Leu Glu
1475                    1480                1485

Arg Thr Arg Glu Ile His Asn Glu Ala Glu Ser Gln Leu Arg Ala
1490                    1495                1500

Ala Gln Gln Gln Trp Gly Asn Asp Phe Tyr Lys Arg Asp Pro Arg
1505                    1510                1515

Ile Ala Pro Leu Arg Gly Ala Leu Ala Thr Tyr Gly Leu Thr Ile
1520                    1525                1530

Asp Asp Leu Gly Val Ala Ser Phe His Gly Thr Ser Thr Lys Ala
1535                    1540                1545

Asn Asp Lys Asn Glu Ser Ala Thr Ile Asn Glu Met Met Lys His
1550                    1555                1560

Leu Gly Arg Ser Glu Gly Asn Pro Val Ile Gly Val Phe Gln Lys
1565                    1570                1575

Phe Leu Thr Gly His Pro Lys Gly Ala Ala Gly Ala Trp Met Met
1580                    1585                1590

Asn Gly Ala Leu Gln Ile Leu Asn Ser Gly Ile Ile Pro Gly Asn
1595                    1600                1605

Arg Asn Ala Asp Asn Val Asp Lys Ile Leu Glu Gln Phe Glu Tyr
1610                    1615                1620

Val Leu Tyr Pro Ser Lys Thr Leu Lys Thr Asp Gly Val Arg Ala
1625                    1630                1635

Val Ser Ile Thr Ser Phe Gly Phe Gly Gln Lys Gly Gly Gln Ala
1640                    1645                1650

Ile Val Val His Pro Asp Tyr Leu Tyr Gly Ala Ile Thr Glu Asp
1655                    1660                1665

Arg Tyr Asn Glu Tyr Val Ala Lys Val Ser Ala Arg Glu Lys Ser
1670                    1675                1680

Ala Tyr Lys Phe Phe His Asn Gly Met Ile Tyr Asn Lys Leu Phe
1685                    1690                1695

Val Ser Lys Glu His Ala Pro Tyr Thr Asp Glu Leu Glu Glu Asp
1700                    1705                1710

Val Tyr Leu Asp Pro Leu Ala Arg Val Ser Lys Asp Lys Lys Ser
1715                    1720                1725

Gly Ser Leu Thr Phe Asn Ser Lys Asn Ile Gln Ser Lys Asp Ser
1730                    1735                1740

Tyr Ile Asn Ala Asn Thr Ile Glu Thr Ala Lys Met Ile Glu Asn
1745                    1750                1755

Met Thr Lys Glu Lys Val Ser Asn Gly Gly Val Gly Val Asp Val
1760                    1765                1770

Glu Leu Ile Thr Ser Ile Asn Val Glu Asn Asp Thr Phe Ile Glu
1775                    1780                1785

Arg Asn Phe Thr Pro Gln Glu Ile Glu Tyr Cys Ser Ala Gln Pro
1790                    1795                1800

Ser Val Gln Ser Ser Phe Ala Gly Thr Trp Ser Ala Lys Glu Ala
1805                    1810                1815

Val Phe Lys Ser Leu Gly Val Lys Ser Leu Gly Gly Gly Ala Ala
```

-continued

```
               1820                1825                1830

Leu Lys Asp Ile Glu Ile Val Arg Val Asn Lys Asn Ala Pro Ala
        1835                1840                1845

Val Glu Leu His Gly Asn Ala Lys Lys Ala Ala Glu Glu Ala Gly
    1850                1855                1860

Val Thr Asp Val Lys Val Ser Ile Ser His Asp Asp Leu Gln Ala
    1865                1870                1875

Val Ala Val Ala Val Ser Thr Lys Lys
    1880                1885

<210> SEQ ID NO 20
<211> LENGTH: 2037
<212> TYPE: PRT
<213> ORGANISM: Candida albicans

<400> SEQUENCE: 20

Met Ser Thr His Arg Pro Phe Gln Leu Thr His Gly Ser Ile Glu His
1               5                   10                  15

Thr Leu Leu Val Pro Asn Asp Leu Phe Phe Asn Tyr Ser Gln Leu Lys
            20                  25                  30

Asp Glu Phe Ile Lys Thr Leu Pro Glu Pro Thr Glu Gly Phe Ala Gly
        35                  40                  45

Asp Asp Glu Pro Ser Ser Pro Ala Glu Leu Tyr Gly Lys Phe Ile Gly
    50                  55                  60

Phe Ile Ser Asn Ala Gln Phe Pro Gln Ile Val Glu Leu Ser Leu Lys
65                  70                  75                  80

Asp Phe Glu Ser Arg Phe Leu Asp Asn Asn Asp Asn Ile His Ser
                85                  90                  95

Phe Ala Val Lys Leu Leu Asp Asp Glu Thr Tyr Pro Thr Thr Ile Ala
            100                 105                 110

Lys Val Lys Glu Asn Ile Val Lys Asn Tyr Tyr Lys Ala Val Lys Ser
        115                 120                 125

Ile Asn Lys Val Glu Ser Asn Leu Leu Tyr His Cys Lys His Asp Ala
    130                 135                 140

Lys Leu Val Ala Ile Phe Gly Gly Gln Gly Asn Thr Asp Asp Tyr Phe
145                 150                 155                 160

Glu Glu Leu Arg Glu Leu Tyr Thr Leu Tyr Gln Gly Leu Ile Glu Asp
                165                 170                 175

Leu Leu Val Ser Ile Ala Glu Lys Leu Asn Gln Leu His Pro Ser Phe
            180                 185                 190

Asp Lys Ile Tyr Thr Gln Gly Leu Asn Ile Leu Ser Trp Leu Lys His
        195                 200                 205

Pro Glu Thr Thr Pro Asp Gln Asp Tyr Leu Leu Ser Val Pro Val Ser
    210                 215                 220

Cys Pro Val Ile Cys Val Ile Gln Leu Cys His Tyr Thr Ile Thr Cys
225                 230                 235                 240

Lys Val Leu Gly Leu Thr Pro Gly Glu Phe Arg Asn Ser Leu Lys Trp
                245                 250                 255

Ser Thr Gly His Ser Gln Gly Leu Val Thr Ala Val Thr Ile Ala Ala
            260                 265                 270

Ser Asp Ser Trp Asp Ser Phe Leu Lys Asn Ser Leu Thr Ala Val Ser
        275                 280                 285

Leu Leu Leu Phe Ile Gly Ser Arg Cys Leu Ser Thr Tyr Pro Arg Thr
    290                 295                 300
```

```
Ser Leu Pro Pro Thr Met Leu Gln Asp Ser Leu Asp Asn Gly Glu Gly
305                 310                 315                 320

Arg Pro Ser Pro Met Leu Ser Val Arg Asp Leu Ser Ile Lys Gln Val
            325                 330                 335

Glu Lys Phe Ile Glu Gln Thr Asn Ser His Leu Pro Arg Glu Lys His
        340                 345                 350

Ile Ala Ile Ser Leu Ile Asn Gly Ala Arg Asn Leu Val Leu Ser Gly
    355                 360                 365

Pro Pro Glu Ser Leu Tyr Gly Phe Asn Leu Asn Leu Arg Asn Gln Lys
370                 375                 380

Ala Pro Met Gly Leu Asp Gln Ser Arg Val Pro Phe Ser Glu Arg Lys
385                 390                 395                 400

Leu Lys Cys Ser Asn Arg Phe Leu Pro Ile Phe Ala Pro Phe His Ser
            405                 410                 415

His Leu Leu Ala Asp Ala Thr Glu Leu Ile Leu Asp Asp Val Lys Glu
        420                 425                 430

His Gly Leu Ser Phe Glu Gly Leu Lys Ile Pro Val Tyr Asp Thr Phe
    435                 440                 445

Asp Gly Ser Asp Phe Gln Ala Leu Lys Glu Pro Ile Ile Asp Arg Val
450                 455                 460

Val Lys Leu Ile Thr Glu Leu Pro Val His Trp Glu Glu Ala Thr Asn
465                 470                 475                 480

His Lys Ala Thr His Ile Leu Asp Phe Gly Pro Gly Gly Val Ser Gly
            485                 490                 495

Leu Gly Val Leu Thr His Arg Asn Lys Glu Gly Thr Gly Ala Arg Ile
        500                 505                 510

Ile Leu Ala Gly Thr Leu Asp Ser Asn Pro Ile Asp Asp Glu Tyr Gly
    515                 520                 525

Phe Lys His Glu Ile Phe Gln Thr Ser Ala Asp Lys Ala Ile Lys Trp
530                 535                 540

Ala Pro Asp Trp Leu Lys Glu Leu Arg Pro Thr Leu Val Lys Asn Ser
545                 550                 555                 560

Glu Gly Lys Ile Tyr Val Lys Thr Lys Phe Ser Gln Leu Leu Gly Arg
            565                 570                 575

Ala Pro Leu Met Val Ala Gly Met Thr Pro Thr Thr Val Asn Thr Asp
        580                 585                 590

Ile Val Ser Ala Ser Leu Asn Ala Gly Tyr His Ile Glu Leu Ala Gly
    595                 600                 605

Gly Gly Tyr Phe Ser Pro Val Met Met Thr Arg Ala Ile Asp Asp Ile
610                 615                 620

Val Ser Arg Ile Lys Pro Gly Tyr Gly Leu Gly Ile Asn Leu Ile Tyr
625                 630                 635                 640

Val Asn Pro Phe Met Leu Gln Trp Gly Ile Pro Leu Ile Lys Asp Leu
            645                 650                 655

Arg Glu Lys Gly Tyr Pro Ile Gln Ser Leu Thr Ile Gly Ala Gly Val
        660                 665                 670

Pro Ser Ile Glu Val Ala Thr Glu Tyr Ile Glu Asp Leu Gly Leu Thr
    675                 680                 685

His Leu Gly Leu Lys Pro Gly Ser Val Asp Ala Ile Ser Gln Val Ile
690                 695                 700

Ala Ile Ala Lys Ala His Pro Thr Phe Pro Ile Val Leu Gln Trp Thr
705                 710                 715                 720

Gly Gly Arg Gly Gly Gly His His Ser Phe Glu Asp Phe His Gln Pro
```

-continued

```
                725                 730                 735
Ile Ile Gln Met Tyr Ser Lys Ile Arg Arg Cys Ser Asn Ile Val Leu
                    740                 745                 750
Val Ala Gly Ser Gly Phe Gly Ser Asp Glu Asp Thr Tyr Pro Tyr Leu
                    755                 760                 765
Ser Gly Tyr Trp Ser Glu Lys Phe Asn Tyr Pro Pro Met Pro Phe Asp
                    770                 775                 780
Gly Val Leu Phe Gly Ser Arg Val Met Thr Ser Lys Glu Ser His Thr
785                 790                 795                 800
Ser Leu Ala Ala Lys Lys Leu Ile Val Glu Cys Lys Gly Val Pro Asp
                    805                 810                 815
Gln Gln Trp Glu Gln Thr Tyr Lys Lys Pro Thr Gly Gly Ile Ile Thr
                    820                 825                 830
Val Arg Ser Glu Met Gly Glu Pro Ile His Lys Ile Ala Thr Arg Gly
                    835                 840                 845
Val Met Phe Trp Lys Glu Leu Asp Asp Thr Ile Phe Asn Leu Pro Lys
                    850                 855                 860
Asn Lys Leu Leu Asp Ala Leu Asn Lys Lys Arg Asp His Ile Ile Lys
865                 870                 875                 880
Lys Leu Asn Asn Asp Phe Gln Lys Pro Trp Phe Gly Lys Asn Ala Asn
                    885                 890                 895
Gly Val Cys Asp Leu Gln Glu Met Thr Tyr Lys Glu Val Ala Asn Arg
                    900                 905                 910
Leu Val Glu Leu Met Tyr Val Lys Lys Ser His Arg Trp Ile Asp Val
                    915                 920                 925
Ser Leu Arg Asn Met Tyr Gly Asp Phe Leu Arg Arg Val Glu Glu Arg
                    930                 935                 940
Phe Thr Ser Ser Ala Gly Thr Val Ser Leu Leu Gln Asn Phe Asn Gln
945                 950                 955                 960
Leu Asn Glu Pro Glu Gln Phe Thr Ala Asp Phe Glu Lys Phe Pro
                    965                 970                 975
Gln Ala Gly Lys Gln Leu Ile Ser Glu Glu Asp Cys Asp Tyr Phe Leu
                    980                 985                 990
Met Leu Ala Ala Arg Pro Gly Gln  Lys Pro Val Pro Phe  Val Pro Val
                    995                1000                1005
Leu Asp  Glu Arg Phe Glu Phe  Phe Phe Lys Lys Asp  Ser Leu Trp
1010                    1015                1020
Gln Ser  Glu Asp Leu Glu Ser  Val Val Asp Glu Asp  Val Gln Arg
1025                    1030                1035
Thr Cys  Ile Leu His Gly Pro  Val Ala Ser Gln Tyr  Thr Ser Lys
1040                    1045                1050
Val Asp  Glu Pro Ile Gly Asp  Ile Leu Asn Ser Ile  His Glu Gly
1055                    1060                1065
His Ile  Ala Arg Leu Ile Lys  Glu Glu Tyr Ala Gly  Asp Glu Ser
1070                    1075                1080
Lys Ile  Pro Val Val Glu Tyr  Phe Gly Gly Lys Lys  Pro Ala Ser
1085                    1090                1095
Val Ser  Ala Thr Ser Val Asn  Ile Ile Asp Gly Asn  Gln Val Val
1100                    1105                1110
Tyr Glu  Ile Asp Ser Glu Leu  Pro Asn Lys Gln Glu  Trp Leu Asp
1115                    1120                1125
Leu Leu  Ala Gly Thr Glu Leu  Asn Trp Leu Gln Ala  Phe Ile Ser
1130                    1135                1140
```

-continued

```
Thr Asp Arg Ile Val Gln Gly Ser Lys His Val Ser Asn Pro Leu
    1145             1150                1155

His Asp Ile Leu Thr Pro Ala Lys His Ser Lys Val Thr Ile Asp
    1160             1165                1170

Lys Lys Thr Lys Lys Leu Thr Ala Phe Glu Asn Ile Lys Gly Asp
    1175             1180                1185

Leu Leu Pro Val Val Glu Ile Glu Leu Val Lys Pro Asn Thr Ile
    1190             1195                1200

Gln Leu Ser Leu Ile Glu His Arg Thr Ala Asp Thr Asn Pro Val
    1205             1210                1215

Ala Leu Pro Phe Leu Tyr Lys Tyr Asn Pro Ala Asp Gly Phe Ala
    1220             1225                1230

Pro Ile Leu Glu Ile Met Glu Asp Arg Asn Glu Arg Ile Lys Glu
    1235             1240                1245

Phe Tyr Trp Lys Leu Trp Phe Gly Ser Ser Val Pro Tyr Ser Asn
    1250             1255                1260

Asp Ile Asn Val Glu Lys Ala Ile Leu Gly Asp Glu Ile Thr Ile
    1265             1270                1275

Ser Ser Gln Thr Ile Ser Glu Phe Thr His Ala Ile Gly Asn Lys
    1280             1285                1290

Cys Asp Ala Phe Val Asp Arg Pro Gly Lys Ala Thr Leu Ala Pro
    1295             1300                1305

Met Asp Phe Ala Ile Val Ile Gly Trp Lys Ala Ile Ile Lys Ala
    1310             1315                1320

Ile Phe Pro Lys Ser Val Asp Gly Asp Leu Leu Lys Leu Val His
    1325             1330                1335

Leu Ser Asn Gly Tyr Lys Met Ile Thr Gly Ala Ala Pro Leu Lys
    1340             1345                1350

Lys Gly Asp Val Val Ser Thr Lys Ala Glu Ile Lys Ala Val Leu
    1355             1360                1365

Asn Gln Pro Ser Gly Lys Leu Val Glu Val Val Gly Thr Ile Tyr
    1370             1375                1380

Arg Glu Gly Lys Pro Val Met Glu Val Thr Ser Gln Phe Leu Tyr
    1385             1390                1395

Arg Gly Glu Tyr Asn Asp Tyr Cys Asn Thr Phe Gln Lys Val Thr
    1400             1405                1410

Glu Thr Pro Val Gln Val Ala Phe Lys Ser Ala Lys Asp Leu Ala
    1415             1420                1425

Val Leu Arg Ser Lys Glu Trp Phe His Leu Glu Lys Asp Val Gln
    1430             1435                1440

Phe Asp Val Leu Thr Phe Arg Cys Glu Ser Thr Tyr Lys Phe Lys
    1445             1450                1455

Ser Ala Asn Val Tyr Ser Ser Ile Lys Thr Thr Gly Gln Val Leu
    1460             1465                1470

Leu Glu Leu Pro Thr Lys Glu Val Ile Gln Val Gly Ser Val Asp
    1475             1480                1485

Tyr Glu Ala Gly Thr Ser Tyr Gly Asn Pro Val Thr Asp Tyr Leu
    1490             1495                1500

Ser Arg Asn Gly Lys Thr Ile Glu Glu Ser Val Ile Phe Glu Asn
    1505             1510                1515

Ala Ile Pro Leu Ser Ser Gly Glu Glu Leu Thr Ser Lys Ala Pro
    1520             1525                1530
```

```
Gly Thr Asn Glu Pro Tyr Ala Ile Val Ser Gly Asp Tyr Asn Pro
1535                1540                1545

Ile His Val Ser Arg Val Phe Ala Ala Tyr Ala Lys Leu Pro Gly
    1550                1555                1560

Thr Ile Thr His Gly Met Tyr Ser Ser Ala Ser Ile Arg Ala Leu
1565                1570                1575

Val Glu Glu Trp Ala Ala Asn Asn Val Ala Ala Arg Val Arg Ala
1580                1585                1590

Phe Lys Cys Asp Phe Val Gly Met Val Leu Pro Asn Asp Thr Leu
1595                1600                1605

Gln Thr Thr Met Glu His Val Gly Met Ile Asn Gly Arg Lys Ile
    1610                1615                1620

Ile Lys Val Glu Thr Arg Asn Val Glu Thr Glu Leu Pro Val Leu
1625                1630                1635

Ile Gly Glu Ala Glu Ile Glu Gln Pro Thr Thr Thr Tyr Val Phe
1640                1645                1650

Thr Gly Gln Gly Ser Gln Glu Gln Gly Met Gly Met Glu Leu Tyr
    1655                1660                1665

Asn Ser Ser Glu Val Ala Arg Glu Val Trp Asp Lys Ala Asp Arg
1670                1675                1680

His Phe Val Asn Asn Tyr Gly Phe Ser Ile Leu Asp Ile Val Gln
    1685                1690                1695

Asn Asn Pro Asn Glu Leu Thr Ile His Phe Gly Ala Lys Gly
1700                1705                1710

Arg Ala Ile Arg Asp Asn Tyr Ile Gly Met Met Phe Glu Thr Ile
    1715                1720                1725

Gly Glu Asp Gly Ala Leu Lys Ser Glu Lys Ile Phe Lys Asp Ile
1730                1735                1740

Asp Glu Thr Thr Thr Ser Tyr Thr Phe Val Ser Pro Thr Gly Leu
    1745                1750                1755

Leu Ser Ala Thr Gln Phe Thr Gln Pro Ala Leu Thr Leu Met Glu
1760                1765                1770

Lys Ala Ala Tyr Glu Asp Ile Lys Ser Lys Gly Leu Ile Pro Ser
    1775                1780                1785

Asp Ile Met Phe Ala Gly His Ser Leu Gly Glu Tyr Ser Ala Leu
    1790                1795                1800

Ser Ser Leu Ala Asn Val Met Pro Ile Glu Ser Leu Val Asp Val
1805                1810                1815

Val Phe Tyr Arg Gly Met Thr Met Gln Val Ala Val Pro Arg Asp
    1820                1825                1830

Glu Leu Gly Arg Ser Asn Tyr Gly Met Val Ala Val Asn Pro Ser
1835                1840                1845

Arg Val Ser Ala Thr Phe Asp Asp Ser Ala Leu Arg Phe Val Val
    1850                1855                1860

Asp Glu Val Ala Asn Lys Thr Lys Trp Leu Leu Glu Ile Val Asn
    1865                1870                1875

Tyr Asn Val Glu Asn Gln Gln Tyr Val Ala Ala Gly Asp Leu Arg
1880                1885                1890

Ala Leu Asp Thr Leu Thr Asn Val Leu Asn Val Leu Lys Ile Asn
    1895                1900                1905

Lys Ile Asp Ile Val Lys Leu Gln Glu Gln Met Ser Ile Glu Lys
1910                1915                1920

Val Lys Glu His Leu Tyr Glu Ile Val Asp Glu Val Ala Ala Lys
```

```
              1925                1930                1935
Ser Leu Ala Lys Pro Gln Pro Ile Asp Leu Glu Arg Gly Phe Ala
    1940                1945                1950

Val Ile Pro Leu Lys Gly Ile Ser Val Pro Phe His Ser Ser Tyr
    1955                1960                1965

Leu Met Ser Gly Val Lys Pro Phe Gln Arg Phe Leu Cys Lys Lys
    1970                1975                1980

Ile Pro Lys Ser Ser Val Lys Pro Gln Asp Leu Ile Gly Lys Tyr
    1985                1990                1995

Ile Pro Asn Leu Thr Ala Lys Pro Phe Glu Leu Thr Lys Glu Tyr
    2000                2005                2010

Phe Gln Ser Val Tyr Asp Leu Thr Lys Ser Glu Lys Ile Lys Ser
    2015                2020                2025

Ile Leu Asp Asn Trp Glu Gln Tyr Glu
    2030                2035

<210> SEQ ID NO 21
<211> LENGTH: 6072
<212> TYPE: DNA
<213> ORGANISM: Candida albicans

<400> SEQUENCE: 21 ggatccttt tttttggggt aatattaaca atccagctta ggccatattg ttgggtgtcc     60
ttaaaaatta tgtgccaatt atttacttat atattgatat agctctcctt ttctcttttt    120 tatattttc aaagttttt ttattcttt actgttatt caactaactt gttttattt        180 ctcccccaat taacaatgaa accagaaatt gaacaagaat tatcccacac tttgttaact    240
gaattgttgg catatcaatt tgcttctcca gttagatgga ttgaaactca agatgtcttt    300
ttaaaacagc ataatactga aagaatcatc gaaattggtc cttcaccaac tttagctggt    360
atggccaata gaactatcaa agccaaatat gaatcctatg atgctgcttt atctttgcaa    420
cgacaagtct tgtgttactc caaagatgct aaggagattt actacaagcc agatccagca    480
gatcttgctc ctaaggaaac accaaagcaa gaagagagta ccccatcagc tcctgccgct    540
gccactccaa cacctgctgc tgccgctgct cctactccag caccagctcc tgcaagtgct    600
ggcccagttg aatctattcc agatgaacca gtcaaggcta acttgttaat ccatgttttg    660
gttgcacaaa aattaagaa acctttagat gctgttccaa tgaccaaggc aattaaggat    720
ttggttaatg gtaaatccac tgttcaaaat gaaattcttg gtgacttggg taaggaattt    780
ggctctactc ctgaaaaacc ggaagacact ccattggaag aattagctga acaattccaa    840
gattcattca gcggtcaatt aggaaagact tctacttcat tgattggtag attaatgtcc    900
tcaaagatgc cgggtggatt ttccatcact actgctagaa agtatttgga atcaagattt    960 ggttgggtg ctggtagaca agattctgtc ttgttgatgg cttttaacaa atgaaccagct   1020 aatagattag gttctgaagc cgatgcaaaa actttctttg atggaattgc tcaaaaatac   1080
gcatcaagtg ctgggatctc cttgtcatca ggagcaggct ccggtgcagg cgccgcaaat   1140
agtggtggtg ctgttgttga tagtgctgcc ttagatgctt aacagctgaa aacaagaaa    1200 ttagccaaac agcaattaga agttttagca agatacttgc aaagtcgact taaacaaggg   1260
agccttaaat ctttatcaa ggaaaggaa gcttctgctg tttacaaaa agagttagat     1320 ttgtgggaag cagaacacgg agaattctat gctaagggta tccaaccaac tttctccgca   1380
ttaaagtcta gaacttatga ctcctattgg aattgggccc gtcaagacgt tttatcaatg   1440
```

```
tatttcgaca ttattttggg caagttaact tctgttgata gagaaaccat caaccaatgt    1500
attcaaatca tgaacagagc caatccaact ttaatcaagt ttatgcaata tcatatcgac    1560
cattgtccag aatataaagg tgaaacttat aaattggcca agagattggg tcaacaattg    1620
attgacaact gtaaacaagt tttgactgaa gatccagttt acaagatgt ttccagaatt     1680 actggtccaa agactaaagt cagtgctaag ggtaacattg aatatgagga aactcaaaag    1740
gattcagtta gaaaatttga acaatatgtg tatgaaatgg cccaaggtgg tgctatgacc    1800
aaagttagtc aaccaactat tcaagaagat ttagctagag tttacaaggc tatttccaaa    1860
caagcttcca aagatagcaa attggaattg caaagagttt acgaagattt attgaaggtg    1920
gttgaaagtt ccaaggaaat cgaaaccgaa caattgacta agatatttt acaagctgct     1980 acagttccaa caaccccaac agaggaagta gacgatcctt gtactccttc ttcggatgat    2040
gaaattgctt ctttaccaga taagacttct atcattcaac ctgtctcgtc tactattcca    2100
tctcaaacta ttccattttt gcacattcag aaaaagacca agacggttg ggaatacaat     2160 aagaaattat cttctctttta cttggatgga ttggaatcag ctgccattaa tggtttaact    2220
ttcaaagaca agtatgtctt agttactggt gctggtgctg gctctattgg tgccgaaatt    2280
ttgcaaggtt taatcagtgg tggtgccaaa gttattgtca caacctctag attttccaag    2340
aaagttaccg agtattatca aaacatgtat gccagatatg gtgctgctgg gtctacttta    2400
attgttgttc cgttcaacca aggttctaaa caagatgttg atgcattggt tcaatacatt    2460
tatgatgagc caaagaaagg tggtttgggt tgggatttgg atgcaatcat tccatttgct    2520
gctattccag aaaatggtaa tggtctcgac aacattgatt ctaaatctga atttgcccac    2580
agaatcatgt tgaccaacct tttaagattg ttaggtgctg ttaaatccaa aaagcccact    2640
gacactagac ctgctcaatg tattttgcca ttatctccaa atcacggaac ttttggtttt    2700
gacgggttgt actctgaatc taaaatctca ttggaaacct tattcaacag atggtattct    2760
gaagattggg gatccaagtt gactgtttgt ggtgccgtaa ttgggtggac tagaggtaca    2820
ggtttgatga gtgccaataa cattattgct gaaggtattg aaaaattggg tgtcagaact    2880
ttctcccaaa aggaaatggc tttcaatatt ttaggtttat tgacaccaga aattgtacaa    2940
ttatgtcaag aagaaccagt tatggctgac ttgaatggtg gtttgcaatt cattgacaac    3000
ttgaaggatt tcacatctaa attaagaacc gacttgttgg aaactgcaga cattagaaga    3060 gctgttttcta ttgaatcagc tatcgagcaa aaagttgtca atggtgacaa tgtcgatgca    3120
aactactcaa aggttatggt tgaacctaga gccaacatga aatttgattt cccaactttg    3180
aaatcttatg atgaaatcaa acaaattgct ccagaattgg aaggtatgtt ggatttggaa    3240
aatgttgtcg ttgtgacagg ttttgctgaa gttggtccat ggggtaactc tagaaccaga    3300
tgggaaatgg aagcttatgg tgagttctca ttggaaggtg ccattgaaat ggcttggatt    3360 atgggttca tcaagtatca taatggtaat ttgcaaggga accatactc tggatgggtt      3420 gatgccaaga ctcaaactcc aattgacgaa aaggatatca aatccaaata tgaagaagaa    3480 atttttagaac attccggtat tagattgatt gagccagaat tgttcaatgg ctatgatcca    3540
aagaaaaaac aaatgattca agaaattgtt gttcaacacg atttagaacc atttgaatgt    3600
tctaaagaaa cagctgagca atacaaacac gaacacggag aaaaatgtga aatttttgaa    3660
attgaagaaa gtggtgaata cacagttaga atcttgaaag gtgcaacatt gtacgttccg    3720
aaagctttga gatttgatag attagttgct ggtcaaattc caactggttg ggacgctcgt    3780
acctatggta tcccagaaga cactattagt caagttgatc caatcacttt gtacgtgttg    3840
```

```
gttgccactg ttgaagcctt gttgtctgct ggtattactg atccatatga attctacaaa    3900
tacgttcatg tgtctgaagt tggtaactgt tctggttccg gtatgggagg tgtctctgct    3960
ttgagaggaa tgttcaaaga tagatatgct gacaaaccag ttcaaaatga cattttgcaa    4020
gaatcattta tcaacactat gtctgcttgg gtcaatatgt tgttgttgtc ttcctctggt    4080
ccaatcaaga caccagtcgg tgcttgtgcc actgctgttg aatcggttga cattggtatt    4140
gaaacaattt tgtctggtaa agctaaagta gttttggtag gtggttacga tgacttccaa    4200
gaagaagggt cttatgaatt cgccaatatg aatgctactt ctaattctat tgaagagttc    4260
aaacacggaa gaacaccaaa ggaaatgtca agaccaacta ctactaccag aaatggtttc    4320
atggaagctc aaggttctgg tattcaagtt atcatgactg ctgatttggc tctcaagatg    4380
ggtgttccaa tccacgctgt attggccatg actgctactg ccactgataa gattggtaga    4440
tctgttccag caccaggtaa aggtattttg accactgcca gagaacatca tggcaacttg    4500
aagtacccat ctccactttt gaacatcaag tacaggaaga gacaattgaa caaaagattg    4560
gaacaaatca atctctggga agaaacagaa cttttcttact tgcaagaaga agccgagttg    4620
gccaaagaag aatttggtga cgaattttct atgcatgagt tcttgaaaga gagaactgaa    4680
gaagtgtacc gtgaatcaaa agacaagtt tctgatgcta agaaacaatg gggtaattca    4740
ttctacaagt ctgatccaag aattgctcca ttgagaggag cattggctgc cttcaactta    4800
accatcgatg atattggtgt tgcatccttc catggtactt ccaccgttgc taacgataag    4860
aatgaatctg ccacaatcaa caatatgatg aaacacttgg gtagatccga aggtaaccca    4920
gtatttggtg ttttccaaaa atacttgaca ggtcatccaa aggtgcagc tggtgcttgg    4980 atgttgaatg gtgccattca aattcttgag tctggtcttg ttccaggtaa cagaaatgcg    5040
gataatgttg ataagctttt agaacaatac gaatatgtat tgtacccatc aagatcaatt    5100
caaaccgatg gtattaaagc cgtttctgtt acatcatttg gtttcggtca aaaaggtgca    5160
caagccgttg ttgttcatcc agattactta tttgctgttt tggatagatc cacttatgaa    5220
gaatatgcta ctaaggtctc tgctagaaat aaaaagacct accgttacat gcacaatgca    5280
atcaccagaa acactatgtt tgttgccaaa gacaaagctc catatagtga cgaattggaa    5340
caaccagttt acttggatcc attggctcgt gttgaagaaa acaagaaaaa gttggtattc    5400
agtgacaaaa caattcaatc gaaccaatct tatgttggag aagttgctca aaaaactgct    5460
aaggcattgt ctacttttaaa caaatcatca aagggagttg gtgtagatgt tgaattgttg    5520
tcagcaatca atatcgacaa tgaaaccttt attgaaagaa actttactgg taatgaagtt    5580
gaatactgtt tgaatactgc tcacccacaa gcttcattca ctggaacttg gtcagcaaag    5640
gaagctgttt tcaaagcctt gggtgttgaa tcaaaaggtg ctggagcaag cttgattgat    5700
attgaaatca ctcgtgacgt taatggtgct cctaaagtaa ttttgcatgg tgaggccaaa    5760
aaagctgctg ctaaagctgg tgttaaaaat gtcaatattt caatttctca tgatgatttc    5820
caagctactg ctgttgcttt aagtgaattt taaaattagt agtgtttaga aatattcgtg    5880
tatatctgat caaaaacttt tttgattttt aatatatgtc cggttgtaca atttttttt    5940 ctgttgattt aaactgatct cattattttg ttctctcaca gctcacagcc tacaaccata    6000
aaaaaagccc aacactcact tttgctcact ggttcaccac cactacggaa aaaataagaa    6060
caacaaataa aa                                                       6072
```

<210> SEQ ID NO 22

<211> LENGTH: 1885
<212> TYPE: PRT
<213> ORGANISM: Candida albicans

<400> SEQUENCE: 22

```
Met Lys Pro Glu Ile Glu Gln Glu Leu Ser His Thr Leu Leu Thr Glu
1               5                   10                  15

Leu Leu Ala Tyr Gln Phe Ala Ser Pro Val Arg Trp Ile Glu Thr Gln
            20                  25                  30

Asp Val Phe Leu Lys Gln His Asn Thr Glu Arg Ile Ile Glu Ile Gly
        35                  40                  45

Pro Ser Pro Thr Leu Ala Gly Met Ala Asn Arg Thr Ile Lys Ala Lys
    50                  55                  60

Tyr Glu Ser Tyr Asp Ala Ala Leu Ser Leu Gln Arg Gln Val Leu Cys
65                  70                  75                  80

Tyr Ser Lys Asp Ala Lys Glu Ile Tyr Tyr Lys Pro Asp Pro Ala Asp
                85                  90                  95

Leu Ala Pro Lys Glu Thr Pro Lys Gln Glu Glu Ser Thr Pro Ser Ala
            100                 105                 110

Pro Ala Ala Ala Thr Pro Thr Pro Ala Ala Ala Ala Pro Thr Pro
        115                 120                 125

Ala Pro Ala Pro Ala Ser Ala Gly Pro Val Glu Ser Ile Pro Asp Glu
    130                 135                 140

Pro Val Lys Ala Asn Leu Leu Ile His Val Leu Val Ala Gln Lys Leu
145                 150                 155                 160

Lys Lys Pro Leu Asp Ala Val Pro Met Thr Lys Ala Ile Lys Asp Leu
                165                 170                 175

Val Asn Gly Lys Ser Thr Val Gln Asn Glu Ile Leu Gly Asp Leu Gly
            180                 185                 190

Lys Glu Phe Gly Ser Thr Pro Glu Lys Pro Glu Asp Thr Pro Leu Glu
        195                 200                 205

Glu Leu Ala Glu Gln Phe Gln Asp Ser Phe Ser Gly Gln Leu Gly Lys
    210                 215                 220

Thr Ser Thr Ser Leu Ile Gly Arg Leu Met Ser Ser Lys Met Pro Gly
225                 230                 235                 240

Gly Phe Ser Ile Thr Thr Ala Arg Lys Tyr Leu Glu Ser Arg Phe Gly
                245                 250                 255

Leu Gly Ala Gly Arg Gln Asp Ser Val Leu Leu Met Ala Leu Thr Asn
            260                 265                 270

Glu Pro Ala Asn Arg Leu Gly Ser Glu Ala Asp Ala Lys Thr Phe Phe
        275                 280                 285

Asp Gly Ile Ala Gln Lys Tyr Ala Ser Ser Ala Gly Ile Ser Leu Ser
    290                 295                 300

Ser Gly Ala Gly Ser Gly Ala Gly Ala Ala Asn Ser Gly Gly Ala Val
305                 310                 315                 320

Val Asp Ser Ala Ala Leu Asp Ala Leu Thr Ala Glu Asn Lys Lys Leu
                325                 330                 335

Ala Lys Gln Gln Leu Glu Val Leu Ala Arg Tyr Leu Gln Ser Arg Leu
            340                 345                 350

Lys Gln Gly Ser Leu Lys Ser Phe Ile Lys Glu Lys Ala Ser Ala
        355                 360                 365

Val Leu Gln Lys Glu Leu Asp Leu Trp Glu Ala Glu His Gly Glu Phe
    370                 375                 380

Tyr Ala Lys Gly Ile Gln Pro Thr Phe Ser Ala Leu Lys Ser Arg Thr
```

-continued

```
            385                 390                 395                 400
Tyr Asp Ser Tyr Trp Asn Trp Ala Arg Gln Asp Val Leu Ser Met Tyr
                405                 410                 415

Phe Asp Ile Ile Phe Gly Lys Leu Thr Ser Val Asp Arg Glu Thr Ile
                420                 425                 430

Asn Gln Cys Ile Gln Ile Met Asn Arg Ala Asn Pro Thr Leu Ile Lys
                435                 440                 445

Phe Met Gln Tyr His Ile Asp His Cys Pro Glu Tyr Lys Gly Glu Thr
                450                 455                 460

Tyr Lys Leu Ala Lys Arg Leu Gly Gln Gln Leu Ile Asp Asn Cys Lys
465                 470                 475                 480

Gln Val Leu Thr Glu Asp Pro Val Tyr Lys Asp Val Ser Arg Ile Thr
                485                 490                 495

Gly Pro Lys Thr Lys Val Ser Ala Lys Gly Asn Ile Glu Tyr Glu Glu
                500                 505                 510

Thr Gln Lys Asp Ser Val Arg Lys Phe Glu Gln Tyr Val Tyr Glu Met
                515                 520                 525

Ala Gln Gly Gly Ala Met Thr Lys Val Ser Gln Pro Thr Ile Gln Glu
                530                 535                 540

Asp Leu Ala Arg Val Tyr Lys Ala Ile Ser Lys Gln Ala Ser Lys Asp
545                 550                 555                 560

Ser Lys Leu Glu Leu Gln Arg Val Tyr Glu Asp Leu Leu Lys Val Val
                565                 570                 575

Glu Ser Ser Lys Glu Ile Glu Thr Glu Gln Leu Thr Lys Asp Ile Leu
                580                 585                 590

Gln Ala Ala Thr Val Pro Thr Thr Pro Thr Glu Glu Val Asp Asp Pro
                595                 600                 605

Cys Thr Pro Ser Ser Asp Asp Glu Ile Ala Ser Leu Pro Asp Lys Thr
                610                 615                 620

Ser Ile Ile Gln Pro Val Ser Ser Thr Ile Pro Ser Gln Thr Ile Pro
625                 630                 635                 640

Phe Leu His Ile Gln Lys Lys Thr Lys Asp Gly Trp Glu Tyr Asn Lys
                645                 650                 655

Lys Leu Ser Ser Leu Tyr Leu Asp Gly Leu Glu Ser Ala Ala Ile Asn
                660                 665                 670

Gly Leu Thr Phe Lys Asp Lys Tyr Val Leu Val Thr Gly Ala Gly Ala
                675                 680                 685

Gly Ser Ile Gly Ala Glu Ile Leu Gln Gly Leu Ile Ser Gly Gly Ala
                690                 695                 700

Lys Val Ile Val Thr Thr Ser Arg Phe Ser Lys Lys Val Thr Glu Tyr
705                 710                 715                 720

Tyr Gln Asn Met Tyr Ala Arg Tyr Gly Ala Ala Gly Ser Thr Leu Ile
                725                 730                 735

Val Val Pro Phe Asn Gln Gly Ser Lys Gln Asp Val Asp Ala Leu Val
                740                 745                 750

Gln Tyr Ile Tyr Asp Glu Pro Lys Lys Gly Gly Leu Gly Trp Asp Leu
                755                 760                 765

Asp Ala Ile Ile Pro Phe Ala Ala Ile Pro Glu Asn Gly Asn Gly Leu
                770                 775                 780

Asp Asn Ile Asp Ser Lys Ser Glu Phe Ala His Arg Ile Met Leu Thr
785                 790                 795                 800

Asn Leu Leu Arg Leu Leu Gly Ala Val Lys Ser Lys Lys Pro Thr Asp
                805                 810                 815
```

-continued

Thr Arg Pro Ala Gln Cys Ile Leu Pro Leu Ser Pro Asn His Gly Thr
            820                 825                 830

Phe Gly Phe Asp Gly Leu Tyr Ser Glu Ser Lys Ile Ser Leu Glu Thr
            835                 840                 845

Leu Phe Asn Arg Trp Tyr Ser Glu Asp Trp Gly Ser Lys Leu Thr Val
            850                 855                 860

Cys Gly Ala Val Ile Gly Trp Thr Arg Gly Thr Gly Leu Met Ser Ala
865                 870                 875                 880

Asn Asn Ile Ile Ala Glu Gly Ile Glu Lys Leu Gly Val Arg Thr Phe
                    885                 890                 895

Ser Gln Lys Glu Met Ala Phe Asn Ile Leu Gly Leu Leu Thr Pro Glu
            900                 905                 910

Ile Val Gln Leu Cys Gln Glu Pro Val Met Ala Asp Leu Asn Gly
            915                 920                 925

Gly Leu Gln Phe Ile Asp Asn Leu Lys Asp Phe Thr Ser Lys Leu Arg
            930                 935                 940

Thr Asp Leu Leu Glu Thr Ala Asp Ile Arg Arg Ala Val Ser Ile Glu
945                 950                 955                 960

Ser Ala Ile Glu Gln Lys Val Val Asn Gly Asp Asn Val Asp Ala Asn
                    965                 970                 975

Tyr Ser Lys Val Met Val Glu Pro Arg Ala Asn Met Lys Phe Asp Phe
            980                 985                 990

Pro Thr Leu Lys Ser Tyr Asp Glu Ile Lys Gln Ile Ala Pro Glu Leu
            995                 1000                1005

Glu Gly Met Leu Asp Leu Glu Asn Val Val Val Thr Gly Phe
            1010                1015                1020

Ala Glu Val Gly Pro Trp Gly Asn Ser Arg Thr Arg Trp Glu Met
            1025                1030                1035

Glu Ala Tyr Gly Glu Phe Ser Leu Glu Gly Ala Ile Glu Met Ala
            1040                1045                1050

Trp Ile Met Gly Phe Ile Lys Tyr His Asn Gly Asn Leu Gln Gly
            1055                1060                1065

Lys Pro Tyr Ser Gly Trp Val Asp Ala Lys Thr Gln Thr Pro Ile
            1070                1075                1080

Asp Glu Lys Asp Ile Lys Ser Lys Tyr Glu Glu Glu Ile Leu Glu
            1085                1090                1095

His Ser Gly Ile Arg Leu Ile Glu Pro Glu Leu Phe Asn Gly Tyr
            1100                1105                1110

Asp Pro Lys Lys Lys Gln Met Ile Gln Glu Ile Val Val Gln His
            1115                1120                1125

Asp Leu Glu Pro Phe Glu Cys Ser Lys Glu Thr Ala Glu Gln Tyr
            1130                1135                1140

Lys His Glu His Gly Glu Lys Cys Glu Ile Phe Glu Ile Glu Glu
            1145                1150                1155

Ser Gly Glu Tyr Thr Val Arg Ile Leu Lys Gly Ala Thr Leu Tyr
            1160                1165                1170

Val Pro Lys Ala Leu Arg Phe Asp Arg Leu Val Ala Gly Gln Ile
            1175                1180                1185

Pro Thr Gly Trp Asp Ala Arg Thr Tyr Gly Ile Pro Glu Asp Thr
            1190                1195                1200

Ile Ser Gln Val Asp Pro Ile Thr Leu Tyr Val Leu Val Ala Thr
            1205                1210                1215

-continued

```
Val Glu Ala Leu Leu Ser Ala Gly Ile Thr Asp Pro Tyr Glu Phe
1220                1225                1230

Tyr Lys Tyr Val His Val Ser Glu Val Gly Asn Cys Ser Gly Ser
1235                1240                1245

Gly Met Gly Gly Val Ser Ala Leu Arg Gly Met Phe Lys Asp Arg
1250                1255                1260

Tyr Ala Asp Lys Pro Val Gln Asn Asp Ile Leu Gln Glu Ser Phe
1265                1270                1275

Ile Asn Thr Met Ser Ala Trp Val Asn Met Leu Leu Leu Ser Ser
1280                1285                1290

Ser Gly Pro Ile Lys Thr Pro Val Gly Ala Cys Ala Thr Ala Val
1295                1300                1305

Glu Ser Val Asp Ile Gly Ile Glu Thr Ile Leu Ser Gly Lys Ala
1310                1315                1320

Lys Val Val Leu Val Gly Gly Tyr Asp Asp Phe Gln Glu Glu Gly
1325                1330                1335

Ser Tyr Glu Phe Ala Asn Met Asn Ala Thr Ser Asn Ser Ile Glu
1340                1345                1350

Glu Phe Lys His Gly Arg Thr Pro Lys Glu Met Ser Arg Pro Thr
1355                1360                1365

Thr Thr Thr Arg Asn Gly Phe Met Glu Ala Gln Gly Ser Gly Ile
1370                1375                1380

Gln Val Ile Met Thr Ala Asp Leu Ala Leu Lys Met Gly Val Pro
1385                1390                1395

Ile His Ala Val Leu Ala Met Thr Ala Thr Ala Thr Asp Lys Ile
1400                1405                1410

Gly Arg Ser Val Pro Ala Pro Gly Lys Gly Ile Leu Thr Thr Ala
1415                1420                1425

Arg Glu His His Gly Asn Leu Lys Tyr Pro Ser Pro Leu Leu Asn
1430                1435                1440

Ile Lys Tyr Arg Lys Arg Gln Leu Asn Lys Arg Leu Glu Gln Ile
1445                1450                1455

Lys Ser Trp Glu Glu Thr Glu Leu Ser Tyr Leu Gln Glu Glu Ala
1460                1465                1470

Glu Leu Ala Lys Glu Glu Phe Gly Asp Glu Phe Ser Met His Glu
1475                1480                1485

Phe Leu Lys Glu Arg Thr Glu Glu Val Tyr Arg Glu Ser Lys Arg
1490                1495                1500

Gln Val Ser Asp Ala Lys Lys Gln Trp Gly Asn Ser Phe Tyr Lys
1505                1510                1515

Ser Asp Pro Arg Ile Ala Pro Leu Arg Gly Ala Leu Ala Ala Phe
1520                1525                1530

Asn Leu Thr Ile Asp Asp Ile Gly Val Ala Ser Phe His Gly Thr
1535                1540                1545

Ser Thr Val Ala Asn Asp Lys Asn Glu Ser Ala Thr Ile Asn Asn
1550                1555                1560

Met Met Lys His Leu Gly Arg Ser Glu Gly Asn Pro Val Phe Gly
1565                1570                1575

Val Phe Gln Lys Tyr Leu Thr Gly His Pro Lys Gly Ala Ala Gly
1580                1585                1590

Ala Trp Met Leu Asn Gly Ala Ile Gln Ile Leu Glu Ser Gly Leu
1595                1600                1605

Val Pro Gly Asn Arg Asn Ala Asp Asn Val Asp Lys Leu Leu Glu
```

```
              1610                1615                1620

Gln Tyr Glu Tyr Val Leu Tyr Pro Ser Arg Ser Ile Gln Thr Asp
    1625                1630                1635

Gly Ile Lys Ala Val Ser Val Thr Ser Phe Gly Phe Gly Gln Lys
    1640                1645                1650

Gly Ala Gln Ala Val Val His Pro Asp Tyr Leu Phe Ala Val
    1655                1660                1665

Leu Asp Arg Ser Thr Tyr Glu Glu Tyr Ala Thr Lys Val Ser Ala
    1670                1675                1680

Arg Asn Lys Lys Thr Tyr Arg Tyr Met His Asn Ala Ile Thr Arg
    1685                1690                1695

Asn Thr Met Phe Val Ala Lys Asp Lys Ala Pro Tyr Ser Asp Glu
    1700                1705                1710

Leu Glu Gln Pro Val Tyr Leu Asp Pro Leu Ala Arg Val Glu Glu
    1715                1720                1725

Asn Lys Lys Lys Leu Val Phe Ser Asp Lys Thr Ile Gln Ser Asn
    1730                1735                1740

Gln Ser Tyr Val Gly Glu Val Ala Gln Lys Thr Ala Lys Ala Leu
    1745                1750                1755

Ser Thr Leu Asn Lys Ser Ser Lys Gly Val Gly Val Asp Val Glu
    1760                1765                1770

Leu Leu Ser Ala Ile Asn Ile Asp Asn Glu Thr Phe Ile Glu Arg
    1775                1780                1785

Asn Phe Thr Gly Asn Glu Val Glu Tyr Cys Leu Asn Thr Ala His
    1790                1795                1800

Pro Gln Ala Ser Phe Thr Gly Thr Trp Ser Ala Lys Glu Ala Val
    1805                1810                1815

Phe Lys Ala Leu Gly Val Glu Ser Lys Gly Ala Gly Ala Ser Leu
    1820                1825                1830

Ile Asp Ile Glu Ile Thr Arg Asp Val Asn Gly Ala Pro Lys Val
    1835                1840                1845

Ile Leu His Gly Glu Ala Lys Lys Ala Ala Ala Lys Ala Gly Val
    1850                1855                1860

Lys Asn Val Asn Ile Ser Ile Ser His Asp Asp Phe Gln Ala Thr
    1865                1870                1875

Ala Val Ala Leu Ser Glu Phe
    1880                1885

<210> SEQ ID NO 23
<211> LENGTH: 3069
<212> TYPE: PRT
<213> ORGANISM: Mycobacterium tuberculosis

<400> SEQUENCE: 23

Met Thr Ile His Glu His Asp Arg Val Ser Ala Asp Arg Gly Gly Asp
1               5                   10                  15

Ser Pro His Thr Thr His Ala Leu Val Asp Arg Leu Met Ala Gly Glu
                20                  25                  30

Pro Tyr Ala Val Ala Phe Gly Gly Gln Gly Ser Ala Trp Leu Glu Thr
            35                  40                  45

Leu Glu Glu Leu Val Ser Ala Thr Gly Ile Glu Thr Glu Leu Ala Thr
        50                  55                  60

Leu Val Gly Glu Ala Glu Leu Leu Leu Asp Pro Val Thr Asp Glu Leu
65                  70                  75                  80
```

-continued

```
Ile Val Val Arg Pro Ile Gly Phe Glu Pro Leu Gln Trp Val Arg Ala
                 85                  90                  95
Leu Ala Ala Glu Asp Pro Val Pro Ser Asp Lys His Leu Thr Ser Ala
            100                 105                 110
Ala Val Ser Val Pro Gly Val Leu Leu Thr Gln Ile Ala Ala Thr Arg
        115                 120                 125
Ala Leu Ala Arg Gln Gly Met Asp Leu Val Ala Thr Pro Pro Val Ala
    130                 135                 140
Met Ala Gly His Ser Gln Gly Val Leu Ala Val Glu Ala Leu Lys Ala
145                 150                 155                 160
Gly Gly Ala Arg Asp Val Glu Leu Phe Ala Leu Ala Gln Leu Ile Gly
                165                 170                 175
Ala Ala Gly Thr Leu Val Ala Arg Arg Gly Ile Ser Val Leu Gly
            180                 185                 190
Asp Arg Pro Pro Met Val Ser Val Thr Asn Ala Asp Pro Glu Arg Ile
        195                 200                 205
Gly Arg Leu Leu Asp Glu Phe Ala Gln Asp Val Arg Thr Val Leu Pro
    210                 215                 220
Pro Val Leu Ser Ile Arg Asn Gly Arg Arg Ala Val Val Ile Thr Gly
225                 230                 235                 240
Thr Pro Glu Gln Leu Ser Arg Phe Glu Leu Tyr Cys Arg Gln Ile Ser
                245                 250                 255
Glu Lys Glu Glu Ala Asp Arg Lys Asn Lys Val Arg Gly Gly Asp Val
            260                 265                 270
Phe Ser Pro Val Phe Glu Pro Val Gln Val Glu Val Gly Phe His Thr
        275                 280                 285
Pro Arg Leu Ser Asp Gly Ile Asp Ile Val Ala Gly Trp Ala Glu Lys
    290                 295                 300
Ala Gly Leu Asp Val Ala Leu Ala Arg Glu Leu Ala Asp Ala Ile Leu
305                 310                 315                 320
Ile Arg Lys Val Asp Trp Val Asp Glu Ile Thr Arg Val His Ala Ala
                325                 330                 335
Gly Ala Arg Trp Ile Leu Asp Leu Gly Pro Gly Asp Ile Leu Thr Arg
            340                 345                 350
Leu Thr Ala Pro Val Ile Arg Gly Leu Gly Ile Gly Ile Val Pro Ala
        355                 360                 365
Ala Thr Arg Gly Gly Gln Arg Asn Leu Phe Thr Val Gly Ala Thr Pro
    370                 375                 380
Glu Val Ala Arg Ala Trp Ser Ser Tyr Ala Pro Thr Val Val Arg Leu
385                 390                 395                 400
Pro Asp Gly Arg Val Lys Leu Ser Thr Lys Phe Thr Arg Leu Thr Gly
                405                 410                 415
Arg Ser Pro Ile Leu Leu Ala Gly Met Thr Pro Thr Thr Val Asp Ala
            420                 425                 430
Lys Ile Val Ala Ala Ala Ala Asn Ala Gly His Trp Ala Glu Leu Ala
        435                 440                 445
Gly Gly Gly Gln Val Thr Glu Glu Ile Phe Gly Asn Arg Ile Glu Gln
    450                 455                 460
Met Ala Gly Leu Leu Glu Pro Gly Arg Thr Tyr Gln Phe Asn Ala Leu
465                 470                 475                 480
Phe Leu Asp Pro Tyr Leu Trp Lys Leu Gln Val Gly Gly Lys Arg Leu
                485                 490                 495
Val Gln Lys Ala Arg Gln Ser Gly Ala Ala Ile Asp Gly Val Val Ile
```

```
                500             505             510
Ser Ala Gly Ile Pro Asp Leu Asp Glu Ala Val Glu Leu Ile Asp Glu
            515             520             525

Leu Gly Asp Ile Gly Ile Ser His Val Val Phe Lys Pro Gly Thr Ile
        530             535             540

Glu Gln Ile Arg Ser Val Ile Arg Ile Ala Thr Glu Val Pro Thr Lys
545             550             555             560

Pro Val Ile Met His Val Glu Gly Gly Arg Ala Gly His His Ser
            565             570             575

Trp Glu Asp Leu Asp Asp Leu Leu Ala Thr Tyr Ser Glu Leu Arg
            580             585             590

Ser Arg Ala Asn Ile Thr Val Cys Val Gly Gly Ile Gly Thr Pro
            595             600             605

Arg Arg Ala Ala Glu Tyr Leu Ser Gly Arg Trp Ala Gln Ala Tyr Gly
        610             615             620

Phe Pro Leu Met Pro Ile Asp Gly Ile Leu Val Gly Thr Ala Ala Met
625             630             635             640

Ala Thr Lys Glu Ser Thr Thr Ser Pro Ser Val Lys Arg Met Leu Val
            645             650             655

Asp Thr Gln Gly Thr Asp Gln Trp Ile Ser Ala Gly Lys Ala Gln Gly
            660             665             670

Gly Met Ala Ser Ser Arg Ser Gln Leu Gly Ala Asp Ile His Glu Ile
        675             680             685

Asp Asn Ser Ala Ser Arg Cys Gly Arg Leu Leu Asp Glu Val Ala Gly
    690             695             700

Asp Ala Glu Ala Val Ala Glu Arg Arg Asp Glu Ile Ile Ala Ala Met
705             710             715             720

Ala Lys Thr Ala Lys Pro Tyr Phe Gly Asp Val Ala Asp Met Thr Tyr
            725             730             735

Leu Gln Trp Leu Arg Arg Tyr Val Glu Leu Ala Ile Gly Glu Gly Asn
            740             745             750

Ser Thr Ala Asp Thr Ala Ser Val Gly Ser Pro Trp Leu Ala Asp Thr
        755             760             765

Trp Arg Asp Arg Phe Glu Gln Met Leu Gln Arg Ala Glu Ala Arg Leu
    770             775             780

His Pro Gln Asp Phe Gly Pro Ile Gln Thr Leu Phe Thr Asp Ala Gly
785             790             795             800

Leu Leu Asp Asn Pro Gln Gln Ala Ile Ala Ala Leu Leu Ala Arg Tyr
            805             810             815

Pro Asp Ala Glu Thr Val Gln Leu His Pro Ala Asp Val Pro Phe Phe
            820             825             830

Val Thr Leu Cys Lys Thr Leu Gly Lys Pro Val Asn Phe Val Pro Val
        835             840             845

Ile Asp Gln Asp Val Arg Arg Trp Trp Arg Ser Asp Ser Leu Trp Gln
    850             855             860

Ala His Asp Ala Arg Tyr Asp Ala Asp Ala Val Cys Ile Ile Pro Gly
865             870             875             880

Thr Ala Ser Val Ala Gly Ile Thr Arg Met Asp Glu Pro Val Gly Glu
            885             890             895

Leu Leu Asp Arg Phe Glu Gln Ala Ile Asp Glu Val Leu Gly Ala
            900             905             910

Gly Val Glu Pro Lys Asp Val Ala Ser Arg Arg Leu Gly Arg Ala Asp
        915             920             925
```

```
Val Ala Gly Pro Leu Ala Val Val Leu Asp Ala Pro Asp Val Arg Trp
        930                 935                 940

Ala Gly Arg Thr Val Thr Asn Pro Val His Arg Ile Ala Asp Pro Ala
945                 950                 955                 960

Glu Trp Gln Val His Asp Gly Pro Glu Asn Pro Arg Ala Thr His Ser
                965                 970                 975

Ser Thr Gly Ala Arg Leu Gln Thr His Gly Asp Asp Val Ala Leu Ser
            980                 985                 990

Val Pro Val Ser Gly Thr Trp Val Asp Ile Arg Phe Thr Leu Pro Ala
            995                 1000                1005

Asn Thr Val Asp Gly Gly Thr Pro Val Ile Ala Thr Glu Asp Ala
    1010                1015                1020

Thr Ser Ala Met Arg Thr Val Leu Ala Ile Ala Ala Gly Val Asp
    1025                1030                1035

Ser Pro Glu Phe Leu Pro Ala Val Ala Asn Gly Thr Ala Thr Leu
    1040                1045                1050

Thr Val Asp Trp His Pro Glu Arg Val Ala Asp His Thr Gly Val
    1055                1060                1065

Thr Ala Thr Phe Gly Glu Pro Leu Ala Pro Ser Leu Thr Asn Val
    1070                1075                1080

Pro Asp Ala Leu Val Gly Pro Cys Trp Pro Ala Val Phe Ala Ala
    1085                1090                1095

Ile Gly Ser Ala Val Thr Asp Thr Gly Glu Pro Val Val Glu Gly
    1100                1105                1110

Leu Leu Ser Leu Val His Leu Asp His Ala Ala Arg Val Val Gly
    1115                1120                1125

Gln Leu Pro Thr Val Pro Ala Gln Leu Thr Val Thr Ala Thr Ala
    1130                1135                1140

Ala Asn Ala Thr Asp Thr Asp Met Gly Arg Val Val Pro Val Ser
    1145                1150                1155

Val Val Val Thr Gly Ala Asp Gly Ala Val Ile Ala Thr Leu Glu
    1160                1165                1170

Glu Arg Phe Ala Ile Leu Gly Arg Thr Gly Ser Ala Glu Leu Ala
    1175                1180                1185

Asp Pro Ala Arg Ala Gly Gly Ala Val Ser Ala Asn Ala Thr Asp
    1190                1195                1200

Thr Pro Arg Arg Arg Arg Asp Val Thr Ile Thr Ala Pro Val
    1205                1210                1215

Asp Met Arg Pro Phe Ala Val Val Ser Gly Asp His Asn Pro Ile
    1220                1225                1230

His Thr Asp Arg Ala Ala Ala Leu Leu Ala Gly Leu Glu Ser Pro
    1235                1240                1245

Ile Val His Gly Met Trp Leu Ser Ala Ala Ala Gln His Ala Val
    1250                1255                1260

Thr Ala Thr Asp Gly Gln Ala Arg Pro Pro Ala Arg Leu Val Gly
    1265                1270                1275

Trp Thr Ala Arg Phe Leu Gly Met Val Arg Pro Gly Asp Glu Val
    1280                1285                1290

Asp Phe Arg Val Glu Arg Val Gly Ile Asp Gln Gly Ala Glu Ile
    1295                1300                1305

Val Asp Val Ala Ala Arg Val Gly Ser Asp Leu Val Met Ser Ala
    1310                1315                1320
```

-continued

```
Ser Ala Arg Leu Ala Ala Pro Lys Thr Val Tyr Ala Phe Pro Gly
1325                1330                1335

Gln Gly Ile Gln His Lys Gly Met Gly Met Glu Val Arg Ala Arg
1340                1345                1350

Ser Lys Ala Ala Arg Lys Val Trp Asp Thr Ala Asp Lys Phe Thr
1355                1360                1365

Arg Asp Thr Leu Gly Phe Ser Val Leu His Val Val Arg Asp Asn
1370                1375                1380

Pro Thr Ser Ile Ile Ala Ser Gly Val His Tyr His His Pro Asp
1385                1390                1395

Gly Val Leu Tyr Leu Thr Gln Phe Thr Gln Val Ala Met Ala Thr
1400                1405                1410

Val Ala Ala Ala Gln Val Ala Glu Met Arg Glu Gln Gly Ala Phe
1415                1420                1425

Val Glu Gly Ala Ile Ala Cys Gly His Ser Val Gly Glu Tyr Thr
1430                1435                1440

Ala Leu Ala Cys Val Thr Gly Ile Tyr Gln Leu Glu Ala Leu Leu
1445                1450                1455

Glu Met Val Phe His Arg Gly Ser Lys Met His Asp Ile Val Pro
1460                1465                1470

Arg Asp Glu Leu Gly Arg Ser Asn Tyr Arg Leu Ala Ala Ile Arg
1475                1480                1485

Pro Ser Gln Ile Asp Leu Asp Asp Ala Asp Val Pro Ala Phe Val
1490                1495                1500

Ala Gly Ile Ala Glu Ser Thr Gly Glu Phe Leu Glu Ile Val Asn
1505                1510                1515

Phe Asn Leu Arg Gly Ser Gln Tyr Ala Ile Ala Gly Thr Val Arg
1520                1525                1530

Gly Leu Glu Ala Leu Glu Ala Glu Val Glu Arg Arg Arg Glu Leu
1535                1540                1545

Thr Gly Gly Arg Arg Ser Phe Ile Leu Val Pro Gly Ile Asp Val
1550                1555                1560

Pro Phe His Ser Arg Val Leu Arg Val Gly Val Ala Glu Phe Arg
1565                1570                1575

Arg Ser Leu Asp Arg Val Met Pro Arg Asp Ala Asp Pro Asp Leu
1580                1585                1590

Ile Ile Gly Arg Tyr Ile Pro Asn Leu Val Pro Arg Leu Phe Thr
1595                1600                1605

Leu Asp Arg Asp Phe Ile Gln Glu Ile Arg Asp Leu Val Pro Ala
1610                1615                1620

Glu Pro Leu Asp Glu Ile Leu Ala Asp Tyr Asp Thr Trp Leu Arg
1625                1630                1635

Glu Arg Pro Arg Glu Met Ala Arg Thr Val Phe Ile Glu Leu Leu
1640                1645                1650

Ala Trp Gln Phe Ala Ser Pro Val Arg Trp Ile Glu Thr Gln Asp
1655                1660                1665

Leu Leu Phe Ile Glu Glu Ala Ala Gly Gly Leu Gly Val Glu Arg
1670                1675                1680

Phe Val Glu Ile Gly Val Lys Ser Ser Pro Thr Val Ala Gly Leu
1685                1690                1695

Ala Thr Asn Thr Leu Lys Leu Pro Glu Tyr Ala His Ser Thr Val
1700                1705                1710

Glu Val Leu Asn Ala Glu Arg Asp Ala Ala Val Leu Phe Ala Thr
```

1715                1720                1725

Asp Thr Asp Pro Glu Pro Glu Pro Glu Asp Glu Pro Val Ala
        1730                1735                1740

Glu Ser Pro Ala Pro Asp Val Val Ser Glu Ala Ala Pro Val Ala
        1745                1750                1755

Pro Ala Ala Ser Ser Ala Gly Pro Arg Pro Asp Leu Val Phe
        1760                1765                1770

Asp Ala Ala Asp Ala Thr Leu Ala Leu Ile Ala Leu Ser Ala Lys
        1775                1780                1785

Met Arg Ile Asp Gln Ile Glu Glu Leu Asp Ser Ile Glu Ser Ile
        1790                1795                1800

Thr Asp Gly Ala Ser Ser Arg Arg Asn Gln Leu Leu Val Asp Leu
        1805                1810                1815

Gly Ser Glu Leu Asn Leu Gly Ala Ile Asp Gly Ala Ala Glu Ser
        1820                1825                1830

Asp Leu Ala Gly Leu Arg Ser Gln Val Thr Lys Leu Ala Arg Thr
        1835                1840                1845

Tyr Lys Pro Tyr Gly Pro Val Leu Ser Asp Ala Ile Asn Asp Gln
        1850                1855                1860

Leu Arg Thr Val Leu Gly Pro Ser Gly Lys Arg Pro Gly Ala Ile
        1865                1870                1875

Ala Glu Arg Val Lys Lys Thr Trp Glu Leu Gly Glu Gly Trp Ala
        1880                1885                1890

Lys His Val Thr Val Glu Val Ala Leu Gly Thr Arg Glu Gly Ser
        1895                1900                1905

Ser Val Arg Gly Gly Ala Met Gly His Leu His Glu Gly Ala Leu
        1910                1915                1920

Ala Asp Ala Ala Ser Val Asp Lys Val Ile Asp Ala Ala Val Ala
        1925                1930                1935

Ser Val Ala Ala Arg Gln Gly Val Ser Val Ala Leu Pro Ser Ala
        1940                1945                1950

Gly Ser Gly Gly Gly Ala Thr Ile Asp Ala Ala Ala Leu Ser Glu
        1955                1960                1965

Phe Thr Asp Gln Ile Thr Gly Arg Glu Gly Val Leu Ala Ser Ala
        1970                1975                1980

Ala Arg Leu Val Leu Gly Gln Leu Gly Leu Asp Asp Pro Val Asn
        1985                1990                1995

Ala Leu Pro Ala Ala Pro Asp Ser Glu Leu Ile Asp Leu Val Thr
        2000                2005                2010

Ala Glu Leu Gly Ala Asp Trp Pro Arg Leu Val Ala Pro Val Phe
        2015                2020                2025

Asp Pro Lys Lys Ala Val Val Phe Asp Asp Arg Trp Ala Ser Ala
        2030                2035                2040

Arg Glu Asp Leu Val Lys Leu Trp Leu Thr Asp Glu Gly Asp Ile
        2045                2050                2055

Asp Ala Asp Trp Pro Arg Leu Ala Glu Arg Phe Glu Gly Ala Gly
        2060                2065                2070

His Val Val Ala Thr Gln Ala Thr Trp Trp Gln Gly Lys Ser Leu
        2075                2080                2085

Ala Ala Gly Arg Gln Ile His Ala Ser Leu Tyr Gly Arg Ile Ala
        2090                2095                2100

Ala Gly Ala Glu Asn Pro Glu Pro Gly Arg Tyr Gly Gly Glu Val
        2105                2110                2115

```
Ala Val Val Thr Gly Ala Ser Lys Gly Ser Ile Ala Ala Ser Val
    2120            2125                2130

Val Ala Arg Leu Leu Asp Gly Gly Ala Thr Val Ile Ala Thr Thr
    2135            2140                2145

Ser Lys Leu Asp Glu Glu Arg Leu Ala Phe Tyr Arg Thr Leu Tyr
    2150            2155                2160

Arg Asp His Ala Arg Tyr Gly Ala Ala Leu Trp Leu Val Ala Ala
    2165            2170                2175

Asn Met Ala Ser Tyr Ser Asp Val Asp Ala Leu Val Glu Trp Ile
    2180            2185                2190

Gly Thr Glu Gln Thr Glu Ser Leu Gly Pro Gln Ser Ile His Ile
    2195            2200                2205

Lys Asp Ala Gln Thr Pro Thr Leu Leu Phe Pro Phe Ala Ala Pro
    2210            2215                2220

Arg Val Val Gly Asp Leu Ser Glu Ala Gly Ser Arg Ala Glu Met
    2225            2230                2235

Glu Met Lys Val Leu Leu Trp Ala Val Gln Arg Leu Ile Gly Gly
    2240            2245                2250

Leu Ser Thr Ile Gly Ala Glu Arg Asp Ile Ala Ser Arg Leu His
    2255            2260                2265

Val Val Leu Pro Gly Ser Pro Asn Arg Gly Met Phe Gly Gly Asp
    2270            2275                2280

Gly Ala Tyr Gly Glu Ala Lys Ser Ala Leu Asp Ala Val Val Ser
    2285            2290                2295

Arg Trp His Ala Glu Ser Ser Trp Ala Ala Arg Val Ser Leu Ala
    2300            2305                2310

His Ala Leu Ile Gly Trp Thr Arg Gly Thr Gly Leu Met Gly His
    2315            2320                2325

Asn Asp Ala Ile Val Ala Ala Val Glu Glu Ala Gly Val Thr Thr
    2330            2335                2340

Tyr Ser Thr Asp Glu Met Ala Ala Leu Leu Leu Asp Leu Cys Asp
    2345            2350                2355

Ala Glu Ser Lys Val Ala Ala Ala Arg Ser Pro Ile Lys Ala Asp
    2360            2365                2370

Leu Thr Gly Gly Leu Ala Glu Ala Asn Leu Asp Met Ala Glu Leu
    2375            2380                2385

Ala Ala Lys Ala Arg Glu Gln Met Ser Ala Ala Ala Val Asp
    2390            2395                2400

Glu Asp Ala Glu Ala Pro Gly Ala Ile Ala Ala Leu Pro Ser Pro
    2405            2410                2415

Pro Arg Gly Phe Thr Pro Ala Pro Pro Pro Gln Trp Asp Asp Leu
    2420            2425                2430

Asp Val Asp Pro Ala Asp Leu Val Val Ile Val Gly Gly Ala Glu
    2435            2440                2445

Ile Gly Pro Tyr Gly Ser Ser Arg Thr Arg Phe Glu Met Glu Val
    2450            2455                2460

Glu Asn Glu Leu Ser Ala Ala Gly Val Leu Glu Leu Ala Trp Thr
    2465            2470                2475

Thr Gly Leu Ile Arg Trp Glu Asp Asp Pro Gln Pro Gly Trp Tyr
    2480            2485                2490

Asp Thr Glu Ser Gly Glu Met Val Asp Glu Ser Glu Leu Val Gln
    2495            2500                2505
```

```
Arg Tyr His Asp Ala Val Val Gln Arg Val Gly Ile Arg Glu Phe
2510                2515                2520

Val Asp Asp Gly Ala Ile Asp Pro Asp His Ala Ser Pro Leu Leu
2525                2530                2535

Val Ser Val Phe Leu Glu Lys Asp Phe Ala Phe Val Val Ser Ser
2540                2545                2550

Glu Ala Asp Ala Arg Ala Phe Val Glu Phe Asp Pro Glu His Thr
2555                2560                2565

Val Ile Arg Pro Val Pro Asp Ser Thr Asp Trp Gln Val Ile Arg
2570                2575                2580

Lys Ala Gly Thr Glu Ile Arg Val Pro Arg Lys Thr Lys Leu Ser
2585                2590                2595

Arg Val Val Gly Gly Gln Ile Pro Thr Gly Phe Asp Pro Thr Val
2600                2605                2610

Trp Gly Ile Ser Ala Asp Met Ala Gly Ser Ile Asp Arg Leu Ala
2615                2620                2625

Val Trp Asn Met Val Ala Thr Val Asp Ala Phe Leu Ser Ser Gly
2630                2635                2640

Phe Ser Pro Ala Glu Val Met Arg Tyr Val His Pro Ser Leu Val
2645                2650                2655

Ala Asn Thr Gln Gly Thr Gly Met Gly Gly Gly Thr Ser Met Gln
2660                2665                2670

Thr Met Tyr His Gly Asn Leu Leu Gly Arg Asn Lys Pro Asn Asp
2675                2680                2685

Ile Phe Gln Glu Val Leu Pro Asn Ile Ala Ala His Val Val
2690                2695                2700

Gln Ser Tyr Val Gly Ser Tyr Gly Ala Met Ile His Pro Val Ala
2705                2710                2715

Ala Cys Ala Thr Ala Ala Val Ser Val Glu Glu Gly Val Asp Lys
2720                2725                2730

Ile Arg Leu Gly Lys Ala Gln Leu Val Val Ala Gly Gly Leu Asp
2735                2740                2745

Asp Leu Thr Leu Glu Gly Ile Ile Gly Phe Gly Asp Met Ala Ala
2750                2755                2760

Thr Ala Asp Thr Ser Met Met Cys Gly Arg Gly Ile His Asp Ser
2765                2770                2775

Lys Phe Ser Arg Pro Asn Asp Arg Arg Arg Leu Gly Phe Val Glu
2780                2785                2790

Ala Gln Gly Gly Gly Thr Ile Leu Leu Ala Arg Gly Asp Leu Ala
2795                2800                2805

Leu Arg Met Gly Leu Pro Val Leu Ala Val Val Ala Phe Ala Gln
2810                2815                2820

Ser Phe Gly Asp Gly Val His Thr Ser Ile Pro Ala Pro Gly Leu
2825                2830                2835

Gly Ala Leu Gly Ala Gly Arg Gly Gly Lys Asp Ser Pro Leu Ala
2840                2845                2850

Arg Ala Leu Ala Lys Leu Gly Val Ala Ala Asp Asp Val Ala Val
2855                2860                2865

Ile Ser Lys His Asp Thr Ser Thr Leu Ala Asn Asp Pro Asn Glu
2870                2875                2880

Thr Glu Leu His Glu Arg Leu Ala Asp Ala Leu Gly Arg Ser Glu
2885                2890                2895

Gly Ala Pro Leu Phe Val Val Ser Gln Lys Ser Leu Thr Gly His
```

```
                2900                2905                2910
Ala Lys Gly Gly Ala Ala Val Phe Gln Met Met Gly Leu Cys Gln
    2915                2920                2925

Ile Leu Arg Asp Gly Val Ile Pro Pro Asn Arg Ser Leu Asp Cys
    2930                2935                2940

Val Asp Asp Glu Leu Ala Gly Ser Ala His Phe Val Trp Val Arg
    2945                2950                2955

Asp Thr Leu Arg Leu Gly Gly Lys Phe Pro Leu Lys Ala Gly Met
    2960                2965                2970

Leu Thr Ser Leu Gly Phe Gly His Val Ser Gly Leu Val Ala Leu
    2975                2980                2985

Val His Pro Gln Ala Phe Ile Ala Ser Leu Asp Pro Ala Gln Arg
    2990                2995                3000

Ala Asp Tyr Gln Arg Arg Ala Asp Ala Arg Leu Leu Ala Gly Gln
    3005                3010                3015

Arg Arg Leu Ala Ser Ala Ile Ala Gly Gly Ala Pro Met Tyr Gln
    3020                3025                3030

Arg Pro Gly Asp Arg Arg Phe Asp His His Ala Pro Glu Arg Pro
    3035                3040                3045

Gln Glu Ala Ser Met Leu Leu Asn Pro Ala Ala Arg Leu Gly Asp
    3050                3055                3060

Gly Glu Ala Tyr Ile Gly
    3065

<210> SEQ ID NO 24
<211> LENGTH: 3076
<212> TYPE: PRT
<213> ORGANISM: Mycobacterium tuberculosis

<400> SEQUENCE: 24

Met Thr Ile His Glu His Asp Gln Val Ser Ala Asp Arg Asn Gly Asn
1               5                   10                  15

Ser Leu His Gly Ser Arg Ala Leu Ala Asp Arg Leu Lys Ala Gly Glu
            20                  25                  30

Pro Tyr Val Val Ala Phe Gly Gly Gln Gly Ser Ala Trp Leu Glu Thr
        35                  40                  45

Leu Glu Glu Leu Val Ser Ser Ala Gly Leu Glu Ala Asp Leu Ala Thr
    50                  55                  60

Leu Val Cys Glu Val Glu Leu Leu Glu Pro Val Ala Lys Glu Leu
65                  70                  75                  80

Val Val Val Arg Pro Ile Gly Phe Glu Pro Leu Gln Trp Val Arg Ala
                85                  90                  95

Leu Leu Ala Glu Asp Leu Val Pro Ser Asp Lys His Leu Thr Ser Ala
            100                 105                 110

Ala Val Ser Val Pro Gly Val Leu Leu Thr Gln Ile Ala Val Gly Arg
        115                 120                 125

Ala Leu Ala Arg Gln Gly Met Asp Leu Ile Ala Thr Pro Pro Val Gly
    130                 135                 140

Ile Val Gly His Ser Gln Gly Val Leu Ala Val Glu Ala Leu Lys Ala
145                 150                 155                 160

Gly Gly Ala Arg Asp Ala Glu Leu Leu Ala Met Ala Gln Leu Ile Gly
                165                 170                 175

Ala Ala Gly Thr Leu Val Ala Arg Arg Gly Ile Ser Val Leu Gly
            180                 185                 190
```

```
-continued

Asp Arg Pro Pro Met Val Ser Val Thr Asn Ala Asp Pro Glu Arg Ile
    195                 200                 205

Arg Arg Leu Leu Asp Glu Phe Ala Gln Asp Val Arg Thr Val Leu Pro
    210                 215                 220

Pro Val Leu Ser Ile Arg Asn Gly Trp Arg Ser Val Val Ile Thr Gly
225                 230                 235                 240

Thr Pro Glu Gln Leu Ser Arg Phe Glu Arg Tyr Cys Arg Gln Ile Ser
                245                 250                 255

Asp Lys Glu Glu Glu Asp Arg Arg Lys Lys Ile Arg Gly Gly Asp Ile
            260                 265                 270

Phe Ala Pro Val Phe Asp Pro Val Gln Val Glu Ile Gly Phe His Thr
        275                 280                 285

Pro His Leu Ala Asp Gly Ile Gly Ile Val Gly Gly Trp Ala Glu Lys
    290                 295                 300

Val Gly Leu Asp Val Thr Leu Ala Arg Glu Leu Thr Glu Ala Ile Leu
305                 310                 315                 320

Val Arg Gly Val Asp Trp Val Arg Glu Ile Thr Arg Val His Gly Ala
                325                 330                 335

Gly Val Arg Trp Ile Ile Asp Leu Gly Pro Gly Asp Ile Leu Thr Arg
            340                 345                 350

Leu Thr Ala Pro Val Ile Arg Gly Leu Gly Val Gly Ile Val Pro Val
        355                 360                 365

Ala Asn Arg Gly Gly Gln Arg Thr Leu Phe Thr Val Gly Ala Val Pro
    370                 375                 380

Glu Val Val Arg Ala Trp Leu Ser Tyr Ala Pro Thr Val Val Gln Leu
385                 390                 395                 400

Pro Asp Gly Arg Ile Lys Leu Ser Thr Lys Phe Thr Arg Leu Thr Gly
                405                 410                 415

Arg Ser Pro Ile Leu Leu Ala Gly Met Thr Pro Thr Thr Val Asp Ala
            420                 425                 430

Asn Ile Val Ala Ala Ala Asn Ala Gly His Trp Ala Glu Leu Ala
        435                 440                 445

Gly Gly Gly Gln Val Thr Glu Glu Ile Phe Ala Asn Arg Val Glu Gln
    450                 455                 460

Leu Ser Gly Leu Leu Glu Pro Gly Arg Thr Tyr Gln Phe Asn Ala Leu
465                 470                 475                 480

Phe Leu Asp Pro Tyr Leu Trp Lys Leu Gln Val Gly Gly Lys Arg Leu
                485                 490                 495

Val Gln Lys Ala Arg Gln Ser Gly Ala Ala Ile Asp Gly Val Val Ile
            500                 505                 510

Ser Gly Gly Ile Leu Asp Leu Glu Asp Ala Val Glu Leu Ile Glu Glu
        515                 520                 525

Leu Gly Gly Ile Gly Ile Ser Tyr Val Val Phe Lys Pro Gly Thr Ile
    530                 535                 540

Glu Gln Ile Arg Ser Val Ile Arg Ile Ala Thr Glu Met Ser Thr Lys
545                 550                 555                 560

Pro Val Ile Met His Val Glu Gly Gly Arg Ala Gly His His Ser
                565                 570                 575

Trp Glu Asp Leu Asp Asp Leu Leu Ala Thr Tyr Ser Glu Leu Arg
            580                 585                 590

Ser His Ala Asn Ile Thr Val Cys Val Gly Gly Ile Gly Thr Pro
        595                 600                 605

Glu Lys Ala Ala Glu Tyr Leu Ser Gly Arg Trp Ala Gln Ala Tyr Gly
```

```
                    610                 615                 620
Phe Pro Leu Met Pro Ile Asp Gly Ile Leu Val Gly Thr Ala Ala Met
625                 630                 635                 640

Ala Thr Lys Glu Ala Thr Thr Ser Pro Ser Val Lys Arg Met Leu Val
                645                 650                 655

Glu Thr Gln Gly Thr Asp Gln Trp Ile Gly Ser Gly Lys Ala Gln Gly
                660                 665                 670

Gly Met Ala Ser Ser Arg Ser Gln Leu Gly Ala Asp Ile His Glu Ile
                675                 680                 685

Asp Asn Ala Ala Ser Arg Cys Gly Arg Leu Leu Asp Glu Val Ala Gly
690                 695                 700

Asp Ala Glu Ala Val Ala Glu Arg Arg Asp Glu Ile Ile Ala Ala Met
705                 710                 715                 720

Ala Asn Thr Ala Lys Pro Tyr Phe Gly Asp Val Ser Glu Met Thr Tyr
                725                 730                 735

Leu Gln Trp Leu Gln Arg Tyr Val Glu Leu Thr Ile Gly Glu Gly Asn
                740                 745                 750

Ser Thr Ala Asp Thr Ala Ser Pro Gly Ser Pro Trp Leu Ala Asp Thr
                755                 760                 765

Trp Arg Asp Arg Phe Gln Lys Met Leu Gln Arg Ala Glu Ser Arg Leu
770                 775                 780

His Pro Ser Asp Phe Gly Leu Ile Lys Thr Ile Phe Thr Asp Pro Val
785                 790                 795                 800

Leu Leu Glu Lys Pro Asn Gln Ala Ile Ala Ala Leu Leu Lys Tyr Tyr
                805                 810                 815

Pro Asp Ala Glu Thr Val Gln Leu His Pro Asp Ala Pro Phe Phe
                820                 825                 830

Val Met Leu Cys Gln Met Leu Gly Lys Pro Val Asn Phe Val Pro Val
                835                 840                 845

Ile Asp Lys Asp Val Arg Arg Trp Trp Arg Ser Asp Ser Leu Trp Gln
850                 855                 860

Ala His Asp Ala Arg Tyr Asp Ala Asp Gln Val Cys Ile Ile Pro Gly
865                 870                 875                 880

Ile Ala Ala Val Ala Gly Ile Thr Gln Met Asp Glu Pro Val Gly Glu
                885                 890                 895

Leu Leu Asp Arg Phe Glu Gln Ala Ala Ile Asp Glu Val Leu Ala Gly
                900                 905                 910

Gly Ala Glu Pro Val Val Met Ser Arg Arg Leu Gly Arg Ala Asp
                915                 920                 925

Val Ala Gly Pro Leu Ala Val Val Leu Asp Ala Pro Asp Val Leu Trp
930                 935                 940

Ala Gly Arg Ile Ala Thr Asn Pro Val His Arg Ile Ala Asp Pro Asn
945                 950                 955                 960

Glu Trp Gln Val Asn Gly Asn Leu Ser Ala Thr His Ser Ser Thr Gly
                965                 970                 975

Ala Gln Leu Gln Val Lys Ser Glu Asp Gln Gln Val Val Leu Ser Val
                980                 985                 990

Pro Val Ser Asn Gly Trp Ile Asp Ile Pro Phe Thr Leu Pro Thr Asn
                995                 1000                1005

Thr Val Asp Gly Gly Ala Leu Leu Val Ser Thr Glu Asp Ala Thr
    1010                1015                1020

Ser Ala Met Arg Ala Val Leu Ala Ile Val Ala Gly Val Asp Gly
    1025                1030                1035
```

-continued

```
Pro Glu Leu Leu Ser Pro Val Lys Asp Gly Thr Ala Ile Val Thr
    1040            1045                1050

Val Asp Trp Asn Pro Glu Arg Val Ala Asp His Thr Gly Val Thr
    1055            1060                1065

Ala Thr Phe Arg Glu Pro Leu Ala Pro Ser Leu Ala Thr Val Pro
    1070            1075                1080

Asp Ala Leu Val Gly Ala Cys Trp Pro Ala Val Phe Ser Ala Ile
    1085            1090                1095

Gly Ser Ala Val Thr Glu Ala Gly Val Leu Val Glu Gly Leu
    1100            1105                1110

Leu Asn Leu Leu His Leu Asp His Ala Val Cys Val Val Gly Lys
    1115            1120                1125

Leu Pro Thr Val Pro Ala Gln Leu Thr Val Thr Ala Thr Val Ser
    1130            1135                1140

Leu Ala Ile Asp Thr Asp Met Gly Arg Val Val Pro Val Ser Val
    1145            1150                1155

Thr Ile Arg Asp Thr Thr Gly Ala Asp Gly Ala Val Leu Ala Thr
    1160            1165                1170

Leu Glu Glu Arg Phe Val Ile Leu Gly Arg Thr Gly Thr Ala Glu
    1175            1180                1185

Leu Thr Gly Pro Val Arg Ala Gly Gly Ala Ile Ser Glu Asn Ala
    1190            1195                1200

Thr Asp Thr Pro Arg Arg Arg Arg Asp Val Thr Leu Thr Ala
    1205            1210                1215

Pro Ile Asp Met Arg Pro Phe Ala Val Val Ser Gly Asp His Asn
    1220            1225                1230

Pro Ile His Thr Asp Arg Thr Ala Ala Leu Leu Ala Gly Leu Glu
    1235            1240                1245

Ser Pro Ile Val His Gly Met Trp Leu Ser Ala Ala Gln His
    1250            1255                1260

Val Val Met Ala Thr Asp Gly Gln Ala Arg Pro Ala Ala Arg Leu
    1265            1270                1275

Ile Gly Trp Thr Ala Arg Phe Leu Gly Met Ala His Pro Gly Asp
    1280            1285                1290

Lys Val Asp Phe Arg Val Asp Arg Ile Gly Ile Asp Gln Gly Ala
    1295            1300                1305

Glu Ile Leu Glu Val Ser Ala Arg Ile Ser Ser Gly Leu Val Met
    1310            1315                1320

Ser Ala Thr Ala Arg Leu Ala Ala Pro Lys Thr Val Tyr Ala Phe
    1325            1330                1335

Pro Gly Gln Gly Ile Gln His Lys Gly Met Gly Met Asp Val Arg
    1340            1345                1350

Ala Arg Ser Lys Ala Ala Arg Arg Val Trp Asp Asp Ala Asp Lys
    1355            1360                1365

Phe Thr Arg Ser Gly Leu Gly Phe Ser Val Leu His Val Val Arg
    1370            1375                1380

Asp Asn Pro Thr Asn Ile Thr Ala Asn Gly Val His Tyr His His
    1385            1390                1395

Pro Asp Gly Val Leu Tyr Leu Thr Gln Phe Thr Gln Val Ala Met
    1400            1405                1410

Ala Thr Val Ala Val Ala Gln Val Ala Glu Met Arg Glu Gln Gly
    1415            1420                1425
```

-continued

```
Ala Phe Val Glu Gly Ala Ile Ala Cys Gly His Ser Val Gly Glu
1430                1435                1440

Tyr Thr Ala Leu Ala Cys Val Met Gly Val Tyr Glu Leu Glu Ala
1445                1450                1455

Leu Leu Glu Thr Val Phe His Arg Gly Ser Lys Met His Asp Ile
1460                1465                1470

Val Leu Arg Asp Glu Leu Gly Arg Ser Asn Tyr Arg Leu Ala Ala
1475                1480                1485

Ile Arg Pro Ser Gln Ile Gly Leu Pro Asp Asp Glu Val Pro Ala
1490                1495                1500

Phe Val Arg Gly Ile Ala Glu Ser Thr Gly Glu Phe Leu Glu Ile
1505                1510                1515

Val Asn Phe Asn Leu Arg Gly Ser Gln Tyr Ala Ile Ala Gly Thr
1520                1525                1530

Val His Gly Leu Glu Ala Leu Glu Ala Glu Val Glu Arg Arg Arg
1535                1540                1545

Glu Leu Thr Gly Gly Arg Arg Ser Phe Ile Leu Val Pro Gly Ile
1550                1555                1560

Asp Val Pro Phe His Ser Arg Val Leu Arg Val Gly Val Ala Glu
1565                1570                1575

Phe Arg Arg Ser Leu Asp Arg Val Leu Pro Gln Asp Gln Asp Pro
1580                1585                1590

Asp Trp Ile Ile Gly Arg Tyr Ile Pro Asn Leu Val Pro Arg Pro
1595                1600                1605

Phe Thr Leu Ala Arg Asp Phe Ile Gln Glu Ile Arg Asp Leu Val
1610                1615                1620

Pro Ala Glu Pro Leu Asp Asp Ile Leu Ala Asp Tyr Asp Thr Trp
1625                1630                1635

Arg Arg Glu Arg Pro Ser Glu Met Ala Arg Arg Val Leu Ile Glu
1640                1645                1650

Leu Leu Ala Trp Gln Phe Ala Ser Pro Val Arg Trp Ile Glu Thr
1655                1660                1665

Gln Asp Leu Leu Phe Thr Glu Glu Ala Ala Gly Gly Leu Gly Val
1670                1675                1680

Glu Arg Phe Val Glu Ile Gly Val Lys Ser Ala Pro Thr Val Ala
1685                1690                1695

Gly Leu Ala Thr Asp Thr Leu Lys Leu Pro Glu Tyr Ser His Asn
1700                1705                1710

Thr Val Glu Val Leu Asn Val Glu Arg Asp Ala Ala Val Leu Phe
1715                1720                1725

Ala Thr Asp Thr Asp Pro Glu Leu Glu Pro Glu Pro Glu Asn Val
1730                1735                1740

Ser Asp Ala Ser Ala Ala Leu Pro Ala Glu Ser Ala Leu Ala Leu
1745                1750                1755

Gly Thr Val Ala Pro Ala Pro Val Val Pro Ser Gly Pro Arg Pro
1760                1765                1770

Glu Asp Ile Ser Phe Gly Ala Ala Asp Ala Thr Leu Ala Leu Ile
1775                1780                1785

Ala Leu Ser Ala Lys Met Arg Leu Asp Gln Ile Glu Glu Met Asp
1790                1795                1800

Ser Ile Glu Ser Ile Thr Asp Gly Ala Ser Ser Arg Arg Asn Gln
1805                1810                1815

Leu Leu Val Asp Leu Gly Ser Glu Leu Ser Leu Gly Ala Ile Asp
```

-continued

```
            1820              1825              1830
Gly Val Ala Glu Ala Asp Leu Ala Gly Leu Arg Ser Gln Val Thr
    1835              1840              1845
Lys Leu Ala Arg Thr Tyr Lys Pro Tyr Gly Pro Val Leu Ser Glu
    1850              1855              1860
Leu Ile Asn Asp Gln Leu Arg Ser Ala Leu Gly Pro Ser Gly Lys
    1865              1870              1875
Arg Pro Gly Val Ile Ala Glu Arg Val Lys Lys Ile Trp Glu Leu
    1880              1885              1890
Gly Asp Gly Trp Val Lys His Val Thr Val Glu Ile Ala Leu Gly
    1895              1900              1905
Thr Arg Glu Gly Thr Ser Val Arg Gly Gly Pro Leu Gly Asn Leu
    1910              1915              1920
Asn Glu Gly Ala Leu Ala Asp Val Asp Ser Val Asp Lys Ala Val
    1925              1930              1935
Asp Ala Ala Val Ala Ser Val Ala Ala Arg His Gly Val Val Val
    1940              1945              1950
Ala Leu Pro Ser Ala Gly Ser Gly Gly Ser Ala Thr Val Asp Val
    1955              1960              1965
Ala Ala Leu Ser Glu Phe Thr Asp Gln Ile Thr Gly His Asp Gly
    1970              1975              1980
Val Leu Ala Ser Ala Ala Arg Leu Val Leu Gly Gln Leu Gly Leu
    1985              1990              1995
Asp Gly Pro Val Thr Ala Ala Pro Ala Thr Thr Asp Thr Gly Leu
    2000              2005              2010
Ile Asp Leu Val Thr Ala Glu Leu Ser Thr Asp Trp Pro Arg Leu
    2015              2020              2025
Val Ala Pro Val Phe Asp Val Lys Lys Ala Val Val Phe Asp Asp
    2030              2035              2040
Arg Trp Ala Ser Ala Arg Glu Asp Leu Val Arg Leu Trp Leu Asn
    2045              2050              2055
Asp Glu Gly Glu Ile Glu Ala Gln Trp Ser His Leu Ser Glu Arg
    2060              2065              2070
Phe Glu Gly Ala Gly His Val Val Ala Thr Gln Ala Thr Trp Trp
    2075              2080              2085
Gln Gly Lys Ser Leu Ala Ala Gly Arg Gln Ile His Ala Ser Leu
    2090              2095              2100
Tyr Gly Arg Ile Ala Ala Gly Ala Gln Asn Pro Asp Arg Gly Leu
    2105              2110              2115
Tyr Ser Ser Glu Ile Ala Val Val Thr Gly Ala Ser Lys Gly Ser
    2120              2125              2130
Ile Ala Ala Ser Val Ala Ala Arg Leu Leu Asp Gly Gly Ala Thr
    2135              2140              2145
Val Ile Ala Thr Thr Ser Lys Leu Asp Glu Glu Arg Ile Thr Phe
    2150              2155              2160
Tyr Arg Ala Leu Tyr Arg Asp His Ala Arg Tyr Gly Ala Ala Leu
    2165              2170              2175
Trp Val Val Ala Ala Asn Met Ala Ser Tyr Ser Asp Ile Asp Ala
    2180              2185              2190
Leu Val Glu Trp Ile Gly Asn Glu Gln Thr Glu Ser Leu Gly Pro
    2195              2200              2205
Gln Ser Ile His Ile Lys Asp Ala Gln Thr Pro Thr Leu Leu Phe
    2210              2215              2220
```

-continued

```
Pro Phe Ala Ala Pro Arg Val Ile Gly Asp Leu Ser Glu Ala Gly
2225                2230                2235

Ala Arg Ser Glu Ile Glu Met Lys Val Leu Leu Trp Ala Val Gln
2240                2245                2250

Arg Leu Ile Val Gly Leu Ser Lys Ile Gly Thr Glu Arg Asp Val
2255                2260                2265

Ala Ser Arg Leu His Val Val Leu Pro Gly Ser Pro Asn Arg Gly
2270                2275                2280

Met Phe Gly Gly Asp Gly Ala Tyr Gly Glu Ala Lys Ser Ala Leu
2285                2290                2295

Asp Ala Val Val Ser Arg Trp His Ala Glu Ser Ser Trp Ala Ala
2300                2305                2310

Arg Val Ser Leu Ala His Ala Leu Ile Gly Trp Thr Arg Gly Thr
2315                2320                2325

Gly Leu Met Gly His Asn Asp Val Ile Val Ser Ala Val Glu Glu
2330                2335                2340

Ala Gly Val Thr Thr Tyr Ser Thr Asp Glu Met Ala Ala Met Leu
2345                2350                2355

Leu Asp Leu Cys Asn Ala Glu Ser Lys Val Ala Ala Ala Gly Thr
2360                2365                2370

Pro Ile Thr Val Asp Leu Thr Gly Gly Leu Gly Glu Val Asp Leu
2375                2380                2385

Asp Met Ala Glu Leu Ala Ala Lys Ala Arg Glu Asp His Ala Ala
2390                2395                2400

Gln Ala Ala Glu Asp Glu Ala Thr Glu Ala Ser Glu Val Ala Gly
2405                2410                2415

Thr Ile Ala Ala Leu Pro Ser Pro Pro Arg Gly Tyr Thr Pro Ala
2420                2425                2430

Ser Pro His Trp Asp Asp Leu Asp Val Asp Pro Ala Asp Leu Val
2435                2440                2445

Val Ile Val Gly Gly Ala Glu Ile Gly Pro Tyr Gly Ser Ser Arg
2450                2455                2460

Thr Arg Phe Glu Met Glu Val Ala Gly Glu Leu Ser Ala Ala Gly
2465                2470                2475

Val Leu Glu Leu Val Trp Thr Thr Gly Leu Ile Arg Trp Glu Asp
2480                2485                2490

Asp Pro Gln Pro Gly Trp Tyr Asp Thr Glu Ser Gly Glu Leu Val
2495                2500                2505

Asp Glu Ser Glu Leu Val Glu Arg Tyr His Asp Thr Val Val Gln
2510                2515                2520

Arg Cys Gly Ile Arg Glu Phe Val Asp Asp Gly Thr Ile Asp Pro
2525                2530                2535

Asp His Ala Tyr Pro Leu Leu Val Ser Val Phe Leu Asp Lys Asp
2540                2545                2550

Phe Ala Phe Val Val Ser Ser Glu Ala Asp Ala Arg Ala Phe Val
2555                2560                2565

Glu Phe Asp Pro Glu His Thr Val Ile Arg Pro Val Pro Asp Ser
2570                2575                2580

Ser Asp Trp Gln Val Ile Arg Lys Ala Gly Thr Glu Ile Arg Val
2585                2590                2595

Pro Arg Lys Met Lys Leu Ser Arg Val Val Gly Gly Gln Ile Pro
2600                2605                2610
```

```
Thr Gly Phe Asp Pro Thr Val Trp Gly Ile Ser Pro Asp Met Val
2615                 2620                2625

Ser Ser Ile Asp Arg Val Ala Val Trp Ser Ile Val Ala Thr Val
2630                 2635                2640

Asp Ala Phe Leu Ser Ala Gly Phe Thr Pro Ala Glu Val Met Arg
2645                 2650                2655

Tyr Val His Pro Ser Leu Val Ala Asn Thr Met Gly Thr Gly Met
2660                 2665                2670

Gly Gly Gly Thr Ser Ile Gln Arg Leu Tyr His Ser Ser Leu Leu
2675                 2680                2685

Gly Arg Asn Lys Pro Asn Asp Ile Phe Gln Glu Ile Leu Pro Asn
2690                 2695                2700

Ile Val Ala Ala His Val Val Gln Ser Tyr Ile Gly Ser Tyr Gly
2705                 2710                2715

Ser Met Ile His Pro Val Ala Ala Cys Ala Thr Ala Ala Val Ser
2720                 2725                2730

Val Glu Glu Gly Val Asp Lys Ile Arg Leu Gly Lys Ala Glu Leu
2735                 2740                2745

Val Val Ala Gly Gly Ile Asp Asp Leu Thr Leu Glu Gly Ile Ile
2750                 2755                2760

Gly Phe Gly Asp Met Ala Ala Thr Ala Asp Thr Ala Met Met Arg
2765                 2770                2775

Gly Arg Gly Ile His Asp Ser Lys Phe Ser Arg Pro Asn Asp Arg
2780                 2785                2790

Arg Arg Leu Gly Phe Val Glu Ala Gln Gly Gly Gly Thr Ile Leu
2795                 2800                2805

Leu Ala Arg Gly Asp Leu Ala Leu Lys Met Gly Leu Pro Val Phe
2810                 2815                2820

Ala Val Val Ala Phe Ala Gln Ser Phe Gly Asp Gly Val His Thr
2825                 2830                2835

Ser Ile Pro Ala Pro Gly Leu Gly Ala Leu Gly Ala Gly Arg Gly
2840                 2845                2850

Gly Lys Asp Ser Pro Leu Val Gln Ser Leu Ala Lys Leu Gly Val
2855                 2860                2865

Ser Ala Asp Asp Ile Ala Val Ile Ser Lys His Asp Thr Ser Thr
2870                 2875                2880

Leu Ala Asn Asp Pro Asn Glu Thr Glu Leu His Glu Arg Leu Ala
2885                 2890                2895

Asp Ala Met Gly Arg Ser Ala Gly Ala Pro Leu Phe Val Val Ser
2900                 2905                2910

Gln Lys Ser Leu Thr Gly His Ala Lys Gly Gly Ala Ala Val Phe
2915                 2920                2925

Gln Met Met Gly Leu Cys Gln Met Leu Arg Asp Gly Val Ile Pro
2930                 2935                2940

Pro Asn Arg Ser Leu Asp Cys Val Asp Glu Glu Leu Ala Gly Ala
2945                 2950                2955

Ala His Phe Val Trp Leu Arg Asp Thr Leu Arg Leu Gly Glu Lys
2960                 2965                2970

Phe Pro Leu Lys Ala Gly Met Leu Thr Ser Leu Gly Phe Gly His
2975                 2980                2985

Val Ser Gly Leu Val Ala Leu Val His Pro Gln Ala Phe Ile Ala
2990                 2995                3000

Ala Leu Asp Pro Gly Gln Arg Asp Asp Tyr Gln Arg Arg Ala Asn
```

```
                    3005                3010                3015
Val Arg Leu Leu Ala Gly Gln Arg Arg Leu Ala Ser Ala Ile Ala
        3020                3025                3030

Gly Gly Ala Pro Met Tyr Glu Arg Pro Pro Asp Arg Arg Phe Asp
        3035                3040                3045

His His Val Pro Glu Lys Leu Gln Glu Ala Ala Met Leu Leu Asn
        3050                3055                3060

Pro Ala Ala Arg Leu Gly Asp Gly Asp Ala Tyr Ile Gly
        3065                3070                3075

<210> SEQ ID NO 25
<211> LENGTH: 2586
<212> TYPE: PRT
<213> ORGANISM: Caenorhabditis elegans

<400> SEQUENCE: 25

Met Asp Pro Thr Gln Trp Trp Gln Lys Gln Asp Ile Val Ile Ser
1               5                   10                  15

Gly Val Ser Gly Arg Phe Pro Arg Cys Asp Asn Val Lys Met Phe Gly
                20                  25                  30

Asp Met Leu Leu Ala Gly Glu Asp Leu Val Thr Glu Asp Ser Leu Arg
            35                  40                  45

Trp Thr Pro Gly Phe Cys Asp Leu Pro Lys Arg His Gly Lys Leu Lys
        50                  55                  60

Val Leu Asn Lys Phe Asp Ala Gly Phe Phe Gln Val Thr Pro Lys Gln
65                  70                  75                  80

Ala Asn Phe Met Asp Pro Gln Val Arg Leu Leu Leu Glu Ala Ser Trp
                    85                  90                  95

Glu Ala Met Val Asp Ala Gly Ile Asn Pro Thr Asp Leu Arg Gly Ser
                100                 105                 110

Lys Thr Gly Val Phe Val Gly Cys Ser Ala Ser Glu Thr Ser Gly Met
            115                 120                 125

Leu Thr Gln Asp Pro Asp Thr Val Thr Gly Tyr Thr Leu Thr Gly Cys
        130                 135                 140

Val Arg Ser Met Phe Ser Asn Arg Ile Ser Tyr Thr Phe Asp Leu Gln
145                 150                 155                 160

Gly Pro Ser Phe Ser Val Asp Thr Ala Cys Ser Ser Leu Leu Ala
                165                 170                 175

Leu Gln Leu Ala Val Asp Ser Ile Arg Gln Gly Gln Cys Asp Ala Ala
            180                 185                 190

Ile Val Ala Gly Ala His Leu Thr Leu Thr Pro Thr Ala Ala Leu Gln
        195                 200                 205

Phe Leu Arg Leu Gly Met Leu Thr Asp Lys Gly Ser Cys Arg Ser Phe
    210                 215                 220

Asp Glu Ser Gly Asp Gly Tyr Cys Arg Thr Glu Gly Val Ala Ala Ile
225                 230                 235                 240

Phe Ile Gln Arg Lys Lys Lys Ala Gln Arg Leu Tyr Ala Thr Val Val
                    245                 250                 255

His Ala Lys Ser Asn Thr Asp Gly His Lys Glu His Gly Ile Thr Phe
                260                 265                 270

Pro Ser Gly Glu Arg Gln Ala Gln Leu Leu Gln Glu Val Tyr Ser Glu
            275                 280                 285

Ala Gly Ile Asp Pro Asn Ser Val Tyr Tyr Val Glu Ala His Gly Thr
        290                 295                 300
```

-continued

```
Gly Thr Lys Val Gly Asp Pro Gln Glu Ala Asn Ala Ile Cys Glu Val
305                 310                 315                 320

Phe Cys Ser Lys Arg Thr Asp Ser Leu Leu Ile Gly Ser Val Lys Ser
            325                 330                 335

Asn Met Gly His Ala Glu Pro Ala Ser Gly Val Cys Ser Leu Thr Lys
        340                 345                 350

Ile Leu Leu Ser Ile Glu Arg Gln Leu Ile Pro Pro Asn Leu His Tyr
    355                 360                 365

Asn Thr Pro Asn Gln Tyr Ile Pro Gly Leu Thr Asp Gly Arg Leu Lys
    370                 375                 380

Val Val Thr Glu Pro Thr Ala Leu Pro Gly Gly Leu Ile Gly Ile Asn
385                 390                 395                 400

Ser Phe Gly Phe Gly Gly Ser Asn Thr His Val Ile Leu Lys Ala Ala
                405                 410                 415

Asp His Ile Ala Pro Pro Ile Thr Pro His Pro Phe Thr Lys Leu Val
            420                 425                 430

Thr Tyr Cys Gly Arg Thr Gln Glu Ala Val Glu Asn Ile Phe Thr Glu
        435                 440                 445

Ile Glu Ser Asn Lys Asp Asp Leu Tyr Leu Gln Ala Leu Leu Ala Asn
    450                 455                 460

Gln Ala Asn Met Pro Ala Asn Leu Leu Pro Phe Arg Gly Tyr Met Leu
465                 470                 475                 480

Leu Asp Arg Glu Asn Asn Val Glu Thr Leu Lys Ser Ile Thr Lys Val
                485                 490                 495

Pro Ile Thr Glu Ala Arg Pro Ile Tyr Phe Ile Tyr Ser Gly Met Gly
            500                 505                 510

Ser Gln Trp Pro Gly Met Ala Ile Lys Leu Met Lys Ile Pro Met Phe
        515                 520                 525

Asp Asp Ser Leu Arg Ala Ser Ser Lys Thr Leu Glu Glu Phe Gly Leu
    530                 535                 540

Asp Val Tyr Gly Met Leu Cys Asn Pro Asp Pro Glu Gln Tyr Ser Asn
545                 550                 555                 560

Asn Thr Met Asn Cys Met Leu Ala Ile Thr Ala Ile Gln Ile Ala Leu
                565                 570                 575

Thr Asp Val Leu Thr Ala Leu Gly Val Ser Pro Asp Gly Ile Ile Gly
        580                 585                 590

His Ser Thr Gly Glu Met Gly Cys Gly Tyr Ala Asp Gly Gly Ile Thr
    595                 600                 605

Arg Glu Gln Thr Met Arg Leu Ala Tyr His Arg Gly Thr Thr Ile Met
    610                 615                 620

Lys His Thr Glu Ile Lys Gly Ala Met Ala Ala Val Gly Leu Thr Trp
625                 630                 635                 640

Glu Gln Val Lys Glu Gln Ala Pro Pro Gly Val Val Ala Ala Cys His
                645                 650                 655

Asn Gly Ala Asp Ser Val Thr Ile Ser Gly Asp Ala Glu Gly Val Ala
            660                 665                 670

Thr Phe Cys Ala Gln Leu Lys Glu Lys Asp Ile Phe Ala Lys Val Val
        675                 680                 685

Asp Thr Ser Gly Ile Pro Phe His Ser Pro Ala Met Leu Ala Val Gln
        690                 695                 700

Asp Glu Met Ile Glu Cys Met Arg Thr Ala Val Pro Glu Pro Lys Pro
705                 710                 715                 720

Arg Ser Ser Lys Trp Ile Ser Thr Ser Ile Pro Glu Asp Asp Trp Glu
```

-continued

```
                725                 730                 735
Ser Asp Leu Ala Ala Thr Cys Ser Ala Glu Tyr His Val His Asn Ala
                740                 745                 750
Cys Ser Pro Val Leu Phe Tyr Glu Ala Ile Gln Lys Ile Pro Ala Asn
                755                 760                 765
Ala Val Thr Ile Glu Met Ala Pro His Ser Leu Met Gln Ala Ile Leu
                770                 775                 780
Arg Arg Ser Leu Gln Lys Thr Val Thr Asn Val Gly Leu Met Asn Arg
785                 790                 795                 800
Pro Lys Ser Glu Asn Asp Asp Glu Leu Glu Ser Phe Leu Gly Ser Leu
                805                 810                 815
Gly Lys Ile Tyr Gln Ala Gly Val Asn Ile Gln Ile Thr Glu Leu Tyr
                820                 825                 830
Pro Gly Gly Gln Tyr Lys Gly Val Val Pro Lys Gly Thr Pro Met Ile
                835                 840                 845
Gly Pro Met Trp Lys Trp Asp His Thr Gln Asp Trp Leu Thr Ile Asp
                850                 855                 860
Gly Arg Gln Val Leu Ala Gly Ser Gly Ser Val Ala Ser Ser Ala
865                 870                 875                 880
Thr Tyr Asn Ile Asp Pro Phe Ala Thr Asp Ser Lys Glu Thr Tyr Leu
                885                 890                 895
Leu Asp His Val Ile Asp Gly Arg Val Leu Tyr Pro Phe Thr Gly His
                900                 905                 910
Met Val Leu Ala Trp Arg Thr Leu Cys Lys Leu Lys Gly Leu Asp Tyr
                915                 920                 925
Thr Lys Thr Pro Val Val Phe Glu Asn Ile Asn Val Phe Ser Ala Thr
                930                 935                 940
Ile Leu Thr Lys Pro Ile Lys Leu Asp Val Val Leu Ser Pro Gly Asn
945                 950                 955                 960
Gly Tyr Phe Glu Ile Ile Ser Asp Asp Gln Val Ala Ala Ser Gly Arg
                965                 970                 975
Ile Tyr Ile Pro Glu Asp Asn Gln Pro Phe Tyr Tyr Gly Lys Leu Glu
                980                 985                 990
Asp Ile Arg Thr Ser Glu Ile Ala  Asp Arg Ile Glu Leu  Asp Thr Glu
                995                1000                1005
Asp Ala  Tyr Lys Glu Phe Leu  Leu Arg Gly Tyr Glu  Tyr Gly Gln
               1010                1015                1020
Ala Phe  Arg Gly Ile Tyr Lys  Thr Cys Asn Ser Gly  Glu Arg Gly
               1025                1030                1035
Phe Leu  Tyr Trp Thr Gly Asn  Trp Val Thr Phe Leu  Asp Ser Leu
               1040                1045                1050
Leu Gln  Thr Ala Leu Leu Ala  Glu Arg Ser Asp Thr  Leu Arg Leu
               1055                1060                1065
Pro Thr  Arg Val Arg His Leu  Arg Ile Asp Pro Asn  Lys His Leu
               1070                1075                1080
Glu His  Val Val Glu Lys Asp  Gly Ile Gln Val Ile  Glu Leu Arg
               1085                1090                1095
Asn Asp  His Ser Thr Asn Gly  Cys Ile Ala Gly Gly  Val Glu Cys
               1100                1105                1110
Cys Asp  Leu Asn Ala His Ser  Val Ala Arg Arg Ile  Gln Val Ser
               1115                1120                1125
Gly Gln  Leu Tyr His Glu Lys  Ile Phe Phe Val Pro  His Phe Asp
               1130                1135                1140
```

-continued

```
His Asn Cys Leu Ser Gly His Lys Lys Thr Ser Thr Ile Leu Lys
    1145                1150                1155

Asp Tyr Ser Ala Val Ile Lys Gln Gln Leu Tyr Thr Gly Phe Ser
    1160                1165                1170

Lys Trp Gln Ser Ala Gly Leu Leu Lys Lys Leu Lys Asn Gly Ala
    1175                1180                1185

Gln Ile Val Lys Ala Leu Ala Val Leu Lys Ala Ser Gln Ser Asp
    1190                1195                1200

Val Val Leu Asp Asp Thr Val Thr Arg Phe Thr His Asp Gly Lys
    1205                1210                1215

Cys Thr Val Leu His His Ile Ala Asp Met Phe Lys Ile Glu Asp
    1220                1225                1230

Cys Glu Asp Phe Glu Asp Arg Val Ala Ala Lys Leu Lys Ser Val
    1235                1240                1245

Arg Gly Ile Phe Glu Leu Asp Arg Leu Trp Ala Gly Ala Val Leu
    1250                1255                1260

Asn Asp Arg Ile Val Lys Ser Leu Gln Asp Ile Cys Ile Glu Asn
    1265                1270                1275

Ser Ala Gly His His Ala Thr Met Ala Ala Val Asp Leu Val Ser
    1280                1285                1290

Thr Asp Gln Ile Arg His Cys Ile Glu Ala Asn Ser Ser His Pro
    1295                1300                1305

Leu Leu Glu Thr Asp Tyr Thr Cys Ile Gly Ala Asn Val Asp His
    1310                1315                1320

Leu Asp Glu Ser Thr Leu Glu Ile Ile Gly Gly Lys Lys Gln Lys
    1325                1330                1335

Ile Asp Leu Glu Asn Asn Phe Thr Gly His Gly Glu Val Lys Asn
    1340                1345                1350

Leu Asp Tyr Val Leu Leu Asp Lys Val Ile Ser Lys Lys Ala Asp
    1355                1360                1365

Pro Ile Ala Phe Ile Glu Ala Cys Lys His Leu Ile Arg Glu Thr
    1370                1375                1380

Gly Phe Leu Leu Val Val Glu Val Thr Ser Gln Tyr Glu Ile Ala
    1385                1390                1395

Leu Ala Ile Glu Gly Leu Leu Gly Asn Glu Met Val Gly Asp Ala
    1400                1405                1410

Ser Arg Lys Tyr Asn Gln Phe Phe Thr His Glu Gln Leu Leu Asp
    1415                1420                1425

Met Phe Lys Ser Thr Gly Phe Leu Ile Cys Asn Phe Gln Ser Asp
    1430                1435                1440

Pro Ala Leu Met Thr Thr Thr Tyr Ala Val Arg Arg Val Ser Pro
    1445                1450                1455

Ile Pro Arg Asp Pro Val Phe Ile Asp Val Asp Val Lys Glu
    1460                1465                1470

Phe Asn Trp Ile Glu Pro Leu Gln Lys Val Ser Glu Glu Arg Leu
    1475                1480                1485

Asn Glu Pro Asp Ser Lys Thr Ile Trp Leu Val Ser Asn Lys Cys
    1490                1495                1500

Arg Asn Asn Gly Ile Val Gly Leu Gly Leu Cys Phe Val Glu Glu
    1505                1510                1515

Asn Leu Lys Ile Asn Arg Phe Arg Ser Ala Phe Asp Met Ser Ala
    1520                1525                1530
```

-continued

```
Asn Lys Glu Ile Arg Asp Gly Pro Pro Val Trp Asn Ile Gly Asp
1535                1540                1545

Glu Glu Thr Lys Lys Ile Val Glu Leu Asp Leu His Ala Asn Asp
1550                1555                1560

Tyr Met Asp Gly Gln Trp Gly Ser Met Arg His Ile Val Val Lys
1565                1570                1575

Asp Glu Asp Val His Val Tyr Lys Asp Cys Glu His Ala Phe Ile
1580                1585                1590

Asn Thr Leu Thr Arg Gly Asp Val Ser Ser Leu Thr Trp Phe Glu
1595                1600                1605

Ser Pro Asn Gln Tyr Phe Asp Ser Met Val Lys Ser Lys Ala Thr
1610                1615                1620

Gln Glu Leu Cys Ser Val Tyr Tyr Ala Pro Ile Asn Phe Arg Asp
1625                1630                1635

Ile Met Leu Ala Tyr Gly Arg Leu Pro Pro Asp Ala Ile Pro Gly
1640                1645                1650

Asn Phe Ala Asp Arg Glu Cys Leu Leu Gly Met Glu Phe Ser Gly
1655                1660                1665

Arg Leu Lys Asp Gly Thr Arg Leu Met Gly Ile Leu Pro Ala Gln
1670                1675                1680

Ala Leu Ala Thr Thr Val Met Val Asp Arg Asp Tyr Ala Trp Glu
1685                1690                1695

Val Pro Arg Asp Trp Thr Leu Ala Glu Ala Ser Thr Val Pro Val
1700                1705                1710

Val Tyr Thr Thr Ala Tyr Tyr Ala Leu Val Arg Arg Gly Leu Met
1715                1720                1725

Lys Lys Gly Asp Lys Ile Leu Ile His Gly Gly Ala Gly Gly Val
1730                1735                1740

Gly Gln Ala Ala Ile Ala Ile Ala Leu Ala Ala Gly Cys Glu Val
1745                1750                1755

Phe Thr Thr Val Gly Ser Ala Glu Lys Arg Glu Phe Leu Lys Asn
1760                1765                1770

Leu Phe Pro Gln Leu Gln Glu His His Phe Ala Asn Ser Arg Ser
1775                1780                1785

Ala Asp Phe Glu Leu His Ile Arg Gln His Thr Lys Gly Arg Gly
1790                1795                1800

Val Asn Ile Val Leu Asn Ser Leu Ala Asn Glu Met Leu Gln Ala
1805                1810                1815

Ser Leu Arg Cys Leu Ala Arg His Gly Arg Phe Leu Glu Ile Gly
1820                1825                1830

Lys Val Asp Leu Ser Gln Asn Ser Ser Leu Gly Met Ala Lys Leu
1835                1840                1845

Leu Asp Asn Val Ser Val His Gly Ile Leu Leu Asp Ser Ile Met
1850                1855                1860

Asp Pro Thr Val Gly Asp Leu Asp Glu Trp Lys Glu Ile Ala Arg
1865                1870                1875

Leu Leu Glu Gln Gly Ile Lys Ser Gly Val Val Lys Pro Leu His
1880                1885                1890

Ser His Ser Phe Pro Ala Asp Lys Ala Glu Glu Ala Phe Arg Phe
1895                1900                1905

Met Ser Ala Gly Lys His Ile Gly Lys Val Ile Met Glu Ile Arg
1910                1915                1920

Pro Asp Glu Gly Thr Lys Val Cys Pro Pro Ser Lys Ile Ser Val
```

-continued

```
             1925                1930                1935

Arg Ala Ile Cys Arg Thr Leu Cys His Pro Gln His  Thr Tyr Leu
    1940                1945                1950

Ile Thr Gly Gly Leu Gly Gly Phe Gly Leu Glu Leu  Ala Gln Trp
    1955                1960                1965

Leu Ile Asn Arg Gly Ala Arg Lys Leu Val Leu Thr  Ser Arg Thr
    1970                1975                1980

Gly Ile Arg Thr Gly Tyr Gln Ala Arg Cys Val His  Phe Trp Arg
    1985                1990                1995

Arg Thr Gly Val Ser Val Leu Val Ser Thr Leu Asn  Ile Ala Lys
    2000                2005                2010

Lys Ser Asp Ala Val Glu Leu Ile Asn Gln Cys Thr  Ala Met Gly
    2015                2020                2025

Pro Ile Gly Gly Ile Phe His Leu Ala Met Val Leu  Arg Asp Cys
    2030                2035                2040

Leu Phe Glu Asn Gln Asn Val Gln Asn Phe Lys Asp  Ala Ala Glu
    2045                2050                2055

Ala Lys Tyr Tyr Gly Thr Ile Asn Leu Asp Tyr Ala  Ser Arg Glu
    2060                2065                2070

His Cys Asp Lys Asn Ile Leu Lys Trp Phe Val Val  Phe Ser Ser
    2075                2080                2085

Ile Thr Ser Gly Arg Gly Asn Ala Gly Gln Thr Asn  Tyr Gly Trp
    2090                2095                2100

Ser Asn Ser Cys Met Glu Arg Met Ile Asp Gln Arg  Arg Ala Asp
    2105                2110                2115

Gly Phe Pro Gly Ile Ala Ile Gln Trp Gly Ala Ile  Gly Asp Val
    2120                2125                2130

Gly Val Ile Leu Glu Asn Met Gly Asp Asn Asn Thr  Val Val Gly
    2135                2140                2145

Gly Thr Leu Pro Gln Arg Met Pro Ser Cys Leu Ser  Ser Leu Asp
    2150                2155                2160

Asn Phe Leu Ser Trp Asn His Pro Ile Val Ser Ser  Phe Ile Lys
    2165                2170                2175

Ala Glu Leu Gly Ser Lys Lys Asn Val Gly Gly Gly  Asp Leu Met
    2180                2185                2190

Ala Thr Ile Ala His Ile Leu Gly Val Asn Asp Ile  Ser Gln Leu
    2195                2200                2205

Asn Ala Asp Ala Asn Leu Ser Asp Leu Gly Leu Asp  Ser Leu Met
    2210                2215                2220

Gly Val Glu Ile Lys Gln Ala Leu Glu Arg Asp His  Asp Ile Val
    2225                2230                2235

Leu Ser Met Lys Glu Ile Arg Thr Leu Thr Leu Asn  Lys Leu Gln
    2240                2245                2250

Gln Leu Ala Asp Gln Gly Gly Thr Gly Arg Thr Ala  Leu Gln Val
    2255                2260                2265

Asn Glu Leu Glu Met Lys Lys Asp Gly Glu Arg Asp  Ala Glu Leu
    2270                2275                2280

Asn Thr Ala Glu Met Leu Glu Gln Gln Met Asn Gln  Leu Phe Lys
    2285                2290                2295

Met Arg Val Asp Val Asn Asp Leu Asp Pro Gln Asp  Ile Ile Val
    2300                2305                2310

Lys Ala Asn Lys Val Glu Glu Gly Pro Ile Thr Phe  Phe Val His
    2315                2320                2325
```

```
Ser Ile Glu Gly Ile Ala Thr Pro Leu Lys Lys Val Met Asn Lys
    2330                2335                2340

Cys Glu Phe Pro Ala Tyr Cys Phe Gln Ser Thr Lys Asn Val Pro
    2345                2350                2355

Gln Thr Ser Ile Glu Asp Val Ala Lys Cys Tyr Ile Arg Glu Met
    2360                2365                2370

Lys Lys Ile Gln Pro Ser Gly Pro Tyr Arg Leu Val Gly Tyr Ser
    2375                2380                2385

Tyr Gly Ala Cys Ile Gly Phe Glu Met Ala Asn Met Leu Gln Glu
    2390                2395                2400

Ser Asp Gly Arg Asp Ala Val Glu Arg Leu Ile Leu Leu Asp Gly
    2405                2410                2415

Ser His Leu Tyr Met Gln Thr Tyr Arg Asn Val Tyr Arg Met Ala
    2420                2425                2430

Phe Gly Val Thr Gly Asp Ser Leu Val Asn Asn Pro Leu Phe Glu
    2435                2440                2445

Ser Glu Ile Met Cys Ala Met Thr Leu Arg Phe Ala Asn Val Asp
    2450                2455                2460

Tyr Lys Lys Phe Arg Phe Glu Leu Leu Gln Gln Pro Gly Phe Lys
    2465                2470                2475

Ala Arg Val Gln Lys Val Val Asp Gln Val Met Leu Thr Gly Leu
    2480                2485                2490

Phe Lys Ser Pro Glu Thr Val Ala Phe Ala Cys Glu Ala Met His
    2495                2500                2505

Ser Lys Phe Leu Met Ala Asp Lys Tyr Lys Pro Arg Arg Asn Phe
    2510                2515                2520

Gly Gly His Ile Thr Leu Ile Arg Ala Glu Gln Gly Ala Ala Arg
    2525                2530                2535

Glu Glu Asp Val Gly Glu Asp Tyr Gly Val Ala Ala Val Ser Glu
    2540                2545                2550

Asp Cys Glu Val Leu Lys Val Lys Gly Asp His Asp Thr Phe Val
    2555                2560                2565

Gln Gly Lys Ser Ser Ser Val Thr Val Glu His Ile Asn Arg Ile
    2570                2575                2580

Ile Leu Gln
    2585

<210> SEQ ID NO 26
<211> LENGTH: 8936
<212> TYPE: DNA
<213> ORGANISM: Rattus norvegicus

<400> SEQUENCE: 26
aggctgggct ctatgggttg cctaagcggt ctggaaagct gaaggatctg tccaagttcg      60
acgcctcctt ttttgggggtc cacccccaagc aggcacacac aatggacccg cagctccggc     120
tgctgctgga agtcagctat gaagctattg tggacgagg tatcaacccg gcctcactcc      180 aggaacaaa cactggtgtc tgggtgggtg tgagtggttc cgaggcgtcg gaggccctga     240
gcagagatcc tgagactctt ctgggctaca gcatggtggg ctgccagaga gcaatgatgg     300
ccaaccggct ctcttttcttc ttcgacttca aggacccag cattgccctg acacagcct     360 gctcctctag cctactggca ctacagaatg cctatcaggc tatccgcagt ggggagtgcc     420
ctgctgccat tgtgggcggg atcaacctgc tgctaaagcc taacacctct gtgcagttca     480
```

```
tgaagctagg catgctcagc cccgatggca cctgcagatc ctttgatgat tcagggaacg    540
ggtattgccg tgctgaggct gtcgtggcag ttctgctgac taagaagtcc ttggctcggc    600
gagtctatgc cactattctg aatgccggga cgaacacaga tggctgcaag gagcaaggcg    660
tgacattccc ctctggagaa gcccaggaac aactcatccg ttctctgtat cagccgggcg    720
gtgtggcccc cgagtctctt gaatatattg aagcccatgg cacgggcacc aaggtggggg    780 accccccagga actgaacggc attactcggt ccctgtgtgc tttccgccag agccctttgt    840
taattggctc caccaaatcc aacatgggac ccctgagcc tgcctcgggg cttgcagccc    900
tgaccaaggt gctgttatcc ctagaaaatg gggtttgggc ccccaacctg catttccaca    960 acccccaaccc tgaaatccca gcacttcttg atgggcggct gcaggtggtc gataggcccc   1020
tgcctgttcg tggtggcatc gtgggcatca actcgtttgg cttcggaggt gccaatgttc   1080
acgtcatcct ccagcccaac acacagcagg ccccagcacc tgccccacat gctgccctac   1140
cgcatttgct gcatgccagt ggacggacca tggaggcagt gcagggcctg ctggaacagg   1200
gccgccagca cagtcaggac ttggcctttg ttagcatgct caatgacatt gcagcaaccc   1260
ctacagcagc catgcccttc agaggttaca ctgtgttagg tgttgagggc catgtccagg   1320
aagtgcagca agtgcctgcc agccagcgcc cactctggtt catctgctca gggatgggca   1380
cacagtggcg tggaatgggg ctgagcctta tgcgcctgga cagtttccgt gagtccatcc   1440
tgcgctctga tgaggctctg aagcccttgg gagtcaaagt gtcagacctg ctgctgagca   1500
ctgatgagca cacctttgat gacatcgtgc attcctttgt gagcctcacc gccatccaga   1560
ttgccctcat cgacctgctg acgtctatgg ggctgaaacc tgatggcatc attgggcact   1620
ccttgggaga ggttgcctgt ggctatgcag atggctgtct ctcccagaga gaggctgtgc   1680
ttgcagccta ctggagaggc cagtgcatta aggatgccaa ccttccggct ggatccatgg   1740
cagctgttgg tttgtcctgg gaagaatgta acaacgctg ccctcctggt gtggtgcctg   1800
cctgccacaa ctctgaggac actgtgacca tctctggacc tcaggctgca gtgaatgaat   1860
ttgtggagca gctaaagcaa gagggcgtgt ttgccaagga ggtgcgaaca ggtgcctgg   1920 ccttccactc ctacttcatg gaaggaattg ccccacgct gctgcaggct ctcaagaagg   1980
tgatccggga gccacggcca cgctcagcac gctggctcag cacctctatc cctgaggccc   2040
agtggcagag cagcctggcc cgcacatctt ctgctgagta caacgtcaac aacctggtga   2100
gccctgtgct cttccaggaa gcactgtggc acgtccccga gcacgccgtg gtgctggaga   2160
ttgcacccca tgcactgttg caggctgtcc tgaagcgagg cgtgaagcct agctgcacca   2220
tcatcccctt gatgaagagg gaccataaag ataacttgga gttcttcctc accaacctcg   2280
gcaaggtgca cctcacaggc atcgacatca accctaatgc cttgttccca cctgtggaat   2340
tcccggttcc ccgagggact cctctcatct cccctcacat caagtgggac cacagtcaga   2400
cttgggatat cccagttgct gaagacttcc ccaacggttc cagctcctcc tcagctacag   2460
tctacaacat tgacgccagt tccgagtcac ctgaccacta cctggtcgac cactgcattg   2520
acggccgtgt cctcttccct ggcactggct acctgtacct ggtgtggaag acactggctc   2580
gaagcctgag cttgtcccta aagagaccc tgtggtgtt tgagaacgtg acatttcatc   2640
aggccaccat cctgccagg acaggaaccg tgcctctgga ggtgcggctg ctagaggcct   2700
cacatgcatt tgaggtgtct gacagtggca acctgatagt gagcgggaaa gtgtaccagt   2760
gggaagaccc tgactccaag ttattcgacc acccagaagt cccgatcccc gccgagtccg   2820
agtctgtctc ccgcttgacg cagggagaag tatacaagga gctgcggcta cgtggctatg   2880
```

```
actatggccc tcatttccag ggcgtctatg aggccaccct cgaaggtgag caaggcaagc    2940
tgctctggaa agacaactgg gtgaccttca tggacacaat gctgcagata tccatcctgg    3000
gcttcagcaa gcagagtctg cagctaccca cccgtgtgac tgccatctat attgaccctg    3060
caacccacct gcagaaggtg tacatgctgg agggagacac tcaagtggct gacgtgacca    3120
cgagccgctg tctgggcgtg accgtctctg gtggtgtcta catttcgaga ctacagacaa    3180
cagcaacctc acggcggcag caggaacagc tggtccccac cctggagaag tttgtcttca    3240
caccccatgt ggagcctgag tgcctgtctg agagtgctat cctgcagaaa gagctgcagc    3300
tgtgcaaggg tctggcaaag gctctgcaga ccaaggccac ccagcaaggg ctgaagatga    3360
cagtgcctgg gctagaggac cttccccagc atggactgcc tcgactcttg gctgctgcct    3420
gccagctgca gctcaacggg aacctgcaac tggagttagg tgaggtactg gctcgagaga    3480
ggctcctgct gccagaagac cctctgatca gtggcctcct taactcccag gccctcaagg    3540
cctgcataga cacagccctg gagaacttgt ctactctcaa gatgaaggtg gtggaggtgc    3600
tggctggaga aggccacttg tattcccaca tctcagcact gctcaacacc cagcctatgc    3660
tgcaactgga gtatacagcc accgaccggc accccaggc cctgaaggat gttcagacca    3720
agctgcagca gcatgatgta gcacagggcc agtgggaccc ttctggtcct gctcctacca    3780
acctgggtgc tcttgacctt gtggtgtgca actgtgcgtt agccaccctg ggggatccag    3840
ccctggccct ggacaacatg gtagctgccc tcaaggatgg tggtttcctg ctaatgcaca    3900
cagtgctcaa aggacatgcc cttggggaga ccctggcctg cctcccttct gaggtgcagc    3960
ctgggcccag cttcttaagc caggaagagt gggagagcct gttctcaagg aaggcactgc    4020
acctggtggg ccttaaaaag tcattctacg gtactgcgct gttcctgtgc cgccgtctca    4080
gcccacagga caagcccatc ttcctgcctg tggaggatac tagtttccag tgggtggact    4140
ctctgaagag cattctggcc acatcctcct cccagcctgt gtggctaaca gccatgaact    4200
gccccacctc aggtgtggta ggcttggtga actgtctccg aaaagagccg ggtggacacc    4260
ggattcggtg tatcctgctg tccaacctca gcagcacatc tcacgtcccc aagctggacc    4320
ctggctcttc agagctacag aaggtgctag agagtgatct ggtgatgaac gtgtacaggg    4380
acggtgcctg gggtgccttc cgtcacttcc agttagagca ggacaagccc gaggagcaga    4440
cagcacatgc ctttgtaaac gtccttaccc gaggggacct tgcctccatc cgctgggtct    4500 cttctccct gaaacacatg cagccgcccc cgagctcagg agcacagctc tgcactgtct    4560
actatgcctc actgaacttc cgagatatca tgctggccac gggcaagctg tcccctgatg    4620
ccattccagg taaatgggcc agccgggact gcatgcttgg catggagttc tcaggccgtg    4680
ataagtgcgg ccggcgtgtg atggggctgg tacccgcaga aggcctggcc acctcagtcc    4740
tgttatcacc cgacttcctc tgggatgtac cctctagctg gaccctggag gaggcggctt    4800
ctgtgcctgt tgtctacacc accgcctact actccttagt agtgcgtggt cgtattcagc    4860
acggggaaac tgtgctcatt cactcgggct ccggtggtgt gggccaagcg ccatttccca    4920
ttgcccttag cctgggctgc cgagtcttca ccactgtggg ctccgctgag aagcgagctt    4980
acctccaggc cagattccct cagctggatg acaccagctt tgctaactct cgagacacat    5040
cgtttgagca gcatgtgtta ctgcacacag gtggcaaagg ggtggacctg gtcctcaact    5100
ccctggcaga agagaagctg caggccagtg tgcggtgctt ggctcagcat ggccgcttcc    5160
tagagatcgg caaatttgat ctttctaaca accaccctct gggcatggcc atcttcttga    5220
```

```
agaacgtcac tttccatggg atcctgctgg atgcactttt tgaggggggcc aacgacagct   5280 ggcgggaggt ggcagagctg ctgaaggccg gcatccgtga tggggttgtg aagcctctca   5340
agtgtacagt gtttcccaag gcccaggtgg aggacgcctt ccgatacatg gctcaaggaa   5400
aacatattgg caaagtcctt gtccaggtac gggaggagga gcccgaggct atgctgccag   5460
gggctcagcc caccctgatt tccgccatct ccaagacctt ctgcccagag cataagagtt   5520
acatcatcac tggtggccta ggtggctttg gcctggaact ggcccggtgg cttgtgcttc   5580
gtggggccca aaggcttgta ctaacttccc gatctggaat ccgcacaggc taccaagcca   5640
agcacgttcg ggagtggagg cgccagggca tccatgtgct agtgtcgaca agcaatgtca   5700
gttcactgga gggggcccgt gctctcatcg ctgaagccac aaagcttggg cccgttggag   5760
gtgtcttcaa cctggccatg gttttaaggg atgccatgct ggagaaccag actcagaac   5820 tcttccagga tgtcaacaag cccaagtaca atggcaccct gaaccttgac agggcgaccc   5880
gggaagcctg tcctgagctg gactactttg tggccttctc ctctgtaagc tgcgggcgtg   5940
gtaatgctgg ccaatccaac tatggcttcg ccaactctac catggagcgt atttgcgaac   6000
agcgccggca cgatggcctc ccaggtcttg ccgtgcaatg gggtgccatt ggtgacgtgg   6060
gcattatctt ggaagcgatg ggtaccaatg acacagtcgt tggcggcaca ctgccacagc   6120
gcatctcctc ctgcatggag gtgctggacc tcttcctgaa tcagcccccac gcagtcctga   6180 gcagttttgt gctggctgag aagaaagctg tggcccatgg tgatggtgaa gcccagaggg   6240
atctggtgaa agcagtggca cacatcctag gcatccgcga cctcgcaggg attaacctgg   6300
acagctcgct ggcagacctc ggcctggact cgctcatggg tgtggaagtg cgccagatcc   6360
tggaacgtga acatgatctg gtgctaccca ttcgtgaagt acggcaactc acactgcgga   6420
agcttcagga aatgtcctcc aaggctggct cagacactga gttggcagcc cccaagtcca   6480
agaatgatac atccctgaag caggcccagc tgaatctgag tatcctgctg gtgaaccctg   6540
agggccctac cttaacacga ctcaactcag tgcagagctc tgagcggcct ctgttcctgg   6600
tgcaccccat tgaaggttcc atcactgtgt tccacagcct ggctgccaag ctcagtgtgc   6660
ccacctacgg tctgcagtgc acccaagcgg cccccctgga cagcattcca aacctggctg   6720
cctactacat tgattgcatc aagcaggtgc agcctgaggg gccctaccga gtggctgggt   6780
attcttttgg agcttgtgta gccttcgaga tgtgctccca gctgcaggcc cagcagggcc   6840
cagcccccgc ccacaacaac ctcttcttgt tgatggctc acacacctac gtattggcgt   6900
acacccagag ctaccgggca aagctgaccc caggctgtga ggctgaggct gaagctgaag   6960
ccatatgctt cttcattaag cagtttgttg atgcagagca tagcaaggtg ctagaggccc   7020
tgctaccact gaagagcctg gaggaccggg ttgctgctgc tgtggacctc atcactagaa   7080
gccaccagag cctggaccgc cgtgacctga gctttgctgc cgtgtccttc tactacaagc   7140
ttcgagccgc cgaccagtat aaacccaagg ccaagtacca cggcaatgtg atcctgctgc   7200
gggccaagac aggtggcacc tacggcgagg acttgggtgc cgattacaac ctgtcccagg   7260
tgtgtgatgg gaaggtgtct gtgcacatca ttgaggtga ccaccgtacg ctgctggagg   7320 gcagggggcct ggagtctatc atcaacatca tccacagctc cctggctgag cctcgagtga   7380
gtgtacggga gggctagacc tgcctaccat gaagccacga cccacaccgg ccaccagaga   7440
tgctccgatc cccaccacac cctgagtgca gggactgggg aggtcctgc tggtgggacc   7500 ccctcacccc agtggcccag caccacccc tcccctggtg gctgctacaa acaggaccat   7560
cacatgtgtc ccagccactt agtgggggttc ccagagccac tgacttggag gcaccctggt   7620
```

-continued

```
ctgtgaagag tcagtggagg ccagcaagag ccaaactgag cctttctgc caagtgacat      7680 ttgtcacact ggttgtttct ccattaaatt ctcatattta ttgcattgct gggaaagacc      7740
gcccacccca gggttaactc attccagaac ccctaaagtg ggaaaagcca tgtggggaag      7800
gctgctggct ggagccccct tttgtcttag ccctgtaccc gctcactgca gggcagggta      7860
tggagagggc tggttcgcgg ggaacgagga ccccagcaga cactgtagcc catggccctt      7920
ggtccccagc actcccggct gcacccatga tgcagggcct accagactct gcggaccgca      7980
ccgggcactc actgtatttg ttttccaaga ttcaaattgc tgcttgggtt ttgaatttac      8040
tgcagctgtc agtgtaaaga acatgtctg aactgtgtcc tttttacacc aacctggtaa      8100
aaatgctctt gatgctgtcc cgttgccaca attaaactgc acgtgagctc tggcttccgt      8160
tcagtctctt tccagtccca gacctgagtc cccagagcct ccacagctct tacagtgaga      8220
atcaaattgg cccactcctt ggaaggcgtg gcattctgtc agagtaaaag gaaagtagag      8280
tgtgctgatt cacgttcagc gtgtggggct ggctagagac cttggcactg tagtgaacag      8340
aatgtgtcca ccttaagtc accctgaagg catcaccata gctacagcct cacccagggg      8400
tagagaatag tactgtctac ttgttgacta cctggcagtt ggtgccagcc cctatagagg      8460
aaaacagcag tgtgtggcca ctgtgagaag catatccctg aaacaggtg accagagcag      8520 agggctaacg cctacctgag tcacacaaaa ctgaccaggc ttgagtgtcc agaagagtct      8580
atcagaaggc cacagcattc agtcctatcc acagagagca gcagactaag ttgtctcctt      8640
gccagcttag aaaactgcag tgctgggta caggtagggt gttcaggagg tccgggcccc      8700
agtgattagt ctaagactga agcatctggt tggctgtggt cccacctaga aaattcttaa      8760
agctcttgtc atgtacttcc tgggaaggac ctaccctgtc tcaataatgt ctctagctcg      8820
ttggagtcta ctgactcaaa catttataaa gtgtcctaga aaggcctgac tccctacaa      8880 ggctgtgtga tccttcaaac tcacatatgt gagccaataa accttgaga ctctag         8936
```

<210> SEQ ID NO 27
<211> LENGTH: 2431
<212> TYPE: PRT
<213> ORGANISM: Rattus norvegicus

<400> SEQUENCE: 27

```
Met Asp Pro Gln Leu Arg Leu Leu Glu Val Ser Tyr Glu Ala Ile
1               5                   10                  15

Val Asp Gly Gly Ile Asn Pro Ala Ser Leu Arg Gly Thr Asn Thr Gly
            20                  25                  30

Val Trp Val Gly Val Ser Gly Ser Glu Ala Ser Glu Ala Leu Ser Arg
        35                  40                  45

Asp Pro Glu Thr Leu Leu Gly Tyr Ser Met Val Gly Cys Gln Arg Ala
    50                  55                  60

Met Met Ala Asn Arg Leu Ser Phe Phe Phe Asp Phe Lys Gly Pro Ser
65                  70                  75                  80

Ile Ala Leu Asp Thr Ala Cys Ser Ser Leu Leu Ala Leu Gln Asn
                85                  90                  95

Ala Tyr Gln Ala Ile Arg Ser Gly Glu Cys Pro Ala Ala Ile Val Gly
            100                 105                 110

Gly Ile Asn Leu Leu Leu Lys Pro Asn Thr Ser Val Gln Phe Met Lys
        115                 120                 125

Leu Gly Met Leu Ser Pro Asp Gly Thr Cys Arg Ser Phe Asp Asp Ser
    130                 135                 140
```

-continued

```
Gly Asn Gly Tyr Cys Arg Ala Glu Ala Val Val Ala Val Leu Leu Thr
145                 150                 155                 160

Lys Lys Ser Leu Ala Arg Arg Val Tyr Ala Thr Ile Leu Asn Ala Gly
            165                 170                 175

Thr Asn Thr Asp Gly Cys Lys Glu Gln Gly Val Thr Phe Pro Ser Gly
        180                 185                 190

Glu Ala Gln Glu Gln Leu Ile Arg Ser Leu Tyr Gln Pro Gly Gly Val
    195                 200                 205

Ala Pro Glu Ser Leu Glu Tyr Ile Glu Ala His Gly Thr Gly Thr Lys
210                 215                 220

Val Gly Asp Pro Gln Glu Leu Asn Gly Ile Thr Arg Ser Leu Cys Ala
225                 230                 235                 240

Phe Arg Gln Ser Pro Leu Leu Ile Gly Ser Thr Lys Ser Asn Met Gly
            245                 250                 255

His Pro Glu Pro Ala Ser Gly Leu Ala Ala Leu Thr Lys Val Leu Leu
        260                 265                 270

Ser Leu Glu Asn Gly Val Trp Ala Pro Asn Leu His Phe His Asn Pro
    275                 280                 285

Asn Pro Glu Ile Pro Ala Leu Leu Asp Gly Arg Leu Gln Val Val Asp
290                 295                 300

Arg Pro Leu Pro Val Arg Gly Ile Val Gly Ile Asn Ser Phe Gly
305                 310                 315                 320

Phe Gly Gly Ala Asn Val His Val Ile Leu Gln Pro Asn Thr Gln Gln
            325                 330                 335

Ala Pro Ala Pro Ala Pro His Ala Ala Leu Pro His Leu Leu His Ala
        340                 345                 350

Ser Gly Arg Thr Met Glu Ala Val Gln Gly Leu Leu Glu Gln Gly Arg
    355                 360                 365

Gln His Ser Gln Asp Leu Ala Phe Val Ser Met Leu Asn Asp Ile Ala
370                 375                 380

Ala Thr Pro Thr Ala Ala Met Pro Phe Arg Gly Tyr Thr Val Leu Gly
385                 390                 395                 400

Val Glu Gly His Val Gln Glu Val Gln Gln Val Pro Ala Ser Gln Arg
            405                 410                 415

Pro Leu Trp Phe Ile Cys Ser Gly Met Gly Thr Gln Trp Arg Gly Met
        420                 425                 430

Gly Leu Ser Leu Met Arg Leu Asp Ser Phe Arg Glu Ser Ile Leu Arg
    435                 440                 445

Ser Asp Glu Ala Leu Lys Pro Leu Gly Val Lys Val Ser Asp Leu Leu
450                 455                 460

Leu Ser Thr Asp Glu His Thr Phe Asp Asp Ile Val His Ser Phe Val
465                 470                 475                 480

Ser Leu Thr Ala Ile Gln Ile Ala Leu Ile Asp Leu Leu Thr Ser Met
            485                 490                 495

Gly Leu Lys Pro Asp Gly Ile Ile Gly His Ser Leu Gly Glu Val Ala
        500                 505                 510

Cys Gly Tyr Ala Asp Gly Cys Leu Ser Gln Arg Glu Ala Val Leu Ala
    515                 520                 525

Ala Tyr Trp Arg Gly Gln Cys Ile Lys Asp Ala Asn Leu Pro Ala Gly
530                 535                 540

Ser Met Ala Ala Val Gly Leu Ser Trp Glu Glu Cys Lys Gln Arg Cys
545                 550                 555                 560
```

-continued

```
Pro Pro Gly Val Val Pro Ala Cys His Asn Ser Glu Asp Thr Val Thr
            565                 570                 575

Ile Ser Gly Pro Gln Ala Ala Val Asn Glu Phe Val Glu Gln Leu Lys
            580                 585                 590

Gln Glu Gly Val Phe Ala Lys Glu Val Arg Thr Gly Gly Leu Ala Phe
            595                 600                 605

His Ser Tyr Phe Met Glu Gly Ile Ala Pro Thr Leu Leu Gln Ala Leu
            610                 615                 620

Lys Lys Val Ile Arg Glu Pro Arg Pro Arg Ser Ala Arg Trp Leu Ser
625                 630                 635                 640

Thr Ser Ile Pro Glu Ala Gln Trp Gln Ser Ser Leu Ala Arg Thr Ser
                    645                 650                 655

Ser Ala Glu Tyr Asn Val Asn Asn Leu Val Ser Pro Val Leu Phe Gln
                    660                 665                 670

Glu Ala Leu Trp His Val Pro Glu His Ala Val Val Leu Glu Ile Ala
                    675                 680                 685

Pro His Ala Leu Leu Gln Ala Val Leu Lys Arg Gly Val Lys Pro Ser
            690                 695                 700

Cys Thr Ile Ile Pro Leu Met Lys Arg Asp His Lys Asp Asn Leu Glu
705                 710                 715                 720

Phe Phe Leu Thr Asn Leu Gly Lys Val His Leu Thr Gly Ile Asp Ile
                    725                 730                 735

Asn Pro Asn Ala Leu Phe Pro Pro Val Glu Phe Pro Val Pro Arg Gly
                    740                 745                 750

Thr Pro Leu Ile Ser Pro His Ile Lys Trp Asp His Ser Gln Thr Trp
            755                 760                 765

Asp Ile Pro Val Ala Glu Asp Phe Pro Asn Gly Ser Ser Ser Ser Ser
            770                 775                 780

Ala Thr Val Tyr Asn Ile Asp Ala Ser Ser Glu Ser Pro Asp His Tyr
785                 790                 795                 800

Leu Val Asp His Cys Ile Asp Gly Arg Val Leu Phe Pro Gly Thr Gly
                    805                 810                 815

Tyr Leu Tyr Leu Val Trp Lys Thr Leu Ala Arg Ser Leu Ser Leu Ser
                    820                 825                 830

Leu Glu Glu Thr Pro Val Val Phe Glu Asn Val Thr Phe His Gln Ala
            835                 840                 845

Thr Ile Leu Pro Arg Thr Gly Thr Val Pro Leu Glu Val Arg Leu Leu
850                 855                 860

Glu Ala Ser His Ala Phe Glu Val Ser Asp Ser Gly Asn Leu Ile Val
865                 870                 875                 880

Ser Gly Lys Val Tyr Gln Trp Glu Asp Pro Asp Ser Lys Leu Phe Asp
                    885                 890                 895

His Pro Glu Val Pro Ile Pro Ala Glu Ser Glu Ser Val Ser Arg Leu
            900                 905                 910

Thr Gln Gly Glu Val Tyr Lys Glu Leu Arg Leu Arg Gly Tyr Asp Tyr
            915                 920                 925

Gly Pro His Phe Gln Gly Val Tyr Glu Ala Thr Leu Glu Gly Glu Gln
            930                 935                 940

Gly Lys Leu Leu Trp Lys Asp Asn Trp Val Thr Phe Met Asp Thr Met
945                 950                 955                 960

Leu Gln Ile Ser Ile Leu Gly Phe Ser Lys Gln Ser Leu Gln Leu Pro
                    965                 970                 975

Thr Arg Val Thr Ala Ile Tyr Ile Asp Pro Ala Thr His Leu Gln Lys
```

-continued

```
              980             985                990
Val Tyr Met Leu Glu Gly Asp Thr Gln Val Ala Asp Val Thr Thr Ser
          995             1000               1005
Arg Cys Leu Gly Val Thr Val Ser Gly Gly Val Tyr Ile Ser Arg
    1010            1015               1020
Leu Gln Thr Thr Ala Thr Ser Arg Arg Gln Gln Glu Gln Leu Val
    1025            1030               1035
Pro Thr Leu Glu Lys Phe Val Phe Thr Pro His Val Glu Pro Glu
    1040            1045               1050
Cys Leu Ser Glu Ser Ala Ile Leu Gln Lys Glu Leu Gln Leu Cys
    1055            1060               1065
Lys Gly Leu Ala Lys Ala Leu Gln Thr Lys Ala Thr Gln Gln Gly
    1070            1075               1080
Leu Lys Met Thr Val Pro Gly Leu Glu Asp Leu Pro Gln His Gly
    1085            1090               1095
Leu Pro Arg Leu Leu Ala Ala Cys Gln Leu Gln Leu Asn Gly
    1100            1105               1110
Asn Leu Gln Leu Glu Leu Gly Glu Val Leu Ala Arg Glu Arg Leu
    1115            1120               1125
Leu Leu Pro Glu Asp Pro Leu Ile Ser Gly Leu Leu Asn Ser Gln
    1130            1135               1140
Ala Leu Lys Ala Cys Ile Asp Thr Ala Leu Glu Asn Leu Ser Thr
    1145            1150               1155
Leu Lys Met Lys Val Val Glu Val Leu Ala Gly Glu Gly His Leu
    1160            1165               1170
Tyr Ser His Ile Ser Ala Leu Leu Asn Thr Gln Pro Met Leu Gln
    1175            1180               1185
Leu Glu Tyr Thr Ala Thr Asp Arg His Pro Gln Ala Leu Lys Asp
    1190            1195               1200
Val Gln Thr Lys Leu Gln Gln His Asp Val Ala Gln Gly Gln Trp
    1205            1210               1215
Asp Pro Ser Gly Pro Ala Pro Thr Asn Leu Gly Ala Leu Asp Leu
    1220            1225               1230
Val Val Cys Asn Cys Ala Leu Ala Thr Leu Gly Asp Pro Ala Leu
    1235            1240               1245
Ala Leu Asp Asn Met Val Ala Ala Leu Lys Asp Gly Gly Phe Leu
    1250            1255               1260
Leu Met His Thr Val Leu Lys Gly His Ala Leu Gly Glu Thr Leu
    1265            1270               1275
Ala Cys Leu Pro Ser Glu Val Gln Pro Gly Pro Ser Phe Leu Ser
    1280            1285               1290
Gln Glu Glu Trp Glu Ser Leu Phe Ser Arg Lys Ala Leu His Leu
    1295            1300               1305
Val Gly Leu Lys Lys Ser Phe Tyr Gly Thr Ala Leu Phe Leu Cys
    1310            1315               1320
Arg Arg Leu Ser Pro Gln Asp Lys Pro Ile Phe Leu Pro Val Glu
    1325            1330               1335
Asp Thr Ser Phe Gln Trp Val Asp Ser Leu Lys Ser Ile Leu Ala
    1340            1345               1350
Thr Ser Ser Ser Gln Pro Val Trp Leu Thr Ala Met Asn Cys Pro
    1355            1360               1365
Thr Ser Gly Val Val Gly Leu Val Asn Cys Leu Arg Lys Glu Pro
    1370            1375               1380
```

```
Gly Gly His Arg Ile Arg Cys Ile Leu Leu Ser Asn Leu Ser Ser
1385                1390                1395

Thr Ser His Val Pro Lys Leu Asp Pro Gly Ser Ser Glu Leu Gln
1400                1405                1410

Lys Val Leu Glu Ser Asp Leu Val Met Asn Val Tyr Arg Asp Gly
1415                1420                1425

Ala Trp Gly Ala Phe Arg His Phe Gln Leu Glu Gln Asp Lys Pro
1430                1435                1440

Glu Glu Gln Thr Ala His Ala Phe Val Asn Val Leu Thr Arg Gly
1445                1450                1455

Asp Leu Ala Ser Ile Arg Trp Val Ser Ser Pro Leu Lys His Met
1460                1465                1470

Gln Pro Pro Ser Ser Ser Gly Ala Gln Leu Cys Thr Val Tyr Tyr
1475                1480                1485

Ala Ser Leu Asn Phe Arg Asp Ile Met Leu Ala Thr Gly Lys Leu
1490                1495                1500

Ser Pro Asp Ala Ile Pro Gly Lys Trp Ala Ser Arg Asp Cys Met
1505                1510                1515

Leu Gly Met Glu Phe Ser Gly Arg Asp Lys Cys Gly Arg Arg Val
1520                1525                1530

Met Gly Leu Val Pro Ala Glu Gly Leu Ala Thr Ser Val Leu Leu
1535                1540                1545

Ser Pro Asp Phe Leu Trp Asp Val Pro Ser Ser Trp Thr Leu Glu
1550                1555                1560

Glu Ala Ala Ser Val Pro Val Val Tyr Thr Thr Ala Tyr Tyr Ser
1565                1570                1575

Leu Val Val Arg Gly Arg Ile Gln His Gly Glu Thr Val Leu Ile
1580                1585                1590

His Ser Gly Ser Gly Gly Val Gly Gln Ala Ala Ile Ser Ile Ala
1595                1600                1605

Leu Ser Leu Gly Cys Arg Val Phe Thr Thr Val Gly Ser Ala Glu
1610                1615                1620

Lys Arg Ala Tyr Leu Gln Ala Arg Phe Pro Gln Leu Asp Asp Thr
1625                1630                1635

Ser Phe Ala Asn Ser Arg Asp Thr Ser Phe Glu Gln His Val Leu
1640                1645                1650

Leu His Thr Gly Gly Lys Gly Val Asp Leu Val Leu Asn Ser Leu
1655                1660                1665

Ala Glu Glu Lys Leu Gln Ala Ser Val Arg Cys Leu Ala Gln His
1670                1675                1680

Gly Arg Phe Leu Glu Ile Gly Lys Phe Asp Leu Ser Asn Asn His
1685                1690                1695

Pro Leu Gly Met Ala Ile Phe Leu Lys Asn Val Thr Phe His Gly
1700                1705                1710

Ile Leu Leu Asp Ala Leu Phe Glu Gly Ala Asn Asp Ser Trp Arg
1715                1720                1725

Glu Val Ala Glu Leu Leu Lys Ala Gly Ile Arg Asp Gly Val Val
1730                1735                1740

Lys Pro Leu Lys Cys Thr Val Phe Pro Lys Ala Gln Val Glu Asp
1745                1750                1755

Ala Phe Arg Tyr Met Ala Gln Gly Lys His Ile Gly Lys Val Leu
1760                1765                1770
```

-continued

```
Val Gln Val Arg Glu Glu Pro Glu Ala Met Leu Pro Gly Ala
    1775            1780            1785

Gln Pro Thr Leu Ile Ser Ala Ile Ser Lys Thr Phe Cys Pro Glu
    1790            1795            1800

His Lys Ser Tyr Ile Ile Thr Gly Gly Leu Gly Gly Phe Gly Leu
    1805            1810            1815

Glu Leu Ala Arg Trp Leu Val Leu Arg Gly Ala Gln Arg Leu Val
    1820            1825            1830

Leu Thr Ser Arg Ser Gly Ile Arg Thr Gly Tyr Gln Ala Lys His
    1835            1840            1845

Val Arg Glu Trp Arg Arg Gln Gly Ile His Val Leu Val Ser Thr
    1850            1855            1860

Ser Asn Val Ser Ser Leu Glu Gly Ala Arg Ala Leu Ile Ala Glu
    1865            1870            1875

Ala Thr Lys Leu Gly Pro Val Gly Gly Val Phe Asn Leu Ala Met
    1880            1885            1890

Val Leu Arg Asp Ala Met Leu Glu Asn Gln Thr Pro Glu Leu Phe
    1895            1900            1905

Gln Asp Val Asn Lys Pro Lys Tyr Asn Gly Thr Leu Asn Leu Asp
    1910            1915            1920

Arg Ala Thr Arg Glu Ala Cys Pro Glu Leu Asp Tyr Phe Val Ala
    1925            1930            1935

Phe Ser Ser Val Ser Cys Gly Arg Gly Asn Ala Gly Gln Ser Asn
    1940            1945            1950

Tyr Gly Phe Ala Asn Ser Thr Met Glu Arg Ile Cys Glu Gln Arg
    1955            1960            1965

Arg His Asp Gly Leu Pro Gly Leu Ala Val Gln Trp Gly Ala Ile
    1970            1975            1980

Gly Asp Val Gly Ile Ile Leu Glu Ala Met Gly Thr Asn Asp Thr
    1985            1990            1995

Val Val Gly Gly Thr Leu Pro Gln Arg Ile Ser Ser Cys Met Glu
    2000            2005            2010

Val Leu Asp Leu Phe Leu Asn Gln Pro His Ala Val Leu Ser Ser
    2015            2020            2025

Phe Val Leu Ala Glu Lys Lys Ala Val Ala His Gly Asp Gly Glu
    2030            2035            2040

Ala Gln Arg Asp Leu Val Lys Ala Val Ala His Ile Leu Gly Ile
    2045            2050            2055

Arg Asp Leu Ala Gly Ile Asn Leu Asp Ser Ser Leu Ala Asp Leu
    2060            2065            2070

Gly Leu Asp Ser Leu Met Gly Val Glu Val Arg Gln Ile Leu Glu
    2075            2080            2085

Arg Glu His Asp Leu Val Leu Pro Ile Arg Glu Val Arg Gln Leu
    2090            2095            2100

Thr Leu Arg Lys Leu Gln Glu Met Ser Ser Lys Ala Gly Ser Asp
    2105            2110            2115

Thr Glu Leu Ala Ala Pro Lys Ser Lys Asn Asp Thr Ser Leu Lys
    2120            2125            2130

Gln Ala Gln Leu Asn Leu Ser Ile Leu Leu Val Asn Pro Glu Gly
    2135            2140            2145

Pro Thr Leu Thr Arg Leu Asn Ser Val Gln Ser Ser Glu Arg Pro
    2150            2155            2160

Leu Phe Leu Val His Pro Ile Glu Gly Ser Ile Thr Val Phe His
```

-continued

|  | 2165 |  |  | 2170 |  |  |  | 2175 |  |  |  |
|---|---|---|---|---|---|---|---|---|---|---|---|
| Ser | Leu | Ala | Ala | Lys | Leu | Ser | Val | Pro | Thr | Tyr | Gly | Leu | Gln | Cys |
|  | 2180 |  |  |  | 2185 |  |  |  | 2190 |  |  |

Ser Leu Ala Ala Lys Leu Ser Val Pro Thr Tyr Gly Leu Gln Cys
          2180                    2185                    2190

Thr Gln Ala Ala Pro Leu Asp Ser Ile Pro Asn Leu Ala Ala Tyr
     2195                    2200                    2205

Tyr Ile Asp Cys Ile Lys Gln Val Gln Pro Glu Gly Pro Tyr Arg
     2210                    2215                    2220

Val Ala Gly Tyr Ser Phe Gly Ala Cys Val Ala Phe Glu Met Cys
     2225                    2230                    2235

Ser Gln Leu Gln Ala Gln Gln Gly Pro Ala Pro Ala His Asn Asn
     2240                    2245                    2250

Leu Phe Leu Phe Asp Gly Ser His Thr Tyr Val Leu Ala Tyr Thr
     2255                    2260                    2265

Gln Ser Tyr Arg Ala Lys Leu Thr Pro Gly Cys Glu Ala Glu Ala
     2270                    2275                    2280

Glu Ala Glu Ala Ile Cys Phe Phe Ile Lys Gln Phe Val Asp Ala
     2285                    2290                    2295

Glu His Ser Lys Val Leu Glu Ala Leu Leu Pro Leu Lys Ser Leu
     2300                    2305                    2310

Glu Asp Arg Val Ala Ala Ala Val Asp Leu Ile Thr Arg Ser His
     2315                    2320                    2325

Gln Ser Leu Asp Arg Arg Asp Leu Ser Phe Ala Ala Val Ser Phe
     2330                    2335                    2340

Tyr Tyr Lys Leu Arg Ala Ala Asp Gln Tyr Lys Pro Lys Ala Lys
     2345                    2350                    2355

Tyr His Gly Asn Val Ile Leu Leu Arg Ala Lys Thr Gly Gly Thr
     2360                    2365                    2370

Tyr Gly Glu Asp Leu Gly Ala Asp Tyr Asn Leu Ser Gln Val Cys
     2375                    2380                    2385

Asp Gly Lys Val Ser Val His Ile Ile Glu Gly Asp His Arg Thr
     2390                    2395                    2400

Leu Leu Glu Gly Arg Gly Leu Glu Ser Ile Ile Asn Ile Ile His
     2405                    2410                    2415

Ser Ser Leu Ala Glu Pro Arg Val Ser Val Arg Glu Gly
     2420                    2425                    2430

<210> SEQ ID NO 28
<211> LENGTH: 9345
<212> TYPE: DNA
<213> ORGANISM: Gallus gallus

<400> SEQUENCE: 28
agaacctgct caatggggtt gatatggtca cagaggacga tcggaggtgg aagccaggga      60
tttatggact gcccaaaaga aatggaaagc tcaaggacat aaaaaaattc gatgcctcct     120
tctttgggtc caccccaaac aagctcatac aatggatcct ccagttcgct tgttgttgga     180
agtttcttat gaggctattt tggatggagg cattaatcca actgccctcc gtggcacaga     240
cacgggtgta tgggttggtg caagtggctc agaagctgct gaagccctta gccaagatcc     300
agaagagctt tgggataca gtatgactgg ctgccagcgt gctatgcttg ccaacaggat     360
ttcttacttc tatgattta caggaccaag cttaactatc gacacagcct gctcctccag     420
tctcatggct ttagaaaatg cttataaagc aattcgtcac ggacagtgca gtgcagccct     480
ggtaggaggg gtcaacattc tgctgaagcc caacacttct gtgcagttca tgaagctggg     540

-continued

```
catgcttagt cctgatggtg cctgcaaggc tttcgatgtt tcaggaaatg ggtattgtcg      600
ctctgaagct gttgttgttg tgctcttgac caagaaatcc atggctaaac gcgtctatgc      660
cactatagtc aatgctggga gtaacactga tggctttaag gagcaaggtg tgacattccc      720
atctggagag atgcagcagc agctggttgg ttctctgtac agagaatgtg gtatcaagcc      780
tggagatgtg gagtatgttg aagctcatgg gacaggcacc aaggttggag atcctcaaga      840
agtaaatggc attgtaaatg tcttctgcca gtgtgagaga gagcctctgt taattggatc      900
aaccaagtca aacatgggtc atccagagcc tgcttctggg cttgctgcat tagccaaggt      960
cattctttct ctggaacatg gactgtgggc tccaaatctt catttcaatg atccaaatcc     1020
agatattcct gctttacacg atggctcctt gaaggtggtt tgcaaaccaa caccggtgaa     1080
aggtggcctt gtcagcatca attcttttgg ctttggaggc tctaatgctc atgttattct     1140
gaggccaaat gagaagaaat gtcagcctca agagacttgt aacttgccaa gactggttca     1200
agtttgtggc agaacacagg aagctgtgga aatactaatt gaagaaagca ggaaacatgg     1260
aggatgcagt ccattttttaa gcctgctcag tgatatctct gcagttcctg tatcttctat     1320
gccctacagg ggctacacac tagttggcac tgagagtgac ataacagaga ttcagcaagt     1380
tcaagcatct ggtagaccac tctggtacat ctgctcaggc atgggaacac agtggaaagg     1440
tatgggcctg agccttatga aattggatct gtttcgccag tctatattgc gctcagatga     1500
ggctttgaag agcacaggac tgaaggtctc agacctgctt ctgaatgcag atgagaacac     1560
ttttgatgac actgtccatg cttttgttgg actagctgct atacagattg cccaaattga     1620
tgtgctaaag gctgcgggtc tgcaacctga tgggattttg ggccactcag tgggagaact     1680
agcttgtggc tatgcagata attccttaag tcatgaagaa gctgttcttg ctgcttattg     1740
gaggggccga tgtgtgaaag aggccaaatt gccccggga gggatggctg ctgttggtct     1800
gacatgggag gaatgtaagc agcgctgtcc tccaaacgtg gtaccagcat gtcacaactc     1860
tgaggatact gtcactgttt cggggcctct ggattctgtg tctgagtttg taaccaaact     1920
gaagaaagat ggggtgtttg caaggaggt gcgcagcgcc ggagttgcat tcattccta     1980 ttacatggca tccattgcac cagcactgct cagtgcactg aaaaaggtca ttccacaccc     2040
taagcctcgt tcagcacggt ggatcagtac atctatccct gaatctcagt ggcagagtga     2100
tcttgctagg aattcctctg cagagtatca tgtgaacaac ctagtgaatc ctgtgctgtt     2160
ccatgaaggc ctgaagcata ttccagagaa tgctgttgta gtggagattg ctccacatgc     2220
tctcttacag gctatcttga ggagaacttt gaagccaact tgcactattc tacctctgat     2280
gaagaaggac cacaaaaata acttggagtt cttcctaacg cagactggaa agattcattt     2340
aactgggata aatgttcttg gaaataactt gttcccacct gtggaatacc ctgtccctgt     2400
gggaacacct ctcatttctc catatatcaa atgggaccac agccaagact gggatgttcc     2460
aaaagctgaa gacttcccct caggttccaa aggctctgcg tctgcttcag tctacaacat     2520
cgatgtgagt cctgactctc ctgaccatta cttggttggc cattgcattg atggcagagt     2580
cctgtaccca gcaactgggt acttagtgct ggcgtggcga actctggcac gatctcttgg     2640
catggtcatg gaacaaacag ctgttatgtt tgaagaagtt acaatccatc aggcaactat     2700
ccttcccaaa aagggatcaa cacagctgga agtacgaatc atgcctgctt ctcacagctt     2760
tgaagtgtca gggaatggga atttggctgt gagtgggaag atctccctcc tagaaaacga     2820
tgctctgaag aactttcata accagctggc tgacttccag agtcaagcaa acgtgactgc     2880
gaagtctggc ctcttgatgg aagatgttta ccaagagctg catcttcgtg gatataacta     2940
```

```
tggaccaact tttcagggtg ttctggaatg caacagtgaa ggaagtgcag ggaaaattct    3000
gtggaatgga aactgggtaa ccttccttga caccctgcta cacttgatag tcttagcaga    3060
gactgggcgc agtctacgat tgcccaccag gattcgctca gtgtatattg accctgtgct    3120
tcatcaggag caggtgtacc agtaccagga caatgtagaa gcttttgatg ttgttgttga    3180
ccgctgtctt gatagcctca aagcaggagg tgttcagatc aatggacttc atgcctcggt    3240
ggcaccacgg cgacaacagg agcggatctc tcccactctg gaaaaattct cctttgttcc    3300
ctatattgag agtgactgtt tgtcttccag tacccagctt catgcctacc tggagcactg    3360
caaaggcctg atccagaaat tacaagctaa gatggcattg cacggagtca aactagttat    3420
ccatggccta gaaaccaacg gggctgctgc aggatcccca cccacacaga agggccttca    3480
gcatatcctt actgaaatct gccatctgga actgaatgga aacctacatt ctgagctgga    3540
acagattgtg actcaggaga agatgcacct ccaggacgat ccccttctca atggcttgct    3600
ggattcttca gagttgaaga cttgcctgga tgtggcaaag gagaacacga ccagtcacag    3660
gatgaagata gtggaggctc tggcaggaag tggacgtctg ttctctcgtg tccaaagtat    3720
tctgaatact cagcccctgt tgcagctgga ctacattgcc actgactgca ccctgaaac    3780
tctttcaaat gatgaaacag agctgcacga tgctggaatc tcctttagcc agtgggatcc    3840
ctctagcctt ccctctggaa atctgaccaa tgctgacctg gcagtatgca actgttcaac    3900
aagtgttctg gggaacacag ctgaaattat ctctaactta gcagctgcag tgaaagaagg    3960
agggtttgtt ttgctgcaca cccttcttaa agaggaaact cttggagaaa ttgtcagctt    4020
tcttacaagt ccagacctac agcaagagca cagcttcctg tctcaggcac agtgggagga    4080
gttattcagc aaggcctcat tgaatctggt tgcaatgaag agatctttct ttggctcagt    4140
tattttcctg tgtcgacggc agtcccctgc caaagcaccc attcttctgc cagtagatga    4200
cactcattat aagtggggttg actccttaaa ggagatcttg gctgactcat cagagcagcc    4260
tctgtggttg actgccacca attgtgggaa ctctggaatt tgggtatgg tgaactgcct    4320
ccgcctggaa gcagagggcc acagaatcag gtgtgtgttt gtttccaacc tgagcccttc    4380
atcaactgtc ccagccacta gtctttcttc cctggagatg cagaagatta ttgagagaga    4440
tctggtgatg aatgtgtatc gtgatggaaa gtggggttcc ttcaggcatc tcccattgca    4500
gcaagctcag cctcaggagc tgacagaata tgcctacgta aatgtgttga ctcgtggaga    4560
tctctcttcc cttcgttgga ttgtttcccc acttcgacac ttccaaacaa ccaatccaaa    4620
tgttcagctc tgcaaagtct actatgcatc tctcaatttc cgggacatta tgctggcaac    4680
aggaaagctt tctccagatg ctatccctgg taactgacg ttgcagcagt gcatgctggg    4740
catggagttc tcaggacggg acctggctgg aaggagagtg atgggattgc tgccagcaaa    4800
agggctggcg acagtggtgg actgtgacaa gaggtttcta tgggaagtgc ctgaaaactg    4860
gactctggaa gaagcagctt cggtgcctgt ggtttatgcc actgcttatt atgctttggt    4920
ggttcgaggt ggtatgaaga agggggagag tgtcctcatt cactctggct caggaggtgt    4980
gggcgcaagc agccattgcc atcgccttga gcatgggctg gcgcgtgttt ttgctactgt    5040
aggctctgct gagaaacgtg agtatctcca agcaaggttc ccacagctgg atgctaatag    5100
ctttgccagc tcccgaaata caacctttga gcaacacata ctgcgagtta ccaatgggaa    5160
aggtgtcaac cttgtgttaa attccttggc agaagagaag ctccaagcca gtttgcgttg    5220
tcttgctcaa catgggcgct tcttggaaat aggcaaattt gatctatcaa acaacagcca    5280
```

```
gcttggaatg gctcttttcc tcaagaatgt ggcgtttcat ggaatcctgc tggattcaat    5340
ctttgaggaa ggaaaccaag agtgggaggt ggtatcagag ttgttgacaa aaggcataaa    5400
agatggtgtg gtaaagcccc tgagaaccac agtcttcggt aaagaagagg tagaagctgc    5460
cttcaggttc atggcgcaag gaaaacatat tggcaaagtt atgatcaaga tccaagaaga    5520
ggagaagcaa tatcctttaa ggtctgaacc agtaaaactc tctgccatct cccgaacttc    5580
ctgcccacct accaagtctt acatcatcac agggggccta ggaggatttg gcttgagtt    5640
ggcacagtgg ctaattgaga gaggagcaca gaagcttgta ctgacatctc gatctggcat    5700
acgaactggc taccaggcta atgtgttag agaatggaag cgctgggaa tccaagtgtt     5760
ggtctctacc agtgatgttg gaactctaga aggaacgcag cttttgatag aagaggcttt    5820
gaagctcgga ccagttgggg gcatctttaa tttggctgtg gtccttaaag atgccatgat    5880
tgaaaatcag accccggaat tattctggga ggtcaacaag cccaagtatt caggcaccct    5940
tcatttggac tgggtgactc gtaagaagtg cccagacctg gactattttg ttgtattctc    6000
ctctgtaagc tgtggaagag gaaatgctgg gcaaagtaat tatggctttg ctaattctgc    6060
catggagcgt atctgtgagc agcggcatca cgatgggctc ccaggcctgg cagtccagtg    6120
gggagccatt ggtgatgtgg gcatcctgaa ggcaatggga acagggagg ttgtgattgg     6180
gggaaccgtt ctccagcaaa tcagctcctg cctggaggtg ctcgatatgt tcctgaatca    6240
acctcatcct gttatgtcca gttttgtcct agcagagaag gtctctgtga aaagtgaagg    6300
aggaagtcaa cgggatcttg tagaagctgt tgctcatatc cttggtgttc gtgacgtgag    6360
cagtctgaat gctgagagct ccctagcaga cttgggcctg gattccttga tgggtgtgga    6420
ggtgcgccag acgctggaga gagactacga catcgtaatg accatgaggg agatccgact    6480
cctcaccatc aacaaactgc gtgaactgtc ctccaagact gggacagcag aggagctgaa    6540
gccatcacaa gtgttgaaga caggcccagg tgagcctcca aaactggatt tgaacaactt    6600
gctggtgaat ccagaagggc caacgattac ccgtctcaat gaagttcaga gcacagaacg    6660
ccctcttttc cttgttcacc ccattgaggg atccattgca gtcttctata ctcttgcctc    6720
caaacttcat atgccctgct atggactcca gtgcacaaaa gctgctccct tggacagcat    6780
acagagcctg gcatcctatt atattgactg tatgaagcag atacagcctg aaggacctta    6840
tcgcattgct ggatactctt ttggtgcctg cgtagccttt gaaatgtgct cccagctgca    6900
agcacaacaa aatgcttccc atgcactcaa cagtttattc ctctttgatg gtctcattc     6960
ctttgtggca gcatacactc agtgttttc cttttctctt tttcagagct acagagcaaa    7020
gctgacccaa ggaaatgagg ctgcgttgga gacagaagca ctgtgtgcct tgttcagca    7080
gtttacaggc attgaataca ataagttgtt ggagattctt ctgcccttgg aagatctgga    7140
ggctcgtgtc aatgctgctg cagaccttat aactcagatt cataaaaaca tcaaccgtga    7200
agcactcagc tttgctgctg cttccttta ccataagctg aaggctgctg acaagtatat     7260
accagaatcc aagtatcatg ggaacgtgac actgatgcgg gcaaagactc acaatgagta    7320
tgaagaaggt ctggggtggag actacagact ctcagaggtc tgcgatggaa aagtatcagt    7380
ccacatcatt gaaggagatc accgcacctt attggaggga gatggtgttg aatcaatcat    7440
tgggatcatc catggctcac tggcagagcc acgtgtcagt gtcagagaag gttaacttct    7500
gccacttact gtcagtggtg aagaaaatgc caacaacatt cctagttatg acagacccca    7560
aggaactctt cctgttgaac aacatctcat ctctctgctg ccagagctgg gaaggccagc    7620
tgaacttgat tggtctcttt gtttcctctc tcactcagtc atctttccta actttcacgt    7680
```

```
gttctctctc tctcctcttc ccttcctatg ctttgtctat ttccccacta tccctgcccg    7740
tgttactgcg gtgctgtgac tgtcactgtg caccggggt tccccggcga tggtggcttc     7800
ccacagcttt ggcagtatgt ttttcaaatt taggagtaga cttctacgtg ctctatattg    7860
ttttgtctta acagtattcc aaagggtaag tgatagcact tgttgaccaa gcccagtgag    7920
cagagagggg aactgcagct gatttcggag atacctgttg tctgtgaaga atctgtctgt    7980
agtgaggtca gaaagagaat tccatttgag gcttttgtaa ctatatttt ttaatttgat    8040 atagtctaag tatttattgt gtcaaatcag agacttcttg ctttgtttta atttatcgtg   8100
ggtatcagaa aaggaaacat ccgttttgaa gggataggtt cattctacaa ggggaggttg    8160
cccatttgtt aaaccaaagt gcatctatgg aacagcccat ttctttttt tttttaagtt    8220 gattttttgt ttgtgtttcg ttttttgttg tttgttttt gtggcgtttt gttaattttg    8280
attagtgatt tttctgtgtg tggtttttct ttccccccc ccccaccct gccttgttca     8340 gaagggtgga agtgaggttc cttgccatca cccacccttg tggggagaga ggcgtggagg   8400
gcaggatgga tggttcaaca gatgccactg tattgaacag ccttaacttg ggctgataca    8460
agcaggcaga gctctcccta ggtatgtact tagtttatat ctctgcaagg ttctgtgctt    8520
tgcattacca gaaacacagt aaagcattac ggctattgct tcacctttgt tccttcccac    8580
ctccagttgc tccatccaac caggcatttg gaatgtcagg gggaatagag ttctccattg    8640
gtcacggtat aaatcctcct acccttgctc tcccataacc aaagttcatg caaacataga    8700
aggcatctac ccagtacccc agtgtatttt atgtagcata ggcttgctta agccttgagt    8760
atgcattttc ctctggcagt gagactggag atcccacata agttagctaa gtaaaagttt    8820
gatggcatga ttttaagata cagtaccttt ttaaaggaaa cttgcataaa attcaattta    8880
aaaatgactg acttttgcta tgctggatct gtcttttcca aaatcagtaa atcctcttga    8940
cgcctatgat acagaggaga cctgaatagc aatgaagtac caaccaggag gcattccact    9000
gcctctcaga acttctgtaa accctgttc tttctgtatt catcccctag tgaagcatcc    9060
tgtgagttca ggagcattcc agtgagagga acagctggtt cctcgtggca ggttctacct    9120
agcgtctctt gcttatacaa ccctctgtgg agagtggctg ggttaactgg ttttagtttt    9180
ataaagtatt tcttttgtga aatctgaaat acaaacaaca taatgtcagc ttaaagcatt    9240
tctagaatta agttttgttt tttactttt tttttttt ttttaatct gaagagtgtc      9300 tttttcctct ttggctttcc tagaattaaa cagaattgat cactg                    9345
```

<210> SEQ ID NO 29
<211> LENGTH: 2447
<212> TYPE: PRT
<213> ORGANISM: Gallus gallus

<400> SEQUENCE: 29

```
Met Asp Pro Pro Val Arg Leu Leu Leu Glu Val Ser Tyr Glu Ala Ile
1               5                   10                  15

Leu Asp Gly Gly Ile Asn Pro Thr Ala Leu Arg Gly Thr Asp Thr Gly
            20                  25                  30

Val Trp Val Gly Ala Ser Gly Ser Glu Ala Ala Glu Ala Leu Ser Gln
        35                  40                  45

Asp Pro Glu Glu Leu Leu Gly Tyr Ser Met Thr Gly Cys Gln Arg Ala
    50                  55                  60

Met Leu Ala Asn Arg Ile Ser Tyr Phe Tyr Asp Phe Thr Gly Pro Ser
65                  70                  75                  80
```

-continued

```
Leu Thr Ile Asp Thr Ala Cys Ser Ser Leu Met Ala Leu Glu Asn
                85                  90                  95
Ala Tyr Lys Ala Ile Arg His Gly Gln Cys Ser Ala Ala Leu Val Gly
            100                 105                 110
Gly Val Asn Ile Leu Leu Lys Pro Asn Thr Ser Val Gln Phe Met Lys
            115                 120                 125
Leu Gly Met Leu Ser Pro Asp Gly Ala Cys Lys Ala Phe Asp Val Ser
        130                 135                 140
Gly Asn Gly Tyr Cys Arg Ser Glu Ala Val Val Val Leu Leu Thr
145                 150                 155                 160
Lys Lys Ser Met Ala Lys Arg Val Tyr Ala Thr Ile Val Asn Ala Gly
                165                 170                 175
Ser Asn Thr Asp Gly Phe Lys Glu Gln Gly Val Thr Phe Pro Ser Gly
            180                 185                 190
Glu Met Gln Gln Gln Leu Val Gly Ser Leu Tyr Arg Glu Cys Gly Ile
        195                 200                 205
Lys Pro Gly Asp Val Glu Tyr Val Glu Ala His Gly Thr Gly Thr Lys
        210                 215                 220
Val Gly Asp Pro Gln Glu Val Asn Gly Ile Val Asn Val Phe Cys Gln
225                 230                 235                 240
Cys Glu Arg Glu Pro Leu Leu Ile Gly Ser Thr Lys Ser Asn Met Gly
                245                 250                 255
His Pro Glu Pro Ala Ser Gly Leu Ala Ala Leu Ala Lys Val Ile Leu
            260                 265                 270
Ser Leu Glu His Gly Leu Trp Ala Pro Asn Leu His Phe Asn Asp Pro
        275                 280                 285
Asn Pro Asp Ile Pro Ala Leu His Asp Gly Ser Leu Lys Val Val Cys
        290                 295                 300
Lys Pro Thr Pro Val Lys Gly Gly Leu Val Ser Ile Asn Ser Phe Gly
305                 310                 315                 320
Phe Gly Gly Ser Asn Ala His Val Ile Leu Arg Pro Asn Glu Lys Lys
                325                 330                 335
Cys Gln Pro Gln Glu Thr Cys Asn Leu Pro Arg Leu Val Gln Val Cys
            340                 345                 350
Gly Arg Thr Gln Glu Ala Val Glu Ile Leu Ile Glu Glu Ser Arg Lys
        355                 360                 365
His Gly Gly Cys Ser Pro Phe Leu Ser Leu Leu Ser Asp Ile Ser Ala
        370                 375                 380
Val Pro Val Ser Ser Met Pro Tyr Arg Gly Tyr Thr Leu Val Gly Thr
385                 390                 395                 400
Glu Ser Asp Ile Thr Glu Ile Gln Gln Val Gln Ala Ser Gly Arg Pro
                405                 410                 415
Leu Trp Tyr Ile Cys Ser Gly Met Gly Thr Gln Trp Lys Gly Met Gly
            420                 425                 430
Leu Ser Leu Met Lys Leu Asp Leu Phe Arg Gln Ser Ile Leu Arg Ser
        435                 440                 445
Asp Glu Ala Leu Lys Ser Thr Gly Leu Lys Val Ser Asp Leu Leu Leu
        450                 455                 460
Asn Ala Asp Glu Asn Thr Phe Asp Asp Thr Val His Ala Phe Val Gly
465                 470                 475                 480
Leu Ala Ala Ile Gln Ile Ala Gln Ile Asp Val Leu Lys Ala Ala Gly
                485                 490                 495
```

-continued

```
Leu Gln Pro Asp Gly Ile Leu Gly His Ser Val Gly Glu Leu Ala Cys
            500                 505                 510
Gly Tyr Ala Asp Asn Ser Leu Ser His Glu Glu Ala Val Leu Ala Ala
        515                 520                 525
Tyr Trp Arg Gly Arg Cys Val Lys Glu Ala Lys Leu Pro Pro Gly Gly
    530                 535                 540
Met Ala Ala Val Gly Leu Thr Trp Glu Glu Cys Lys Gln Arg Cys Pro
545                 550                 555                 560
Pro Asn Val Val Pro Ala Cys His Asn Ser Glu Asp Thr Val Thr Val
                565                 570                 575
Ser Gly Pro Leu Asp Ser Val Ser Glu Phe Val Thr Lys Leu Lys Lys
            580                 585                 590
Asp Gly Val Phe Ala Lys Glu Val Arg Ser Ala Gly Val Ala Phe His
        595                 600                 605
Ser Tyr Tyr Met Ala Ser Ile Ala Pro Ala Leu Leu Ser Ala Leu Lys
    610                 615                 620
Lys Val Ile Pro His Pro Lys Pro Arg Ser Ala Arg Trp Ile Ser Thr
625                 630                 635                 640
Ser Ile Pro Glu Ser Gln Trp Gln Ser Asp Leu Ala Arg Asn Ser Ser
                645                 650                 655
Ala Glu Tyr His Val Asn Asn Leu Val Asn Pro Val Leu Phe His Glu
            660                 665                 670
Gly Leu Lys His Ile Pro Glu Asn Ala Val Val Glu Ile Ala Pro
    675                 680                 685
His Ala Leu Leu Gln Ala Ile Leu Arg Arg Thr Leu Lys Pro Thr Cys
        690                 695                 700
Thr Ile Leu Pro Leu Met Lys Lys Asp His Lys Asn Asn Leu Glu Phe
705                 710                 715                 720
Phe Leu Thr Gln Thr Gly Lys Ile His Leu Thr Gly Ile Asn Val Leu
                725                 730                 735
Gly Asn Asn Leu Phe Pro Pro Val Glu Tyr Pro Val Pro Val Gly Thr
            740                 745                 750
Pro Leu Ile Ser Pro Tyr Ile Lys Trp Asp His Ser Gln Asp Trp Asp
        755                 760                 765
Val Pro Lys Ala Glu Asp Phe Pro Ser Gly Ser Lys Gly Ser Ala Ser
    770                 775                 780
Ala Ser Val Tyr Asn Ile Asp Val Ser Pro Asp Ser Pro Asp His Tyr
785                 790                 795                 800
Leu Val Gly His Cys Ile Asp Gly Arg Val Leu Tyr Pro Ala Thr Gly
                805                 810                 815
Tyr Leu Val Leu Ala Trp Arg Thr Leu Ala Arg Ser Leu Gly Met Val
            820                 825                 830
Met Glu Gln Thr Ala Val Met Phe Glu Glu Val Thr Ile His Gln Ala
        835                 840                 845
Thr Ile Leu Pro Lys Lys Gly Ser Thr Gln Leu Glu Val Arg Ile Met
    850                 855                 860
Pro Ala Ser His Ser Phe Glu Val Ser Gly Asn Gly Asn Leu Ala Val
865                 870                 875                 880
Ser Gly Lys Ile Ser Leu Leu Glu Asn Asp Ala Leu Lys Asn Phe His
                885                 890                 895
Asn Gln Leu Ala Asp Phe Gln Ser Gln Ala Asn Val Thr Ala Lys Ser
            900                 905                 910
Gly Leu Leu Met Glu Asp Val Tyr Gln Glu Leu His Leu Arg Gly Tyr
```

```
                915                 920                 925
Asn Tyr Gly Pro Thr Phe Gln Gly Val Leu Glu Cys Asn Ser Glu Gly
930                 935                 940

Ser Ala Gly Lys Ile Leu Trp Asn Gly Asn Trp Val Thr Phe Leu Asp
945                 950                 955                 960

Thr Leu Leu His Leu Ile Val Leu Ala Glu Thr Gly Arg Ser Leu Arg
                965                 970                 975

Leu Pro Thr Arg Ile Arg Ser Val Tyr Ile Asp Pro Val Leu His Gln
                980                 985                 990

Glu Gln Val Tyr Gln Tyr Gln Asp Asn Val Glu Ala Phe Asp Val Val
                995                 1000                1005

Val Asp Arg Cys Leu Asp Ser Leu Lys Ala Gly Gly Val Gln Ile
    1010                1015                1020

Asn Gly Leu His Ala Ser Val Ala Pro Arg Arg Gln Gln Glu Arg
    1025                1030                1035

Ile Ser Pro Thr Leu Glu Lys Phe Ser Phe Val Pro Tyr Ile Glu
    1040                1045                1050

Ser Asp Cys Leu Ser Ser Ser Thr Gln Leu His Ala Tyr Leu Glu
    1055                1060                1065

His Cys Lys Gly Leu Ile Gln Lys Leu Gln Ala Lys Met Ala Leu
    1070                1075                1080

His Gly Val Lys Leu Val Ile His Gly Leu Glu Thr Asn Gly Ala
    1085                1090                1095

Ala Ala Gly Ser Pro Pro Thr Gln Lys Gly Leu Gln His Ile Leu
    1100                1105                1110

Thr Glu Ile Cys His Leu Glu Leu Asn Gly Asn Leu His Ser Glu
    1115                1120                1125

Leu Glu Gln Ile Val Thr Gln Glu Lys Met His Leu Gln Asp Asp
    1130                1135                1140

Pro Leu Leu Asn Gly Leu Leu Asp Ser Ser Glu Leu Lys Thr Cys
    1145                1150                1155

Leu Asp Val Ala Lys Glu Asn Thr Thr Ser His Arg Met Lys Ile
    1160                1165                1170

Val Glu Ala Leu Ala Gly Ser Gly Arg Leu Phe Ser Arg Val Gln
    1175                1180                1185

Ser Ile Leu Asn Thr Gln Pro Leu Leu Gln Leu Asp Tyr Ile Ala
    1190                1195                1200

Thr Asp Cys Thr Pro Glu Thr Leu Ser Asn Asp Glu Thr Glu Leu
    1205                1210                1215

His Asp Ala Gly Ile Ser Phe Ser Gln Trp Asp Pro Ser Ser Leu
    1220                1225                1230

Pro Ser Gly Asn Leu Thr Asn Ala Asp Leu Ala Val Cys Asn Cys
    1235                1240                1245

Ser Thr Ser Val Leu Gly Asn Thr Ala Glu Ile Ile Ser Asn Leu
    1250                1255                1260

Ala Ala Ala Val Lys Glu Gly Gly Phe Val Leu Leu His Thr Leu
    1265                1270                1275

Leu Lys Glu Glu Thr Leu Gly Glu Ile Val Ser Phe Leu Thr Ser
    1280                1285                1290

Pro Asp Leu Gln Gln Glu His Ser Phe Leu Ser Gln Ala Gln Trp
    1295                1300                1305

Glu Glu Leu Phe Ser Lys Ala Ser Leu Asn Leu Val Ala Met Lys
    1310                1315                1320
```

```
Arg Ser Phe Phe Gly Ser Val Ile Phe Leu Cys Arg Arg Gln Ser
    1325                1330                1335

Pro Ala Lys Ala Pro Ile Leu Leu Pro Val Asp Asp Thr His Tyr
    1340                1345                1350

Lys Trp Val Asp Ser Leu Lys Glu Ile Leu Ala Asp Ser Ser Glu
    1355                1360                1365

Gln Pro Leu Trp Leu Thr Ala Thr Asn Cys Gly Asn Ser Gly Ile
    1370                1375                1380

Leu Gly Met Val Asn Cys Leu Arg Leu Glu Ala Glu Gly His Arg
    1385                1390                1395

Ile Arg Cys Val Phe Val Ser Asn Leu Ser Pro Ser Ser Thr Val
    1400                1405                1410

Pro Ala Thr Ser Leu Ser Ser Leu Glu Met Gln Lys Ile Ile Glu
    1415                1420                1425

Arg Asp Leu Val Met Asn Val Tyr Arg Asp Gly Lys Trp Gly Ser
    1430                1435                1440

Phe Arg His Leu Pro Leu Gln Gln Ala Gln Pro Gln Glu Leu Thr
    1445                1450                1455

Glu Tyr Ala Tyr Val Asn Val Leu Thr Arg Gly Asp Leu Ser Ser
    1460                1465                1470

Leu Arg Trp Ile Val Ser Pro Leu Arg His Phe Gln Thr Thr Asn
    1475                1480                1485

Pro Asn Val Gln Leu Cys Lys Val Tyr Tyr Ala Ser Leu Asn Phe
    1490                1495                1500

Arg Asp Ile Met Leu Ala Thr Gly Lys Leu Ser Pro Asp Ala Ile
    1505                1510                1515

Pro Gly Asn Trp Thr Leu Gln Gln Cys Met Leu Gly Met Glu Phe
    1520                1525                1530

Ser Gly Arg Asp Leu Ala Gly Arg Arg Val Met Gly Leu Leu Pro
    1535                1540                1545

Ala Lys Gly Leu Ala Thr Val Val Asp Cys Asp Lys Arg Phe Leu
    1550                1555                1560

Trp Glu Val Pro Glu Asn Trp Thr Leu Glu Glu Ala Ala Ser Val
    1565                1570                1575

Pro Val Val Tyr Ala Thr Ala Tyr Tyr Ala Leu Val Val Arg Gly
    1580                1585                1590

Gly Met Lys Lys Gly Glu Ser Val Leu Ile His Ser Gly Ser Gly
    1595                1600                1605

Gly Val Gly Ala Ser Ser His Cys His Arg Leu Glu His Gly Leu
    1610                1615                1620

Ala Arg Val Phe Ala Thr Val Gly Ser Ala Glu Lys Arg Glu Tyr
    1625                1630                1635

Leu Gln Ala Arg Phe Pro Gln Leu Asp Ala Asn Ser Phe Ala Ser
    1640                1645                1650

Ser Arg Asn Thr Thr Phe Glu Gln His Ile Leu Arg Val Thr Asn
    1655                1660                1665

Gly Lys Gly Val Asn Leu Val Leu Asn Ser Leu Ala Glu Glu Lys
    1670                1675                1680

Leu Gln Ala Ser Leu Arg Cys Leu Ala Gln His Gly Arg Phe Leu
    1685                1690                1695

Glu Ile Gly Lys Phe Asp Leu Ser Asn Asn Ser Gln Leu Gly Met
    1700                1705                1710
```

-continued

```
Ala Leu Phe Leu Lys Asn Val Ala Phe His Gly Ile Leu Leu Asp
    1715                1720                1725

Ser Ile Phe Glu Glu Gly Asn Gln Glu Trp Glu Val Val Ser Glu
    1730                1735                1740

Leu Leu Thr Lys Gly Ile Lys Asp Gly Val Val Lys Pro Leu Arg
    1745                1750                1755

Thr Thr Val Phe Gly Lys Glu Val Glu Ala Ala Phe Arg Phe
    1760                1765                1770

Met Ala Gln Gly Lys His Ile Gly Lys Val Met Ile Lys Ile Gln
    1775                1780                1785

Glu Glu Lys Gln Tyr Pro Leu Arg Ser Glu Pro Val Lys Leu
    1790                1795                1800

Ser Ala Ile Ser Arg Thr Ser Cys Pro Pro Thr Lys Ser Tyr Ile
    1805                1810                1815

Ile Thr Gly Gly Leu Gly Gly Phe Gly Leu Glu Leu Ala Gln Trp
    1820                1825                1830

Leu Ile Glu Arg Gly Ala Gln Lys Leu Val Leu Thr Ser Arg Ser
    1835                1840                1845

Gly Ile Arg Thr Gly Tyr Gln Ala Lys Cys Val Arg Glu Trp Lys
    1850                1855                1860

Ala Leu Gly Ile Gln Val Leu Val Ser Thr Ser Asp Val Gly Thr
    1865                1870                1875

Leu Glu Gly Thr Gln Leu Leu Ile Glu Glu Ala Leu Lys Leu Gly
    1880                1885                1890

Pro Val Gly Gly Ile Phe Asn Leu Ala Val Val Leu Lys Asp Ala
    1895                1900                1905

Met Ile Glu Asn Gln Thr Pro Glu Leu Phe Trp Glu Val Asn Lys
    1910                1915                1920

Pro Lys Tyr Ser Gly Thr Leu His Leu Asp Trp Val Thr Arg Lys
    1925                1930                1935

Lys Cys Pro Asp Leu Asp Tyr Phe Val Val Phe Ser Ser Val Ser
    1940                1945                1950

Cys Gly Arg Gly Asn Ala Gly Gln Ser Asn Tyr Gly Phe Ala Asn
    1955                1960                1965

Ser Ala Met Glu Arg Ile Cys Glu Gln Arg His His Asp Gly Leu
    1970                1975                1980

Pro Gly Leu Ala Val Gln Trp Gly Ala Ile Gly Asp Val Gly Ile
    1985                1990                1995

Leu Lys Ala Met Gly Asn Arg Glu Val Val Ile Gly Gly Thr Val
    2000                2005                2010

Leu Gln Gln Ile Ser Ser Cys Leu Glu Val Leu Asp Met Phe Leu
    2015                2020                2025

Asn Gln Pro His Pro Val Met Ser Ser Phe Val Leu Ala Glu Lys
    2030                2035                2040

Val Ser Val Lys Ser Glu Gly Gly Ser Gln Arg Asp Leu Val Glu
    2045                2050                2055

Ala Val Ala His Ile Leu Gly Val Arg Asp Val Ser Ser Leu Asn
    2060                2065                2070

Ala Glu Ser Ser Leu Ala Asp Leu Gly Leu Asp Ser Leu Met Gly
    2075                2080                2085

Val Glu Val Arg Gln Thr Leu Glu Arg Asp Tyr Asp Ile Val Met
    2090                2095                2100

Thr Met Arg Glu Ile Arg Leu Leu Thr Ile Asn Lys Leu Arg Glu
```

```
            2105                2110                2115

Leu Ser Ser Lys Thr Gly Thr Ala Glu Glu Leu Lys Pro Ser Gln
    2120                2125                2130

Val Leu Lys Thr Gly Pro Gly Glu Pro Pro Lys Leu Asp Leu Asn
    2135                2140                2145

Asn Leu Leu Val Asn Pro Glu Gly Pro Thr Ile Thr Arg Leu Asn
    2150                2155                2160

Glu Val Gln Ser Thr Glu Arg Pro Leu Phe Leu Val His Pro Ile
    2165                2170                2175

Glu Gly Ser Ile Ala Val Phe Tyr Thr Leu Ala Ser Lys Leu His
    2180                2185                2190

Met Pro Cys Tyr Gly Leu Gln Cys Thr Lys Ala Pro Leu Asp
    2195                2200                2205

Ser Ile Gln Ser Leu Ala Ser Tyr Tyr Ile Asp Cys Met Lys Gln
    2210                2215                2220

Ile Gln Pro Glu Gly Pro Tyr Arg Ile Ala Gly Tyr Ser Phe Gly
    2225                2230                2235

Ala Cys Val Ala Phe Glu Met Cys Ser Gln Leu Gln Ala Gln Gln
    2240                2245                2250

Asn Ala Ser His Ala Leu Asn Ser Leu Phe Leu Phe Asp Gly Ser
    2255                2260                2265

His Ser Phe Val Ala Ala Tyr Thr Gln Cys Phe Ser Phe Ser Leu
    2270                2275                2280

Phe Gln Ser Tyr Arg Ala Lys Leu Thr Gln Gly Asn Glu Ala Ala
    2285                2290                2295

Leu Glu Thr Glu Ala Leu Cys Ala Phe Val Gln Gln Phe Thr Gly
    2300                2305                2310

Ile Glu Tyr Asn Lys Leu Leu Glu Ile Leu Pro Leu Glu Asp
    2315                2320                2325

Leu Glu Ala Arg Val Asn Ala Ala Ala Asp Leu Ile Thr Gln Ile
    2330                2335                2340

His Lys Asn Ile Asn Arg Glu Ala Leu Ser Phe Ala Ala Ala Ser
    2345                2350                2355

Phe Tyr His Lys Leu Lys Ala Ala Asp Lys Tyr Ile Pro Glu Ser
    2360                2365                2370

Lys Tyr His Gly Asn Val Thr Leu Met Arg Ala Lys Thr His Asn
    2375                2380                2385

Glu Tyr Glu Glu Gly Leu Gly Gly Asp Tyr Arg Leu Ser Glu Val
    2390                2395                2400

Cys Asp Gly Lys Val Ser Val His Ile Ile Glu Gly Asp His Arg
    2405                2410                2415

Thr Leu Leu Glu Gly Asp Gly Val Glu Ser Ile Ile Gly Ile Ile
    2420                2425                2430

His Gly Ser Leu Ala Glu Pro Arg Val Ser Val Arg Glu Gly
    2435                2440                2445

SEQ ID NO 30
LENGTH: 8391

TYPE: DNA
ORGANISM: Mycobacterium bovis

SEQUENCE: 30
```

```
atgggtacgc gcactggcgg ccgaggaccc ggttccgtcc gacaagcacc tgacgtcggc    60
cgccgtgtcg gtgcccggcg tgttgcttac ccagatcgcg gcgacccggg cgctggcccg   120
tcaaggcatg gacctcgtgg ccaccccgcc ggtcgccatg gcgggcattc gcaaggtgtg   180
ctggcggtgg aagccctcaa ggctggtggg cacgcgacg tcgagctgtt tgccttggcc    240
cagttgatcg gtgccgccgg aacgctggtg gcccgccggc gcgaatttcc gtcctgggcg   300
atcgcgccga tggtatcggt caccaacgcc gaccccgagc gcatcggccg gttgctcgac   360
gagttcgccc aggacgtgcg cacggtgctg ccaccggtgt tgtccatccg caacggccgg   420
cgtgccgtcg tcatcaccgg cacccccgag cagctgtcgc gtttcgagct ttattgccgc   480
cagatctccg agaaggaaga agccgaccgc aagaacaagg tccgcggcgg cgacgtcttc   540
tcgccggtct tcgagccggt gcaggtggag gtgggctttc acaccccgcg gctatccgac   600
gggatcgaca tcgtcgcggg ctgggccgag aaggcgggcc tcgatgtcgc cttggctcgg   660
gagctggccg atgccatctt gatcagaaag gtcgactggg tcgacgagat cacccgtgtc   720
caccgggccg cgcccgctg atcctcgac ctggggccgg cgacatcct gacccgactg     780 accgcaccgg tgatccgcgg cctgggcatc ggcatcgtgc cggcgcgtac ccgcggtggc   840
cagcgcaacc tgttcaccgt cggcgccacc ccgaggttg cccgggcctg gtcgagctac    900
gcaccgaccg tggttcgcct ccccgacggc agggtcaagc tctcgacgaa gttcacccgg   960
ctgacccgcc gctcgccgat cctgctcgcg ggcatgaccc cgaccaccgt ggacgccaag  1020
atcgtcgccg cggcggccaa cggccggcac tgggccgagc tggcggcgcg gggcaggtca  1080
ccgaagagat cttcggtaac cgcatcgaac aaatggccgg cctgctcgag ccgggccgca  1140
cctatcagtt caacgcgctg ttcctcgatc cctacctgtg aagcttcagg tgggcggcaa  1200
gcggttggtg cagaaggccc gccagtccgg cgccgcgatc gacggcgtgg tgatcagcgc  1260
cggcatccca gacctcgacg aggccgtcga gctgatcgac gaactgggcg acatcggcat  1320
cagccacgtc gtgttcaaac ccgggaccat cgagcagatc cgctcggtga ttcgcatcgc  1380
caccgaggtg cccaccaagc cggtgatcat gcacgtcgag ggccgggcgc gccggcgggc  1440
accattcctg ggaggatctc acacctgctg ctggctacct actcggcaga tcggcaccg   1500 cgccaacatc acgtgtgcgt cggcggcggc catctcggca ccccgaagaa gggctgcgga  1560
tatttgtccg ggcctgggcg cagcgtacgg cttcccattg atgccgatcg acgcatcctg  1620
gtcggcaccg cggcgatggc caccaaggaa tccaccacgt cgccatcggt caagcggatg  1680
ctcgtcgaca ctcagggcac cgaccaatgg atcagcgccg gaaaagcgca gggccgcatg  1740
cctccagccg agtcagctcg gtgccgacat ccacgagatc gacacagcgc atccgtgcgg  1800
cgctgctcga cgaggtggcc ggtgacgcgg aggcggtcgc ggagcgtcgc atggccaaga  1860
ccgccaagcc ctacttgccg acgtcgccga catgacctac ctgcagtggc tgcgggcgct  1920
acgtcgaact ggccatcggg gaaggcaact cgaccgccga caccgcctcg gtgggcagcc  1980
cgtggctggc cgacactggc gggaccgctt cgagcagatg ctgcagcgtg ccgaagcccg  2040
gttgcaccca caggatttcg gcccgatcca gacgctattc accgatgctg gcctgctgga  2100
caatccgcag cagcgatcgc cgccctcgtg gcgcgctacc ccgacgccga gaccgtgcag  2160
ttgcatcccg cggatgtgcc cttttttcgtg acgttgtgca agacgctggg caagccggtc  2220
aacttcgtgc cggcgatcga cctcgtcgtg gcgcgctggtg gcgcagcgac tgctgtggc   2280 aggcccacga cgcccgctac gacgccgatg cggtgtgcat cattccgggc acgcgtcggt  2340
```

```
agccgcatca cccggatgga tgaacccgtc ggtgagttgc tggacgcttt cgagcaagcc   2400
gcaatcgatg aagtgctcgg cgccggtgtc gagccgaagg atgtcgcgtc cggccggctg   2460
ggccgggccg acgtggccgg accgttggct gtcgtcctcg acgcacccga tgtgcgctgg   2520
gccggtcgca ccgtgaccaa cccggtgcat cggatccgcg acccggccga atggcaggtg   2580
cacgatggac ccgaaaaccc gcgcgccgca cactcatcca ccggcgcccg gctgcagacg   2640
cacggcgacg acgtcgcctt gagcgtcgcg cgtctcgggc acctgggtcg acatccgatt   2700
cacgttgccg gccaacaccg tcgatggcgg caccccggtg atcgccaccg aggacgccac   2760
cacgccatgc gcacggtgct gcgatcgccg ccggtgtcga cagcccggag ttcttgctgc   2820
ggtggccaac gggacggcca ctttgacggt ggactggcac cccgagcgtg ttgccgacca   2880
caccgtcacc gccacgttcg gtgcgcgctg gcacccagcc tcaccaacgt gccgacgcga   2940
ctcgtcggcc cttgttggcc agcggttttc gcggccatcg gatcggcggt caccgacacc   3000
ggtgagccgg tggtggaagg cctgctgagc ctggtgcatc tggacacgcg gccgcgcgtg   3060
gtcggtcagc tgcccacggt cccggcccaa ttgaccgtca cgcaacgcct gccaacgcaa   3120
ccgatacgga catgggccgc gtcgtgccgg tctcggtcgt cgttcaccgc atggcgccgt   3180
gatcgccact ctcgaggagc gattcgcgat cctgggtcgc accggttcgc cgagctggac   3240
cggcgcgagc cggtggcgcg tgtcgcgaac gccaccgac accccgcgcg tcgccgccgc   3300
gacgtcacga tcaccgcgcc ggtcgacatg cgcccgttcg cggtggtgtc cggcgaccac   3360
aaccccattc acaccgaccg ggccgccgct gcttgccggc ctggagtcgc cgatcgtgca   3420
cggcatgtgg ctgtcggccg cggcgcaaca cgccggtgacc ggcaccgacg ggcaggcccg   3480
ccaccggccc ggctggtcgg ctggaccgcg cggttttttgg gcatggtggc cccggcgacg   3540
aggtggactt ccggtcgagc gcgtcggatc gaccagggcg cagagattgt ggacgtggcc   3600
gcgcgcgtcg ggtcggatct agtgatgtcg gcctccgcgc gactggccgc acccaagacg   3660
gtctacgcat tccccggcca gggcatccaa cacaagggca tgggcatgga ggtgcgcgcc   3720
gctccaaggc ggcccgcaag gtgtgggaca ccgcggacaa gttcaccgc gacaccctgg   3780 gcttctcggt actgcacgtg gtccgcgaca acccgaccag catcatcgcc agcggtgtgc   3840
actaccacca ccgacggggt gctctacctg acgcagttca cccaggtcgc gatggcgacg   3900
gtggcggccg ggcaggtcgc cgagatgcgt gaacagggag ccttcgtcga aggcgccatc   3960
gcgtgcggcc actcggtcgg cgagtacacc gcgctggcct gcgtgaccgg catctaccaa   4020
ctggaagcct tgctggagat ggtgtttcac cgcgggtcga agatgcacga catcgttccg   4080
cgcgacgagc tcggccgctc caactatcgg ctgtcggcca tccggccgtc ccagatcgac   4140
ctcgacgacg ccgacgtgcc cgcgttcgtc gccgggatcg cggagagcac cggtgaattc   4200
ctggagatcg agaatttcaa cctcggtggc tcgcaatacg cgatcgcggg cacggtacgc   4260
ggcctcgagg cgctcgaggc cgaggtggag cggcgccgcg agctcaccgg cggccgacgg   4320
tcgttcattt tggtgcccgg catcgatgtt ccgttccact ccgcgagtgct gcgggtcggg   4380 gtggccgaat tccggcgctc gctggaccgg gtcatgcggc cgacgcggac ccgacctgat   4440
catcgggcgc tacattccca acctggtgcc gcggaagttc aaccctggac cgcgacttca   4500
tccaggaaat ccgggatttg gtgccccgcc gagccgctcg acgagatcct cgccgactac   4560
gacacctggc ttcgcgacga ccggcgagat ggcgcgcacg gtgttcatcg agctgctggc   4620
atggcaattc gccagcccgg tgcgctggat cgagacgcag gatctgctgt tcatcgagga   4680
```

```
ggcgccggcg ggctgggtgt ggagcgattc gtcgagatcg gtgtgaagag ctcaccgacg   4740
gtggcgggt cttgccacca acaccctcaa actgcccgaa tacgcccaca gcacagtgaa   4800
gtgctcaacg ccgagcgtga tgcgcggtgc tgttcgccac cgacaccgac ccggagccgg   4860
agccggagga agacgagccg gtcgcggaat cgcccgcgcc ggacgtcgtc tcggaagccg   4920
cccccgtcgc gccggccgct tcgtcggcgg gcccgcgtcc cgacgatctg gttttcgacg   4980
ccgccgatgc cacgctgcgt gatcgcgctc tcggccaaga tgcgcatcga ccagatcgaa   5040
gaactcgact ccatcgagtc catcaccgac ggtgcgtcgt cgcggcgcaa ccagctgctg   5100
gtggacctgg gctccgagct gaacctcggt gccattgaac ggcgccgccg aatcggacct   5160
ggccggtctg cgctcacagg tgaccaaact ggcgcgcacc tacaacgtta cggcccagtg   5220
ctttccgacg ccatcaacga ccacgttcgc accgtcctcg gaccgtcggg caagcggccc   5280
ggcgccatcg ccgagcgggt gaagaagacc tgggagctcg gtgaggctgg gccaagcatg   5340
tcaccgtcga ggtcgcgctg gcacccgcg agggcagcag cgttcgcggc ggcgccatgg   5400
gccacctgca cgagggcgcg ctggccgatg ccgcctccgt cgacaaggtc atcgacgcgg   5460
cggtcgcatc ggtggccgcg gccagggcgt ttcggtagcg ctgcgtcggc cggtagtggc   5520
ggcgccacca tcgacgcggc cgcgctcagc gagttcaccg accaaatcac cggccgtgag   5580
ggcgtgctgc ctccgcggcc cgcctggtgc tggggcagct gggactggac gaccccatca   5640
accgttgccg gccgccccga ttccgagctg atcgacttgg tcaccgccga actgggacgg   5700
actggccgcg gttggtggca ccggtgttcg accccaagaa ggccgtcgta ttcgacgacc   5760
gctggccagc gcccgcgagg acctggtgaa gctgtggctg accgacggaa ggaccgaagg   5820
cgacatcgac gccgactggc cgcgctggcg gagcgcttcg agggtgccgc cacgtcgtgg   5880
cgacccaggc tacctggtgg caaggtaagt cgctcgcgcg ggccggcaga tccatgcatc   5940
gctgtacggc cgcatgccgc cggcgccgag aaccccgaac cccgcgtacg gcggcgaagt   6000
tgccgtggtg accggcgctt cgaagggttc gatcgccgcg tcggtggtgg ctcggctgct   6060
cgacgcggag ccaccgtcat cgcgaccacc tccaagctcg acgaggagcg gctgcggttc   6120
taccgcacgc tgtatcgcga ccacgcccgt tacgcgcgg cgctgtggct ggtcgcggcg   6180
aacatggcgt cctactccga cgtcgacgcc ctggtcgaat ggatcggcac cgaacagacc   6240
gaaagccttg ggccgcagtc gattcacatc aaagacgcgc agaccccgac gctgctgttc   6300
cgttcgcggc gcacgcgtgt cgggactgtc ggaggccggt tcgcgcgccg agatggagat   6360
gaaagtgctg ctgtggcggt gcaacggctg atcggcggcc tgtcgacgat cggcgccgaa   6420
cgcgacatgc cgtcgcggct cgagcgtggt gctgcccggc tcgcccaacc gtggcatgtt   6480
cggcggcgac gggccctacg gcgaagccaa gtccgcgctg gatgccgtgg tgacgcgctg   6540
gcacgccgag tcgtcctggg cggcacgggt cagcctggcg cacgcgctca tcggctggac   6600
ccgcggcacc gggctgatgg ccacaacga tgccatcgtg gccgcgtcg aagaggccgg   6660
ggtcaccacc tactcgaccg acgagatggc gcggctgctg ctcgacctgt gtcatgcgga   6720
atccaaggtg gctgcggccg ttcgccgatc aaggccgacc tgaccggggg cctgccgagg   6780
ccaacctcga catggccgag ctggcggcca aggcgcgcga gcagatgtcg gcagcggcgg   6840
ccgtcgacga ggacgccgag gcccctggcg ccatcgccgc gctgccgtcg ccgcccggt   6900
ttcaccccg caccgccgcc gcaatgggac gacctcgatg tcgacccggc cgacctggtg   6960
gtgatcgtcg gcgccgcga aatcggcccg tacggctcgt cacgcacccg gttcgagatg   7020
gaggtcgaaa acgagctgtc ggcggccggc gtgctggagc tggcctggac cactgggttg   7080
```

-continued

```
atcgctggga gacgacccgc aacccggttg gtacgacacc gaatccggcg aaatggtcga    7140
cgaatccgag ttggtgcagc gctacacgac gccgtggtgc agcgcgtcgg cattcgcgaa    7200
ttcgttgatg acggcgcgat cgaccccgac cacgcctcgc cgctgctggt gtcggtgttc    7260
ctggagaagg acttcgcgtt cgtggtgtcc tcggaggccg atgcgcgcgc cttcgtcgag    7320
ttcgatcccg agcacacggt catccggccg gtgcccgact ccaccgactg gcaggtcatc    7380
cgcaaggccg gcaccgagat ccgggtgccg cgaaagacca agctgtcccg cgtcgtcggc    7440
ggccagatcc cgaccgggtt cgacccgacg gtgtggggca tcagcgcaga catggccggt    7500
tccatcgacc ggttggcggt atggaacatg tggcggaccg tcgaccggtt cctgtcgtcc    7560
ggtttcagcc cggccgaggt gatgcgttac gtgcacccga gtttggtggc aacacccag    7620 ggcaccggca tgggcggcgg cacgtcgatg cagacgatgt accacggcaa tctgttgggc    7680
cgcaacaagc cgaacgacat cttccaggaa gtcttgccga tatcattcgc cgcgcacgtg    7740
gttcagtcct acgtcggtag ctacggtgcg atgatccacc cggtagccgc gtgcgccacc    7800
gccgcggtgt cggtcgagga aggtgtcgac aagatccggt tgggaaggct caactggtgg    7860
tcggcggccg tggatgacct gacgctggag ggcatcatcg gattcggtga catggccgcc    7920
accgccgaca cgtccatgat gcgcggccgc ggcatccacg actcgaagtt tccccggccc    7980
aacgaccgcc gccgtctggc ttcgtcgaag cccaaggcgg cgggacgatc ctgttgggcg    8040
cggggacctg gcgctgcgga tggggctgcc ggtgctggcg gtggtgggtt cgcgcagtcg    8100
ttcggcgacg gcgtgcacac ctcgatccgc cccgggcctg ggcgcgctgg gggcggcgcg    8160
cggcggcaag gattcagctg cggcgggcgc tggccaagct gcgtggccgc cgacgacgtg    8220
gcggtcatct ccaagcacga cacctcgacg ctggccaacg atcccaacga gaccgagttg    8280
catgaacggc tcgccgacgc cctgggccgt tccgagggcg ccccgctgtt cgtggtgtcg    8340
cagaagagcc tgaccggcca gccaagggcg gcgcggcggt cttccagatg a            8391
```

<210> SEQ ID NO 31
<211> LENGTH: 2796
<212> TYPE: PRT
<213> ORGANISM: Mycobacterium bovis

<400> SEQUENCE: 31

```
Met Gly Thr Arg Thr Gly Gly Arg Gly Pro Gly Ser Val Arg Gln Ala
1               5                   10                  15

Pro Asp Val Gly Arg Arg Val Gly Ala Arg Arg Val Ala Tyr Pro Asp
            20                  25                  30

Arg Gly Asp Pro Gly Ala Gly Pro Ser Arg His Gly Pro Arg Gly His
        35                  40                  45

Pro Ala Gly Arg His Gly Gly His Ser Gln Gly Val Leu Ala Val Glu
    50                  55                  60

Ala Leu Lys Ala Gly Ala Arg Asp Val Glu Leu Phe Ala Leu Ala
65                  70                  75                  80

Gln Leu Ile Gly Ala Ala Gly Thr Leu Val Ala Arg Arg Glu Phe
                85                  90                  95

Pro Ser Trp Ala Ile Ala Pro Met Val Ser Val Thr Asn Ala Asp Pro
            100                 105                 110

Glu Arg Ile Gly Arg Leu Leu Asp Glu Phe Ala Gln Asp Val Arg Thr
        115                 120                 125

Val Leu Pro Pro Val Leu Ser Ile Arg Asn Gly Arg Arg Ala Val Val
    130                 135                 140
```

-continued

```
Ile Thr Gly Thr Pro Glu Gln Leu Ser Arg Phe Glu Leu Tyr Cys Arg
145                 150                 155                 160

Gln Ile Ser Glu Lys Glu Ala Asp Arg Lys Asn Lys Val Arg Gly
                165                 170                 175

Gly Asp Val Phe Ser Pro Val Phe Glu Pro Val Gln Val Glu Val Gly
                180                 185                 190

Phe His Thr Pro Arg Leu Ser Asp Gly Ile Asp Ile Val Ala Gly Trp
                195                 200                 205

Ala Glu Lys Ala Gly Leu Asp Val Ala Leu Ala Arg Glu Leu Ala Asp
        210                 215                 220

Ala Ile Leu Ile Arg Lys Val Asp Trp Val Asp Glu Ile Thr Arg Val
225                 230                 235                 240

His Arg Ala Gly Ala Arg Trp Ile Leu Asp Leu Gly Pro Gly Asp Ile
                245                 250                 255

Leu Thr Arg Leu Thr Ala Pro Val Ile Arg Gly Leu Gly Ile Gly Ile
                260                 265                 270

Val Pro Ala Arg Thr Arg Gly Gly Gln Arg Asn Leu Phe Thr Val Gly
                275                 280                 285

Ala Thr Pro Glu Val Ala Arg Ala Trp Ser Ser Tyr Ala Pro Thr Val
        290                 295                 300

Val Arg Leu Pro Asp Gly Arg Val Lys Leu Ser Thr Lys Phe Thr Arg
305                 310                 315                 320

Leu Thr Arg Arg Ser Pro Ile Leu Leu Ala Gly Met Thr Pro Thr Thr
                325                 330                 335

Val Asp Ala Lys Ile Val Ala Ala Ala Asn Gly Arg His Trp Ala
                340                 345                 350

Glu Leu Ala Ala Arg Gly Arg Ser Pro Lys Arg Ser Ser Val Thr Ala
                355                 360                 365

Ser Asn Lys Trp Pro Ala Cys Ser Ser Arg Ala Ala Pro Ile Ser Ser
        370                 375                 380

Thr Arg Cys Ser Ser Ile Pro Thr Cys Glu Ala Ser Gly Gly Arg Gln
385                 390                 395                 400

Ala Val Gly Ala Glu Gly Pro Pro Val Arg Arg Asp Arg Arg
                405                 410                 415

Gly Asp Gln Arg Arg His Pro Arg Pro Arg Arg Gly Arg Arg Ala Asp
                420                 425                 430

Arg Arg Thr Gly Arg His Arg His Gln Pro Arg Arg Val Gln Thr Arg
                435                 440                 445

Asp His Arg Ala Asp Pro Leu Gly Asp Ser His Arg His Arg Gly Ala
        450                 455                 460

His Gln Ala Gly Asp His Ala Arg Arg Gly Pro Gly Ala Pro Ala Gly
465                 470                 475                 480

Thr Ile Pro Gly Arg Ile Ser His Leu Leu Ala Thr Tyr Ser Ala
                485                 490                 495

Asp Arg Ala Pro Arg Gln His His Val Cys Val Gly Gly His Leu
                500                 505                 510

Gly Thr Pro Lys Lys Gly Cys Gly Tyr Leu Ser Gly Pro Gly Arg Ser
        515                 520                 525

Val Arg Leu Pro Ile Asp Ala Asp Arg Arg Ile Leu Val Gly Thr Ala
                530                 535                 540

Ala Met Ala Thr Lys Glu Ser Thr Thr Ser Pro Ser Val Lys Arg Met
545                 550                 555                 560
```

-continued

```
Leu Val Asp Thr Gln Gly Thr Asp Gln Trp Ile Ser Ala Gly Lys Ala
            565                 570                 575
Gln Gly Arg Met Pro Pro Ala Glu Ser Ala Arg Cys Arg His Pro Arg
        580                 585                 590
Asp Arg His Ser Ala Ser Val Arg Arg Cys Ser Thr Arg Trp Pro Val
            595                 600                 605
Thr Arg Arg Arg Ser Arg Ser Val Ala Trp Pro Arg Pro Ser Pro
    610                 615                 620
Thr Cys Arg Arg Arg His Asp Leu Pro Ala Val Ala Gly Ala
625                 630                 635                 640
Thr Ser Asn Trp Pro Ser Gly Lys Ala Thr Arg Pro Thr Pro Pro
            645                 650                 655
Arg Trp Ala Ala Arg Gly Trp Pro Thr Leu Ala Gly Pro Leu Arg Ala
                660                 665                 670
Asp Ala Ala Cys Arg Ser Pro Val Ala Pro Thr Gly Phe Arg Pro
            675                 680                 685
Asp Pro Asp Ala Ile His Arg Cys Trp Pro Ala Gly Gln Ser Ala Ala
        690                 695                 700
Ala Ile Ala Ala Leu Val Ala Arg Tyr Pro Asp Ala Glu Thr Val Gln
705                 710                 715                 720
Leu His Pro Ala Asp Val Pro Phe Phe Val Thr Leu Cys Lys Thr Leu
                725                 730                 735
Gly Lys Pro Val Asn Phe Val Pro Ala Ile Asp Leu Val Val Arg Ala
            740                 745                 750
Gly Gly Ala Ala Thr Arg Cys Gly Arg Pro Thr Thr Pro Ala Thr Thr
        755                 760                 765
Pro Met Arg Cys Ala Ser Phe Arg Ala Arg Val Gly Ser Arg Ile Thr
    770                 775                 780
Arg Met Asp Glu Pro Val Gly Glu Leu Leu Asp Ala Phe Glu Gln Ala
785                 790                 795                 800
Ala Ile Asp Glu Val Leu Gly Ala Gly Val Glu Pro Lys Asp Val Ala
                805                 810                 815
Ser Gly Arg Leu Gly Arg Ala Asp Val Ala Gly Pro Leu Ala Val Val
            820                 825                 830
Leu Asp Ala Pro Asp Val Arg Trp Ala Gly Arg Thr Val Thr Asn Pro
        835                 840                 845
Val His Arg Ile Arg Asp Pro Ala Glu Trp Gln Val His Asp Gly Pro
    850                 855                 860
Glu Asn Pro Arg Ala Ala His Ser Ser Thr Gly Ala Arg Leu Gln Thr
865                 870                 875                 880
His Gly Asp Asp Val Ala Leu Ser Val Ala Arg Leu Gly His Leu Gly
                885                 890                 895
Arg His Pro Ile His Val Ala Gly Gln His Arg Arg Trp Arg His Pro
            900                 905                 910
Gly Asp Arg His Arg Gly Arg His Ala Met Arg Thr Val Leu Arg
        915                 920                 925
Ser Pro Pro Val Ser Thr Ala Arg Ser Cys Cys Gly Gly Gln Arg
    930                 935                 940
Asp Gly His Phe Asp Gly Gly Leu Ala Pro Arg Ala Cys Cys Arg Pro
945                 950                 955                 960
His Arg His Arg His Val Arg Cys Ala Leu Ala Pro Ser Leu Thr Asn
                965                 970                 975
Val Pro Thr Arg Leu Val Gly Pro Cys Trp Pro Ala Val Phe Ala Ala
```

-continued

```
            980             985             990
Ile Gly Ser Ala Val Thr Asp Thr  Gly Glu Pro Val  Glu Gly Leu
            995            1000            1005
Leu Ser Leu Val His Leu Asp  Thr Arg Pro Arg Val  Val Gly Gln
        1010            1015            1020
Leu Pro Thr Val Pro Ala Gln  Leu Thr Val Thr Gln  Arg Leu Pro
        1025            1030            1035
Thr Gln Pro Ile Arg Thr Trp  Ala Ala Ser Cys Arg  Ser Arg Ser
        1040            1045            1050
Ser Phe Thr Ala Trp Arg Arg  Asp Arg His Ser Arg  Gly Ala Ile
        1055            1060            1065
Arg Asp Pro Gly Ser His Arg  Phe Ala Glu Leu Asp  Arg Arg Glu
        1070            1075            1080
Pro Val Ala Arg Cys Arg Glu  Arg His Arg His Pro  Ala Arg Arg
        1085            1090            1095
Arg Arg Asp Val Thr Ile Thr  Ala Pro Val Asp Met  Arg Pro Phe
        1100            1105            1110
Ala Val Val Ser Gly Asp His  Asn Pro Ile His Thr  Asp Arg Ala
        1115            1120            1125
Ala Ala Ala Cys Arg Pro Gly  Val Ala Asp Arg Ala  Arg His Val
        1130            1135            1140
Ala Val Gly Arg Gly Ala Thr  Arg Gly Asp Arg His  Arg Arg Ala
        1145            1150            1155
Gly Pro Pro Pro Ala Arg Leu  Val Gly Trp Thr Ala  Arg Phe Leu
        1160            1165            1170
Gly Met Val Ala Pro Ala Thr  Arg Trp Thr Ser Gly  Arg Ala Arg
        1175            1180            1185
Arg Ile Asp Gln Gly Ala Glu  Ile Val Asp Val Ala  Ala Arg Val
        1190            1195            1200
Gly Ser Asp Leu Val Met Ser  Ala Ser Ala Arg Leu  Ala Ala Pro
        1205            1210            1215
Lys Thr Val Tyr Ala Phe Pro  Gly Gln Gly Ile Gln  His Lys Gly
        1220            1225            1230
Met Gly Met Glu Val Arg Ala  Ala Pro Arg Arg Pro  Ala Arg Cys
        1235            1240            1245
Gly Thr Pro Arg Thr Ser Ser  Pro Ala Thr Pro Trp  Ala Ser Arg
        1250            1255            1260
Tyr Cys Thr Trp Ser Ala Thr  Thr Arg Pro Ala Ser  Ser Pro Ala
        1265            1270            1275
Val Cys Thr Thr Thr Asp  Gly Val Leu Tyr Leu  Thr Gln Phe
        1280            1285            1290
Thr Gln Val Ala Met Ala Thr  Val Ala Ala Gly Gln  Val Ala Glu
        1295            1300            1305
Met Arg Glu Gln Gly Ala Phe  Val Glu Gly Ala Ile  Ala Cys Gly
        1310            1315            1320
His Ser Val Gly Glu Tyr Thr  Ala Leu Ala Cys Val  Thr Gly Ile
        1325            1330            1335
Tyr Gln Leu Glu Ala Leu Leu  Glu Met Val Phe His  Arg Gly Ser
        1340            1345            1350
Lys Met His Asp Ile Val Pro  Arg Asp Glu Leu Gly  Arg Ser Asn
        1355            1360            1365
Tyr Arg Leu Ser Ala Ile Arg  Pro Ser Gln Ile Asp  Leu Asp Asp
        1370            1375            1380
```

```
Ala Asp Val Pro Ala Phe Val Ala Gly Ile Ala Glu Ser Thr Gly
    1385                1390                1395

Glu Phe Leu Glu Ile Glu Asn Phe Asn Leu Gly Gly Ser Gln Tyr
    1400                1405                1410

Ala Ile Ala Gly Thr Val Arg Gly Leu Glu Ala Leu Glu Ala Glu
    1415                1420                1425

Val Glu Arg Arg Arg Glu Leu Thr Gly Gly Arg Arg Ser Phe Ile
    1430                1435                1440

Leu Val Pro Gly Ile Asp Val Pro Phe His Ser Arg Val Leu Arg
    1445                1450                1455

Val Gly Val Ala Glu Phe Arg Arg Ser Leu Asp Arg Val Met Arg
    1460                1465                1470

Pro Thr Arg Thr Arg Pro Asp His Arg Ala Leu His Ser Gln Pro
    1475                1480                1485

Gly Ala Ala Glu Val Gln Pro Trp Thr Ala Thr Ser Ser Arg Lys
    1490                1495                1500

Ser Gly Ile Trp Cys Pro Ala Glu Pro Leu Asp Glu Ile Leu Ala
    1505                1510                1515

Asp Tyr Asp Thr Trp Leu Arg Asp Asp Arg Arg Asp Gly Ala His
    1520                1525                1530

Gly Val His Arg Ala Ala Gly Met Ala Ile Arg Gln Pro Gly Ala
    1535                1540                1545

Leu Asp Arg Asp Ala Gly Ser Ala Val His Arg Gly Gly Ala Gly
    1550                1555                1560

Gly Leu Gly Val Glu Arg Phe Val Glu Ile Gly Val Lys Ser Ser
    1565                1570                1575

Pro Thr Val Ala Gly Ser Cys His Gln His Pro Gln Thr Ala Arg
    1580                1585                1590

Ile Arg Pro Gln His Ser Glu Val Leu Asn Ala Glu Arg Asp Ala
    1595                1600                1605

Arg Cys Cys Ser Pro Pro Thr Pro Thr Arg Ser Arg Ser Arg Arg
    1610                1615                1620

Lys Thr Ser Arg Ser Arg Asn Arg Pro Arg Arg Thr Ser Ser Arg
    1625                1630                1635

Lys Pro Pro Pro Ser Arg Arg Pro Leu Arg Arg Arg Ala Arg Val
    1640                1645                1650

Pro Thr Ile Trp Phe Ser Thr Pro Pro Met Pro Arg Cys Val Ile
    1655                1660                1665

Ala Leu Ser Ala Lys Met Arg Ile Asp Gln Ile Glu Glu Leu Asp
    1670                1675                1680

Ser Ile Glu Ser Ile Thr Asp Gly Ala Ser Ser Arg Arg Asn Gln
    1685                1690                1695

Leu Leu Val Asp Leu Gly Ser Glu Leu Asn Leu Gly Ala Ile Glu
    1700                1705                1710

Arg Arg Arg Arg Ile Gly Pro Gly Arg Ser Ala Leu Thr Gly Asp
    1715                1720                1725

Gln Thr Gly Ala His Leu Gln Arg Tyr Gly Pro Val Leu Ser Asp
    1730                1735                1740

Ala Ile Asn Asp His Val Arg Thr Val Leu Gly Pro Ser Gly Lys
    1745                1750                1755

Arg Pro Gly Ala Ile Ala Glu Arg Val Lys Lys Thr Trp Glu Leu
    1760                1765                1770
```

```
Gly Glu Ala Gly Pro Ser Met Ser Pro Ser Arg Ser Arg Trp Ala
    1775                1780                1785

Pro Ala Arg Ala Ala Ala Phe Ala Ala Pro Trp Ala Thr Cys
    1790                1795                1800

Thr Arg Ala Arg Trp Pro Met Pro Pro Pro Ser Thr Arg Ser Ser
    1805                1810                1815

Thr Arg Arg Ser His Arg Trp Pro Arg Pro Gly Arg Phe Gly Ser
    1820                1825                1830

Ala Ala Ser Ala Gly Ser Gly Gly Ala Thr Ile Asp Ala Ala Ala
    1835                1840                1845

Leu Ser Glu Phe Thr Asp Gln Ile Thr Gly Arg Glu Gly Val Leu
    1850                1855                1860

Pro Pro Arg Pro Ala Trp Cys Trp Gly Ser Trp Asp Trp Thr Thr
    1865                1870                1875

Pro Ser Thr Val Ala Gly Arg Pro Asp Ser Glu Leu Ile Asp Leu
    1880                1885                1890

Val Thr Ala Glu Leu Gly Arg Thr Gly Arg Gly Trp Trp His Arg
    1895                1900                1905

Cys Ser Thr Pro Arg Arg Pro Ser Tyr Ser Thr Thr Ala Gly Gln
    1910                1915                1920

Arg Pro Arg Gly Pro Gly Glu Ala Val Ala Asp Arg Arg Lys Asp
    1925                1930                1935

Arg Arg Arg His Arg Arg Arg Leu Ala Ala Leu Ala Glu Arg Phe
    1940                1945                1950

Glu Gly Ala Ala Thr Ser Trp Arg Pro Arg Leu Pro Gly Gly Lys
    1955                1960                1965

Val Ser Arg Ser Arg Gly Pro Ala Asp Pro Cys Ile Ala Val Arg
    1970                1975                1980

Pro His Ala Ala Gly Ala Glu Asn Pro Glu Pro Arg Val Arg Arg
    1985                1990                1995

Arg Ser Cys Arg Gly Asp Arg Arg Phe Glu Gly Phe Asp Arg Arg
    2000                2005                2010

Val Gly Gly Gly Ser Ala Ala Arg Arg Gly Ala Thr Val Ile Ala
    2015                2020                2025

Thr Thr Ser Lys Leu Asp Glu Glu Arg Leu Arg Phe Tyr Arg Thr
    2030                2035                2040

Leu Tyr Arg Asp His Ala Arg Tyr Gly Ala Ala Leu Trp Leu Val
    2045                2050                2055

Ala Ala Asn Met Ala Ser Tyr Ser Asp Val Asp Ala Leu Val Glu
    2060                2065                2070

Trp Ile Gly Thr Glu Gln Thr Glu Ser Leu Gly Pro Gln Ser Ile
    2075                2080                2085

His Ile Lys Asp Ala Gln Thr Pro Thr Leu Leu Phe Arg Ser Arg
    2090                2095                2100

Arg Thr Arg Val Gly Thr Val Gly Gly Arg Phe Ala Arg Arg Asp
    2105                2110                2115

Gly Asp Glu Ser Ala Ala Val Ala Val Gln Arg Leu Ile Gly Gly
    2120                2125                2130

Leu Ser Thr Ile Gly Ala Glu Arg Asp Met Pro Ser Arg Leu Glu
    2135                2140                2145

Arg Gly Ala Ala Arg Leu Ala Gln Pro Trp His Val Arg Arg Arg
    2150                2155                2160

Arg Ala Leu Arg Arg Ser Gln Val Arg Ala Gly Cys Arg Gly Asp
```

-continued

```
            2165                2170                2175

Ala Leu Ala Arg Arg Val Val Leu Gly Gly Thr Gly Gln Pro Gly
        2180                2185                2190

Ala Arg Ala His Arg Leu Asp Pro Arg His Arg Ala Asp Gly Pro
        2195                2200                2205

Gln Arg Cys His Arg Gly Arg Arg Arg Gly Arg Gly His His
        2210                2215                2220

Leu Leu Asp Arg Arg Asp Gly Ala Ala Ala Arg Pro Val Ser
        2225                2230                2235

Cys Gly Ile Gln Gly Gly Cys Gly Arg Ser Pro Ile Lys Ala Asp
        2240                2245                2250

Leu Thr Gly Gly Leu Pro Arg Pro Thr Ser Thr Trp Pro Ser Trp
        2255                2260                2265

Arg Pro Arg Arg Ala Ser Arg Cys Arg Gln Arg Pro Ser Thr
        2270                2275                2280

Arg Thr Pro Arg Pro Leu Ala Pro Ser Pro Arg Cys Arg Arg Arg
        2285                2290                2295

Pro Gly Phe Thr Pro Ala Pro Pro Gln Trp Asp Asp Leu Asp
        2300                2305                2310

Val Asp Pro Ala Asp Leu Val Val Ile Val Gly Gly Arg Glu Ile
        2315                2320                2325

Gly Pro Tyr Gly Ser Ser Arg Thr Arg Phe Glu Met Glu Val Glu
        2330                2335                2340

Asn Glu Leu Ser Ala Ala Gly Val Leu Glu Leu Ala Trp Thr Thr
        2345                2350                2355

Gly Leu Ile Ala Gly Arg Arg Pro Ala Thr Arg Leu Val Arg His
        2360                2365                2370

Arg Ile Arg Arg Asn Gly Arg Arg Ile Arg Val Gly Ala Ala Leu
        2375                2380                2385

His Asp Ala Val Val Gln Arg Val Gly Ile Arg Glu Phe Val Asp
        2390                2395                2400

Asp Gly Ala Ile Asp Pro Asp His Ala Ser Pro Leu Leu Val Ser
        2405                2410                2415

Val Phe Leu Glu Lys Asp Phe Ala Phe Val Val Ser Ser Glu Ala
        2420                2425                2430

Asp Ala Arg Ala Phe Val Glu Phe Asp Pro Glu His Thr Val Ile
        2435                2440                2445

Arg Pro Val Pro Asp Ser Thr Asp Trp Gln Val Ile Arg Lys Ala
        2450                2455                2460

Gly Thr Glu Ile Arg Val Pro Arg Lys Thr Lys Leu Ser Arg Val
        2465                2470                2475

Val Gly Gly Gln Ile Pro Thr Gly Phe Asp Pro Thr Val Trp Gly
        2480                2485                2490

Ile Ser Ala Asp Met Ala Gly Ser Ile Asp Arg Leu Ala Val Trp
        2495                2500                2505

Asn Met Trp Arg Thr Val Asp Arg Phe Leu Ser Ser Gly Phe Ser
        2510                2515                2520

Pro Ala Glu Val Met Arg Tyr Val His Pro Ser Leu Val Ala Asn
        2525                2530                2535

Thr Gln Gly Thr Gly Met Gly Gly Gly Thr Ser Met Gln Thr Met
        2540                2545                2550

Tyr His Gly Asn Leu Leu Gly Arg Asn Lys Pro Asn Asp Ile Phe
        2555                2560                2565
```

| Gln | Glu | Val | Leu | Pro | Ile | Ser | Phe | Ala | Ala | His | Val | Val | Gln | Ser |
|---|---|---|---|---|---|---|---|---|---|---|---|---|---|---|
| | 2570 | | | | 2575 | | | | | 2580 | | | | |

| Tyr | Val | Gly | Ser | Tyr | Gly | Ala | Met | Ile | His | Pro | Val | Ala | Ala | Cys |
|---|---|---|---|---|---|---|---|---|---|---|---|---|---|---|
| 2585 | | | | | 2590 | | | | | 2595 | | | | |

| Ala | Thr | Ala | Ala | Val | Ser | Val | Glu | Glu | Gly | Val | Asp | Lys | Ile | Arg |
|---|---|---|---|---|---|---|---|---|---|---|---|---|---|---|
| 2600 | | | | | 2605 | | | | | 2610 | | | | |

| Leu | Gly | Arg | Leu | Asn | Trp | Trp | Ser | Ala | Ala | Val | Asp | Asp | Leu | Thr |
|---|---|---|---|---|---|---|---|---|---|---|---|---|---|---|
| 2615 | | | | | 2620 | | | | | 2625 | | | | |

| Leu | Glu | Gly | Ile | Ile | Gly | Phe | Gly | Asp | Met | Ala | Ala | Thr | Ala | Asp |
|---|---|---|---|---|---|---|---|---|---|---|---|---|---|---|
| 2630 | | | | | 2635 | | | | | 2640 | | | | |

| Thr | Ser | Met | Met | Arg | Gly | Arg | Gly | Ile | His | Asp | Ser | Lys | Phe | Ser |
|---|---|---|---|---|---|---|---|---|---|---|---|---|---|---|
| 2645 | | | | | 2650 | | | | | 2655 | | | | |

| Arg | Pro | Asn | Asp | Arg | Arg | Arg | Leu | Ala | Ser | Ser | Lys | Pro | Lys | Ala |
|---|---|---|---|---|---|---|---|---|---|---|---|---|---|---|
| 2660 | | | | | 2665 | | | | | 2670 | | | | |

| Ala | Gly | Arg | Ser | Cys | Trp | Ala | Arg | Gly | Pro | Gly | Ala | Ala | Asp | Gly |
|---|---|---|---|---|---|---|---|---|---|---|---|---|---|---|
| 2675 | | | | | 2680 | | | | | 2685 | | | | |

| Ala | Ala | Gly | Ala | Gly | Gly | Gly | Phe | Ala | Gln | Ser | Phe | Gly | Asp |
|---|---|---|---|---|---|---|---|---|---|---|---|---|---|
| 2690 | | | | | 2695 | | | | | 2700 | | | | |

| Gly | Val | His | Thr | Ser | Ile | Arg | Pro | Gly | Pro | Gly | Arg | Ala | Gly | Gly |
|---|---|---|---|---|---|---|---|---|---|---|---|---|---|---|
| 2705 | | | | | 2710 | | | | | 2715 | | | | |

| Gly | Ala | Arg | Arg | Gln | Gly | Phe | Ser | Cys | Gly | Gly | Arg | Trp | Pro | Ser |
|---|---|---|---|---|---|---|---|---|---|---|---|---|---|---|
| 2720 | | | | | 2725 | | | | | 2730 | | | | |

| Cys | Val | Ala | Ala | Asp | Asp | Val | Ala | Val | Ile | Ser | Lys | His | Asp | Thr |
|---|---|---|---|---|---|---|---|---|---|---|---|---|---|---|
| 2735 | | | | | 2740 | | | | | 2745 | | | | |

| Ser | Thr | Leu | Ala | Asn | Asp | Pro | Asn | Glu | Thr | Glu | Leu | His | Glu | Arg |
|---|---|---|---|---|---|---|---|---|---|---|---|---|---|---|
| 2750 | | | | | 2755 | | | | | 2760 | | | | |

| Leu | Ala | Asp | Ala | Leu | Gly | Arg | Ser | Glu | Gly | Ala | Pro | Leu | Phe | Val |
|---|---|---|---|---|---|---|---|---|---|---|---|---|---|---|
| 2765 | | | | | 2770 | | | | | 2775 | | | | |

| Val | Ser | Gln | Lys | Ser | Leu | Thr | Gly | Gln | Pro | Arg | Ala | Ala | Arg | Arg |
|---|---|---|---|---|---|---|---|---|---|---|---|---|---|---|
| 2780 | | | | | 2785 | | | | | 2790 | | | | |

| Ser | Ser | Arg |
|---|---|---|
| 2795 | | |

<210> SEQ ID NO 32
<211> LENGTH: 675
<212> TYPE: DNA
<213> ORGANISM: Bacillus subtilis

<400> SEQUENCE: 32

```
atgaagattt acggaattta tatggaccgc ccgctttcac aggaagaaaa tgaacggttc    60
atgactttca tatccctga aaaacgggag aaatgccgga gatttttatca taaagaagat   120
gctcaccgca ccctgctggg agatgtgctc gttcgctcag tcataagcag gcagtatcag   180
ttggacaaat ccgatatccg ctttagcacg caggaatacg ggaagccgtg catccctgat   240
cttcccgacg ctcatttcaa catttctcac tccggccgct gggtcattgg tgcgtttgat   300
tcacagccga tcggcataga tatcgaaaaa acgaaaccga tcagccttga gatcgccaag   360
cgcttctttt caaaaacaga gtacagcgac ttttagcaa agacaaggcga cgagcagaca   420
gactattttt atcatctatg gtcaatgaaa gaaagcttta tcaaacagga aggcaaaggc   480
ttatcgcttc cgcttgattc cttttcagtg cgcctgcatc aggacggaca agtatccatt   540
gagcttccgg acagccattc ccatgctat atcaaaacgt atgaggtcga tcccggctac   600
aaaatggctg tatgcgccgc acaccctgat ttccccgagg atatcacaat ggtctcgtac   660
```
gaagagcttt tataa                                                                                                                                675

<210> SEQ ID NO 33
<211> LENGTH: 224
<212> TYPE: PRT
<213> ORGANISM: Bacillus subtilis

<400> SEQUENCE: 33

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 34
<211> LENGTH: 714
<212> TYPE: DNA
<213> ORGANISM: Brevibacillus brevis

<400> SEQUENCE: 34
atgatagaaa tgttatttgt aaaggttcca acgaaatcg ataggcatgt gtttaacttc        60
ttgtcatcaa atgtgagtaa ggaaaaacag caggcgtttg ttcgatacgt taatgtgaaa       120
gatgcttatc gttctctttt aggggaattg cttattagaa atatttgat acaagtatta       180 aacattccta tgaaaacat tctatttagg aaaaatgaat atggaaaacc ttttgttgat       240
ttcgatattc attttaatat ttcccactct gatgaatggg ttgtatgtgc aatttcaaat       300
catcctgttg gaattgatat cgagcgtatt tcggagatag acattaaaat agcagaacaa       360 tttttttcatg aaaatgaata tatatggttg cagtctaaag cccaaaatag tcaagtttct       420
tctttttttg agctttggac tattaaagaa agttatataa agctattgg taaaggtatg       480 tacataccga ttaattcatt ttggattgat aagaatcaaa cacaaactgt aatttacaaa       540
cagaataaaa aagaacctgt tactattttat gaaccagagt tgtttgaggg ctacaagtgt       600

```
tcttgttgtt ctttgttttc ttctgtaacg aacttgtcta ttactaaatt gcaagtgcaa    660
gagttatgta atttgtttct agattctaca ttttctgaaa ataataactt ttag          714
```

<210> SEQ ID NO 35
<211> LENGTH: 237
<212> TYPE: PRT
<213> ORGANISM: Brevibacillus brevis

<400> SEQUENCE: 35

```
Met Ile Glu Met Leu Phe Val Lys Val Pro Asn Glu Ile Asp Arg His
1               5                   10                  15

Val Phe Asn Phe Leu Ser Ser Asn Val Ser Lys Glu Lys Gln Gln Ala
            20                  25                  30

Phe Val Arg Tyr Val Asn Val Lys Asp Ala Tyr Arg Ser Leu Leu Gly
        35                  40                  45

Glu Leu Leu Ile Arg Lys Tyr Leu Ile Gln Val Leu Asn Ile Pro Asn
    50                  55                  60

Glu Asn Ile Leu Phe Arg Lys Asn Glu Tyr Gly Lys Pro Phe Val Asp
65                  70                  75                  80

Phe Asp Ile His Phe Asn Ile Ser His Ser Asp Glu Trp Val Val Cys
                85                  90                  95

Ala Ile Ser Asn His Pro Val Gly Ile Asp Ile Glu Arg Ile Ser Glu
            100                 105                 110

Ile Asp Ile Lys Ile Ala Glu Gln Phe Phe His Glu Asn Gly Tyr Ile
        115                 120                 125

Trp Leu Gln Ser Lys Ala Gln Asn Ser Gln Val Ser Ser Phe Phe Glu
    130                 135                 140

Leu Trp Thr Ile Lys Glu Ser Tyr Ile Lys Ala Ile Gly Lys Gly Met
145                 150                 155                 160

Tyr Ile Pro Ile Asn Ser Phe Trp Ile Asp Lys Asn Gln Thr Gln Thr
                165                 170                 175

Val Ile Tyr Lys Gln Asn Lys Lys Glu Pro Val Thr Ile Tyr Glu Pro
            180                 185                 190

Glu Leu Phe Glu Gly Tyr Lys Cys Ser Cys Cys Ser Leu Phe Ser Ser
        195                 200                 205

Val Thr Asn Leu Ser Ile Thr Lys Leu Gln Val Gln Glu Leu Cys Asn
    210                 215                 220

Leu Phe Leu Asp Ser Thr Phe Ser Glu Asn Asn Asn Phe
225                 230                 235
```

<210> SEQ ID NO 36
<211> LENGTH: 648
<212> TYPE: DNA
<213> ORGANISM: Escherichia coli

<400> SEQUENCE: 36

```
ttgtcatcag tctcgaatat ggtcgatatg aaaactacgc atacctccct cccctttgcc    60
ggacatacgc tgcattttgt tgagttcgat ccggcgaatt ttgtgagca ggatttactc    120 tggctgccgc actacgcaca actgcaacac gctggacgta acgtaaaac agagcattta    180 gccggacgga tcgctgctgt ttatgctttg cggaatatg gctataaatg tgtgcccgca    240
atcggcgagc tacgccaacc tgtctggcct gcggaggtat acggcagtat tagccactgt    300
gggactacgg cattagccgt ggtatctcgt caaccgattg gcattgatat agaagaaatt    360
ttttctgtac aaaccgcaag agaattgaca gacaacatta ttacaccagc ggaacacgag    420
```

```
cgactcgcag actgcggttt agccttttct ctggcgctga cactggcatt ttccgccaaa      480
gagagcgcat ttaaggcaag tgagatccaa actgatgcag gttttctgga ctatcagata      540
attagctgga ataaacagca ggtcatcatt catcgtgaga atgagatgtt tgctgtgcac      600
tggcagataa aagaaaagat agtcataacg ctgtgccaac acgattaa                   648
```

<210> SEQ ID NO 37
<211> LENGTH: 215
<212> TYPE: PRT
<213> ORGANISM: Escherichia coli

<400> SEQUENCE: 37

```
Met Ser Ser Val Ser Asn Met Val Asp Met Lys Thr Thr His Thr Ser
1               5                   10                  15

Leu Pro Phe Ala Gly His Thr Leu His Phe Val Glu Phe Asp Pro Ala
            20                  25                  30

Asn Phe Cys Glu Gln Asp Leu Leu Trp Leu Pro His Tyr Ala Gln Leu
        35                  40                  45

Gln His Ala Gly Arg Lys Arg Lys Thr Glu His Leu Ala Gly Arg Ile
    50                  55                  60

Ala Ala Val Tyr Ala Leu Arg Glu Tyr Gly Tyr Lys Cys Val Pro Ala
65                  70                  75                  80

Ile Gly Glu Leu Arg Gln Pro Val Trp Pro Ala Glu Val Tyr Gly Ser
                85                  90                  95

Ile Ser His Cys Gly Thr Thr Ala Leu Ala Val Val Ser Arg Gln Pro
            100                 105                 110

Ile Gly Ile Asp Ile Glu Glu Ile Phe Ser Val Gln Thr Ala Arg Glu
        115                 120                 125

Leu Thr Asp Asn Ile Ile Thr Pro Ala Glu His Glu Arg Leu Ala Asp
    130                 135                 140

Cys Gly Leu Ala Phe Ser Leu Ala Leu Thr Leu Ala Phe Ser Ala Lys
145                 150                 155                 160

Glu Ser Ala Phe Lys Ala Ser Glu Ile Gln Thr Asp Ala Gly Phe Leu
                165                 170                 175

Asp Tyr Gln Ile Ile Ser Trp Asn Lys Gln Gln Val Ile Ile His Arg
            180                 185                 190

Glu Asn Glu Met Phe Ala Val His Trp Gln Ile Lys Glu Lys Ile Val
        195                 200                 205

Ile Thr Leu Cys Gln His Asp
    210                 215
```

<210> SEQ ID NO 38
<211> LENGTH: 741
<212> TYPE: DNA
<213> ORGANISM: Streptomyces verticillus

<400> SEQUENCE: 38

```
gtgatcgccg ccctcctgcc ctcctgggcc gtcaccgaac acgccttcac cgacgcccg       60 gacgacccgg tgagcctcct cttccccgag gaggccgccc acgtcgcccg cgccgtcccc      120
aagcgcctgc acgagttcgc caccgtccgg gtgtgcgccc gcgccgccct cggccggctg      180
ggcctcccgc ccggtccgct gctgcccggc cgacggggcg cgccgagctg gcggacggg       240 gtggtgggga gcatgacgca ctgtcagggc ttcggggcg ccgcggtcgc ccgggccgcc       300
gacgccgcgt cgctcgggat agacgccgag ccgaacgggc gctcccggga cggcgtcctc      360
```

```
gccatggtct cgctgccgtc cgagcgcgag tggctcgccg gactggcggc ccgccggccg      420
gacgtgcact gggaccggct gctgttcagc gccaaggaga gcgtcttcaa ggcgtggtac      480
ccgctgaccg gcctggagct ggacttcgac gaggccgagc tggccgtcga tccggacgcc      540
gggacgttca cggcccggct gctggtgccg ggaccggtgg tcggcggccg tcggctggac      600
gggttcgagg ggcgctgggc ggcgggcgag ggcctcgtcg tcaccgccat cgccgtcgcg      660
gcgccggccg gtaccgcgga ggaatcggcg aaggggccg ggaaggaagc gactgcggac       720
gaccggaccg ccgtcccgta a                                                741
```

<210> SEQ ID NO 39
<211> LENGTH: 246
<212> TYPE: PRT
<213> ORGANISM: Streptomyces verticillus

<400> SEQUENCE: 39

```
Met Ile Ala Ala Leu Leu Pro Ser Trp Ala Val Thr Glu His Ala Phe
1               5                   10                  15

Thr Asp Ala Pro Asp Asp Pro Val Ser Leu Leu Phe Pro Glu Glu Ala
            20                  25                  30

Ala His Val Ala Arg Ala Val Pro Lys Arg Leu His Glu Phe Ala Thr
        35                  40                  45

Val Arg Val Cys Ala Arg Ala Ala Leu Gly Arg Leu Gly Leu Pro Pro
    50                  55                  60

Gly Pro Leu Leu Pro Gly Arg Arg Gly Ala Pro Ser Trp Pro Asp Gly
65                  70                  75                  80

Val Val Gly Ser Met Thr His Cys Gln Gly Phe Arg Gly Ala Ala Val
                85                  90                  95

Ala Arg Ala Ala Asp Ala Ala Ser Leu Gly Ile Asp Ala Glu Pro Asn
            100                 105                 110

Gly Pro Leu Pro Asp Gly Val Leu Ala Met Val Ser Leu Pro Ser Glu
        115                 120                 125

Arg Glu Trp Leu Ala Gly Leu Ala Ala Arg Arg Pro Asp Val His Trp
    130                 135                 140

Asp Arg Leu Leu Phe Ser Ala Lys Glu Ser Val Phe Lys Ala Trp Tyr
145                 150                 155                 160

Pro Leu Thr Gly Leu Glu Leu Asp Phe Asp Glu Ala Glu Leu Ala Val
                165                 170                 175

Asp Pro Asp Ala Gly Thr Phe Thr Ala Arg Leu Leu Val Pro Gly Pro
            180                 185                 190

Val Val Gly Gly Arg Arg Leu Asp Gly Phe Glu Gly Arg Trp Ala Ala
        195                 200                 205

Gly Glu Gly Leu Val Val Thr Ala Ile Ala Val Ala Ala Pro Ala Gly
    210                 215                 220

Thr Ala Glu Glu Ser Ala Glu Gly Ala Gly Lys Glu Ala Thr Ala Asp
225                 230                 235                 240

Asp Arg Thr Ala Val Pro
                245
```

<210> SEQ ID NO 40
<211> LENGTH: 819
<212> TYPE: DNA
<213> ORGANISM: Saccharomyces cerevisiae

<400> SEQUENCE: 40

```
atggttaaaa cgactgaagt agtaagcgaa gtttcaaagg tggcaggtgt aagaccatgg      60
```

```
gcaggtatat tcgttgttga aattcaagag gatatactcg cggatgagtt tacgttcgag    120
gcattaatga gaactttgcc attggcgtct caagccagaa tcctcaataa aaaatcgttt    180
cacgatagat gttcaaatct atgcagccag ctgctgcagt tgtttggctg ctctatagta    240
acgggcttaa attttcaaga gctgaaattt gacaagggca gcttcggtaa gccattctta    300
gacaacaatc gttttcttcc atttagcatg accatcggtg aacaatatgt agctatgttc    360
ctcgtaaaat gtgtaagtac agatgaatac caggatgtcg gaattgatat cgcttctccg    420
tgcaattatg gcgggaggga agagttggag ctatttaaag aagttttttag tgaaagagaa    480 tttaacggtt tactgaaagc gtctgatcca tgcacaatat ttacttactt atggtccttg    540
aaggagtcgt atacaaaatt tactggaact ggccttaaca cagacttgtc actaatagat    600
tttggcgcta tcagcttttt tccggctgag ggagcttcta tgtgcataac tctggatgaa    660
gttccattga ttttccattc tcaatggttc aataacgaaa ttgtcactat ctgtatgcca    720
aagtccatca gtgataaaat caacacgaac agaccaaaat tatataatat cagcttatct    780
acgttgattg attatttcat cgaaaatgat ggtttataa                          819
```

<210> SEQ ID NO 41
<211> LENGTH: 272
<212> TYPE: PRT
<213> ORGANISM: Saccharomyces cerevisiae

<400> SEQUENCE: 41

```
Met Val Lys Thr Thr Glu Val Val Ser Glu Val Ser Lys Val Ala Gly
1               5                   10                  15

Val Arg Pro Trp Ala Gly Ile Phe Val Val Glu Ile Gln Glu Asp Ile
            20                  25                  30

Leu Ala Asp Glu Phe Thr Phe Glu Ala Leu Met Arg Thr Leu Pro Leu
        35                  40                  45

Ala Ser Gln Ala Arg Ile Leu Asn Lys Lys Ser Phe His Asp Arg Cys
    50                  55                  60

Ser Asn Leu Cys Ser Gln Leu Leu Gln Leu Phe Gly Cys Ser Ile Val
65                  70                  75                  80

Thr Gly Leu Asn Phe Gln Glu Leu Lys Phe Asp Lys Gly Ser Phe Gly
                85                  90                  95

Lys Pro Phe Leu Asp Asn Asn Arg Phe Leu Pro Phe Ser Met Thr Ile
            100                 105                 110

Gly Glu Gln Tyr Val Ala Met Phe Leu Val Lys Cys Val Ser Thr Asp
        115                 120                 125

Glu Tyr Gln Asp Val Gly Ile Asp Ile Ala Ser Pro Cys Asn Tyr Gly
    130                 135                 140

Gly Arg Glu Glu Leu Glu Leu Phe Lys Glu Val Phe Ser Glu Arg Glu
145                 150                 155                 160

Phe Asn Gly Leu Leu Lys Ala Ser Asp Pro Cys Thr Ile Phe Thr Tyr
                165                 170                 175

Leu Trp Ser Leu Lys Glu Ser Tyr Thr Lys Phe Thr Gly Thr Gly Leu
            180                 185                 190

Asn Thr Asp Leu Ser Leu Ile Asp Phe Gly Ala Ile Ser Phe Phe Pro
        195                 200                 205

Ala Glu Gly Ala Ser Met Cys Ile Thr Leu Asp Glu Val Pro Leu Ile
    210                 215                 220

Phe His Ser Gln Trp Phe Asn Asn Glu Ile Val Thr Ile Cys Met Pro
225                 230                 235                 240
```

```
Lys Ser Ile Ser Asp Lys Ile Asn Thr Asn Arg Pro Lys Leu Tyr Asn
            245                 250                 255

Ile Ser Leu Ser Thr Leu Ile Asp Tyr Phe Ile Glu Asn Asp Gly Leu
        260                 265                 270
```

<210> SEQ ID NO 42
<211> LENGTH: 588
<212> TYPE: DNA
<213> ORGANISM: Escherichia coli

<400> SEQUENCE: 42

```
atggtggacc aggcgcagga caccctgcgc ccgaataaca gattgtcaga tatgcaggca      60
acaatggaac aaacccaggc ctttgaaaac cgtgtgcttg agcgtctgaa tgctggcaaa     120
accgtgcgaa gctttctgat caccgccgtc gagctcctga ccgaggcggt aaatcttctg     180
gtgcttcagg tattccgcaa agacgattac gcggtgaagt atgctgtaga accgttactc     240
gacggcgatg gtccgctggg cgatctttct gtgcgtttaa aactcattta cgggttgggc     300
gtcattaacc gccaggaata cgaagatgcg gaactgctga tggcattgcg tgaagagcta     360
aatcacgacg gcaacgagta cgcctttacc gacgacgaaa tccttggacc ctttggtgaa     420
ctgcactgcg tggcggcgtt accaccgccg ccacagtttg aaccagcaga ctccagtttg     480
tatgcaatgc aaattcagcg ctatcaacag gctgtgcgat caacaatggt cctttcactg     540
actgagctga tttccaaaat cagcttaaaa aaagcctttc aaaagtaa                  588
```

<210> SEQ ID NO 43
<211> LENGTH: 195
<212> TYPE: PRT
<213> ORGANISM: Escherichia coli

<400> SEQUENCE: 43

```
Met Val Asp Gln Ala Gln Asp Thr Leu Arg Pro Asn Asn Arg Leu Ser
1               5                   10                  15

Asp Met Gln Ala Thr Met Glu Gln Thr Gln Ala Phe Glu Asn Arg Val
            20                  25                  30

Leu Glu Arg Leu Asn Ala Gly Lys Thr Val Arg Ser Phe Leu Ile Thr
        35                  40                  45

Ala Val Glu Leu Leu Thr Glu Ala Val Asn Leu Val Leu Gln Val
    50                  55                  60

Phe Arg Lys Asp Asp Tyr Ala Val Lys Tyr Ala Val Glu Pro Leu Leu
65                  70                  75                  80

Asp Gly Asp Gly Pro Leu Gly Asp Leu Ser Val Arg Leu Lys Leu Ile
            85                  90                  95

Tyr Gly Leu Gly Val Ile Asn Arg Gln Glu Tyr Glu Asp Ala Glu Leu
            100                 105                 110

Leu Met Ala Leu Arg Glu Glu Leu Asn His Asp Gly Asn Glu Tyr Ala
        115                 120                 125

Phe Thr Asp Asp Glu Ile Leu Gly Pro Phe Gly Glu Leu His Cys Val
    130                 135                 140

Ala Ala Leu Pro Pro Pro Pro Gln Phe Glu Pro Ala Asp Ser Ser Leu
145                 150                 155                 160

Tyr Ala Met Gln Ile Gln Arg Tyr Gln Gln Ala Val Arg Ser Thr Met
            165                 170                 175

Val Leu Ser Leu Thr Glu Leu Ile Ser Lys Ile Ser Leu Lys Lys Ala
        180                 185                 190
```

```
Phe Gln Lys
      195

<210> SEQ ID NO 44
<211> LENGTH: 16
<212> TYPE: PRT
<213> ORGANISM: Artificial
<220> FEATURE:
<223> OTHER INFORMATION: Peptide Sequence

<400> SEQUENCE: 44

Ser Lys His Asp Thr Ser Thr Asn Ala Asn Asp Pro Asn Glu Ser Glu
1               5                   10                  15

<210> SEQ ID NO 45
<211> LENGTH: 14
<212> TYPE: PRT
<213> ORGANISM: Artificial
<220> FEATURE:
<223> OTHER INFORMATION: Peptide Sequence

<400> SEQUENCE: 45

Gln Asn Lys Ile Arg Gln Asp Gln Ile Asn Asp Ser Asp Thr
1               5                   10

<210> SEQ ID NO 46
<211> LENGTH: 16
<212> TYPE: PRT
<213> ORGANISM: artificial
<220> FEATURE:
<223> OTHER INFORMATION: Peptide Sequence

<400> SEQUENCE: 46

Arg Ile Asn Ser Asp Ser Tyr Trp Asp Asn Leu Pro Glu Glu Gln Arg
1               5                   10                  15

<210> SEQ ID NO 47
<211> LENGTH: 14
<212> TYPE: PRT
<213> ORGANISM: Artificial
<220> FEATURE:
<223> OTHER INFORMATION: Peptide Sequence

<400> SEQUENCE: 47

Thr Leu Val Glu Arg Asp Glu Asn Gly Asn Ser Asn Tyr Gly
1               5                   10

<210> SEQ ID NO 48
<211> LENGTH: 21
<212> TYPE: DNA
<213> ORGANISM: Artificial
<220> FEATURE:
<223> OTHER INFORMATION: Primer Sequence

<400> SEQUENCE: 48
ttcataagat gtcacgccag g                                              21

<210> SEQ ID NO 49
<211> LENGTH: 20
<212> TYPE: DNA
<213> ORGANISM: artificial
<220> FEATURE:
<223> OTHER INFORMATION: Primer Sequence

<400> SEQUENCE: 49
ggtacgcgtc atattccttg                                                20
```